US009475824B2

(12) United States Patent
Zhou et al.

(10) Patent No.: US 9,475,824 B2
(45) Date of Patent: *Oct. 25, 2016

(54) FUSED PYRIMIDINES AS INHIBITORS OF P97 COMPLEX

(71) Applicant: Cleave Biosciences, Inc., Burlingame, CA (US)

(72) Inventors: Han-Jie Zhou, Foster City, CA (US); Francesco Parlati, San Francisco, CA (US); David Wustrow, Los Gatos, CA (US)

(73) Assignee: Cleave Biosciences, Inc., Burlingame, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/416,033

(22) PCT Filed: Jul. 19, 2013

(86) PCT No.: PCT/US2013/051358
§ 371 (c)(1),
(2) Date: Jan. 20, 2015

(87) PCT Pub. No.: WO2014/015291
PCT Pub. Date: Jan. 23, 2014

(65) Prior Publication Data
US 2015/0239907 A1    Aug. 27, 2015

Related U.S. Application Data

(60) Provisional application No. 61/674,144, filed on Jul. 20, 2012, provisional application No. 61/737,666, filed on Dec. 14, 2012.

(51) Int. Cl.
| | |
|---|---|
| *C07D 403/04* | (2006.01) |
| *C07D 471/04* | (2006.01) |
| *C07D 495/04* | (2006.01) |
| *C07D 491/048* | (2006.01) |
| *C07D 491/052* | (2006.01) |
| *A61K 31/517* | (2006.01) |
| *A61K 31/519* | (2006.01) |
| *C07D 513/04* | (2006.01) |
| *C07D 405/04* | (2006.01) |
| *C07D 473/34* | (2006.01) |
| *C07D 487/04* | (2006.01) |

(52) U.S. Cl.
CPC .......... *C07D 513/04* (2013.01); *C07D 403/04* (2013.01); *C07D 405/04* (2013.01); *C07D 471/04* (2013.01); *C07D 473/34* (2013.01); *C07D 487/04* (2013.01); *C07D 491/048* (2013.01); *C07D 491/052* (2013.01); *C07D 495/04* (2013.01)

(58) Field of Classification Search
None
See application file for complete search history.

(56) References Cited

U.S. PATENT DOCUMENTS
| | | | |
|---|---|---|---|
| 7,741,432 B2 | 6/2010 | Parlati et al. | |
| 9,062,026 B2* | 6/2015 | Zhou | .......... C07D 403/04 |
| 2014/0024661 A1 | 1/2014 | Zhou et al. | |

FOREIGN PATENT DOCUMENTS
| | | |
|---|---|---|
| JP | 2015526420 A | 9/2015 |
| WO | WO-9810779 A1 | 3/1998 |
| WO | WO-2008152390 A1 | 12/2008 |
| WO | WO-2010151601 A1 | 12/2010 |
| WO | WO-2011140527 A2 | 11/2011 |
| WO | WO-2011152485 A1 | 12/2011 |
| WO | WO-2014015291 A1 | 1/2014 |

OTHER PUBLICATIONS

U.S. Appl. No. 13/946,795, Non Final Office Action mailed Jul. 30, 2014, 7 pgs.
International Application Serial No. PCT/US2013/051358, Amendement and Response filed Sep. 5, 2014 to Written Opinion mailed Jul. 16, 2014, 27 pgs.
International Application Serial No. PCT/US2013/051358, International Preliminary Report on Patentability mailed Oct. 7, 2014, 6 pgs.
International Application Serial No. PCT/US2013/051358, International Search Report mailed Sep. 23, 2013, 3 pgs.
International Application Serial No. PCT/US2013/051358, Letter under Article 19(1) filed Nov. 22, 2013 in response to International Search Report mailed Sep. 23, 2013, 46 pgs.
International Application Serial No. PCT/US2013/051358, Written Opinion mailed Jul. 16, 2014, 5 pgs.
International Application Serial No. PCT/US2013/051358, Written Opinion mailed Sep. 23, 2013, 6 pgs.
Ali, Amjad, et al., "Novel pyrazolo[3,4-d]pyrimidine-based inhibitors of *Staphlococcus aureus* DNA polymerase III: design, synthesis, and biological evaluation", J. Med. Chem., 46(10), (May 2003), 1824-1830.

(Continued)

Primary Examiner — Emily Bernhardt
(74) Attorney, Agent, or Firm — Schwegman Lundberg & Woessner, P.A.

(57) ABSTRACT

Disclosed are fused pyrimidine compounds having scaffolds composed of left and right rings, the left ring being a saturated carbocyclic or heterocyclic ring and the right ring being a pyrimidine ring. The left saturated ring is fused to the pyrimidine ring at the 5 and 6 carbons of the pyrimidine. The saturated ring may be 5 or 6 members in size and may be all carbon or may contain a single oxygen, sulfur or nitrogen atom as one of the non-fused members of the ring. The pyrimidine ring is substituted at the two position by a 5:6 bicyclic aromatic heterocycle such as indole, benzimidazole or benzopyrazole and at the four position by an aryl methyl amino group. The 5:6 bicyclic aromatic heterocycle is substituted at its 2 position by hydrogen or an aliphatic or functional aliphatic group and at the 4 position by a functional group as described herein. The aryl methyl amino group may be aminobenzyl or aminomethyl-substituted phenyl. These fused pyrimidine compounds are inhibitors of the AAA proteosome complex containing the enzyme complex p97 and are effective medicinal agents for the treatment of diseases associated with p97 bioactivity such as cancer.

14 Claims, No Drawings

(56) References Cited

OTHER PUBLICATIONS

Annunziata, C. M, et al., "Frequent engagement of the classical and alternative NF-kappaB pathways by diverse genetic abnormalities in multiple myeloma", Cancer Cell, 12(2), [online]. Retrieved from the Internet: <URL: http://www.ncbi.nlm.nih.gov/pmc/articles/PMC2730509/pdf/nihms29121.pdf>, (Aug. 2007), 115-130.
Baraldi, Pier G, et al., "Pyrrolo- and pyrazolo-[3,4-e][1,2,4]triazolo[1,5-c]pyrimidines as adenosine receptor antagonists", Bioorganic & Medicinal Chemistry, 20(2), (Jan. 15, 2012), 1046-1059.
Boelens, Jerina, et al., "The Endoplasmic Reticulum: A Target for New Anticancer Drugs", in vivo, 21(2). Review., [online]. Retrieved from the Internet: <URL: http://iv.iiarjournals.org/content/21/2/215.long>, (2007), 215-226.
Cao, K., et al., "The AAA-ATPase Cdc48/p97 regulates spindle disassembly at the end of mitosis", Cell, 115(3), (Oct. 31, 2003), 355-367.
Carvalho, Pedro, et al., "Distinct Ubiquitin-Ligase Complexes Define Convergent Pathways for the Degradation of ER Proteins", Cell, 126(2), [online]. Retrieved from the Internet: <URL: http://ac.els-cdn.com/S0092867406008579/1-s2.0-S0092867406008579-main.pdf?_tid=acf9a38e-ca4a-11e3-b0c1-00000aacb360&acdnat=1398190963_2fb1b92e21209d20fba5993698cdd088>, (Jul. 2006), 361-373.
Christianson, J. C, et al., "Defining human ERAD networks through an integrative mapping strategy", Nat. Cell Biol., 14(1), [online]. Retrieved from the Internet: <URL: http://www.ncbi.nlm.nih.gov/pmc/articles/PMC3250479/pdf/nihms333655.pdf>, (Nov. 27, 2011), 93-105.
Dai, Ren-Ming, et al., "Involvement of Valosin-containing Protein, an ATPase Co-purified with I ?Ba and 26 S Proteasome, in Ubiquitin-Proteasome-mediated Degradation of I ?Ba", J. Biol. Chem., 273, [online]. Retrieved from the Internet: <URL: http://www.jbc.org/content/273/6/3562.full.pdf+html?sid=d525591d-cb88-4f17-a3f8-a022854301a8>, (1998), 3562-3573.
Delabarre, B., et al., "Complete structure of p97/valosin-containing protein reveals communication between nucleotide domains", Nat. Struct. Biol., 10(10), (2003), 856-863.
Fu, Xinrong, et al., "Cdc48p is required for the cell cycle commitment point at Start via degradation of the G1-CDK inhibitor Far1p", The Journal of Cell Biology, 163(1), [online]. Retrieved from the Internet: <URL: http://www.ncbi.nlm.nih.gov/pmc/articles/PMC2173437/pdf/200307025.pdf>, (Oct. 13, 2003), 21-26.
Giaever, G., et al., "Functional profiling of the *Saccharomyces cerevisiae* genome", Nature, 418, (Jul. 25, 2002), 387-391.
Golbik, R., et al., "The Janus face of the archaeal Cdc48/p97 homologue VAT: protein folding versus unfolding", Biol. Chem., 380(9), (Sep. 1999), 1049-1062.
Heffron, T. P, et al., "Rational design of phosphoinositide 3-kinase a inhibitors that exhibit selectivity over the phosphoinositide 3-kinase β isoform", J. Med. Chem., 54(22), (2011), 7815-7833.
Huyton, T., et al., "The crystal structure of murine p97/VCP at 3.6A", J. Struct. Biol., 144(3), (Dec. 2003), 337-348.
Janiesch, P. C, et al., "The ubiquitin-selective chaperone CDC-48/p97 links myosin assembly to human myopathy", Nat. Cell. Biol., 9(4), (2007), 379-390.
Keats, J. J, et al., "Promiscuous mutations activate the noncanonical NF-kappaB pathway in multiple myeloma", Cancer Cell, 12(2), [online]. Retrieved from the Internet: <URL: http://www.ncbi.nlm.nih.gov/pmc/articles/PMC2083698/pdf/nihms31045.pdf>, (Aug. 2007), 131-144.
Muller, J. M M., et al., "Targeted deletion of p97 (VCP/CDC48) in mouse results in early embryonic lethality", Biochem. Biophys. Res. Commun., 354(2), (2007), 459-465.
Rabouille, Catherine, et al., "An NSF-like ATPase, p97, and NSF mediate cisternal regrowth from mitotic golgi fragments", Cell, 82(6), (Sep. 22, 1995), 905-914.
Richly, H., et al., "A series of ubiquitin binding factors connects CDC48/p97 to substrate multiubiquitylation and proteasomal targeting", Cell, 120(1), (Jan. 14, 2005), 73-84.

Song, Changcheng, et al., "ATPase Activity of p97-Valosin-containing Protein (VCP): D2 Mediates the Major Enzyme Activity, and D1 Contributes to the Heat-Induced Activity", J. Biol. Chem., 278, [online]. Retrieved from the Internet: <URL: http://www.jbc.org/content/278/6/3648.full.pdf+html>, (2003), 9 pgs.
Srinivasan, Ananthachari, et al., "Pyridopyrimidines. 14. Conformational studies of 5,6,7,8-tetrahydropyrido[3,2-d]pyrimidines. Potential multisubstrate analog inhibitors of thymidylate synthetase", J. Org. Chem., 47(23), (1982), 4391-4396.
Voorhees, P. M, et al., "The proteasome as a target for cancer therapy", Clin. Cancer Res., 9(17), [online]. Retrieved from the Internet: <URL: http://clincancerres.aacrjournals.org/content/9/17/6316.full.pdf+html>, (Dec. 15, 2003), 6316-6325.
Wang, Qing, et al., "Hexamerization of p97-VCP is promoted by ATP binding to the D1 domain and required for ATPase and biological activities", Biochemical and Biophysical Research Communications, 300(2), (Jan. 10, 2003), 253-260.
Weihl, Conrad C, et al., "Inclusion body myopathy-associated mutations in p97/VCP impair endoplasmic reticulum-associated degradation", Hum. Mol. Genet., 15(2), [online]. Retrieved from the Internet: <URL: http://hmg.oxfordjournals.org/content/15/2/189.full.pdf+html?sid=30a4acff-2565-4dd8-858c-68cfbb8d21c5>, (2006), 189-199.
Yamamoto, S., et al., "Expression level of valosin-containing protein (p97) is correlated with progression and prognosis of non-small-cell lung carcinoma", Ann. Surg. Oncol., 11(7), (Jul. 2004), 697-704.
Yamamoto, S., et al., "Increased expression of valosin-containing protein (p97) is associated with lymph node metastasis and prognosis of pancreatic ductal adenocarcinoma.", Ann. Surg. Oncol., 11(2), (Feb. 2004), 165-172.
Yamamoto, S., et al., "Increased expression of valosin-containing protein (p97) is correlated with disease recurrence in follicular thyroid cancer", Ann. Surg. Oncol., 12(11), (2005), 925-934.
Yamamoto, Shinji, et al., "Expression Level of Valosin-Containing Protein (p97) is Associated with Prognosis of Esophageal Carcinoma", Clin. Cancer Res., 10(16), [online]. Retrieved from the Internet: <URL: http://clincancerres.aacrjournals.org/content/10/16/5558.full.pdf+html>, (Aug. 15, 2004), 5588-5565.
Ye, Y., et al., "Function of the p97-Ufd1-Npl4 complex in retrotranslocation from the ER to the cytosol: dual recognition of nonubiquitinated polypeptide segments and polyubiquitin chains", J. Cell. Biol., 162(1), [online]. Retrieved from the Internet: <URL: http://www.ncbi.nlm.nih.gov/pmc/articles/PMC2172719/pdf/200302169.pdf>, (Jul. 7, 2003), 71-84.
U.S. Appl. No. 13/946,795, Notice of Allowance mailed Feb. 27, 2015, 5 pgs.
U.S. Appl. No. 13/946,795, PTO Response to Rule 312 Communication mailed May 1, 2015, 2 pgs.
U.S. Appl. No. 13/946,795, Responsse filed Jan. 22, 2015 to Non Final Office Action mailed Jul. 30, 2014, 15 pgs.
Chinese Application Serial No. 201380048509.7, Notification to Make Rectification mailed Apr. 1, 2015, 2 pgs.
Chinese Application Serial No. 201380048509.7, Office Action mailed Nov. 3, 2015, 10 pgs.
Israel Application Serial No. 236812, Office Action mailed Aug. 27, 2015, 3 pgs.
Ye, Y., et al., "A membrane protein complex mediates retrotranslocation from the ER lumen nto the cytosol", Nature, 429(6994), (Jun. 24, 2004), 841-847.
Ye, Y., et al., "The AAA ATPase Cdc48/p97 and its partners transport proteins from the ER into the cytosol", Nature 414(6864), (Dec. 6, 2001), 652-656.
Chilean Application Serial No. 132-2015, Office Action mailed Mar. 31, 2016, (w/ English translation), 9 pgs.
Chinese Application Serial No. 201380048509.7, Response filed Mar. 10, 2016 to Office Action mailed Nov. 3, 2015, (with English translation of claims), 39 pgs.
Eurasian Application Serial No. 201590255, Office Action mailed Feb. 1, 2016, (w/ English Translation), 5 pgs.

\* cited by examiner

FUSED PYRIMIDINES AS INHIBITORS OF P97 COMPLEX

This application is a U.S. National Stage Filing under 35 U.S.C. §371 from International Application No. PCT/US2013/051358, filed on Jul. 19, 2013, and published as WO 2014/015291 A1 on Jan. 23, 2014, which claims the benefit of priority under 35 U.S.C. §119(e) to U.S. Provisional Patent Application No. 61/737,666, filed on Dec. 14, 2012, and also claims the benefit of priority under 35 U.S.C. §119(e) to U.S. Provisional Patent Application No. 61/674,144, filed on Jul. 20, 2012, which are hereby incorporated by reference herein in their entireties.

BACKGROUND OF THE INVENTION

The AAA (ATPase Associated with a variety of Activities) ATPase p97 having the descriptive name, Valosin containing protein, is conserved across all eukaryotes and is essential for life in budding yeast (Giaever, G., et. al. *Nature* (2002) 418, 387-391) and mice (Muller, J. M. et al. *Biochem. Biophys. Res. Commun.* (2007) 354, 459-465). Humans bearing reduction-of-function alleles of p97 are afflicted with a syndrome that includes inclusion body myopathy and frontotemporal lobar degeneration (Weihl, C. et al. *Hum. Mol. Genet.* (2006) 15, 189-199). Loss-of-function studies in model organisms indicate that p97 plays a critical role in a broad array of cellular processes including Golgi membrane reassembly (Rabouille, C. et al. *Cell* (1995) 82, 905-914), membrane transport (Ye, Y. et al *Nature* (2001) 414, 652-656; Ye, Y. et al. *Nature* (2004) 429, 841-847) degradation of misfolded membrane and secretory proteins by the ubiquitin-proteasome system (UPS) (Golbik, R. et al. *Biol. Chem.* (1999) 380, 1049-1062; Richly, H. et al. *Cell* (2005) 120, 73-84), regulation of myofibril assembly (Janiesch, P. C. et al. *Nat. Cell Biol.* (2007) 9, 379-390), and cell division (Cao, K. et al. *Cell* (2003) 115, 355-367). The broad range of cellular functions for this protein is thought to derive from its ability to unfold proteins or disassemble protein complexes. The mechanochemical activity of p97 is linked to substrate proteins by an array of at least 14 UBX domain adapters that bind p97, as well as the non-UBX domain adaptors Ufdl and Np14 (Meyer, H. H. et al. *EMBO J.* (2000) 19, 2181-2192).

The sequence of p97 reveals three domains (N-domain, D1 ATPase domain, and D2 ATPase domain) joined by linker regions. X-ray crystallography of p97 revealed that it forms a homohexamer of 97 kilodalton subunits that assemble to form two stacked rings. The two rings are formed by the ATPase domains (Huyton, T. et al., *Struct. Biol.* (2003) 144, 337-348; DeLaBarre, B. et al. *Nat. Struct. Biol.* (2003) 10, 856-863). The 'top' ring is formed by a hexamer of the D1 domains, whereas the 'bottom' ring is formed by a hexamer of the D2 domains. The N-domain extends outward from the D1 domain ring. Although it is clear that the D2 domain hydrolyzes ATP in vitro, the level of D1-specific ATPase activity reported by different investigators varies. Nevertheless, genetic studies in yeast suggest that ATP hydrolysis by both the D1 and D2 domains is essential for the function of p97 (Song, C. et al. *J. Biol. Chem.* (2003) 278, 3648-3655; Ye, Y. et al. *J. Cell Biol.* (2004) 162, 71-84). Binding of ATP to the D1 domain is also required for assembly of p97 (Wang, Q. et al. *Biochem. Biophys. Res. Commun.* (2003) 300, 253-260). Although ATP hydrolysis by the D2 domain is not required for assembly of p97 hexamer, it is thought that ATP hydrolysis by the D2 domain is a substrate conversion, resulting in their unfolding or dissociation from bound partners.

A prominent cellular function for p97 that has received considerable scrutiny is its role in the turnover of misfolded secretory proteins via the UPS (ubiquitin proteasome system). In this process, which is known as ERAD (for endoplasmic reticulum-associated degradation), proteins that fail to fold within the ER are retrotranslocated in a p97-dependent manner into the cytoplasm where they are degraded by the UPS (Ye, Y. et al. *Nature* (2004) 429, 841-847). In this process, p97 is thought to mediate extraction of substrates from the ER membrane. The complex p97 is also required for the turnover of cytosolic substrates of the UPS (Janiesch, P. C. et al. *Nat. Cell Biol.* (2007) 9, 379-390; Cao, K. et al. *Cell* (2003) 115, 355-367; Fu, X. et al. *J. Cell Biol.* (2003) 163, 21-26), although its role in turnover of cytosolic proteins is less understood.

The Valosin containing protein, p97, represents a suitable target for cancer therapeutics. The complex p97 and its function are essential for continued cellular viability, and so drugs that inhibit it should be antiproliferative. In other words, inhibition of p97 will cause undesirable protein concentration within the target cell. A consequential cellular reaction is often apoptosis or at least amelioration of cellular growth and mitosis. Also, p97 is known to be overproduced in multiple cancers (Yamamoto, S. et al. *Ann. Surg. Oncol.* (2005) 12, 925-934; Yamamoto, S. et al. *Clin. Cancer Res.* (2004) 10, 5558-5565; Yamamoto, S. et al. *Ann. Surg. Oncol.* (2004) 11, 697-704; Yamamoto, S. et al. *Ann. Surg. Oncol.* (2004) 11, 165-172) suggesting that its activity may be rate-limiting for the development of at least some cancers. p97 is known to be essential for ERAD (Carvalho, P. et al. *Cell* (2006) 126, 361-373), and recent studies suggest that cancer cells may be particularly dependent upon ERAD (Boelens, J. et al. *In Vivo* (2007) 21, 215-226). Furthermore, p97 has been linked to the turnover of IlcB and consequent activation of NF-kB (Dai, R. M. et al. *J. Biol. Chem.* (1998) 273, 3562-3573). NF-kB activity is important for the survival of some tumor cells, particularly in multiple myeloma (Keats, J. J. et. al. *Cancer Cell* (2007) 12, 131-144; Annunziata, C. M. et. al. *Cancer Cell* (2007) 12, 115-130). It has been suggested that bortezomib is active in multiple myeloma due to its ability to block turnover of proteins via the ERAD pathway and its ability to block turnover of 1 kB, thereby squelching the activity of NF-kB. Given that p97 is implicated in both ERAD and IlcB turnover but otherwise has a more restricted role in the UPS compared to the proteasome itself, drugs that target p97 may retain much of the efficacy of bortezomib but with less toxicity. In addition, compounds intersecting with the p97 complex are disclosed in PCT/US2011/035654, filed May 6, 2011 and published as WO2011/140527 on Nov. 10, 2011.

GOALS OF THE INVENTION

Thus, there is a need to develop compounds suitable for inhibition of p97 activity and for methods of inhibiting the activity of p97 using such compounds. There is a need to develop such compounds for use in treatment of neoplastic malconditions.

SUMMARY OF THE INVENTION

These and other needs are met by aspects of the present invention, one of which is directed to a fused two ring scaffold having a pyrimidine as one of the rings and having a plurality of substituents bonded to either or both rings. In various embodiments the substituents are not bonded to the nitrogens of the pyrimidine ring. Another aspect of the invention is directed to a fused pyrimidine scaffold having a saturated ring fused to the pyrimidine ring. A further aspect of the invention is directed to the saturated ring/pyrimidine ring scaffold in which the saturated ring optionally contains a heteroatom including nitrogen, oxygen and/or sulfur. A further aspect of the invention is directed to a fused pyrimidine scaffold in which the scaffold is a quinazoline. These aspects of the invention based upon a fused pyrimidine scaffold include an optional plurality of substituents bonded to the scaffold. In another aspect of the invention, the fused pyrimidine compounds of the invention have an ability to inhibit Valosin containing protein p97 and to ameliorate, diminish, shrink, moderate and/or eliminate cells exhibiting neoplastic tendencies and/or abnormal function. In a further aspect of the invention, such compounds inhibit the ATPase activity of p97. Another aspect of the invention concerns treatment of malconditions and/or disease such as cancer through use of such compounds.

One aspect of the invention is directed to the fused two ring scaffold having pyrimidine as one of the rings, having an amine substituent at position 4 of the pyrimidine ring, a heterocyclic group or aliphatic heterocyclic group at position 2 of the pyrimidine ring, and a five or six membered saturated or unsaturated ring as the other ring with zero, one, two or three heteroatoms in other ring and optional multiple aliphatic, functional and/or aromatic components as substituents on the other ring. The ring fused to the pyrimidine ring can be fused to the 5,6-positions of the pyrimidine.

More specifically, the fused two ring scaffold aspect of the invention is a fused pyrimidine compound of the generic Formula X

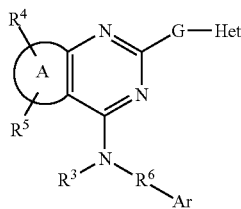

Formula X

The A ring of Formula X is fused to the pyrimidine ring and is a saturated, unsaturated, or aromatic four, five, six, or seven member ring having zero, one, two or three heteroatoms in the ring, the remaining atoms of the ring being carbon, each heteroatom being independently selected from the group consisting of nitrogen, oxygen and sulfur; G is a bond, $NR^1$, O or $(CR^1R^2)_n$; $R^1$ and $R^2$ are each independently hydrogen or alkyl of one to four carbons in length; n is an integer from 1 to 4; $R^3$ is selected from the group consisting of hydrogen, an aliphatic component and an aromatic component, each component being substituted by zero, one or two aliphatic, functional or aromatic components. $R^4$ and $R^5$ are each independently bound to carbon or nitrogen and are each independently selected from the group consisting of hydrogen, an aliphatic component, a functional component, an aromatic component, and a combination thereof. $R^6$ is a covalent bond joining nitrogen to Ar or is an alkyl group of 1 to 4 carbons or an alkenyl group of 2 to 4 carbons. Ar is an unsubstituted or substituted aromatic component. Het is a saturated, unsaturated, or aromatic 5:5 or 5:6 bicyclic ring having zero, one, two or three heteroatoms in the bicyclic ring, the remaining atoms being carbon, the bicyclic ring being substituted with zero, one, two or three substituents each independently selected from the group consisting of an aliphatic component, a functional component, an aromatic component and any combination thereof. The aliphatic component, functional component and aromatic component are defined in the following Definitions section.

The fused pyrimidines of generic Formula X do not include certain substituents as described by the following proviso. When the A ring is benzo or substituted benzo, the Het ring is not unsubstituted indolinyl, unsubstituted benzoxazol-2-one, unsubstituted 2-aminobenzimidazole, 5,6-dimethyl-2-aminobenzamidazole, unsubstituted benzimidazole or an unsubstituted 2-aminoimidazole fused to a unsubstituted cyclopentane, cyclohexane or cycloheptane ring; and when the A ring is an unsubstituted 4, 5, 6 or 7 membered ring containing a ring oxygen, a ring aminomethyl, a ring aminoethyl or a ring aminophenyl moiety, the Het ring is not a 2-aminobenzimidazole with no substituent or with a methyl, fluoro, chloro, bromo or methoxyl substituent. The compounds depicted in Table 1 are also part of this proviso.

Another aspect of the invention is directed to preferred subgeneric embodiments of the fused pyrimidine scaffold of Formula X. Except for the atoms forming the fusion between the A ring and the pyrimidine ring, the A ring of these subgeneric embodiments may be saturated and may optionally contain a heteroatom such as oxygen, nitrogen or sulfur. Alternatively, the A ring of these preferred subgeneric embodiments may be aromatic such that the fused pyrimidine scaffold is a quinazoline ring. In addition, the Het substituent at the 2 position of these subgeneric embodiments may be a benzimidazole or indole optionally substituted at the 2 position and 4 position. Included in this aspect of subgeneric embodiments of generic Formula X are preferred fused pyrimidines of the following formulas I/II III/IV and V/VI.

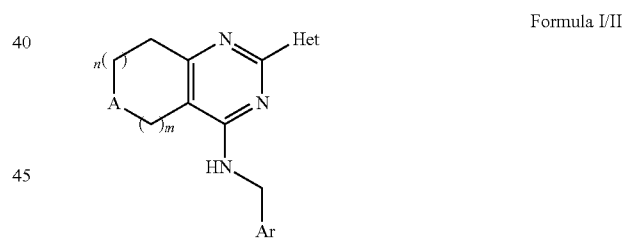

Formula I/II

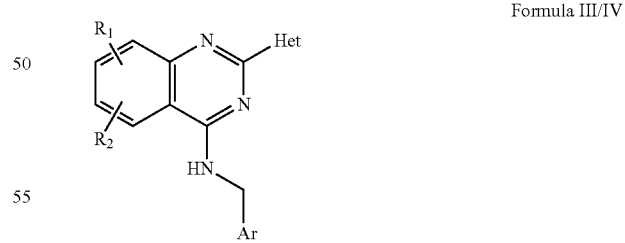

Formula III/IV

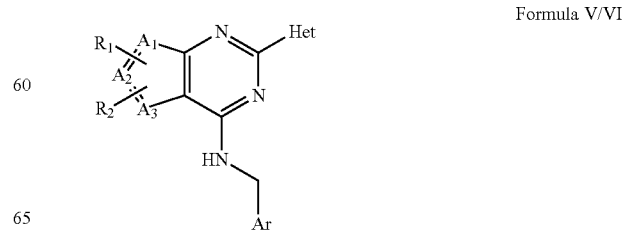

Formula V/VI

For Formula I/II A may be $CH_2$, $NR^1$, O or S; m may be an integer of 1, 2 or 3; n may be 0 or an integer of 1 or 2; the sum of m+n may be no greater than 4 and no less than 1; and Ar may be an unsubstituted or substituted aromatic component. The atoms indicated by $A_1$, $A_2$ and $A_3$ may be CH, $CH_2$, N, NH, O or S. The bonding arrangement among $A_1$, $A_2$ and $A_3$ is discussed in the Detailed Description.

The Het substituent at the 2 position of the pyrimidine ring of these preferred fused pyrimidine scaffolds may be a Het group as defined above or it may be a an indole or a benzimidazole of Formula XIV or XB or a neterocycle of Formula XIII:

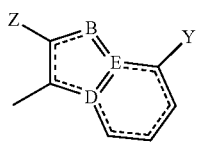

Formula XIII

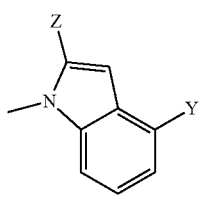

Formula XIV

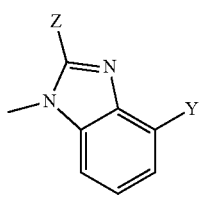

Formula XV

The Het group is directly bonded to the 2 position of the fused pyrimidine. For formula XIII, B may be $CH_2$, CH, C=O, N or O; D and E are each independently selected from C or N provided that not all of B, D and E are carbon.

In terms of the relation to the generic formula X which covers all of these subgeneric fused pyrimidines compounds, G of the generic formula X would be a bond.

The symbols Z, Y, $R^1$, $R_1$ and $R_2$ may be substituted or unsubstituted aliphatic or aromatic groups or functional groups as defined in the following Definitions section provided that these groups conform to accepted chemical bonding principles. Preferred groups for these substituents include hydrogen, functional groups such as halogen, nitrile, carboxyl, sulfonoxy, amino, as well as aliphatic groups as defined below. More preferred groups for these substituents are defined in the following Detailed Description.

Another aspect of the invention is a fused pyrimidine scaffold which is a quinazoline having a 2-aromatic, heteroaromatic or aliphatic substituent, a 4-aminoalkylenylaromatic substituent and multiple aliphatic, aromatic and/or functional components joined to the quinazoline, the 2 substituent and the 4 substituent. More specifically, the quinazoline scaffold of the invention is a quinazoline of formula XX.

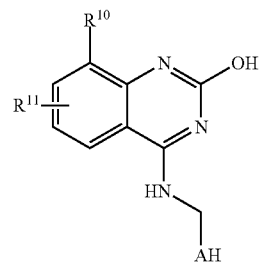

FORMULA XX

For Formula XX, $R^{10}$ and $R^{11}$ are each independently hydrogen, an aliphatic, functional or aromatic component with the location of $R^{11}$ being any of positions 5, 6 or 7 of the benzo group. The group AH is a phenyl, thiophenyl, pyridinyl, pyrrolyl or furanyl, or substituted versions thereof wherein the substituent can be optional, independent and optionally multiple and can be an aliphatic, functional or aromatic component. The substituent QH is phenyl, alkylenylphenyl with its alkylenyl group having from 1 to 6 carbons, indolyl, benzimidazolyl, 2-ketobenzimidazolyl, imidazolyl, α-amino acid amide, α, ω diaminoalkane of 1 to 6 carbons or a substituted version of phenyl, alkylenylphenyl, indolyl, benzimidazolyl or 2-ketobenimidazolyl wherein the substituent of any of these groups can be independent, optional and optionally multiple and can be an aliphatic, functional or aromatic component. However, the quinazoline scaffold of formula III excludes the following: QH may not be an unsubstituted indolinyl, unsubstituted indolyl, unsubstituted benzimidazolyl, or unsubstituted imidazolyl when AH is unsubstituted phenyl and $R^{10}$ and $R^{11}$ are both hydrogen or when $R^{10}$ is methoxyl and $R^{11}$ is hydrogen and AH is unsubstituted phenyl.

An additional aspect of the invention is directed to a pharmaceutical composition of a pharmaceutically acceptable carrier and the above described fused two ring scaffold, more specifically the above described fused two ring scaffold having pyrimidine as one of the rings, especially more specifically the fused pyrimidine compounds of Formula X and the subgeneric formulas encompassed within Formula X including but not limited to Formula I/II, Formula III/IV, Formula V/VI and Formula XXX as well as Formulas I, II, III, IV-A. IV-B, V, VI, VII, VIII, IX and XX set forth in the following Detailed Description.

Another aspect of the invention is directed to a method of decreasing Valosin containing protein (p97) activity or decreasing degradation of a proteasome system substrate, especially a ubiquitin substrate, by administration to a patent in need an effective therapeutic amount of the foregoing fused two ring scaffold, more specifically the above described fused two ring scaffold having pyrimidine as one of the rings and especially more specifically the fused pyrimidine compounds of Formula X and all subgeneric Formulas encompassed within Formula X.

Yet another aspect of the invention is directed to the treatment of neoplastic malconditions, cancer and other malconditions associated with p97 by administration to a patient in need the foregoing pharmaceutical composition.

Another aspect of the invention is directed to methods for selecting a candidate that will inhibit Valosin containing protein (p97) and for determining the inhibitory activity of such candidates. The method is applied in vitro and involves testing a positive standard containing substrate and a biological enzyme (e.g., p97) and comparing the test results of the positive standard with the test results produced from an experimental text with the candidate compound, substrate and the biological enzyme. The substrate is marked in a typical fashion to enable determination whether or not it has been subjected to the biological action of the bioactive enzyme. Comparison of the standard result with the experimental result will show whether or not the candidate will inhibit or ameliorate the activity of the bioactive enzyme, show the physiological profile and will preferably show the degree of inhibition or amelioration. Such methods and substrates useful for determining the degree of inhibition or amelioration of p97 include assays, substrates and protocols such as the p97 in vitro assay and p97 cellular assay.

DETAILED DESCRIPTION OF THE INVENTION

Definitions

Unless defined otherwise, all technical and scientific terms used herein have the same meaning as commonly understood by a person of ordinary skill in the art.

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

All average molecular weights of polymers are weight-average molecular weights, unless otherwise specified.

As used herein, "individual" (as in the subject of the treatment) or "patient" means both mammals and non-mammals. Mammals include, for example, humans; non-human primates, e.g. apes and monkeys; and non-primates, e.g. dogs, cats, cattle, horses, sheep, and goats. Non-mammals include, for example, fish and birds.

The term "may" in the context of this application means "is permitted to" or "is able to" and is a synonym for the term "can." The term "may" as used herein does not mean possibility or chance.

The term "disease" or "disorder" or "malcondition" are used interchangeably, and are used to refer to diseases or conditions wherein X plays a role in the biochemical mechanisms involved in the disease or malcondition or symptom(s) thereof such that a therapeutically beneficial effect can be achieved by acting on X. "Acting on" X, or "modulating" X, can include binding to X and/or inhibiting the bioactivity of X and/or allosterically regulating the bioactivity of X in vivo.

The expression "effective amount", when used to describe therapy to an individual suffering from a disorder, refers to the amount of a drug, pharmaceutical agent or compound of the invention that will elicit the biological or medical response of a cell, tissue, system, animal or human that is being sought, for instance, by a researcher or clinician. Such responses include but are not limited to amelioration, inhibition or other action on a disorder, malcondition, disease, infection or other issue with or in the individual's tissues wherein the disorder, malcondition, disease and the like is active, wherein such inhibition or other action occurs to an extent sufficient to produce a beneficial therapeutic effect. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects.

Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

An "analog" of a chemical structure, as the term is used herein, refers to a chemical structure that preserves substantial similarity with the parent structure, although it may not be readily derived synthetically from the parent structure. A related chemical structure that is readily derived synthetically from a parent chemical structure is referred to as a "derivative."

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended, unless a particular stereochemistry or isomeric form is specifically indicated. In several instances though an individual stereoisomer is described among specifically claimed compounds, the stereochemical designation does not imply that alternate isomeric forms are less preferred, undesired, or not claimed. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

As used herein, the terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

Selected substituents within the compounds described herein are present to a recursive degree. In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis. Recursive substituents are an intended aspect of the disclosed subject matter. One of ordinary skill in the art of medicinal and organic chemistry understands the versatility of such substituents. To the degree that recursive substituents are present in a claim of the disclosed subject matter, the total number should be determined as set forth above.

When a group is recited, wherein the group can be present in more than a single orientation within a structure resulting in more than single molecular structure, e.g., a carboxamide group C(=O)NR, it is understood that the group can be present in any possible orientation, e.g., X—C(=O)N(R)—Y or X—N(R)C(=O)—Y, unless the context clearly limits the orientation of the group within the molecular structure.

When a group, e.g., an "alkyl" group, is referred to without any limitation on the number of atoms in the group, it is understood that the claim is definite and limited with respect the size of the alkyl group, both by definition; i.e., the size (the number of carbon atoms) possessed by a group such as an alkyl group is a finite number, less than the total number of carbon atoms in the universe and bounded by the understanding of the person of ordinary skill as to the size of the group as being reasonable for a molecular entity; and by functionality, i.e., the size of the group such as the alkyl group is bounded by the functional properties the group bestows on a molecule containing the group such as solubility in aqueous or organic liquid media. Therefore, a claim reciting an "alkyl" or other chemical group or moiety is definite and bounded, as the number of atoms in the group cannot be infinite.

In general, "substituted" refers to an organic group as defined herein in which one or more bonds to a hydrogen atom contained therein are replaced by one or more bonds to a non-hydrogen atom. More particularly, the term "chemical substituent" refers to any and all aliphatic, aromatic and functional groups listed in this section that can be appended to an organic molecule. A functional group is an inorganic moiety such as halogen, sulfate, nitro, amino and the like as well as monocarbon functional groups such as carboxyl, carbonyl, carboxamide that are ordinary and typical optional substituents of organic molecules. In the context of this invention, recitation of this term without indication of specific groups constitutes the definition given above. Recitation of this term in combination with a Markush recitation of specific groups constitutes a subgenus of the understanding conveyed by the foregoing definition. The term "substituent" generally means any appropriate group named below that has an "yl", "y" or "o" ending to designate that it is appended, attached or covalently bonded to another moiety such as but not limited to an aromatic framework. Examples include but are not limited to, a halogen (i.e., F, Cl, Br, and I); an oxygen atom in groups such as hydroxyl groups, alkoxy groups, aryloxy groups, aralkyloxy groups, oxo (carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents J that can be bonded to a substituted carbon (or other) atom include F, Cl, Br, I, OR', OC(O)N(R')$_2$, CN, NO, NO$_2$, ONO$_2$, azido, CF$_3$, OCF$_3$, R', O (oxo), S (thiono), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R)C(O)R', (CH$_2$)$_{0-2}$N(R)N(R)$_2$, N(R')N(R')C(O)R', N(R)N(R)C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted; for example, wherein R' can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R' can be independently mono- or multi-substituted with J; or wherein two R' groups bonded to a nitrogen atom or to adjacent nitrogen atoms can together with the nitrogen atom or atoms form a heterocyclyl, which can be mono- or independently multi-substituted with J.

In various embodiments, J can be halo, nitro, cyano, OR, NR$_2$, or R, or is C(O)OR, C(O)NR$_2$, OC(O)OR, OC(O)NR$_2$, N(R)C(O)OR, N(R)C(O)NR$_2$ or thio/thiono analogs thereof. By "thio/thiono analogs thereof", with respect to a group containing an O, is meant that any or all O atoms in the group can be replaced by an S atom; e.g., for group C(O)OR, a "thio/thiono analog thereof" includes C(S)OR, C(O)SR, and C(S)SR; e.g., for group OC(O)NR$_2$, a "thio/thiono analog thereof" includes SC(O)NR$_2$, OC(S)NR$_2$, and SC(S)NR$_2$; and so forth.

When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (=O) group, the oxygen substituent is termed an "oxo" group. When a divalent substituent such as NR is double-bonded to a carbon atom, the resulting C(=NR) group is termed an "imino" group. When a divalent substituent such as S is double-bonded to a carbon atom, the results C(=S) group is termed a "thiocarbonyl" or "thiono" group.

Alternatively, a divalent substituent such as O or S can be connected by two single bonds to two different carbon atoms. For example, O, a divalent substituent, can be bonded to each of two adjacent carbon atoms to provide an epoxide group, or the O can form a bridging ether group, termed an "oxy" group, between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as $(CH_2)_n$ or $(CR'_2)_n$ wherein n is 1, 2, 3, or more, and each R' is independently selected.

For all substituents, the first atom of the molecular formula of the substituent is the atom bonding the substituent to its corresponding moiety, e.g., for the functional group, $N(R^a)C(O)R^a$, the N is bonded to the corresponding moiety substituted by this group. If the substituent is described in words, such as alkyenylamine, the phrase ending in "enyl" indicates the carbon atom bonding the substituent to its corresponding moiety. For substituents that display a single bonding site, such as carboxylic acid, sulfonic acid, fluoro, methyl and the like, the bonding arrangement is the expected arrangement.

"Aliphatic substituent, group or component" refers to any organic group that is non-aromatic. Included are acyclic and cyclic organic compounds composed of carbon, hydrogen and optionally of oxygen, nitrogen, sulfur and other heteroatoms. This term encompasses all of the following organic groups except the following defined aromatic and heteroaromatic groups. Examples of such groups include but are not limited to alkyl, alkenyl, alkynyl, corresponding groups with heteroatoms, cyclic analogs, heterocyclic analogs, branched and linear versions and such groups optionally substituted with functional groups, as these groups and others meeting this definition of "aliphatic" are defined below.

"Aromatic substituent, group or component" refers to any and all aromatic groups including but not limited to aryl, aralkyl, heteroalkylaryl, heteroalkylheteroaryl and heteroaryl groups. The term "aromatic" is general in that it encompasses all compounds containing aryl groups optionally substituted with functional groups (all carbon aromatic groups) and all compounds containing heteroaryl groups optionally substituted with functional groups (carbon-heteroatom aromatic groups), as these groups and others meeting this definition of "aromatic" are defined below.

As used herein, the term "optionally" means that the corresponding substituent or thing may or may not be present. It includes both possibilities.

"Alkyl" refers to a straight or branched hydrocarbon chain radical consisting solely of carbon and hydrogen atoms, containing no unsaturation, having from one to ten carbon atoms (e.g., $C_1$-$C_{10}$ alkyl). Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated. In some embodiments, it is a $C_1$-$C_4$ alkyl group. Typical alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, septyl, octyl, nonyl, decyl, and the like. The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like.

Unless stated otherwise specifically in the specification, an alkyl group is optionally substituted by one or more of substituents as defined above. Such substituents further independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N($R^a)_2$, —C(O)N($R^a)_2$, —N($R^a$)C(O)O$R^a$, —N($R^a$)C(O)$R^a$, —N($R^a$)C(O)N($R^a)_2$, N($R^a$)C(N$R^a$)N($R^a)_2$, —N($R^a$)S(O)$_t R^a$ (where t is 1 or 2), —S(O)$_t$O$R^a$ (where t is 1 or 2), —S(O)$_t$N($R^a)_2$ (where t is 1 or 2), or PO$_3$($R^a)_2$ where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkylaryl" refers to an -(alkyl)aryl radical where aryl and alkyl are as disclosed herein and which are optionally substituted by one or more of the substituents described as suitable substituents for aryl and alkyl respectively.

"Alkylhetaryl" refers to an -(alkyl)hetaryl radical where hetaryl and alkyl are as disclosed herein and which are optionally substituted by one or more of the substituents described as suitable substituents for aryl and alkyl respectively.

"Alkylheterocycloalkyl" refers to an -(alkyl) heterocycyl radical where alkyl and heterocycloalkyl are as disclosed herein and which are optionally substituted by one or more of the substituents described as suitable substituents for heterocycloalkyl and alkyl respectively.

An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

"Alkenyl" refers to a straight or branched hydrocarbon chain radical group consisting solely of carbon and hydrogen atoms, containing at least one double bond, and having from two to ten carbon atoms (i.e., $C_2$-$C_{10}$ alkenyl). Whenever it appears herein, a numerical range such as "2 to 10" refers to each integer in the given range; e.g., "2 to 10 carbon atoms" means that the alkenyl group may consist of 2 carbon atoms, 3 carbon atoms, etc., up to and including 10 carbon atoms. In certain embodiments, an alkenyl comprises two to eight carbon atoms. In other embodiments, an alkenyl comprises two to five carbon atoms (e.g., $C_2$-$C_5$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like.

Unless stated otherwise specifically in the specification, an alkenyl group is optionally substituted by one or more substituents as defined above. Such substituents further independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N (R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl.

"Alkenyl-cycloalkyl" refers to an -(alkenyl)cycloalkyl radical where alkenyl and cyclo alkyl are as disclosed herein and which are optionally substituted by one or more of the substituents described as suitable substituents for alkenyl and cycloalkyl respectively.

"Alkynyl" refers to a straight or branched hydrocarbon chain radical group consisting solely of carbon and hydrogen atoms, containing at least one triple bond, having from two to ten carbon atoms (i.e., C2-C10 alkynyl). Whenever it appears herein, a numerical range such as "2 to 10" refers to each integer in the given range; e.g., "2 to 10 carbon atoms" means that the alkynyl group may consist of 2 carbon atoms, 3 carbon atoms, etc., up to and including 10 carbon atoms. In certain embodiments, an alkynyl comprises two to eight carbon atoms. In other embodiments, an alkynyl has two to five carbon atoms (e.g., C2-C5 alkynyl). The alkynyl is attached to the rest of the molecule by a single bond, for example, ethynyl, propynyl, butynyl, pentynyl, hexynyl, and the like.

Unless stated otherwise specifically in the specification, an alkynyl group is optionally substituted by one or more substituents as defined above. Such substituents further independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SW, —OC(O)—R$^a$, —N(R$^a$)2, —C(O)R$^a$, —C(O)OR$^a$, —C(O)N(R$^a$)2, —C(O)N(R$^a$)2, —N(R$^a$)C(O)OR$^a$, —N(R$^a$)C(O)R$^a$, —N(R$^a$)C(O)N(R$^a$)2, N(R$^a$)C(NR$^a$)N(R$^a$)2, —N(R$^a$)S(O)$_t$R$^a$ (where t is 1 or 2), —S(O)$_t$OR$^a$ (where t is 1 or 2), —S(O)$_t$N(R$^a$)2 (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl.

"Alkynyl-cycloalkyl" refers to refers to an -(alkynyl)cycloalkyl radical where alkynyl and cycloalkyl are as disclosed herein and which are optionally substituted by one or more of the substituents described as suitable substituents for alkynyl and cycloalkyl respectively.

"Carboxaldehyde" refers to a —(C=O)H radical.

"Carboxyl" refers to a —(C=O)OH radical.

"Cyano" refers to a —CN radical.

"Cycloalkyl" refers to a monocyclic or polycyclic radical that contains only carbon and hydrogen, and may be saturated, or partially unsaturated. Cycloalkyl groups include groups having from 3 to 10 ring atoms (i.e., C$_2$-C$_{10}$ cycloalkyl). Whenever it appears herein, a numerical range such as "3 to 10" refers to each integer in the given range; e.g., "3 to 10 carbon atoms" means that the cycloalkyl group may consist of 3 carbon atoms, etc., up to and including 10 carbon atoms. In some embodiments, it is a C$_3$-C$_8$ cycloalkyl radical. In some embodiments, it is a C$_3$-C$_5$ cycloalkyl radical. Illustrative examples of cycloalkyl groups include, but are not limited to the following moieties: cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like.

Unless stated otherwise specifically in the specification, a cycloalkyl group is optionally substituted by one or more substituents as defined above. Such substituents further independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl.

"Cycloalkyl-alkenyl" refers to a -(cycloalkyl) alkenyl radical where cycloalkyl and heterocycloalkyl are as disclosed herein and which are optionally substituted by one or more of the substituents described as suitable substituents for heterocycloalkyl and cycloalkyl respectively.

"Cycloalkyl-heterocycloalkyl" refers to a -(cycloalkyl) heterocycyl radical where cycloalkyl and heterocycloalkyl are as disclosed herein and which are optionally substituted by one or more of the substituents described as suitable substituents for heterocycloalkyl and cycloalkyl respectively.

"Cycloalkyl-heteroaryl" refers to a -(cycloalkyl) heteroaryl radical where cycloalkyl and heterocycloalkyl are as disclosed herein and which are optionally substituted by one or more of the substituents described as suitable substituents for heterocycloalkyl and cycloalkyl respectively.

"Alkoxy" refers to the group —O-alkyl, including from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. "Lower alkoxy" refers to alkoxy groups containing one to six carbons. In some embodiments, C$_1$-C$_4$ alkyl is an alkyl group which encompasses both straight and branched chain alkyls of from 1 to 4 carbon atoms.

"Substituted alkoxy" refers to alkoxy wherein the alkyl constituent is substituted (i.e., —O-(substituted alkyl)).

Unless stated otherwise specifically in the specification, the alkyl moiety of an alkoxy group is optionally substituted by one or more substituents as defined above. Such substituents further independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, SR$^a$, —OC(O)—R$^a$, —N(R$^a$)$_2$, —C(O)R$^a$, —C(O)OR$^a$, —C(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl.

"Alkoxycarbonyl" refers to a group of the formula (alkoxy)(C=O)— attached through the carbonyl carbon wherein the alkoxy group has the indicated number of carbon atoms. Thus a C$_1$-C$_6$ alkoxycarbonyl group is an alkoxy group having from 1 to 6 carbon atoms attached through its oxygen to a carbonyl linker. "Lower alkoxycarbonyl" refers to an alkoxycarbonyl group wherein the alkoxy group is a lower alkoxy group. In some embodiments, C$_1$-C$_4$ alkoxy, is an alkoxy group which encompasses both straight and branched chain alkoxy groups of from 1 to 4 carbon atoms.

"Substituted alkoxycarbonyl" refers to the group (substituted alkyl)-O—C(O)— wherein the group is attached to the parent structure through the carbonyl functionality.

Unless stated otherwise specifically in the specification, the alkyl moiety of an alkoxycarbonyl group is optionally substituted by one or more substituents as defined above. Such substituents further independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl.

"Acyl" refers to the groups (alkyl)-C(O)—, (aryl)-C(O)—, (heteroaryl)-C(O)—, (heteroalkyl)-C(O)—, and (heterocycloalkyl)-C(O)—, wherein the group is attached to the parent structure through the carbonyl functionality. In some embodiments, it is a C$_1$-C$_{10}$ acyl radical which refers to the total number of chain or ring atoms of the alkyl, aryl, heteroaryl or heterocycloalkyl portion of the acyloxy group plus the carbonyl carbon of acyl, i.e. three other ring or chain atoms plus carbonyl. If the R radical is heteroaryl or heterocycloalkyl, the hetero ring or chain atoms contribute to the total number of chain or ring atoms.

Unless stated otherwise specifically in the specification, the "R" of an acyloxy group is optionally substituted by one or more substituents as defined above. Such substituents further independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl. "Acyloxy" refers to a R(C═O)O— radical wherein "R" is alkyl, aryl, heteroaryl, heteroalkyl, or heterocycloalkyl, which are as described herein. In some embodiments, it is a C$_1$-C$_4$ acyloxy radical which refers to the total number of chain or ring atoms of the alkyl, aryl, heteroaryl or heterocycloalkyl portion of the acyloxy group plus the carbonyl carbon of acyl, i.e. three other ring or chain atoms plus carbonyl. If the R radical is heteroaryl or heterocycloalkyl, the hetero ring or chain atoms contribute to the total number of chain or ring atoms.

Unless stated otherwise specifically in the specification, the "R" of an acyloxy group is optionally substituted by one or more substituents as defined above. Such substituents further independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2-S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl.

"Amino" or "amine" refers to a —N(R$^a$)$_2$ radical group, where each R$^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl, unless stated otherwise specifically in the specification. When a —N(R$^a$)$_2$ group has two Ra other than hydrogen they can be combined with the nitrogen atom to form a 4-, 5-, 6-, or 7-membered ring. For example, —N(R$^a$)$_2$ is meant to include, but not be limited to, 1-pyrrolidinyl and 4-morpholinyl.

Unless stated otherwise specifically in the specification, an amino group is optionally substituted by one or more substituents as defined above. Such substituents further independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl and each of these moieties may be optionally substituted as defined herein.

"Substituted amino" also refers to N-oxides of the groups —NHR$^d$, and NR$^d$R$^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

An "ammonium" ion includes the unsubstituted ammonium ion NH$_4^+$, but unless otherwise specified, it also includes any protonated or quaternarized forms of amines. Thus, trimethylammonium hydrochloride and tetramethylammonium chloride are both ammonium ions, and amines, within the meaning herein.

"Amide" or "amido" refers to a chemical moiety with formula —C(O)N(R)$_2$ or —NHC(O)R, where R is selected from the group consisting of hydrogen, alkyl, cycloalkyl, aryl, heteroaryl (bonded through a ring carbon) and heteroalicyclic (bonded through a ring carbon), each of which moiety may itself be optionally substituted. In some embodiments it is a C$_1$-C$_4$ amido or amide radical, which includes the amide carbonyl in the total number of carbons in the radical. The R$_2$ of —N(R)$_2$ of the amide may optionally be taken together with the nitrogen to which it is attached to form a 4-, 5-, 6-, or 7-membered ring. Unless stated otherwise specifically in the specification, an amido group is optionally substituted independently by one or more of the substituents as described herein for alkyl, cycloalkyl, aryl, heteroaryl, or heterocycloalkyl. An amide may be an amino acid or a peptide molecule attached to a compound of Formula (I), thereby forming a prodrug. Any amine, hydroxy, or carboxyl side chain on the compounds described herein can be amidified. The procedures and specific groups to make such amides are known to those of skill in the art and can readily be found in reference sources such as Greene and Wuts, Protective Groups in Organic Synthesis, 3rd Ed., John Wiley & Sons, New York, N.Y., 1999, which is incorporated herein by reference in its entirety.

"Aryl" refers to a conjugated pi radical with six or ten ring atoms which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. The term includes monocyclic or fused-ring polycyclic (i.e., rings which share adjacent pairs of ring atoms) groups.

Unless stated otherwise specifically in the specification, an aryl moiety is optionally substituted by one or more substituents as defined above. Such substituents further are independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —OC(O)N$(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl.

"Aralkyl" or "arylalkyl" refers to an (aryl)alkyl-radical where aryl and alkyl are as disclosed herein and which are optionally substituted by one or more of the substituents described as suitable substituents for aryl and alkyl respectively.

"Ester" refers to a chemical radical of formula —COOR, where R is selected from the group consisting of alkyl, cycloalkyl, aryl, heteroaryl (bonded through a ring carbon) and heteroalicyclic (bonded through a ring carbon). Any amine, hydroxy, or carboxyl side chain on the compounds described herein can be esterified. The procedures and specific groups to make such esters are known to those of skill in the art and can readily be found in reference sources such as Greene and Wuts, Protective Groups in Organic Synthesis, 3rd Ed., John Wiley & Sons, New York, N.Y., 1999, which is incorporated herein by reference in its entirety.

Unless stated otherwise specifically in the specification, an ester group is optionally substituted by one or more substituents as defined above. Such substituents further independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —OC(O)N$(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Functional substituent, group or component" refers to a substituent capable of displaying functionality such as hydroxyl, ester, amide, amine, enamine, halogen, cyano, thio, oxidized sulfur, nitrogen or phosphorus groups, alkoxy, olefinic, aldehyde, ketone, carboxylic acid, anhydride, urethane, urea, imine, amidine, hydroxylimine, hydroxylamine, nitrile, organometallic, and any other group capable of displaying dipole interaction and/or reactivity. See *Basic Principles of Organic Chemistry*, Roberts & Casario, W. A. Benjamin, publisher New York, N.Y. 1965, Chapter 10. Additional examples include hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, C(O)N$(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), —$R^a$—$N(R^a)_2$ or $PO_3(R^a)_2$ where each $R^a$ is independently hydrogen, alkyl, fluoroalkyl, carbocyclyl, carbocyclylalkyl, aryl, aralkyl, heterocyclyl, heterocyclylalkyl, heteroaryl, heteroarylalkyl or any combination thereof.

"Halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroalkyl" "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given, e.g. $C_1$-$C_4$ heteroalkyl which refers to the chain length in total, which in this example is 4 atoms long. For example, a —$CH_2OCH_2CH_3$ radical is referred to as a "$C_4$" heteroalkyl, which includes the heteroatom center in the atom chain length description. Connection to the rest of the molecule may be through either a heteroatom or a carbon in the heteroalkyl chain.

A heteroalkyl group may be substituted with one or more substituents as defined above. Such substituents further independently include: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —$OR^a$, —$SR^a$, —OC(O)—$R^a$, —$N(R^a)_2$, —$C(O)R^a$, —$C(O)OR^a$, —$C(O)N(R^a)_2$, —$N(R^a)C(O)OR^a$, —$N(R^a)C(O)R^a$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl.

"Heteroalkylaryl" refers to an -(heteroalkyl)aryl radical where heteroalkyl and aryl are as disclosed herein and which are optionally substituted by one or more of the substituents described as suitable substituents for heteroalkyl and aryl respectively.

"Heteroalkylheteroaryl" refers to an -(heteroalkyl)heteroaryl radical where heteroalkyl and heteroaryl are as disclosed herein and which are optionally substituted by one or more of the substituents described as suitable substituents for heteroalkyl and heteroaryl respectively.

"Heteroalkylheterocycloalkyl" refers to an -(heteroalkyl)heterocycloalkyl radical where heteroalkyl and heteroaryl are as disclosed herein and which are optionally substituted by one or more of the substituents described as suitable substituents for heteroalkyl and heterocycloalkyl respectively.

"Heteroalkylcycloalkyl" refers to an -(heteroalkyl)cycloalkyl radical where heteroalkyl and cycloalkyl are as disclosed herein and which are optionally substituted by one or more of the substituents described as suitable substituents for heteroalkyl and cycloalkyl respectively.

"Heteroaryl" refers to a 5, 6 or 10-membered aromatic radical (e.g., $C_5$-$C_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range refers to each integer in the given range. An N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to adeninyl, azabenzimidazolyl, azaindolyl, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocyclooctа[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, imidazopyridinyl, isoxazolopyridinyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thianaphthalenyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e., thienyl), xanthinyl, guaninyl, quinoxalinyl, and quinazolinyl groups.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl, 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

Unless stated otherwise specifically in the specification, a heteroaryl moiety is optionally substituted by one or more substituents as defined above. Such substituents further independently include: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl.

Substituted heteroaryl also includes ring systems substituted with one or more oxide (—O—) substituents, such as pyridinyl N-oxides.

"Heterocyclyl" refers to any monocyclic or polycyclic moiety comprising at least one heteroatom selected from nitrogen, oxygen and sulfur. As used herein, heterocyclyl moieties can be aromatic or nonaromatic.

Unless stated otherwise, heterocyclyl moieties are optionally substituted by one or more substituents as defined above. Such substituents further independently include: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heteroaryl or heteroarylalkyl.

"Heteroarylalkyl" refers to a moiety having an aryl moiety, as described herein, connected to an alkylene moiety, as described herein, wherein the connection to the remainder of the molecule is through the alkylene group.

"Heterocyclylalkyl" refers to a stable 5, 6 or 10-membered non-aromatic ring radical having from one to six heteroatoms selected from nitrogen, oxygen and sulfur. Unless stated otherwise specifically in the specification, the heterocycloalkyl radical is a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl.

Unless stated otherwise specifically in the specification, a heterocycloalkyl moiety is optionally substituted by one or more substituents as defined above. Such substituents further independently include: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heteroaryl or heteroarylalkyl.

"Heterocyclylalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

The term "(C$_x$-C$_y$)perfluoroalkyl," wherein x<y, means an alkyl group with a minimum of x carbon atoms and a maximum of y carbon atoms, wherein all hydrogen atoms are replaced by fluorine atoms. Preferred is —(C$_1$-C$_6$)perfluoroalkyl, more preferred is —(C$_1$-C$_3$)perfluoroalkyl, most preferred is —CF$_3$.

The term "(C$_x$-C$_y$)perfluoroalkylene," wherein x<y, means an alkyl group with a minimum of x carbon atoms and a maximum of y carbon atoms, wherein all hydrogen atoms are replaced by fluorine atoms. Preferred is —(C$_1$-C$_6$)perfluoroalkylene, more preferred is —(C$_1$-C$_3$)perfluoroalkylene, most preferred is —CF$_2$—.

"Sulfanyl" refers to the groups: —S-(optionally substituted alkyl), —S-(optionally substituted aryl), —S-(optionally substituted heteroaryl), and —S-(optionally substituted heterocycloalkyl).

"Sulfinyl" refers to the groups: —S(O)—H, —S(O)-(optionally substituted alkyl), —S(O)-(optionally substituted amino), —S(O)-(optionally substituted aryl), —S(O)-(optionally substituted heteroaryl), and —S(O)-(optionally substituted heterocycloalkyl).

"Sulfonyl" refers to the groups: —S(O$_2$)—H, —S(O$_2$)-(optionally substituted alkyl), —S(O$_2$)-(optionally substituted amino), —S(O$_2$)-(optionally substituted aryl), —S(O$_2$)-(optionally substituted heteroaryl), and —S(O$_2$)-(optionally substituted heterocycloalkyl).

"Sulfonamidyl" or "sulfonamido" refers to a —S(=O)$_2$—NRR radical, where each R is selected independently from the group consisting of hydrogen, alkyl, cycloalkyl, aryl, heteroaryl (bonded through a ring carbon) and heteroalicyclic (bonded through a ring carbon). The R groups in —NRR or the —S(=O)$_2$—NRR radical may be taken together with the nitrogen to which it is attached to form a 4-, 5-, 6-, or 7-membered ring. In some embodiments, it is a C$_1$-C$_{10}$ sulfonamido, wherein each R in sulfonamido contains 1 carbon, 2 carbons, 3 carbons, or 4 carbons total. A sulfonamido group is optionally substituted by one or more of the substituents described for alkyl, cycloalkyl, aryl, heteroaryl respectively.

"Sulfoxyl" refers to a —S(=O)$_2$OH radical.

"Sulfonate" refers to a —S(=O)$_2$—OR radical, where R is selected from the group consisting of alkyl, cycloalkyl, aryl, heteroaryl (bonded through a ring carbon) and heteroalicyclic (bonded through a ring carbon). A sulfonate group is optionally substituted on R by one or more of the substituents described for alkyl, cycloalkyl, aryl, heteroaryl respectively.

"Azido" refers to an N$_3$ group. An "azide" can be an organic azide or can be a salt of the azide (N$_3^-$) anion. The term "nitro" refers to an NO$_2$ group bonded to an organic moiety. The term "nitroso" refers to an NO group bonded to an organic moiety. The term nitrate refers to an ONO$_2$ group bonded to an organic moiety or to a salt of the nitrate (NO$_3^-$) anion.

"Urethane" ("carbamoyl" or "carbamyl") includes N- and O-urethane groups, i.e., —NRC(O)OR and —OC(O)NR$_2$ groups, respectively.

"Sulfonamide" (or "sulfonamido") includes S- and N-sulfonamide groups, i.e., —SO$_2$NR$_2$ and —NRSO$_2$R groups, respectively. Sulfonamide groups therefore include but are not limited to sulfamoyl groups (—SO$_2$NH$_2$). An organosulfur structure represented by the formula —S(O)(NR)— is understood to refer to a sulfoximine, wherein both the oxygen and the nitrogen atoms are bonded to the sulfur atom, which is also bonded to two carbon atoms.

"Amidine" or "amidino" includes groups of the formula —C(NR)NR$_2$. Typically, an amidino group is —C(NH)NH$_2$.

"Guanidine" or "guanidino" includes groups of the formula —NRC(NR)NR$_2$. Typically, a guanidino group is —NHC(NH)NH$_2$.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as $NH_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", *J. Pharm. Sci.* 66: 1-19.)

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula (I) compounds, for example in their purification by recrystallization. All of these salts may be prepared by conventional means from the corresponding compound according to Formula (I) by reacting, for example, the appropriate acid or base with the compound according to Formula (I). The term "pharmaceutically acceptable salts" refers to nontoxic inorganic or organic acid and/or base addition salts, see, for example, Lit et al., Salt Selection for Basic Drugs (1986), *Int J. Pharm.*, 33, 201-217, incorporated by reference herein.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometric or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemicals within the patient's body, such as enzymes, to the active pharmaceutical ingredient. Examples of prodrugs include esters of carboxylic acid groups, which can be hydrolyzed by endogenous esterases as are found in the bloodstream of humans and other mammals. Conventional procedures for the selection and preparation of suitable prodrug derivatives are described, for example, in "Design of Prodrugs", ed. H. Bundgaard, Elsevier, 1985.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or sub-combinations of the above-listed embodiments.

In various embodiments, a compound as shown in any of the Examples, or among the exemplary compounds, is provided. Provisos may apply to any of the disclosed categories or embodiments wherein any one or more of the other above disclosed embodiments or species may be excluded from such categories or embodiments.

The term "amino protecting group" or "N-protected" as used herein refers to those groups intended to protect an amino group against undesirable reactions during synthetic procedures and which can later be removed to reveal the amine. Commonly used amino protecting groups are disclosed in Protective Groups in Organic Synthesis, Greene, T. W.; Wuts, P. G. M., John Wiley & Sons, New York, N.Y., (3rd Edition, 1999). Amino protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxy-carbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Amine protecting groups also include cyclic amino protecting groups such as phthaloyl and dithiosuccinimidyl, which incorporate the amino nitrogen into a heterocycle. Typically, amino protecting groups include formyl, acetyl, benzoyl, pivaloyl, t-butylacetyl, phenylsulfonyl, Alloc, Teoc, benzyl, Fmoc, Boc and Cbz. It is well within the skill of the ordinary artisan to select and use the appropriate amino protecting group for the synthetic task at hand.

The term "hydroxyl protecting group" or "O-protected" as used herein refers to those groups intended to protect an OH group against undesirable reactions during synthetic procedures and which can later be removed to reveal the amine. Commonly used hydroxyl protecting groups are disclosed in Protective Groups in Organic Synthesis, Greene, T. W.; Wuts, P. G. M., John Wiley & Sons, New York, N.Y., (3rd Edition, 1999). Hydroxyl protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. It is well within the skill of the ordinary artisan to select and use the appropriate hydroxyl protecting group for the synthetic task at hand.

At various places in the present specification substituents of compounds of the invention are disclosed in groups or in ranges. It is specifically intended that the invention include each and every individual subcombination of the members of such groups and ranges. For example, the term "C1-C6 alkyl" is specifically intended to individually disclose methyl, ethyl, propyl, isopropyl, n-butyl, sec-butyl, isobutyl, etc. For a number qualified by the term "about", a variance of 2%, 5%, 10% or even 20% is within the ambit of the qualified number.

Standard abbreviations for chemical groups such as are well known in the art are used; e.g., Me=methyl, Et=ethyl, i-Pr=isopropyl, Bu=butyl, t-Bu=tert-butyl, Ph=phenyl, Bn=benzyl, Ac=acetyl, Bz=benzoyl, and the like.

COMPOUNDS

The invention is directed to compounds that inhibit ATPase Associated with a variety of Activities (AAA), the ATPase having the descriptive name Valosin containing protein, also known as p97, as well as methods to treat or prevent a disease or condition in a subject that would benefit by inhibition of p97. The compounds embodying of the invention are fused two ring scaffolds having pyrimidine as one of the rings and a saturated, unsaturated or aromatic five or six membered carbocyclic or heterocyclic ring as the other ring (A ring) The A ringe may be a 4, 5, 6 or 7 membered ring, preferably a 5 or 6 membered ring. Compounds embodying the invention are also quinazoline scaffolds.

The two ring scaffold is embodied by a fused pyrimidine compound of Formula X:

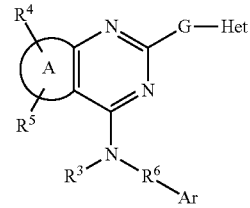

Formula X wherein the variable groups are as defined herein. The descriptions of the A ring, the Ar component, the G component, the Het component and $R^1$ through $R^6$ are given above in the Summary of the Invention, and in the Claims.

Exemplary embodiments of the A ring include a benzo ring, a cyclohexadieno ring, a cyclohexeno ring, a cyclohexano ring, a cyclopentadieno ring, a cyclopenteno ring, a cyclopentano ring, or a heterocycle ring. Exemplary embodiments of the heterocycle ring include a pyridino ring, a pyrimidino ring, a pyrazidino ring, a thiapiperidino, a morpholino, a pyrrolo ring, a thiopheno ring, a furano ring, an oxazolo ring, a thiazolo ring or any saturated, partially unsaturated or positional isomer of any of the heterocycle rings.

The Het feature of formula X includes the fused two rings B and C of Formula XXX

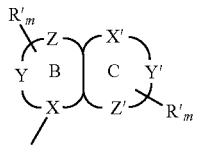

Formula XXX

The B ring is a five membered aliphatic or aromatic ring. The C ring is a five or six membered aliphatic or aromatic ring. The symbol X is nitrogen or carbon and is the atom to which the G group is covalently bonded. The symbols Y, Z, X', Y' and Z' are each independently absent or are each independently selected from the group consisting of nitrogen, oxygen and sulfur. Each of the B and C rings is substituted by zero, one, two or three R' groups. Each R' group is independently selected from the group consisting of an aliphatic component, a functional component and an aromatic component. The symbol m is 0 or an integer from 1 to 3.

Embodiments of the B and C rings of the Het moiety Formula XXX include indolyl, indolinyl, isoindolyl, benzothiophenyl, benzofuranyl, benzoimidazolyl, benzothiazolyl, benzooxazolyl, pyridinopyrrolyl, pyridinothiophenyl, pyridinofuranyl, pyridinoimidazolyl, pyridinothiazolyl, pyridinooxazolyl, pyrimidinopyrrolyl, pyrimidinothiophenyl, pyrimidinofuranyl, pyrimidinoimidazolyl, pyrimidineothiazolyl, pyrimidinooxazolyl, pyrazolinopyrrolyl, pyrazolinothiophenyl, pyrazolinofuranyl, pyrazolinoimidazolyl, pyrazolinothiazolyl, pyrazolinooxazolyl, thiophenopyrrolyl, thiophenothiophenyl, thiophenofuranyl, thiophenoimidazolyl, thiophenothiazolyl, thiophenooxazolyl, pyrrolopyrrolyl, pyrrolothiophenyl, pyrrolofuranyl, pyrroloimidazolyl, pyrrolothiazolyl, pyrrolooxazolyl, furanopyrrolyl, furanothiophenyl, furanofuranyl, furanoimidazolyl, furanothiazolyl, furanooxazolyl or a partially saturated version thereof or a substituted version thereof wherein from one to three substituents are bound to each ring, the substituents being an aliphatic component, functional component or an aromatic component.

Provisos apply to Het of Formula X. When Z is nitrogen, Z is located at either junction between rings B and C or at another position of the B ring, the total number of nitrogen, sulfur and oxygen atoms in rings B and C is no greater than 4, the total number of oxygen atoms is 0 or 1, the total number of sulfur atoms is 0 or 1. When the A ring is benzo or a methoxy substituted benzo, the Het ring is not unsubstituted indolinyl, unsubstituted benzoxazol-2-one, unsubstituted 2-aminobenzimidazole, 5,6-dimethyl-2-aminobenzamidazole, unsubstituted benzimidazole or an unsubstituted 2-aminoimidazole fused to a unsubstituted cyclopentane, cyclohexane or cycloheptane ring. When the A ring is an unsubstituted cyclobutane, cyclopentane, cyclohexane or cycloheptane ring containing a ring oxygen, a ring aminomethyl, a ring aminoethyl or a ring aminophenyl moiety, the Het ring is not a 2-aminobenzamidazole with no substituent or with a methyl, fluoro, chloro, bromo or methoxyl substituent.

In particular, the exclusions or provisos for Formula X include any of the compounds shown in Table I.

TABLE I

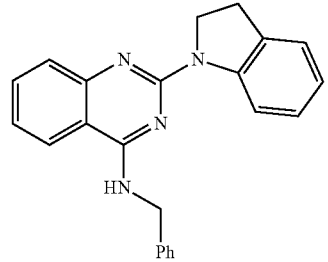 [SMILES: c1ccc(CNc2nc(N3CCc4ccccc43)nc3ccccc23)cc1]

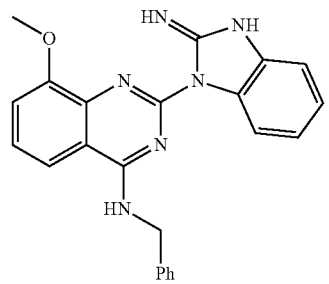 [SMILES: COc1cccc2c(NCc3ccccc3)nc(-n3c(=N)[nH]c4ccccc43)nc12]

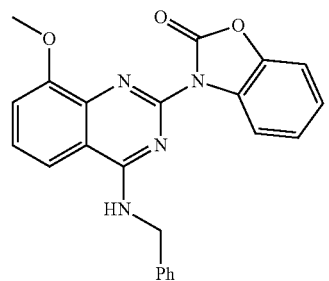 [SMILES: COc1cccc2c(NCc3ccccc3)nc(-n3c(=O)oc4ccccc43)nc12]

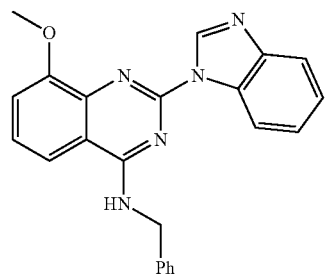 [SMILES: COc1cccc2c(NCc3ccccc3)nc(-n3cnc4ccccc43)nc12]

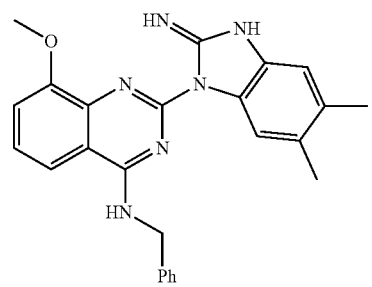 [SMILES: COc1cccc2c(NCc3ccccc3)nc(-n3c(=N)[nH]c4cc(C)c(C)cc43)nc12]

TABLE I-continued
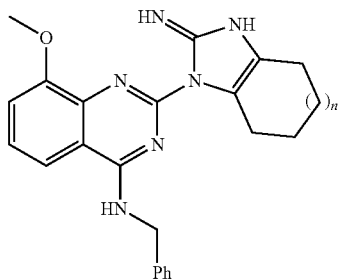 [SMILES: COc1cccc2c(NCc3ccccc3)nc(-n3c4c([nH]c3=N)CCCC4)nc12]
n = 0, 1, 2
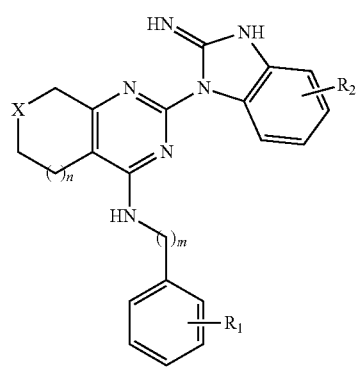
R1, R2 = H, Me, F, Cl, Br, OMe
n = -1, 0, 1, 2; m = 1, 2, 3
X = O NMe, NEt, NPh
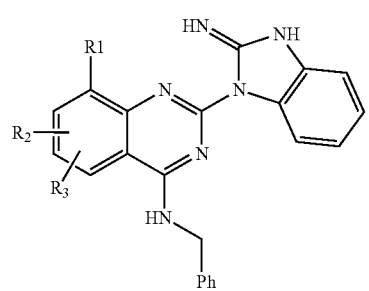
R1, E2, R3 can reach independently be
H, (ACH2)nCH3, A(CH2)nX where n = 0-5
A = O, S, NH; X is heteroaryl, O(alkyl, S(alkyl),
O(alkyl)₂ S(alkyl)₂
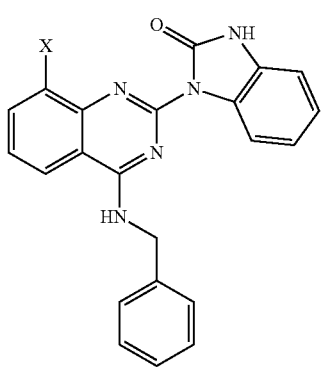
TABLE I-continued
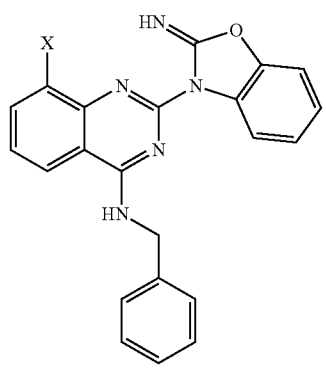
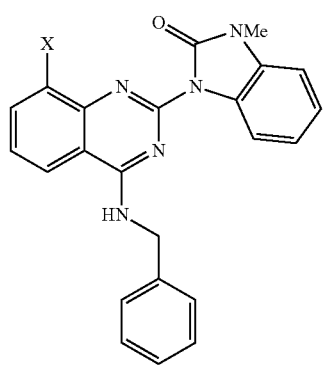
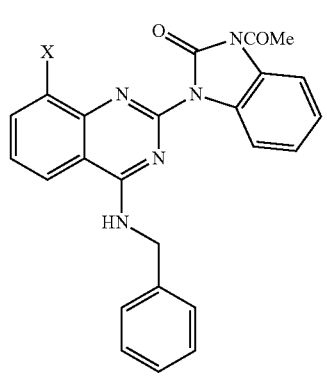
In the four foregoing formulas, X is 8-OMe 8-OH, 8-Ph, 8-OCH₂CH₂OH, 8-OCH₂CH₂NEt₂, 8-p-OMePh and 8-OCH₂CH₂OMe.
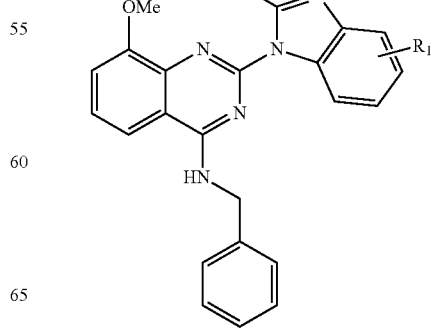

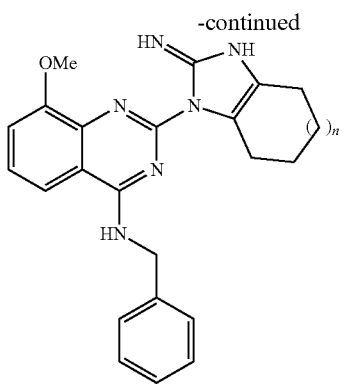

In the foregoing two formulas, $R_1$ is 5,6-dimethyl (left formula) and n is 0, 1 or 2 (right formula).

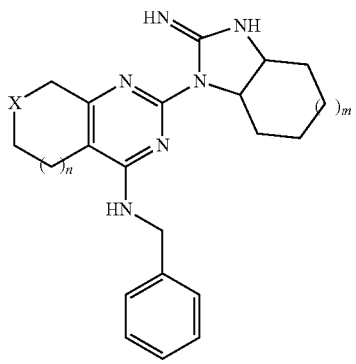

In this formula, n is selected from −1, 0, 1 and 2 and m is selected from 0, 1, and 2; X is selected from CH2, O, NMe, NEt and NPh. The final compound is

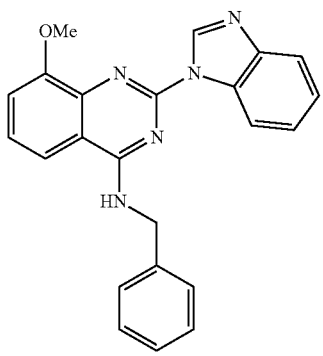 [SMILES: COc1cccc2c(NCc3ccccc3)nc(-n3cnc4ccccc43)nc12]

Preferred embodiments of Formula X include the fused pyrimidine compounds of formulas VII, VIII and IX.

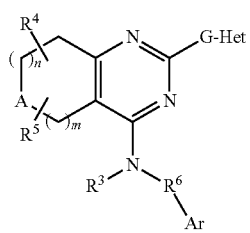

Formula VII

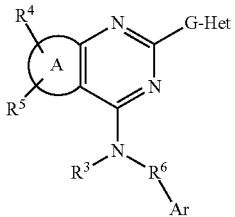

Formula VIII

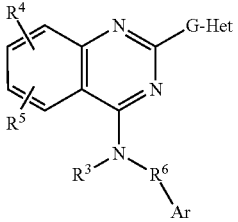

Formula IX

The fused pyrimidine of Formula VII and the fused pyrimidine of Formula VIII do not overlap because the A ring of Formula VIII contains at least one unsaturated carbon in addition to the two carbons of the ring fusion. The A ring of the fused pyrimidine of Formula VIII contains saturated carbons and optional saturated heteroatoms other than the two carbons of the ring fusion. For the preferred fused pyrimidine of Formula VII A is O, S, $NR^7$, $CH_2$; G is a bond, $NR^1$, O or $(CR^1R^2)_q$; $R^1$, $R^2$ and $R^7$ are each independently hydrogen or alkyl of one to four carbons in length; m is zero or an integer from 1 to 3; n is zero or an integer from 1 to 3; the sum of m+n is no more than 4 and no less than 1; q is an integer from 1 to 4. $R^3$ is selected from the group consisting of hydrogen, an aliphatic component and an aromatic component, each component being substituted by zero, one or two aliphatic or aromatic components. $R^4$ and $R^5$ are each independently bound to carbon and are each independently selected from the group consisting of hydrogen, an aliphatic component, a functional component, an aromatic component, and a combination thereof. $R^6$ is a covalent bond joining nitrogen to Ar or is an alkyl group of 1 to 4 carbons or an alkenyl group of 2 to 4 carbons. Ar is an unsubstituted or substituted aromatic component. Het is a saturated, unsaturated, or aromatic 5:5 or 5:6 bicyclic ring having zero, one, two or three heteroatoms independently selected from O, S or N in the bicyclic ring, the remaining atoms being carbon, the bicyclic ring being substituted with zero, one, two or three substituents each independently selected from the group consisting of an aliphatic group, a functional group, an aromatic group and any combination thereof; and provided that the Het ring is not an unsubstituted 2-aminobenzamidazole or a 2-aminobenzamidazole with a methyl, fluoro, chloro, bromo or methoxyl substituent.

For the preferred fused pyrimidine of Formula VIII, the A ring is an unsaturated or aromatic five, six or seven membered ring having one, two or three heteroatoms independently selected from the group consisting of nitrogen, oxygen and sulfur. When nitrogen is present in the A ring, the nitrogen is single or double bonded to adjacent atoms. When oxygen and/or sulfur are present in the A ring, the oxygen and/or sulfur are singled bonded to the adjacent atoms. There is at least one unsaturated carbon in the A ring in addition to the double bonded carbons of the bicyclic ring fusion, and the atoms of the A ring are bonded according to the valence bonding requirements of the molecular identities of the atoms of the A ring. The variable G is a bond, $NR^1$, O or $(CR^1R^2)_q$; $R^1$ and $R^2$ are each independently hydrogen or alkyl of one to four carbons in length; q is an integer from 1 to 4. $R^3$ is selected from the group consisting of hydrogen, an aliphatic component and an aromatic component, each component being substituted by zero, one or two aliphatic or aromatic components. $R^4$ and $R^5$ are each independently bound to carbon or nitrogen and are each independently selected from the group consisting of hydrogen, an aliphatic component, a functional component, an aromatic component, and a combination thereof. $R^6$ is a covalent bond joining nitrogen to Ar or is an alkyl group of 1 to 4 carbons or an alkenyl group of 2 to 4 carbons. Ar is an unsubstituted or substituted aromatic component. Het is a saturated, unsaturated, or aromatic 5:5 or 5:6 bicyclic ring having zero, one, two or three heteroatoms independently selected from O, S or N in the bicyclic ring, the remaining atoms being carbon, the bicyclic ring being substituted with zero, one, two or three substituents each independently selected from the group consisting of an aliphatic group, a functional group, an aromatic group and any combination thereof.

For the preferred fused pyrimidine of Formula IX (quinazoline), G is a bond, $NR^1$, O or $(CR^1R^2)_q$; $R^1$ and $R^2$ are each independently hydrogen or alkyl of one to four carbons in length; q is an integer from 1 to 4. $R^3$ is selected from the group consisting of hydrogen, an aliphatic component and an aromatic component, each component being substituted by zero, one or two aliphatic or aromatic components. $R^4$ and $R^5$ are each independently bound to carbon or nitrogen and are each independently selected from the group consisting of hydrogen, an aliphatic component, a functional component, an aromatic component, and a combination thereof. $R^6$ is a covalent bond joining nitrogen to Ar or is an alkyl group of 1 to 4 carbons or an alkenyl group of 2 to 4 carbons. Ar is an unsubstituted or substituted aromatic component. Het is a saturated, unsaturated, or aromatic 5:5 or 5:6 bicyclic ring having zero, one, two or three heteroatoms independently selected from O, S or N in the bicyclic ring, the remaining atoms being carbon, the bicyclic ring being substituted with zero, one, two or three substituents each independently selected from the group consisting of an aliphatic group, a functional group, an aromatic group and any combination thereof. A proviso applies that the Het ring is not unsubstituted indolinyl, unsubstituted benzoxazol-2-one, unsubstituted 2-aminobenzimidazole, 5,6-dimethyl-2-aminobenzamidazole, unsubstituted benzimidazole or an unsubstituted 2-aminoimidazole fused to a unsubstituted cyclopentane, cyclohexane or cycloheptane ring.

Especially preferred fused pyrimidine compounds are represented by Formulas I, IIA, IIB, III, IVA, IVB, V and VI.

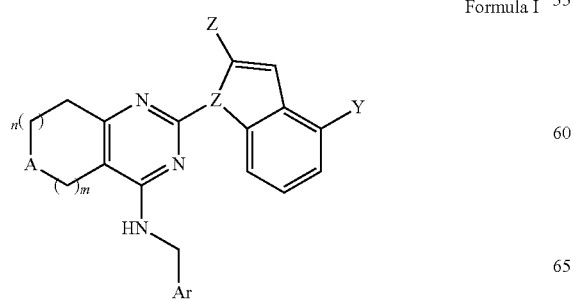

Formula I

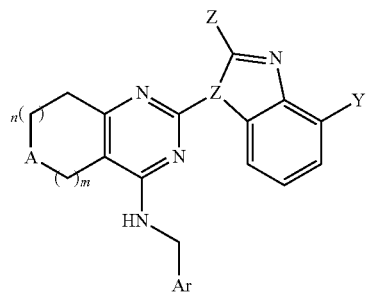

Formula IIA

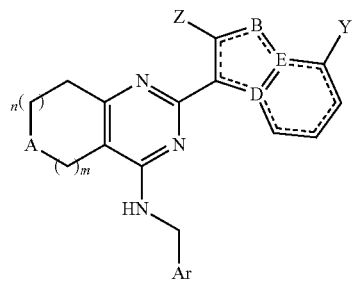

Formula IIB

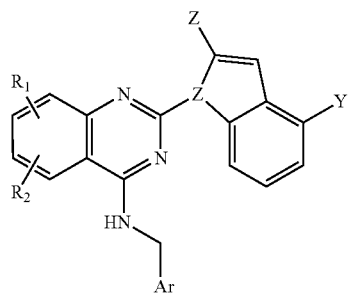

Formula III

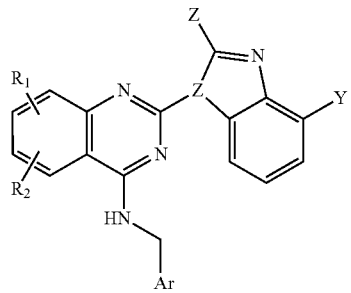

Formula IVA

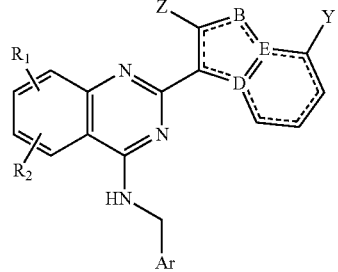

Formula IVB

Formula V

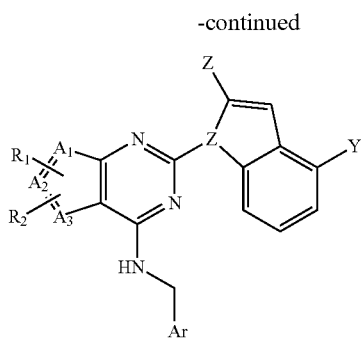

Formula VI

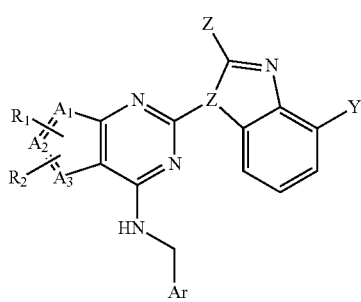

For Formulas I, IIA and IIB, A is $CH_2$, $NR^1$, O or S; m is an integer of 1-3; n is 0 or an integer of 1-2; the sum of m+n is no greater than 4 and no less than 1.

For Formula I, Y is selected from the group consisting of hydrogen, halogen, $R^c$, $OR^c$, CN, $CO_2H$, $CON(R^c)_2$, $C(NR^c)N(R^c)_2$, $SO_2N(R^c)_2$ and $SO_2R^c$ wherein each $R^c$ is independently selected from the group consisting of hydrogen, alkyl, fluoroalkyl, carbocyclyl, carbocyclylalkyl, aryl, aralkyl, heterocyclyl, heterocyclylalkyl, heteroaryl, heteroarylalkyl and any combination thereof. In other words, these groups constitute Y when the 2-substituent of the pyrimidine ring of formula I is an indole moiety. For Formula IIA and IIB, Y is the same except that halogen, $R^c$ and $OR^c$ are excluded. In other words, these groups of Y except for halogen, $R^c$ and $OR^c$ constitute Y when the 2 substituent of the pyrimidine ring of Formula II is a benzimidazole moiety.

For Formulas I, IIA and IIB, Z is selected from the group consisting of halogen, unsubstituted alkyl of 1 to 6 carbons, substituted alkyl of 1 to 4 carbons, and substituted alkoxy of 1 to 4 carbons; wherein the substituted alkyl group is substituted with $OR^a$ $SR^a$, OC(O) $R^a$, $C(O)R^a$, $C(O)OR^a$, $OC(O)N(R^a)_2$, $C(O)N(R^a)_2$, $N(R^a)C(O)OR^a$, $N(R^a)C(O)R^a$, $N(R^a)C(O)N(R^a)_2$, $N(R^a)C(NR^a)N(R^a)_2$, $N(R^a)S(O)_tR^a$, $S(O)_tOR^a$, $S(O)_tN(R^a)_2$, $R^aN(R^a)_2$ or $PO_3(R^a)_2$ wherein each $R^a$ is independently hydrogen, alkyl, fluoroalkyl, carbocyclyl, carbocyclylalkyl, aryl, aralkyl, heterocyclyl, heterocyclylalkyl, heteroaryl, heteroarylalkyl or any combination thereof and, the substituted alkoxy group is substituted with $OR^b$, $R^b$, $OC(O)R^b$, $N(R^b)_2$, $C(O)R^b$, $C(O)OR^b$ $OC(O)N(R^b)_2$, $C(O)N(R^b)_2$, $N(R^b)C(O)OR^b$, $N(R^b)C(O)R^b$, $N(R^b)C(O)N(R^b)_2$, $N(R^b)C(NR^b)N(R^b)_2$, $N(R^b)$ $S(O)_tR^b$, $S(O)_tOR^b$, $S(O)_tN(R^b)_2$, $R^bN(R^b)_2$ or $PO_3(R^b)_2$ wherein each $R^b$ is independently hydrogen, alkyl, fluoroalkyl, carbocyclyl, carbocyclylalkyl, aryl, aralkyl, heterocyclyl, heterocyclylalkyl, heteroaryl, heteroarylalkyl or any combination thereof.

For Formulas I, IIA and IIB, $R^1$ is selected from a group consisting of hydrogen, unsubstituted alkyl of 1 to 6 carbons, substituted alkyl of 1 to 4 carbons and $-C(O)R^d$; wherein, the substituted alkyl is substituted with $OR^d$, $SR^d$, OC(O) $R^d$, $C(O)R^d$, $C(O)OR^d$, $-OC(O)N(R^d)_2$, $C(O)N(R^d)_2$, $N(R^d)C(O)OR^d$, $N(R^d)C(O)R^d$, $N(R^d)C(O)N(R^d)_2$, $N(R^d)C(NR^d)N(R^d)_2$, $N(R^d)S(O)_tR$, $S(O)_tOR^d$, $S(O)_tN(R^d)_2$, $R^dN(R^d)_2$ or $PO_3(R^d)_2$; and wherein each $R^d$ is independently selected from the group consisting of hydrogen, alkyl, fluoroalkyl, carbocyclyl, carbocyclylalkyl, aryl, aralkyl, heterocyclyl, heterocyclylalkyl, heteroaryl, heteroarylalkyl alkenyl, alkynyl or any combination thereof; each t is independently selected from an integer of 1 or 2.

For Formula IIB, B is $CH_2$, CH, C=O, N or O; D and E are each independently selected from C or N.

For all Formulas I, IIA, IIB, III, IVA, IVB, V and VI, Ar is an unsubstituted or substituted aromatic component.

For Formulas III, IVA, IVB, V and VI, the substituents Y and Z are the same as given for Formulas I and II provided that when the 2-substituent of the pyrimidine ring of each of these formulas is a benzimidazole moiety, the exclusion for Y given for Formula II applies. For these Formulas, the substituents $R_1$, $R_2$ as well as the designations for $A_1$, $A_2$, $A_3$ B, D and E have the following designations.

$R_1$ is selected from the group consisting of hydrogen, $OR^d$, $SR^4$, $OC(O)R^d$, $C(O)R^d$, $C(O)OR^d$, $OC(O)N(R^d)_2$, $C(O)N(R^d)_2$, $N(R^d)C(O)OR^d$, $N(R^d)C(O)R^d$, $-N(R^d)C(O)N(R^d)_2$, $N(R^d)C(NR^d)N(R^d)_2$, $N(R^d)S(O)_tR^d$ $S(O)_tOR^d$, $S(O)_tN(R^d)_2$, $N(R^d)_2$, $(CH_2)_tN(R^d)_2$, $PO_3(R^d)_2$ and $C(O)R^d$, wherein each $R^d$ is independently hydrogen, alkyl, fluoroalkyl, carbocyclyl, carbocyclylalkyl, aryl, aralkyl, heterocyclyl, heterocyclylalkyl, heteroaryl, heteroarylalkyl alkenyl, alkynyl or any combination thereof.

$R_2$ is selected from the group consisting of hydrogen, $OR^d$, $SR^d$, $OC(O)R^d$, $C(O)R^d$, $C(O)OR^d$ $OC(O)N(R^d)_2$, $C(O)N(R^d)_2$, $N(R^d)C(O)OR^d$, $N(R^d)C(O)R^d$, $-N(R^d)C(O)N(R^d)_2$, $N(R^d)C(NR^d)N(R^d)_2$, $N(R^d)S(O)_tR^d$ $S(O)_tOR^d$, $S(O)_tN(R^d)_2$, $N(R^d)_2$, $(CH_2)_tN(R^d)_2$ and $PO_3(R^d)_2$ wherein each $R^d$ is independently hydrogen, alkyl, fluoroalkyl, carbocyclyl, carbocyclylalkyl, aryl, aralkyl, heterocyclyl, heterocyclylalkyl, heteroaryl, heteroarylalkyl alkenyl, alkynyl or any combination thereof. Each t is independently selected from the group of integers of 1 and 2.

One of $A_1$, $A_2$ and $A_3$ is CH or $CH_2$; one of $A_1$, $A_2$ and $A_3$ is N, NH or S; one of $A_1$, $A_2$ and $A_3$ is N, NH, O or S; and $A_1$, $A_2$ and $A_3$ are bonded to each other and to the carbons of the pyrimidine ring according to valence bonding requirements of the molecular identities of $A_1$, $A_2$ and $A_3$; or, Two of $A_1$, $A_2$ and $A_3$ are CH; and one of $A_1$, $A_2$ and $A_3$ is N, NH, O or S; and $A_1$, $A_2$ and $A_3$ are bonded to each other and to the carbons of the pyrimidine ring according to valence bonding requirements of the molecular identities of $A_1$, $A_2$ and $A_3$.

B is $CH_2$, CH, C=O, N or O;

D and E are each independently selected from C or N;

Especially preferred Y and Z substituents for Formulas I, HA, IIB, III, IVA, IVB, V and VI include the following groups. Y is selected from the group consisting of hydrogen, cyano, methyl, ethyl, propyl, butyl, amino, methylamino, dimethylamino, aminoalkylenyl, methylaminoalkylenyl, dimethylaminoalkylenyl, hydroxyalkylenyl, methoxy, ethoxy, propoxy, methoxymethyl, methoxyethyl, methoxyethoxy, N-alkylenylacetamide, N-alkylenylurea, N-alkylenylcarbamate, methyl N-alkylenylcarbamate, N-alkylenylsulfonamide, N-alkylenylpropynamide, N-alkylenylacrylamide, morpholinyl, piperidinyl, piperazinyl, pyrrolidonyl, pyrrolidinyl, N-alkylenylmorpholine, trifluoromethyl, pentafluoroethyl, cyanoalkylenyl, fluoro, chloro, bromo, carboxylic acid, sulfonic acid, carboxamide, sulfonamide, N-alkyl carboxamide, N,N-dialkylcarboxamide, N-alkylsulfonamide, N,N-dialkylsulfonamide, wherein the alkylenyl group is $-(CH_2)_n-$ of one to six carbons and the alkyl group is 1 to 4 carbons. Z is selected from the group consisting of methyl, ethyl, propyl, cyclopropyl, methoxy, ethoxy, propoxy, methoxymethyl, methoxyethyl, methoxymethoxy, methoxyethoxy, N-alkylenylacetamide, N-alkylenylurea, N-alkylenylcarbamate, methyl N-alkylenylcarbamate, N-alkylenylsulfonamide, N-alkylenylpropynamide, N-alkylenylacrylamide, morpholinyl, piperidinyl, piperazinyl, pyrrolidonyl, pyrrolidinyl, N-alkylenylmorpholine, trifluoromethyl, pentafluoroethyl, wherein the alkylenyl group is —$(CH_2)_n$— of one to six carbons.

For each of Formulas I, IIA and IIB, A is preferred to be $CH_2$. A is also preferred to be $NR^1$. A is also preferred to be O.

For all preferred Formulas I, IIS, IIB, III, IVA, IVB, V and VI, the aromatic component may be aryl, aralkyl, heteroalkylaryl, heteroalkylheteroaryl and heteroaryl, wherein the aromatic component is a monocyclic or fused ring polycyclic group with at least one ring having a conjugated electron system. More preferred groups for the aromatic component for all of the foregoing Formulas include phenyl, naphthyl, benzyl, ethylphenyl, pyridyl, pyrimidinyl, purinyl, methylenylpyridyl, methylenylpyrimidinyl, methylenylpurinyl, ethylenyl pyridyl, ethylenylpyrimidinyl, ethylenylpurinyl, thiophenyl, furanyl, imidazolyl, pyrrolyl, thiazolyl, oxazolyl, trifluoromethylphenyl or trifluoromethylbenzyl.

The more preferred groups of the aromatic component may be substituted by a functional component selected from the group consisting of hydroxy, halo, cyano, trifluoromethyl, trifluoromethoxy, nitro, trimethylsilanyl, $OR^a$, $SR^a$, OC(O) $R^a$, $N(R^a)_2$, $C(O)R^a$, $C(O)OR^a$, —$OC(O)N(R^a)_2$, $C(O)N(R^a)_2$, $N(R^a)C(O)OR^a$, $N(R^a)C(O)R^a$, $N(R^a)C(O)N(R^a)_2$, $N(R^a)C(NR^a)N(R^a)_2$, $N(R^a)S(O)_tR^a$, $S(O)_tOR^a$, $S(O)_tN(R^a)_2$, —$R^aN(R^a)_2$, $PO_3(R^a)_2$ and any combination thereof; wherein each $R^a$ is independently hydrogen, alkyl, fluoroalkyl, carbocyclyl, carbocyclylalkyl, aryl, aralkyl, heterocyclyl, heterocyclylalkyl, heteroaryl, heteroarylalkyl or any combination thereof; and wherein each t independently is an integer of 1 or 2.

A most preferred group for the aromatic component is an unsubstituted phenyl.

When the fused pyrimidine scaffold is a quinazoline, this aspect is also embodied by the 2,4 substituted quinazoline of formula XX.

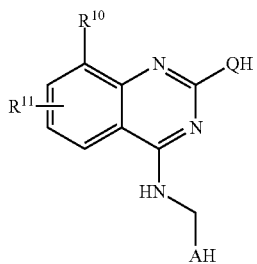

XX wherein $R^{10}$ and $R^{11}$ are each independently hydrogen, an aliphatic, functional or aromatic component with the location of $R^{11}$ being any of positions 5, 6 or 7 of the benzo group; AH is a phenyl, thiophenyl, pyridinyl, pyrrolyl, furanyl or substituted versions thereof wherein the substituents can be optional, independent and optionally multiple and are an aliphatic, functional or aromatic component; and QH is phenyl, alkylenylphenyl with its alkylenyl group having from 1 to 6 carbons, indolyl, benzimidazolyl, 2-ketobenzimidazolyl, imidazolyl, α-amino acid amide, α, ω diaminoalkane of 1 to 6 carbons or a substituted version of phenyl, alkylenylphenyl, indolyl, benzimidazolyl or 2-ketobenimidazolyl wherein the substituents can be optional, independent and optionally multiple and are an aliphatic, functional or aromatic component; and provided that QH is not unsubstituted indolinyl, unsubstituted indolyl, unsubstituted benzimidazolyl, or unsubstituted imidazolyl when AH is unsubstituted phenyl or when $R^{10}$ is methoxyl and $R^{11}$ is hydrogen and AH is unsubstituted phenyl.

Preferred embodiments of formula XX include those wherein QH contains a nitrogen and the nitrogen of the QH group is bonded to the 2 position of the quinazoline. Further preferred embodiments include those wherein the AH group is a phenyl or substituted phenyl, the QH group is indolyl, benzimidazolyl or imidazolyl or a substituted version thereof, and one of $R^{10}$ and $R^{11}$ is not hydrogen when AH is phenyl and QH is one of indolyl, benimidazolyl and imidazol.

For the Formulas VII, VIII, IX, X and XX embodying the fused pyrimidine compounds of the invention, the following descriptions provide the preferred versions of these variables.

The substituents of the fused pyrimidine ring, the Het moiety, $R^3$-$R^6$ and R' as well as the substituents of the quinazoline scaffold, $R^{10}$ and $R^{11}$ and the substituents of AH and QH may be independently selected from a linear, branched or cyclic saturated or unsaturated organic moiety composed of carbon, hydrogen and optional heteroatoms including boron, oxygen, nitrogen, sulfur, phosphorus, halogen, alkali metal and alkali earth metal. More particularly, $R^3$ to $R^6$, R', $R^{10}$ and $R^{11}$ and the substituents of AH and QH may each independently be an aliphatic component as defined above. Preferably, each aliphatic component may be independently selected from a linear or branched alkyl group, a cycloalkyl group, a linear or branched alkenyl group, a cycloalkenyl group, a linear or branched alkynyl group, a cycloalkynyl group, each group optionally containing heteroatoms, the number of carbon atoms in each alkyl or cycloalkyl group being from 1 to 20 and the number of carbon atoms in each alkenyl, cycloalkenyl, alkynyl or cycloalkynyl group being from 2 to 20. Additionally the aliphatic component may be optionally substituted by an alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), —$R^a$—$N(R^a)_2$ or $PO_3(R^a)_2$ where each $R^a$ is independently hydrogen, alkyl, fluoroalkyl, carbocyclyl, carbocyclylalkyl, aryl, aralkyl, heterocyclyl, heterocyclylalkyl, heteroaryl, heteroarylalkyl or any combination thereof.

The substituents of the fused pyrimidine ring, the Het moiety, $R^3$-$R^6$ and R' as well as the substituents of the quinazoline scaffold, QH, AH, $R^{10}$ and $R^{11}$ also may be independently selected from a functional component as defined above. Preferably each functional component may be independently selected from hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(N-R^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), —$R^a$—$N(R^a)_2$ or $PO_3(R^a)_2$ where each $R^a$ is independently hydrogen, alkyl, fluoroalkyl, carbocyclyl, carbocyclylalkyl, aryl, aralkyl, heterocyclyl, heterocyclylalkyl, heteroaryl, heteroarylalkyl or any combination thereof.

The substituents of the fused pyrimidine ring, the Het moiety, $R^3$-$R^6$ and R' as well as the substituents of the quinazoline scaffold, QH, AH, $R^{10}$ and $R^{11}$ also may be an aromatic component as defined above.

Each aromatic component of all Formulas VII, VIII, IX, X and XX preferably is independently selected from the group consisting of aryl, aralkyl, heteroalkylaryl, heteroalkylheteroaryl and heteroaryl, wherein the aromatic component is a monocyclic or fused ring polycyclic group with at least one ring having a conjugated electron system. The aromatic component may be aliphatic in part and olefinically conjugated in part or may be fully aromatic. Exemplary embodiments of the aromatic component include those described above in the Definitions section. Preferred embodiments include phenyl, naphthyl, benzyl, ethylphenyl, pyridyl, pyrimidinyl, purinyl, methylenylpyridyl, methylenylpyrimidinyl, methylenylpurinyl, ethylenyl pyridyl, ethylenylpyrimidinyl, ethylenylpurinyl, thiophenyl, furanyl, imidazolyl, pyrrolyl, thiazolyl, oxazolyl, trifluoromethylphenyl, and trifluoromethylbenzyl.

The aromatic component may optionally be substituted by a group J selected from an alkyl, heteroalkyl, alkenyl, alkynyl, cycloalkyl, heterocycloalkyl, aryl, arylalkyl, heteroaryl, heteroarylalkyl, —$R^a$—N($R^a$)$_2$ or PO$_3$($R^a$)$_2$ where each $R^a$ is independently hydrogen, alkyl, fluoroalkyl, carbocyclyl, carbocyclylalkyl, aryl, aralkyl, heterocyclyl, heterocyclylalkyl, heteroaryl, heteroarylalkyl or any combination thereof, F, Cl, Br, I, OR", OC(O)N(R")$_2$, CN, NO, NO$_2$, ONO$_2$, azido, CF$_3$, OCF$_3$, R", O (oxo), S (thiono), methylenedioxy, ethylenedioxy, N(R")$_2$, SR", SOR', SO$_2$R''', SO$_2$N(R''')$_2$, SO$_3$R", C(O)R", C(O)C(O)R", C(O)CH$_2$C(O)R", C(S)R', C(O)OR", OC(O)R", C(O)N($R^1$)$_2$, OC(O)N(R")$_2$, C(S)N(R")$_2$, (CH$_2$)$_{0-2}$N($R^1$)C(O)R", (CH$_2$)$_{0-2}$N(R")N(R")$_2$, N($R^1$)$_2$, N($R^1$)C(O)R", N($R^1$)$_2$C(O)OR", N(R")$_2$CON($R^1$)$_2$, N(R")$_2$C(NR")N($R^1$)$_2$, N(R")SO$_2$R", N($R^1$)SO$_2$N($R^1$)$_2$, N(R")C(O)OR", N($R^1$)C(O)R", N($R^1$)C(S)R", N($R^1$)C(O)N($R^1$)$_2$, N($R^1$)C(S)N(R")$_2$, N(COR")COR", N(OR")R", C(=NH)N(R")$_2$, C(O)N(OR")R", or C(=NOR")R" wherein R" can be hydrogen or a carbon-based moiety including alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R" is optionally and independently mono- or multi-substituted with J; or wherein two R" groups bonded to a nitrogen atom or to adjacent nitrogen atoms together with the nitrogen atom or atoms optionally form a heterocyclyl, which optionally is mono- or independently multi-substituted with J.

Embodiments of the fused pyrimidine compounds of Formulas I, II, III, IV-A, IV-B, V and VI include the specific compounds named in the following Tables. The tables are coordinated with the individual preferred Formulas I, II, III, IV-A, IV-B, V and VI. All fused pyrimidine compounds of these tables have been synthesized and demonstrate appropriate biological activity in one or more Biological Assays described herein. Not all fused pyrimidine compounds of these tables are listed in BioAssay Table III. The compounds listed in Table III relate to the compounds of the Synthesized Tables according to their IUPAC names.

The especially preferred species of the fused pyrimidine compounds of Formula I include the following synthesized compounds. These compounds are identified by their IUPAC names. Except where specifically noted all of these species of the fused pyrimidine compounds have been synthesized.

N-benzyl-2-(2-methyl-1H-indol-1-yl)-5,6,7,8-tetrahydroquinazolin-4-amine;
N-benzyl-2-(2-ethyl-1H-indol-1-yl)-5,6,7,8-tetrahydroquinazolin-4-amine;
2-[2-(aminomethyl)-1H-indol-1-yl]-N-benzyl-5,6,7,8-tetrahydroquinazolin-4-amine;
2-[2-(1-aminoethyl)-1H-indol-1-yl]-N-benzyl-5,6,7,8-tetrahydroquinazolin-4-amine;
2-[5-(aminomethyl)-4H-pyrrolo[2,3-d][1,3]thiazol-4-yl]-N-benzyl-5,6,7,8-tetrahydroquinazolin-4-amine;
N-benzyl-2-(2-methoxy-1H-indol-1-yl)-5,6,7,8-tetrahydroquinazolin-4-amine;
{1-[4-(benzylamino)-5,6,7,8-tetrahydroquinazolin-2-yl]-1H-indol-2-yl}methanol
N-benzyl-2-[2-(methoxymethyl)-1H-indol-1-yl]-5,6,7,8-tetrahydroquinazolin-4-amine;
N-benzyl-2-{2-[(methylamino)methyl]-1H-indol-1-yl}-5,6,7,8-tetrahydroquinazolin-4-amine;
N-benzyl-2-{2-[(dimethylamino)methyl]-1H-indol-1-yl}-5,6,7,8-tetrahydroquinazolin-4-amine;
N-({1-[4-(benzylamino)-5,6,7,8-tetrahydroquinazolin-2-yl]-1H-indol-2-yl}methyl)acetamide;
({1-[4-(benzylamino)-5,6,7,8-tetrahydroquinazolin-2-yl]-1H-indol-2-yl}methyl)urea;
methyl N-({1-[4-(benzylamino)-5,6,7,8-tetrahydroquinazolin-2-yl]-1H-indol-2-yl}methyl)carbamate;
N-({1-[4-(benzylamino)-5,6,7,8-tetrahydroquinazolin-2-yl]-1H-indol-2-yl}methyl)methanesulfonamide;
4-N-benzyl-2-N-[1-(1H-indol-2-yl)ethyl]-5,6,7,8-tetrahydroquinazoline-2,4-diamine;
N-benzyl-2-[2-(morpholin-4-ylmethyl)-1H-indol-1-yl]-5,6,7,8-tetrahydroquinazolin-4-amine;
N-benzyl-2-(2-methyl-1H-indol-3-yl)-5,6,7,8-tetrahydroquinazolin-4-amine
1-[4-(benzylamino)-5,6,7,8-tetrahydroquinazolin-2-yl]-2-methyl-1H-indole-4-carbonitrile;
1-[4-(benzylamino)-5,6,7,8-tetrahydroquinazolin-2-yl]-2-methoxy-1H-indole-4-carbonitrile;
N-benzyl-2-(2-ethoxy-1H-indol-1-yl)-5,6,7,8-tetrahydroquinazolin-4-amine
N-benzyl-2-[2-(trifluoromethyl)-1H-indol-1-yl]-5,6,7,8-tetrahydroquinazolin-4-amine;
N-benzyl-2-(2-chloro-1H-indol-1-yl)-5,6,7,8-tetrahydroquinazolin-4-amine
N-({1-[4-(benzylamino)-5,6,7,8-tetrahydroquinazolin-2-yl]-1H-indol-2-yl}methyl)prop-2-ynamide;
N-({1-[4-(benzylamino)-5,6,7,8-tetrahydroquinazolin-2-yl]-1H-indol-2-yl}methyl)prop-2-enamide;
1-[4-(benzylamino)-5,6,7,8-tetrahydroquinazolin-2-yl]-2-methyl-1H-indole-4-carboxamide;
1-[4-(benzylamino)-5,6,7,8-tetrahydroquinazolin-2-yl]-2-methoxy-1H-indole-4-carboxamide;
2-(aminomethyl)-1-[4-(benzylamino)-5,6,7,8-tetrahydroquinazolin-2-yl]-1H-indole-4-carboxamide;
1-[4-(benzylamino)-5,6,7,8-tetrahydroquinazolin-2-yl]-2-methyl-1H-indole-4-carboxylic acid;
1-[4-(benzylamino)-5,6,7,8-tetrahydroquinazolin-2-yl]-2-methyl-1H-indole-4-sulfonamide;
N-benzyl-2-(4-methanesulfonyl-2-methyl-1H-indol-1-yl)-5,6,7,8-tetrahydroquinazolin-4-amine;
1-[4-(benzylamino)-5,6,7,8-tetrahydroquinazolin-2-yl]-2-ethyl-1H-indole-4-carboxamide;
N-benzyl-2-[2-methyl-4-(1H-1,2,3,4-tetrazol-5-yl)-1H-indol-1-yl]-5,6,7,8-tetrahydroquinazolin-4-amine;
1-[4-(benzylamino)-5,6,7,8-tetrahydroquinazolin-2-yl]-2-(2-methoxyethoxy)-1H-indole-4-carboxamide;

2-[4-(aminomethyl)-2-methyl-1H-indol-1-yl]-N-benzyl-5,6,7,8-tetrahydroquinazolin-4-amine;

1-[4-(benzylamino)-5,6,7,8-tetrahydroquinazolin-2-yl]-2-(propan-2-yl)-1H-indole-4-carboxamide;

1-[4-(benzylamino)-5,6,7,8-tetrahydroquinazolin-2-yl]-2-cyclopropyl-1H-indole-4-carboxamide;

1-[4-(benzylamino)-5,6,7,8-tetrahydroquinazolin-2-yl]-N,2-dimethyl-1H-indole-4-carboxamide;

1-[4-(benzylamino)-5,6,7,8-tetrahydroquinazolin-2-yl]-N,N,2-trimethyl-1H-indole-4-carboxamide;

1-[4-(benzylamino)-5,6,7,8-tetrahydroquinazolin-2-yl]-N-ethyl-2-methyl-1H-indole-4-carboxamide;

1-[4-(benzylamino)-5,6,7,8-tetrahydroquinazolin-2-yl]-N-(2-methoxyethyl)-2-methyl-1H-indole-4-carboxamide;

N-(2-aminoethyl)-1-[4-(benzylamino)-5,6,7,8-tetrahydroquinazolin-2-yl]-2-methyl-1H-indole-4-carboxamide;

1-[4-(benzylamino)-5,6,7,8-tetrahydroquinazolin-2-yl]-2-ethoxy-1H-indole-4-carboxamide;

1-[4-(benzylamino)-5,6,7,8-tetrahydroquinazolin-2-yl]-2-(2-methoxyethoxy)-1H-indole-4-carbonitrile;

2-[2-(1-aminoethyl)-1H-indol-1-yl]-N-benzyl-5H,7H,8H-pyrano[4,3-d]pyrimidin-4-amine;

N-benzyl-2-(2-methoxy-1H-indol-1-yl)-5H,7H,8H-pyrano[4,3-d]pyrimidin-4-amine;

N-benzyl-2-(2-methyl-1H-indol-1-yl)-5H,7H,8H-pyrano[4,3-d]pyrimidin-4-amine;

2-[2-(aminomethyl)-1H-indol-1-yl]-N-benzyl-5H,7H,8H-pyrano[4,3-d]pyrimidin-4-amine;

1-[4-(benzylamino)-5H,7H,8H-pyrano[4,3-d]pyrimidin-2-yl]-2-methoxy-1H-indole-4-carbonitrile;

1-[4-(benzylamino)-5H,7H,8H-pyrano[4,3-d]pyrimidin-2-yl]-2-methyl-1H-indole-4-carbonitrile;

1-[4-(benzylamino)-5H,7H,8H-pyrano[4,3-d]pyrimidin-2-yl]-2-methoxy-1H-indole-4-carboxamide;

1-[4-(benzylamino)-5H,7H,8H-pyrano[4,3-d]pyrimidin-2-yl]-2-methyl-1H-indole-4-carboxamide;

2-(aminomethyl)-1-[4-(benzylamino)-5H,7H,8H-pyrano[4,3-d]pyrimidin-2-yl]-1H-indole-4-carboxamide;

1-[4-(benzylamino)-5H,7H,8H-pyrano[4,3-d]pyrimidin-2-yl]-2-[(dimethylamino)methyl]-1H-indole-4-carboxamide;

1-[4-(benzylamino)-5H,7H,8H-pyrano[4,3-d]pyrimidin-2-yl]-2-(hydroxymethyl)-1H-indole-4-carboxamide;

1-[4-(benzylamino)-5H,7H,8H-pyrano[4,3-d]pyrimidin-2-yl]-N,2-dimethyl-1H-indole-4-carboxamide;

1-[4-(benzylamino)-5H,7H,8H-pyrano[4,3-d]pyrimidin-2-yl]-N,N,2-trimethyl-1H-indole-4-carboxamide;

1-[4-(benzylamino)-5H,7H,8H-pyrano[4,3-d]pyrimidin-2-yl]-2-methyl-N-(propan-2-yl)-1H-indole-4-carboxamide;

1-[4-(benzylamino)-5H,7H,8H-pyrano[4,3-d]pyrimidin-2-yl]-Nutan-2-yl)-2-methyl-1H-indole-4-carboxamide;

1-[4-(benzylamino)-5H,7H,8H-pyrano[4,3-d]pyrimidin-2-yl]-N-[2-(dimethylamino)ethyl]-2-methyl-1H-indole-4-carboxamide;

N-benzyl-2-{2-methyl-4-[(morpholin-4-yl)carbonyl]-1H-indol-1-yl}-5H,7H,8H-pyrano[4,3-d]pyrimidin-4-amine;

N-benzyl-2-{2-methyl-4-[(piperazin-1-yl)carbonyl]-1H-indol-1-yl}-5H,7H,8H-pyrano[4,3-d]pyrimidin-4-amine;

N-(2-aminoethyl)-1-[4-(benzylamino)-5H,7H,8H-pyrano[4,3-d]pyrimidin-2-yl]-2-methyl-1H-indole-4-carboxamide;

1-[4-(benzylamino)-5H,7H,8H-pyrano[4,3-d]pyrimidin-2-yl]-2-methyl-1H-indole-4-carboxylic acid;

1-[4-(benzylamino)-5H,7H,8H-pyrano[4,3-d]pyrimidin-2-yl]-2-methyl-1H-indole-4-sulfonamide;

1-[4-(benzylamino)-5H,7H,8H-pyrano[4,3-d]pyrimidin-2-yl]-2-ethyl-1H-indole-4-carboxamide;

N-benzyl-2-(4-methanesulfonyl-2-methyl-1H-indol-1-yl)-5H,7H,8H-pyrano[4,3-d]pyrimidin-4-amine;

1-[4-(benzylamino)-5H,7H,8H-pyrano[4,3-d]pyrimidin-2-yl]-2-methyl-1H-indole-4-carboximidamide;

N-benzyl-2-[2-methyl-4-(1H-1,2,3,4-tetrazol-5-yl)-1H-indol-1-yl]-5H,7H,8H-pyrano[4,3-d]pyrimidin-4-amine;

1-(4-{[(4-fluorophenyl)methyl]amino}-5H,7H,8H-pyrano[4,3-d]pyrimidin-2-yl)-2-methyl-1H-indole-4-carboxamide;

1-(4-{[(2-fluorophenyl)methyl]amino}-5H,7H,8H-pyrano[4,3-d]pyrimidin-2-yl)-2-methyl-1H-indole-4-carboxamide;

2-[4-(aminomethyl)-2-methyl-1H-indol-1-yl]-N-benzyl-5H,7H,8H-pyrano[4,3-d]pyrimidin-4-amine;

1-[4-(benzylamino)-5H,7H,8H-pyrano[4,3-d]pyrimidin-2-yl]-2-[(carbamoylamino)methyl]-1H-indole-4-carboxamide;

1-[4-(benzylamino)-5H,7H,8H-pyrano[4,3-d]pyrimidin-2-yl]-2-(propan-2-yl)-1H-indole-4-carboxamide;

1-[4-(benzylamino)-5H,7H,8H-pyrano[4,3-d]pyrimidin-2-yl]-2-cyclopropyl-1H-indole-4-carboxamide;

1-(4-{[(3-fluorophenyl)methyl]amino}-5H,7H,8H-pyrano[4,3-d]pyrimidin-2-yl)-2-methyl-1H-indole-4-carboxamide;

2-[2-(1-aminoethyl)-1H-indol-1-yl]-N-benzyl-5H,6H,8H-pyrano[3,4-d]pyrimidin-4-amine;

N-benzyl-2-(2-methyl-1H-indol-1-yl)-5H,7H-furo[3,4-d]pyrimidin-4-amine;

N-benzyl-2-(2-methyl-1H-indol-1-yl)-5H,6H,7H,8H-pyrido[4,3-d]pyrimidin-4-amine;

1-[4-(benzylamino)-2-(2-methyl-1H-indol-1-yl)-5H,6H,7H,8H-pyrido[4,3-d]pyrimidin-6-yl]ethan-1-one;

2-[2-(1-aminoethyl)-1H-indol-1-yl]-N-benzyl-5H,6H,7H,8H-pyrido[4,3-d]pyrimidin-4-amine;

N-benzyl-2-(2-methoxy-1H-indol-1-yl)-5H,6H,7H,8H-pyrido[4,3-d]pyrimidin-4-amine;

2-[2-(aminomethyl)-1H-indol-1-yl]-N-benzyl-5H,6H,7H,8H-pyrido[4,3-d]pyrimidin-4-amine;

2-[2-(aminomethyl)-1H-indol-1-yl]-N-[(4-fluorophenyl)methyl]-5H,6H,7H,8H-pyrido[4,3-d]pyrimidin-4-amine;

N-benzyl-2-(2-ethoxy-1H-indol-1-yl)-5H,6H,7H,8H-pyrido[4,3-d]pyrimidin-4-amine;

N-benzyl-2-[2-(morpholin-4-ylmethyl)-1H-indol-1-yl]-5H,6H,7H,8H-pyrido[4,3-d]pyrimidin-4-amine;

N-benzyl-2-(2-methoxy-1H-indol-1-yl)-6-methyl-5H,6H,7H,8H-pyrido[4,3-d]pyrimidin-4-amine;

{1-[4-(benzylamino)-5H,6H,7H,8H-pyrido[4,3-d]pyrimidin-2-yl]-1H-indol-2-yl}methanol;

1-{1-[4-(benzylamino)-5H,6H,7H,8H-pyrido[4,3-d]pyrimidin-2-yl]-1H-indol-2-yl}ethan-1-ol;

N-benzyl-2-[2-(methoxymethyl)-1H-indol-1-yl]-5H,6H,7H,8H-pyrido[4,3-d]pyrimidin-4-amine;

N-benzyl-2-{2-[(dimethylamino)methyl]-1H-indol-1-yl}-5H,6H,7H,8H-pyrido[4,3-d]pyrimidin-4-amine;

N-({1-[4-(benzylamino)-5H,6H,7H,8H-pyrido[4,3-d]pyrimidin-2-yl]-1H-indol-2-yl}methyl)acetamide;

({1-[4-(benzylamino)-5H,6H,7H,8H-pyrido[4,3-d]pyrimidin-2-yl]-1H-indol-2-yl}methyl)urea;

methyl N-({1-[4-(benzylamino)-5H,6H,7H,8H-pyrido[4,3-d]pyrimidin-2-yl]-1H-indol-2-yl}methyl)carbamate;

N-({1-[4-(benzylamino)-5H,6H,7H,8H-pyrido[4,3-d]pyrimidin-2-yl]-1H-indol-2-yl}methyl)methanesulfonamide;

1-[4-(benzylamino)-5H,6H,7H,8H-pyrido[4,3-d]pyrimidin-2-yl]-2,3-dihydro-1H-indol-2-one;

{1-[4-(benzylamino)-5H,6H,7H,8H-pyrido[4,3-d]pyrimidin-2-yl]-1H-indol-2-yl}methyl carbamate;

N-benzyl-2-(2,4-dimethyl-1H-indol-1-yl)-5H,6H,7H,8H-pyrido[4,3-d]pyrimidin-4-amine;
N-benzyl-2-(4-fluoro-2-methyl-1H-indol-1-yl)-5H,6H,7H,8H-pyrido[4,3-d]pyrimidin-4-amine;
1-[4-(benzylamino)-5H,6H,7H,8H-pyrido[4,3-d]pyrimidin-2-yl]-2-methyl-1H-indole-4-carbonitrile;
1-[4-(benzylamino)-5H,6H,7H,8H-pyrido[4,3-d]pyrimidin-2-yl]-2-methyl-1H-indole-6-carbonitrile;
N-benzyl-2-(4-methoxy-2-methyl-1H-indol-1-yl)-5H,6H,7H,8H-pyrido[4,3-d]pyrimidin-4-amine;
N-benzyl-2-[2-(trifluoromethyl)-1H-indol-1-yl]-5H,6H,7H,8H-pyrido[4,3-d]pyrimidin-4-amine;
N-benzyl-6-methyl-2-(2-methyl-1H-indol-1-yl)-5H,6H,7H,8H-pyrido[4,3-d]pyrimidin-4-amine;
N-benzyl-2-[2-(propan-2-yl)-1H-indol-1-yl]-5H,6H,7H,8H-pyrido[4,3-d]pyrimidin-4-amine;
N-benzyl-2-(2-ethyl-1H-indol-1-yl)-5H,6H,7H,8H-pyrido[4,3-d]pyrimidin-4-amine;
1-[4-(benzylamino)-5H,6H,7H,8H-pyrido[4,3-d]pyrimidin-2-yl]-1H-indole-2-carboxamide;
N-benzyl-2-(4-chloro-2-methyl-1H-indol-1-yl)-5H,6H,7H,8H-pyrido[4,3-d]pyrimidin-4-amine;
N-benzyl-6-ethyl-2-(2-methyl-1H-indol-1-yl)-5H,6H,7H,8H-pyrido[4,3-d]pyrimidin-4-amine;
N-benzyl-2-(2-methyl-1H-indol-1-yl)-6-(propan-2-yl)-5H,6H,7H,8H-pyrido[4,3-d]pyrimidin-4-amine;
N-benzyl-2-(2-methyl-1H-indol-1-yl)-6-propyl-5H,6H,7H,8H-pyrido[4,3-d]pyrimidin-4-amine;
1-[4-(benzylamino)-5H,6H,7H,8H-pyrido[4,3-d]pyrimidin-2-yl]-2-methyl-1H-indole-4-carboxamide;
1-[4-(benzylamino)-5H,6H,7H,8H-pyrido[4,3-d]pyrimidin-2-yl]-2-methoxy-1H-indole-4-carbonitrile;
4-(benzylamino)-2-(2-methyl-1H-indol-1-yl)-5H,6H,7H,8H-pyrido[4,3-d]pyrimidin-6-ol;
1-[4-(benzylamino)-6-methyl-5H,6H,7H,8H-pyrido[4,3-d]pyrimidin-2-yl]-2-methyl-1H-indole-4-carbonitrile;
N-benzyl-2-[2-methyl-4-(trifluoromethyl)-1H-indol-1-yl]-5H,6H,7H,8H-pyrido[4,3-d]pyrimidin-4-amine;
N-benzyl-2-(2-chloro-1H-indol-1-yl)-5H,6H,7H,8H-pyrido[4,3-d]pyrimidin-4-amine;
1-[4-(benzylamino)-6-ethyl-5H,6H,7H,8H-pyrido[4,3-d]pyrimidin-2-yl]-2-methyl-1H-indole-4-carbonitrile;
1-[4-(benzylamino)-2-(2-methyl-1H-indol-1-yl)-5H,6H,7H,8H-pyrido[4,3-d]pyrimidin-6-yl]prop-2-yn-1-one;
1-[4-(benzylamino)-2-(2-methyl-1H-indol-1-yl)-5H,6H,7H,8H-pyrido[4,3-d]pyrimidin-6-yl]prop-2-en-1-one;
4-(benzylamino)-2-(2-methyl-1H-indol-1-yl)-5H,6H,7H,8H-pyrido[4,3-d]pyrimidine-6-carbaldehyde;
N-{1-[4-(benzylamino)-5H,6H,7H,8H-pyrido[4,3-d]pyrimidin-2-yl]-2-methyl-1H-indol-4-yl}acetamide;
1-[4-(benzylamino)-5H,6H,7H,8H-pyrido[4,3-d]pyrimidin-2-yl]-N,2-dimethyl-1H-indole-4-carboxamide;
1-[4-(benzylamino)-5H,6H,7H,8H-pyrido[4,3-d]pyrimidin-2-yl]-N,N,2-trimethyl-1H-indole-4-carboxamide;
1-[4-(benzylamino)-5H,6H,7H,8H-pyrido[4,3-d]pyrimidin-2-yl]-2-methyl-N-(propan-2-yl)-1H-indole-4-carboxamide;
1-[4-(benzylamino)-5H,6H,7H,8H-pyrido[4,3-d]pyrimidin-2-yl]-N-(butan-2-yl)-2-methyl-1H-indole-4-carboxamide;
1-[4-(benzylamino)-5H,6H,7H,8H-pyrido[4,3-d]pyrimidin-2-yl]-1H-indole-4-carboxamide;
1-[4-(benzylamino)-5H,6H,7H,8H-pyrido[4,3-d]pyrimidin-2-yl]-2-methyl-2,3-dihydro-1H-indole-4-carboxamide;
1-[4-(benzylamino)-5H,6H,7H,8H-pyrido[4,3-d]pyrimidin-2-yl]-2-methyl-2,3-dihydro-1H-indole-4-carbonitrile;
1-[6-(2-aminoacetyl)-4-(benzylamino)-5H,6H,7H,8H-pyrido[4,3-d]pyrimidin-2-yl]-2-methyl-1H-indole-4-carbonitrile;
1-[4-(benzylamino)-6-(2-methoxyacetyl)-5H,6H,7H,8H-pyrido[4,3-d]pyrimidin-2-yl]-2-methyl-1H-indole-4-carbonitrile;
1-[4-(benzylamino)-5H,6H,7H,8H-pyrido[4,3-d]pyrimidin-2-yl]-2-methoxy-1H-indole-4-carboxamide;
1-[4-(benzylamino)-5H,6H,7H,8H-pyrido[4,3-d]pyrimidin-2-yl]-2-methyl-1H-indole-4-sulfonamide;
1-[4-(benzylamino)-5H,6H,7H,8H-pyrido[4,3-d]pyrimidin-2-yl]-2-methyl-1H-indole-4-carboxylic acid;
N-benzyl-2-(4-methanesulfonyl-2-methyl-1H-indol-1-yl)-5H,6H,7H,8H-pyrido[4,3-d]pyrimidin-4-amine;
1-[4-(benzylamino)-5H,6H,7H,8H-pyrido[4,3-d]pyrimidin-2-yl]-2-(2-methoxyethoxy)-1H-indole-4-carboxamide;
N-benzyl-2-(2-methyl-1H-indol-1-yl)-5H,6H,7H,8H-pyrido[3,4-d]pyrimidin-4-amine;
tert-butyl 4-(benzylamino)-2-(2-methyl-1H-indol-1-yl)-5H,6H,7H,8H-pyrido[3,4-d]pyrimidine-7-carboxylate;
1-[4-(benzylamino)-2-(2-methyl-1H-indol-1-yl)-5H,6H,7H,8H-pyrido[3,4-d]pyrimidin-7-yl]ethan-1-one;
tert-butyl 4-(benzylamino)-2-(2-methoxy-1H-indol-1-yl)-8-oxo-5H,6H,7H,8H-pyrido[3,4-d]pyrimidine-7-carboxylate;
2-[2-(aminomethyl)-1H-indol-1-yl]-N-benzyl-5H,6H,7H,8H-pyrido[3,4-d]pyrimidin-4-amine;
N-benzyl-2-(2-methoxy-1H-indol-1-yl)-5H,6H,7H,8H-pyrido[3,4-d]pyrimidin-4-amine;
1-{2-[2-(aminomethyl)-1H-indol-1-yl]-4-(benzylamino)-5H,6H,7H,8H-pyrido[3,4-d]pyrimidin-7-yl}ethan-1-one;
2-[2-(aminomethyl)-1H-indol-1-yl]-N-benzyl-7-ethyl-5H,6H,7H,8H-pyrido[3,4-d]pyrimidin-4-amine;
methyl 2-[2-(aminomethyl)-1H-indol-1-yl]-4-(benzylamino)-5H,6H,7H,8H-pyrido[3,4-d]pyrimidine-7-carboxylate;
N-benzyl-2-(2-methyl-1H-indol-1-yl)-5H,6H,7H,8H-pyrido[3,4-d]pyrimidin-4-amine;
N-benzyl-2-(2-methyl-1H-indol-1-yl)-5H,6H,7H-pyrrolo[3,4-d]pyrimidin-4-amine;
1-[4-(benzylamino)-2-(2-methyl-1H-indol-1-yl)-5H,6H,7H-pyrrolo[3,4-d]pyrimidin-6-yl]ethan-1-one.

The following compounds are further examples of formula I other than those already synthesized that are also preferred species which can be prepared by the methodology described herein:
1-[4-(benzylamino)-5,6,7,8-tetrahydroquinazolin-2-yl]-2-[(carbamoylamino)methyl]-1H-indole-4-carboxamide;
1-[4-(benzylamino)-5H,7H-furo[3,4-d]pyrimidin-2-yl]-2-methyl-1H-indole-4-carboxamide;
1-[4-(benzylamino)-5H,6H,7H-pyrrolo[3,4-d]pyrimidin-2-yl]-2-methyl-1H-indole-4-carboxamide;
1-[4-(benzylamino)-6-methyl-5H,6H,7H-pyrrolo[3,4-d]pyrimidin-2-yl]-2-methyl-1H-indole-4-carboxamide;
1-[6-acetyl-4-(benzylamino)-5H,6H,7H-pyrrolo[3,4-d]pyrimidin-2-yl]-2-methyl-1H-indole-4-carboxamide.

The especially preferred species of the fused pyrimidine compounds of Formula II include the following synthesized compounds. These compounds are identified by their IUPAC names. Except where specifically noted all of these species of the fused pyrimidine compounds have been synthesized.
1-[4-(benzylamino)-5,6,7,8-tetrahydroquinazolin-2-yl]-2-methyl-1H-1,3-benzodiazole-4-carbonitrile;
N-benzyl-2-(2-methoxy-1H-1,3-benzodiazol-1-yl)-5,6,7,8-tetrahydroquinazolin-4-amine;
2-[2-(aminomethyl)-1H-1,3-benzodiazol-1-yl]-N-benzyl-5,6,7,8-tetrahydroquinazolin-4-amine;

2-[2-(1-aminoethyl)-1H-1,3-benzodiazol-1-yl]-N-benzyl-5,6,7,8-tetrahydroquinazolin-4-amine;
N-benzyl-2-(2-methyl-1H-1,3-benzodiazol-1-yl)-5,6,7,8-tetrahydroquinazolin-4-amine;
{1-[4-(benzylamino)-5,6,7,8-tetrahydroquinazolin-2-yl]-1H-1,3-benzodiazol-2-yl}methanol;
N-benzyl-2-{2-[(dimethylamino)methyl]-1H-1,3-benzodiazol-1-yl}-5,6,7,8-tetrahydroquinazolin-4-amine;
N-benzyl-2-[2-(morpholin-4-ylmethyl)-1H-1,3-benzodiazol-1-yl]-5,6,7,8-tetrahydroquinazolin-4-amine;
N-({1-[4-(benzylamino)-5,6,7,8-tetrahydroquinazolin-2-yl]-1H-1,3-benzodiazol-2-yl}methyl)acetamide;
({1-[4-(benzylamino)-5,6,7,8-tetrahydroquinazolin-2-yl]-1H-1,3-benzodiazol-2-yl}methyl)urea;
N-benzyl-2-[2-(morpholin-4-yl)-1H-1,3-benzodiazol-1-yl]-5,6,7,8-tetrahydroquinazolin-4-amine;
1-[4-(benzylamino)-5,6,7,8-tetrahydroquinazolin-2-yl]-2-methyl-1H-1,3-benzodiazole-4-carbonitrile;
1-[4-(benzylamino)-5,6,7,8-tetrahydroquinazolin-2-yl]-2-methyl-1H-1,3-benzodiazole-4-carboxamide;
2-(aminomethyl)-1-[4-(benzylamino)-5,6,7,8-tetrahydroquinazolin-2-yl]-1H-1,3-benzodiazole-4-carbonitrile;
2-(aminomethyl)-1-[4-(benzylamino)-5,6,7,8-tetrahydroquinazolin-2-yl]-1H-1,3-benzodiazole-4-carboxamide;
1-[4-(benzylamino)-5,6,7,8-tetrahydroquinazolin-2-yl]-2-methoxy-1H-1,3-benzodiazole-4-carboxamide;
1-[4-(benzylamino)-5,6,7,8-tetrahydroquinazolin-2-yl]-2-methoxy-1H-1,3-benzodiazole-4-carboxylic acid;
N-benzyl-2-(2-ethoxy-1H-1,3-benzodiazol-1-yl)-5H,6H,7H,8H-pyrido[4,3-d]pyrimidin-4-amine;
N-benzyl-2-(2-methoxy-1H-1,3-benzodiazol-1-yl)-5H,6H,7H,8H-pyrido[4,3-d]pyrimidin-4-amine;
N-benzyl-2-(2-methyl-1H-1,3-benzodiazol-1-yl)-5H,6H,7H,8H-pyrido[4,3-d]pyrimidin-4-amine;
{1-[4-(benzylamino)-5H,6H,7H,8H-pyrido[4,3-d]pyrimidin-2-yl]-1H-1,3-benzodiazol-2-yl}methanol;
1-[4-(benzylamino)-5H,6H,7H,8H-pyrido[4,3-d]pyrimidin-2-yl]-1H-1,3-benzodiazol-2-yl carbamate;
{1-[4-(benzylamino)-5H,6H,7H,8H-pyrido[4,3-d]pyrimidin-2-yl]-1H-1,3-benzodiazol-2-yl}urea;
N-benzyl-2-[2-(trifluoromethyl)-1H-1,3-benzodiazol-1-yl]-5H,6H,7H,8H-pyrido[4,3-d]pyrimidin-4-amine;
1-[4-(benzylamino)-5H,6H,7H,8H-pyrido[4,3-d]pyrimidin-2-yl]-2-methyl-1H-1,3-benzodiazole-4-carbonitrile;
1-[4-(benzylamino)-5H,6H,7H,8H-pyrido[4,3-d]pyrimidin-2-yl]-2-methyl-1H-1,3-benzodiazole-4-carboxamide.

The following compounds are further examples of formula II other than those already synthesized that are also preferred species which can be prepared by the methodology described here in:
2-(aminomethyl)-1-[4-(benzylamino)-5H,7H,8H-pyrano[4,3-d]pyrimidin-2-yl]-1H-1,3-benzodiazole-4-carboxamide
2-amino-1-[4-(benzylamino)-5,6,7,8-tetrahydroquinazolin-2-yl]-1H-1,3-benzodiazole-4-carboxamide;
2-amino-1-[4-(benzylamino)-5H,6H,7H,8H-pyrido[4,3-d]pyrimidin-2-yl]-1H-1,3-benzodiazole-4-carboxamide;
2-amino-1-[4-(benzylamino)-5H,7H,8H-pyrano[4,3-d]pyrimidin-2-yl]-1H-1,3-benzodiazole-4-carboxamide.

The especially preferred species of the fused pyrimidine compounds of Formula III include the following synthesized compounds. These compounds are identified by their IUPAC names. Except where specifically noted all of these species of the fused pyrimidine compounds have been synthesized.
8-(aminomethyl)-N-benzyl-2-(2-methyl-1H-indol-1-yl)quinazolin-4-amine
N-benzyl-8-methoxy-2-(2-methyl-1H-indol-3-yl)quinazolin-4-amine;
N-benzyl-8-methoxy-2-(2-methyl-2,3-dihydro-1H-indol-1-yl)quinazolin-4-amine;
1-[4-(benzylamino)-8-methoxyquinazolin-2-yl]-2,3-dihydro-1H-indol-2-one;
N-benzyl-8-methoxy-2-(2-methyl-1H-indol-1-yl)quinazolin-4-amine;
N-benzyl-2-(2-ethyl-1H-indol-1-yl)-8-methoxyquinazolin-4-amine;
N-benzyl-8-methoxy-2-(2-methoxy-1H-indol-1-yl)quinazolin-4-amine;
2-[2-(aminomethyl)-1H-indol-1-yl]-N-benzyl-8-methoxyquinazolin-4-amine;
4-(benzylamino)-2-(2-methyl-1H-indol-1-yl)quinazoline-8-carboxamide;
4-(benzylamino)-2-(2-methyl-1H-indol-1-yl)quinazoline-8-carbonitrile;
2-[2-(aminomethyl)-1H-indol-1-yl]-N-benzyl-8-(2-methoxyethoxy)quinazolin-4-amine;
N-({1-[4-(benzylamino)-8-methoxyquinazolin-2-yl]-1H-indol-2-yl}methyl)acetamide;
N-({1-[4-(benzylamino)-8-methoxyquinazolin-2-yl]-1H-indol-2-yl}methyl)prop-2-enamide;
(2E)-3-{1-[4-(benzylamino)-8-methoxyquinazolin-2-yl]-1H-indol-2-yl}prop-2-enenitrile;
(2Z)-3-{1-[4-(benzylamino)-8-methoxyquinazolin-2-yl]-1H-indol-2-yl}-2-cyanoprop-2-enamide;
(2E)-3-{3-[({2-[2-(aminomethyl)-1H-indol-1-yl]-8-methoxyquinazolin-4-yl}amino)methyl]phenyl}prop-2-enenitrile;
(2Z)-3-{3-[({2-[2-(aminomethyl)-1H-indol-1-yl]-8-methoxyquinazolin-4-yl}amino)methyl]phenyl}-2-cyanoprop-2-enamide;
2-[2-(aminomethyl)-1H-indol-1-yl]-N-({3-[(E)-2-(benzenesulfonyl)ethenyl]phenyl}methyl)-8-methoxyquinazolin-4-amine;
2-[2-(aminomethyl)-1H-indol-1-yl]-N-({3-[(E)-2-methanesulfonylethenyl]phenyl}methyl)-8-methoxyquinazolin-4-amine;
N-benzyl-2-{2-[(E)-2-methanesulfonylethenyl]-1H-indol-1-yl}-8-methoxyquinazolin-4-amine;
2-{2-[(E)-2-(benzenesulfonyl)ethenyl]-1H-indol-1-yl}-N-benzyl-8-methoxyquinazolin-4-amine;
2-[2-(1-aminoethyl)-1H-indol-1-yl]-N-benzyl-8-methoxyquinazolin-4-amine;
2-[2-(1-aminoethyl)-1H-indol-1-yl]-N-benzyl-8-(2-methoxyethoxy)quinazolin-4-amine;
(2Z)-3-{1-[4-(benzylamino)-8-methoxyquinazolin-2-yl]-1H-indol-2-yl}prop-2-enenitrile;
3-[({2-[2-(aminomethyl)-1H-indol-1-yl]-8-methoxyquinazolin-4-yl}amino)methyl]benzonitrile;
N-benzyl-2-(2-methoxy-1H-indol-1-yl)-8-(2-methoxyethoxy)quinazolin-4-amine
{1-[4-(benzylamino)-8-(2-methoxyethoxy)quinazolin-2-yl]-1H-indol-2-yl}methanol;
N-benzyl-8-(2-methoxyethoxy)-2-(2-methyl-1H-indol-1-yl)quinazolin-4-amine;
N-benzyl-2-{2-[(dimethylamino)methyl]-1H-indol-1-yl}-8-(2-methoxyethoxy)quinazolin-4-amine;
N-benzyl-8-(2-methoxyethoxy)-2-[2-(morpholin-4-ylmethyl)-1H-indol-1-yl]quinazolin-4-amine;
N-({1-[4-(benzylamino)-8-(2-methoxyethoxy)quinazolin-2-yl]-1H-indol-2-yl}methyl)acetamide;
({1-[4-(benzylamino)-8-(2-methoxyethoxy)quinazolin-2-yl]-1H-indol-2-yl}methyl)urea;
methyl N-({1-[4-(benzylamino)-8-(2-methoxyethoxy)quinazolin-2-yl]-1H-indol-2-yl}methyl)carbamate;

N-({1-[4-(benzylamino)-8-(2-methoxyethoxy)quinazolin-2-yl]-1H-indol-2-yl}methyl)methanesulfonamide;
1-[4-(benzylamino)-8-(2-methoxyethoxy)quinazolin-2-yl]-2-methyl-1H-indole-4-carbonitrile;
1-[4-(benzylamino)-8-(2-methoxyethoxy)quinazolin-2-yl]-2-methoxy-1H-indole-4-carbonitrile;
1-[4-(benzylamino)-8-methoxy-quinazolin-2-yl]-2-methyl-indole-4-carboxamide.

The especially preferred species of the fused pyrimidine compounds of Formula IV-A include the following synthesized compounds. These compounds are identified by their IUPAC. Except where specifically noted all of these species of the fused pyrimidine compounds have been synthesized.
2-[2-(aminomethyl)-1H-1,3-benzodiazol-1-yl]-N-benzyl-8-(2-methoxyethoxy)quinazolin-4-amine;
2-[2-(1-aminoethyl)-1H-1,3-benzodiazol-1-yl]-N-benzyl-8-(2-N-benzyl-8-methoxy-2-(2-methyl-1H-1,3-benzodiazol-1-yl)quinazolin-4-amine;
N-benzyl-8-methoxy-2-(2-methoxy-1H-1,3-benzodiazol-1-yl)quinazolin-4-amine;
N-{1-[4-(benzylamino)-8-methoxyquinazolin-2-yl]-1H-1,3-benzodiazol-2-yl}acetamide;
N-[(4-fluorophenyl)methyl]-8-methoxy-2-(2-methoxy-1H-1,3-benzodiazol-1-yl)quinazolin-4-amine;
N-benzyl-2-(2-methoxy-1H-1,3-benzodiazol-1-yl)-8-(2-methoxyethoxy)quinazolin-4-amine;
N-benzyl-8-(2-methoxyethoxy)-2-(2-methyl-1H-1,3-benzodiazol-1-yl)quinazolin-4-amine;
{1-[4-(benzylamino)-8-(2-methoxyethoxy)quinazolin-2-yl]-1H-1,3-benzodiazol-2-yl}methanol;
2-(aminomethyl)-1-[4-(benzylamino)-8-(2-methoxyethoxy)quinazolin-2-yl]-1H-1,3-benzodiazole-4-carboxamide.

The especially preferred species of the fused pyrimidine compounds of Formula V include the following synthesized compounds. These compounds are identified by their IUPAC names. Except where specifically noted all of these species of the fused pyrimidine compounds have been synthesized.
1-[7-(benzylamino)thiazolo[5,4-d]pyrimidin-5-yl]-2-methyl-indole-4-carboxamide;
1-[6-(benzylamino)-9H-purin-2-yl]-2-methyl-indole-4-carboxamide;
1-[7-(benzylamino)oxazolo[5,4-d]pyrimidin-5-yl]-2-methyl-indole-4-carboxamide;
1-[7-(benzylamino)oxazolo[4,5-d]pyrimidin-5-yl]-2-methyl-indole-4-carboxamide;
1-[7-(benzylamino)thiazolo[4,5-d]pyrimidin-5-yl]-2-methyl-indole-4-carboxamide;
1-[4-(benzylamino)thieno[2,3-d]pyrimidin-2-yl]-2-methyl-indole-4-carboxamide.

The following compounds are further examples of formula V other than those already synthesized that are also preferred species which can be prepared by the methodology described here in: 1-[7-(benzylamino)-[1,3]thiazolo[5,4-d]pyrimidin-5-yl]-2-methyl-1H-indole-4-carboxamide;
1-[6-(benzylamino)-9H-purin-2-yl]-2-methyl-1H-indole-4-carboxamide;
1-[7-(benzylamino)-[1,3]oxazolo[5,4-d]pyrimidin-5-yl]-2-methyl-1H-indole-4-carboxamide;
1-[7-(benzylamino)-[1,3]oxazolo[4,5-d]pyrimidin-5-yl]-2-methyl-1H-indole-4-carboxamide;
1-[4-(benzylamino)thieno[2,3-d]pyrimidin-2-yl]-2-methyl-1H-indole-4-carboxamide.

The especially preferred species of the fused pyrimidine compounds of Formula V include the following synthesized compounds. These compounds are identified by their IUPAC names. Except where specifically noted all of these species of the fused pyrimidine compounds have been synthesized.
1-[7-(benzylamino)thiazolo[5,4-d]pyrimidin-5-yl]-2-methyl-indole-4-carboxamide;
1-[6-(benzylamino)-9H-purin-2-yl]-2-methyl-indole-4-carboxamide;
1-[7-(benzylamino)oxazolo[5,4-d]pyrimidin-5-yl]-2-methyl-indole-4-carboxamide;
1-[7-(benzylamino)oxazolo[4,5-d]pyrimidin-5-yl]-2-methyl-indole-4-carboxamide;
1-[7-(benzylamino)thiazolo[4,5-d]pyrimidin-5-yl]-2-methyl-indole-4-carboxamide;
1-[4-(benzylamino)thieno[2,3-d]pyrimidin-2-yl]-2-methyl-indole-4-carboxamide.

The especially preferred species of the fused pyrimidine compounds of Formula VI include the synthesized compounds of Table II-G. These compounds are identified by their IUPAC names. Except where specifically noted all of these species of the fused pyrimidine compounds have been synthesized.
N-benzyl-5-(2-methoxy-1H-1,3-benzodiazol-1-yl)-[1,3]thiazolo[5,4-d]pyrimidin-7-amine The especially preferred species of the fused pyrimidine compounds of Formula IV-B include the following synthesized compounds. These compounds are identified by their IUPAC names. Except where specifically noted all of these species of the fused pyrimidine compounds have been synthesized.
N-benzyl-8-methoxy-2-(2-methyl-1H-indol-3-yl)quinazolin-4-amine;
N-benzyl-2-(2,3-dihydro-1H-isoindol-1-yl)-8-methoxyquinazolin-4-amine;
3-[4-(benzylamino)-8-methoxyquinazolin-2-yl]-2,3-dihydro-1H-isoindol-1-one;
N-benzyl-2-(2,3-dihydro-1H-indol-3-yl)-8-methoxyquinazolin-4-amine;
N-benzyl-8-methoxy-2-(2-methyl-2,3-dihydro-1H-isoindol-1-yl)quinazolin-4-amine;
N-benzyl-8-methoxy-2-(2-methyl-1-benzofuran-3-yl)quinazolin-4-amine.

The especially preferred species of the fused pyrimidine compounds of Formula II-B include the following synthesized compounds. These compounds are identified by their IUPAC names. Except where specifically noted all of these species of the fused pyrimidine compounds have been synthesized.
N-benzyl-2-{2-methylimidazo[1,2-a]pyridin-3-yl}-5,6,7,8-tetrahydroquinazolin-4-amine;
N-benzyl-2-{2-methylpyrazolo[1,5-a]pyridin-3-yl}-5,6,7,8-tetrahydroquinazolin-4-amine;
N-benzyl-2-(2-methyl-1H-indol-3-yl)-5H,6H,7H,8H-pyrido[4,3-d]pyrimidin-4-amine;
N-benzyl-2-(2-methyl-1H-indol-3-yl)-5,6,7,8-tetrahydroquinazolin-4-amine.

The most especially preferred fused pyrimidine compounds of the invention include the following examples. These examples are also included in the foregoing synthesized compounds tables.
a) 1-[4-(benzylamino)-5,6,7,8-tetrahydroquinazolin-2-yl]-2-methyl-1H-indole-4-carbonitrile;
b) 1-[4-(benzylamino)-5,6,7,8-tetrahydroquinazolin-2-yl]-2-methyl-1H-indole-4-carboxamide;
c) 1-[4-(benzylamino)-5,6,7,8-tetrahydroquinazolin-2-yl]-2-methoxy-1H-indole-4-carboxamide;
d) 1-[4-(benzylamino)-5,6,7,8-tetrahydroquinazolin-2-yl]-2-ethoxy-1H-indole-4-carboxamide;
e) 1-[4-(benzylamino)-5,6,7,8-tetrahydroquinazolin-2-yl]-2-(2-methoxyethoxy)-1H-indole-4-carbonitrile;

f) 1-[4-(benzylamino)-5,6,7,8-tetrahydroquinazolin-2-yl]-2-cyclopropyl-1H-indole-4-carboxamide;
g) N-({1-[4-(benzylamino)-5,6,7,8-tetrahydroquinazolin-2-yl]-1H-indol-2-yl}methyl)prop-2-ynamide;
h) N-benzyl-2-[2-methyl-4-(1H-1,2,3,4-tetrazol-5-yl)-1H-indol-1-yl]-5,6,7,8-tetrahydroquinazolin-4-amine;
i) 1-[4-(benzylamino)-5H,7H,8H-pyrano[4,3-d]pyrimidin-2-yl]-2-methoxy-1H-indole-4-carboxamide;
j) 1-[4-(benzylamino)-5H,7H,8H-pyrano[4,3-d]pyrimidin-2-yl]-2-methyl-1H-indole-4-carboxamide;
k) 1-(4-{[(3-fluorophenyl)methyl]amino}-5H,7H,8H-pyrano[4,3-d]pyrimidin-2-yl)-2-methyl-1H-indole-4-carboxamide;
l) 1-[4-(benzylamino)-5H,7H,8H-pyrano[4,3-d]pyrimidin-2-yl]-2-methyl-1H-indole-4-carboxylic acid;
m) -benzyl-2-(2-methyl-1H-indol-1-yl)-5H,6H,7H,8H-pyrido[4,3-d]pyrimidin-4-amine;
n) 1-[4-(benzylamino)-5H,6H,7H,8H-pyrido[4,3-d]pyrimidin-2-yl]-2-methyl-1H-indole-4-carboxamide;
o) 1-[4-(benzylamino)-5H,6H,7H,8H-pyrido[4,3-d]pyrimidin-2-yl]-2-methyl-1H-indole-4-carboxylic acid;
p) 2-[4-(aminomethyl)-2-methyl-1H-indol-1-yl]-N-benzyl-5,6,7,8-tetrahydroquinazolin-4-amine;
q) 1-[4-(benzylamino)-2-(2-methyl-1H-indol-1-yl)-5H,6H,7H,8H-pyrido[3,4-d]pyrimidin-7-yl]prop-2-yn-1-one;
r) 1-[4-(benzylamino)-5,6,7,8-tetrahydroquinazolin-2-yl]-2-methyl-1H-indole-4-sulfonamide;
s) N-benzyl-2-(4-methanesulfonyl-2-methyl-1H-indol-1-yl)-5,6,7,8-tetrahydroquinazolin-4-amine;
t) 1-[4-(benzylamino)-5,6,7,8-tetrahydroquinazolin-2-yl]-N-methyl-2-methyl-1H-indole-4-carboxamide;
u) 1-[4-(benzylamino)-5H,7H,8H-pyrano[4,3-d]pyrimidin-2-yl]-N,2-dimethyl-1H-indole-4-carboxamide;
v) 1-[4-(benzylamino)-5,6,7,8-tetrahydroquinazolin-2-yl]-2-methoxy-1H-1,3-benzodiazole-4-carboxylic acid;
w) 1-[4-(benzylamino)-5,6,7,8-tetrahydroquinazolin-2-yl]-2-methoxy-1H-1,3-benzodiazole-4-carboxamide;
x) N-benzyl-2-(2-methoxy-1H-1,3-benzodiazol-1-yl)-5,6,7,8-tetrahydroquinazolin-4-amine.

Synthetic Preparation

The novel compounds of the present invention can be prepared in a variety of ways known to one skilled in the art of organic synthesis. The compounds of the present invention can be synthesized using the methods as hereinafter described below, together with synthetic methods known in the art of synthetic organic chemistry or variations thereon as appreciated by those skilled in the art.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene and Wuts, *Protective Groups in Organic Synthesis,* 44th. Ed., Wiley & Sons, 2006, as well as in Jerry March, *Advanced Organic Chemistry,* 4$^{th}$ edition, John Wiley & Sons, publisher, New York, 1992 which are incorporated herein by reference in their entirety.

The fused pyrimidine scaffolds can be prepared by the literature methods cited in the following text. The following schemes depict established, known syntheses of these scaffolds.

The -G-Het moiety and the amine substituents of the fused pyrimidine scaffolds can be synthesized and attached to these scaffolds by the literature methods cited in the following text. The following schemes depict the known techniques for accomplishing this joinder.

General Synthetic Schemes for Fused Pyrmidines

Compounds of the present invention can be synthesized using the following methods. General reaction conditions are given and reaction products can be purified by general known methods including crystallization, silica gel chromatography using various organic solvents such as hexane, cyclohexane, ethyl acetate, methanol and the like, preparative high pressure liquid chromatography or preparative reverse phase high pressure liquid chromatography.

A cyclic ketoester of the general structure 1 can be reacted with urea in the presence of acid such as HCl in a solvent such as ethanol at refluxing temperature for 6 to 48 hours to give the pyrimidine dione of the general structure 2. The fused pyrimidine of the general structure 2 can be produced by reaction of the cyclic ketoester of the general formula 1 with urea in the presence of a base such as sodium methoxide in a solvent such as methanol at refluxing temperatures for 6 to 48 hours. A third method used to produce fused pyrimidines of the general structure 2 is to react a cyclic or heterocyclic ketone with of structure 3 with chlorocarbonyl isocyanate (4) in at temperatures from 60 to 130 C for 2-4 hours. The resulting intermediate is then isolated and treated with ammonium hydroxide at 80 C to give the desired compound 2.

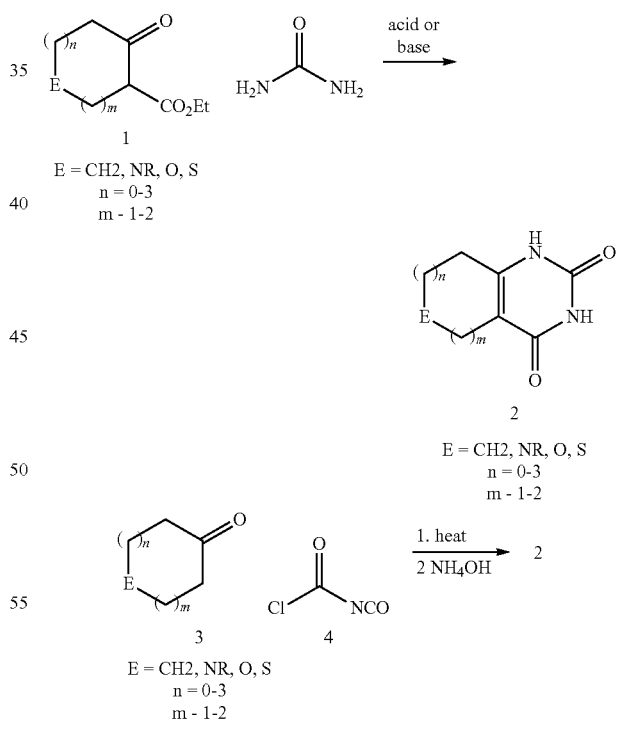

Pyrmidinedione 2 can be reacted with an excess of POCl$_3$ at reflux for 3-12 hours optionally in the presence of a teriary amine such as triethyl amine, diisopropyl ethyl amine or dimethyl analine to give the fused dicholorpyrimidine of the general structure 5. Other chlorinating agents such as thionyl chloride or PCL$_5$ can be substituted for POCL$_3$.

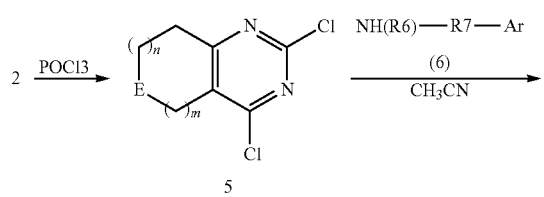

5

E = CH2, NR, O, S
n = 0-3
m - 1-2

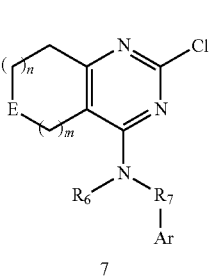

7

E = CH2, NR, O, S
n = 0-3
m - 1-2

Fused dichloropyrimidines of the general structure 5 can be reacted with excess amounts of various substituted amines of the general structure 6 at temperatures ranging from room temperature to reflux in a solvent such as acetonitrile or dimethylformamide to give 4-amino-2-chloro fused pyrimidines of the general structure 7.

Target compounds of the general structure 9 where can be prepared by reacting the fused 2-chloropyrimidine 7 with heterocyclic of the general structure 8 in the presence of an organometallic catalyst such as Pd(dba)₂ with or without an added phosphine ligand such as x-phos, triphenyl phosphine or the like in a solvent such as THF or dioxane at temperatures ranging from room temperature to reflux.

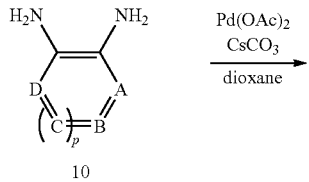

8

Y, Z = CR, N
A, B, C, D =
CX, CR, N, O, S
R = C1-C6 alkyl or
substituted C1-C6 alkyl
X = halogen, alkoxy, or nitrile
p = 0, 1

-continued

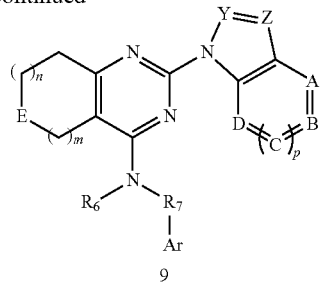

9

E = CH2, NR, O, S
A, B, C, D =
CR, CX, N, O, S
Y, Z = CR', N
R = H, C1-C6 alkyl
or C1-C6 substituted alkyl
R' = H, alkoxy, C1-C6 alkyl
or C1-C6 substituted alkyl
X = halogen, alkoxy, or nitrile
m - 1-2
n = 0-3
p = 0, 1

In some cases compounds of the general structure 9 where Y is CR and Z is N can be prepared by reacting a diamino aryl or heteroaryl compound of the general structure 10 with a fused 2-chloropyrimidine 7 in the presence of a catalytic amount of a organometallic catalyst such as Pd(OAc)₂ and a base such as cesium carbonate in a solvent such as THF or dioxane at a temperature between room temperature and reflux to give the diamines of the general structure 11.

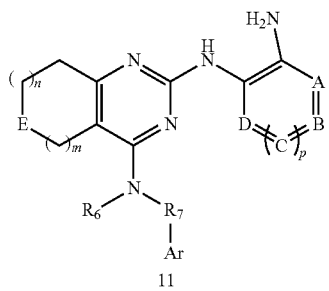

10

A, B, C, D =
CX, CR, N, O, S
R = H, C1-C6 alkyl or
substituted C1-C6 alkyl
X = halogen, alkoxy, or nitrile
p = 0, 1

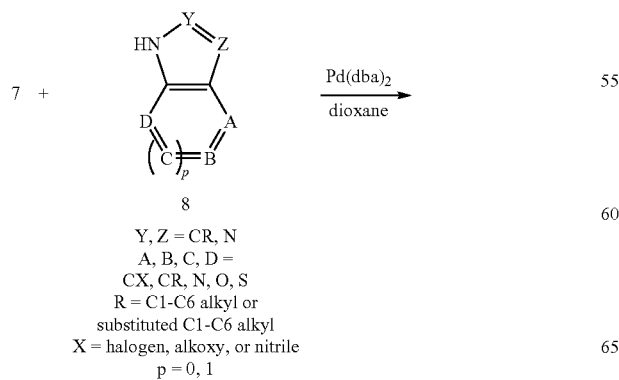

11

E = CH2, NR, O, S
A, B, C, D =
CX, CR, N, O, S
R = H, C1-C6 alkyl or
substituted C1-C6 alkyl
X = halogen, alkoxy, or nitrile
m - 1-2
n = 0-3
p = 0, 1

The diamine 11 can be converted to the general structure 12 by reacting it with cyanogen bromide in the presence of a solvent such as acetonitrile to give a general structure such as 12. Alternatively compounds of the general structure 7 can be reacted with tetramethoxy methane in the presence of acetic acid at reflux to give the compounds of the general structure 13. In other cases compounds of the general structure 7 can be prepared by heating diamines of the general structure of 11 with carboxylic acids to obtain compounds of the general structure 14.

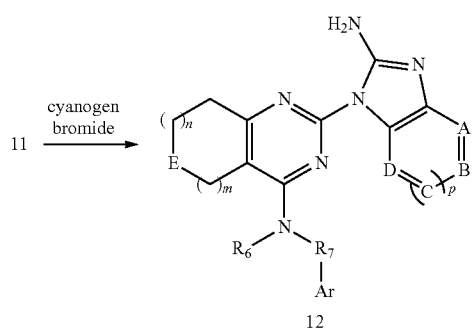

12
E = CH2, NR, O, S
A, B, C, D =
CX, CR, N, O, S
R = H, C1-C6 alkyl or
substituted C1-C6 alkyl
X = halogen, alkoxy, or nitrile
m - 1-2
n = 0-3
p = 0, 1

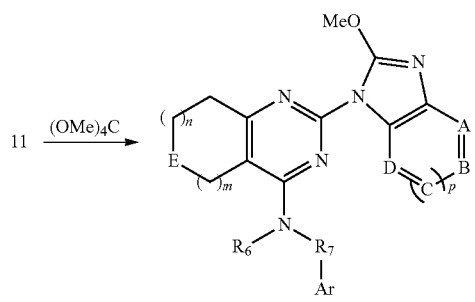

13
E = CH2, NR, O, S
A, B, C, D =
CX, CR, N, O, S
R = H, C1-C6 alkyl or
substituted C1-C6 alkyl
X = halogen, alkoxy, or nitrile
m - 1-2
n = 0-3
p = 0, 1

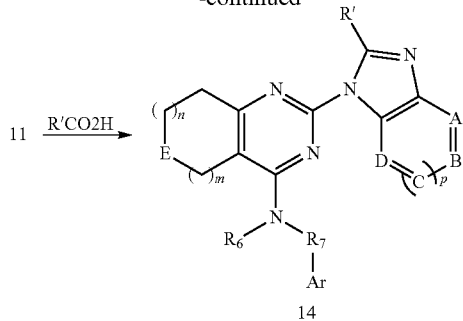

14
E = CH2, NR, O, S
A, B, C, D =
CX, CR, N, O, S
R, R' = H, C1-C6 alkyl or
substituted C1-C6 alkyl
X = halogen, alkoxy, or nitrile
m - 1-2
n = 0-3
p = 0, 1

Target compounds of the general structure 16 can be prepared by reacting boronic esters of the general structure 15 with fused chloropyrimidines of the general structure 7 in the presence of a of an organometallic catalyst such as Pd(dba)$_2$ and a phosphine ligand like x-phos.

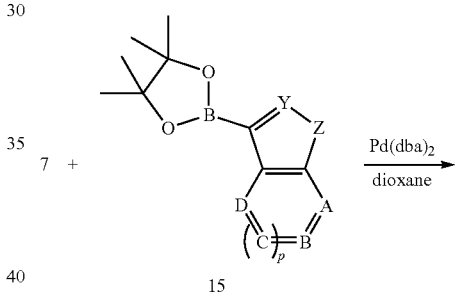

15
Y = CR, N; Z = NR, O, S
A, B, C, D =
CX, CR, N, O, S
R = H, C1-C6 alkyl or
substituted C1-C6 alkyl
X = halogen, alkoxy, or nitrile
p = 0, 1

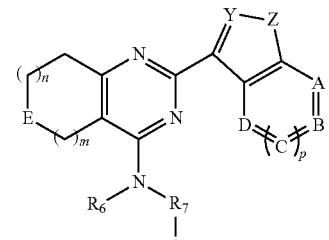

16
E = CH2, NR, O, S
Y = CR, N; Z = NR, O, S
A, B, C, D =
CX, CR, N, O, S
R = H, C1-C6 alkyl or
substituted C1-C6 alkyl
X = halogen, alkoxy, or nitrile
m - 1-2
n = 0-3
p = 0, 1

Boronate esters of the general structure 15 can be prepared from their corresponding bromides 17 by reacting them with the diborane ester 18 in a solvent such as THF at temperatures ranging from 0 to 70° C.

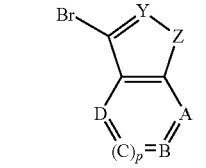
17
Y = CR, N;
Z = NR, O, S
A, B, C, D = CX, CR, N, O, S
R = H, C1-C6 alkyl or
    substituted C1-C6 alkyl
X = halogen, alkoxy, or nitrile
p = 0, 1

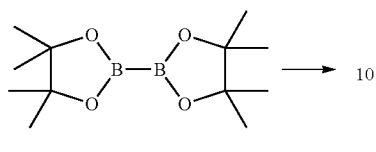
18

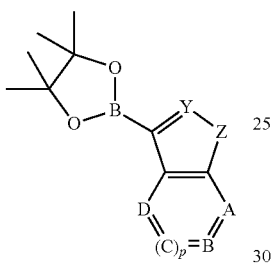
15
Y = CR, N;
Z = NR, O, S
A, B, C, D = CX, CR, N, O, S
R = H, C1-C6 alkyl or
    substituted C1-C6 alkyl
X = halogen, alkoxy, or nitrile
p = 0, 1

Fused dicholoropyrimidines of the general structure 19 prepared using literature methods (Heffron, T P. et al J. Med. Chem. 2011 54, 7815) can be reacted with excess amounts of various substituted amines of the general structure 6 at temperatures ranging from room temperature to reflux in a solvent such as acetonitrile or dimethylformamide to give 4-amino-2-chloro fused pyrimidines of the general structure 20. Compounds of the structure 20 can be further reacted with heterocyclic of the general structure 8 in the presence of an organometallic catalyst such as Pd(dba)₂ with or without an added phosphine ligand such as x-phos, triphenyl phosphine or the like in a solvent such as THF or dioxane at temperatures ranging from room temperature to reflux to give the target compound 21.

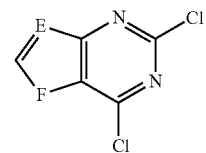
19
E = CR, N; F = NR, O, S
R = H, C1-C6 alkyl or C1-C6
    subtituted alkyl

6

-continued

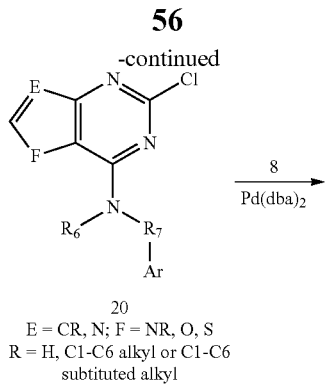
20
E = CR, N; F = NR, O, S
R = H, C1-C6 alkyl or C1-C6
    substituted alkyl

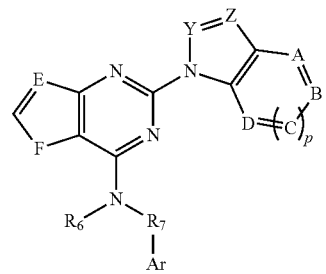
21
E = CH, N; F = NR, O, S
A, B, C, D = CR, CX, N, O, S
Y, Z = CR', N
R = H, C1-C6 alkyl or
    C1-C6 substituted alkyl
R' = H, alkoxy, C1-C6 alkyl or
    C1-C6 substituted alkyl
X = halogen, alkoxy, or nitrile
p = 0, 1

Alternatively compounds of the general structure 20 can be reacted with diamines of the general structure 10 to give diamine 22 using methods previously described for the synthesis of compound 11. Compound 22 can be converted to target compounds with the general structures 23, 24 and 25 using methodology similar to that used to prepare 12 13 and 14.

20 + 10 ⟶ 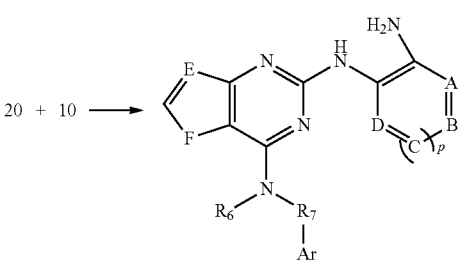
22
E = CH, N; F = NR, O, S
A, B, C, D =
    CX, CR, N, O, S
R = H, C1=C6 alkyl or
    substituted C1-C6 alkyl
X = halogen, alkoxy, or nitrile
p = 0, 1

23

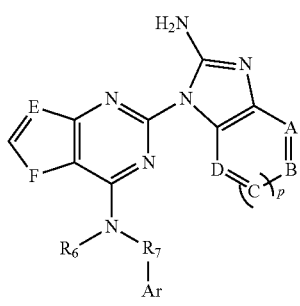

A, B, C, D =
CX, CR, N, O, S
E = CH, N; F = NR, O, S
R = H, C1-C6 alkyl or
C1-C6 subtituted alkyl
X = halogen, alkoxy, or nitrile
p = 0, 1

24

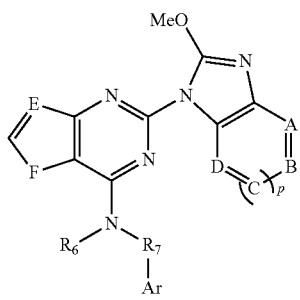

A, B, C, D =
CX, CR, N, O, S
E = CH, N; F = NR, O, S
R = H, C1-C6 alkyl or
C1-C6 subtituted alkyl
X = halogen, alkoxy, or nitrile
p = 0, 1

25

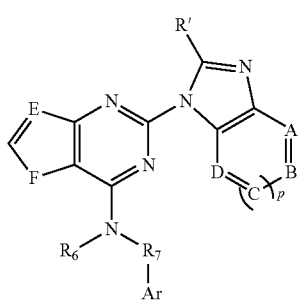

A, B, C, D =
CX, CR, N, O, S
E = CH, N; F = NR, O, S
R = H, C1-C6 alkyl or
C1-C6 subtituted alkyl
X = halogen, alkoxy, or nitrile
p = 0, 1

Target compounds of the general structure 26 can be prepared by reacting boronic esters of the general structure 15 with fused chloropyrimidines of the general structure 20 in the presence of a of an organometallic catalyst such as Pd(dba)$_2$ and a phosphine ligand like x-phos.

26

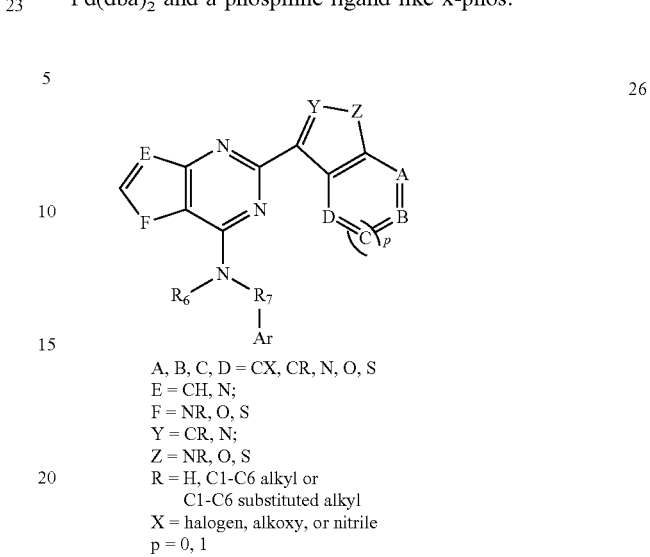

A, B, C, D = CX, CR, N, O, S
E = CH, N;
F = NR, O, S
Y = CR, N;
Z = NR, O, S
R = H, C1-C6 alkyl or
C1-C6 substituted alkyl
X = halogen, alkoxy, or nitrile
p = 0, 1

Fused dicholoropyrimidines of the general structure 27 prepared using literature methods (Hancox, Timothy Colin et al PCT Int. Appl., 2008152390) can be reacted with excess amounts of various substituted amines of the general structure 6 at temperatures ranging from room temperature to reflux in a solvent such as acetonitrile or dimethylformamide to give 4-amino-2-chloro fused pyrimidines of the general structure 28. Compounds of the structure 28 can be further reacted with heterocyclic of the general structure 8 in the presence of an organometallic catalyst such as Pd(dba)$_2$ with or without an added phosphine ligand such as x-phos, triphenyl phosphine or the like in a solvent such as THF or dioxane at temperatures ranging from room temperature to reflux to give the target compound 29.

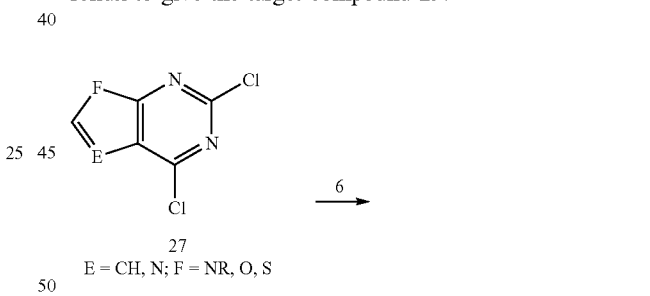

27
E = CH, N; F = NR, O, S

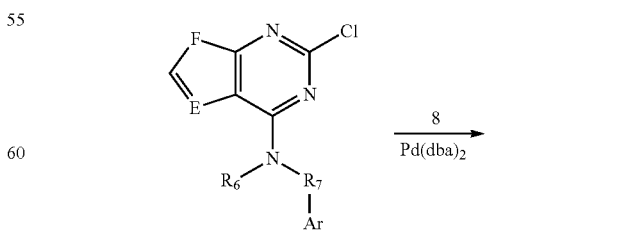

28
E = CH, N; F = NR, O, S

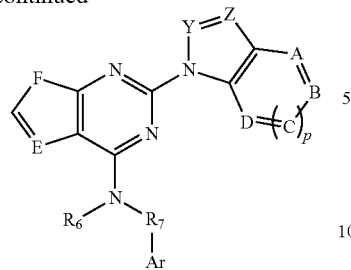

29
E = CH, N; F = NR, O, S
A, B, C, D = CR, CX, N, O, S
Y, Z = CR', N
R = H, C1-C6 alkyl or
   C1-C6 substituted alkyl
R' = H, alkoxy, C1-C6 alkyl or
   C1-C6 substituted alkyl
X = halogen, alkoxy, or nitrile
p = 0, 1

Alternatively compounds of the general structure 28 can be reacted with diamines of the general structure 10 to give diamine 30 using methods previously described for the synthesis of compound 11. Compound 30 can be converted to target compounds with the general structures 31, 32 and 33 using methodology similar to that used to prepare 12, 13 and 14.

28 + 10 ⟶ 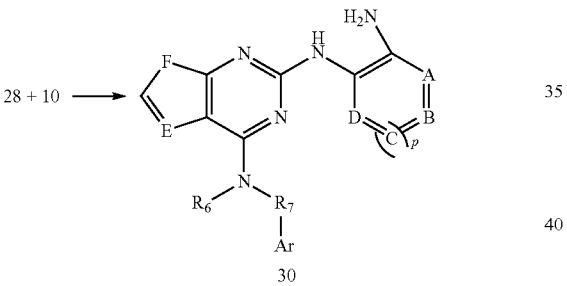

30
E = CR, N;
F = NR, O, S
A, B, C, D = CX, CR, N, O, S
R = H, C1-C6 alkyl or
   substituted C1-C6 alkyl
X = halogen, alkoxy, or nitrile
p = 0, 1

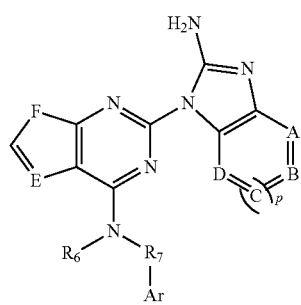

31
E = CR, N;
F = NR, O, S
A, B, C, D = CX, CR, N, O, S
R = H, C1-C6 alkyl or
   substituted C1-C6 alkyl
X = halogen, alkoxy, or nitrile
p = 0, 1

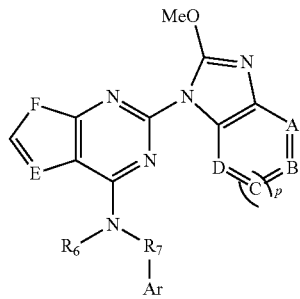

32
E = CR, N;
F = NR, O, S
A, B, C, D = CX, CR, N, O, S
R = H, C1-C6 alkyl or
   substituted C1-C6 alkyl
X = halogen, alkoxy, or nitrile
p = 0, 1

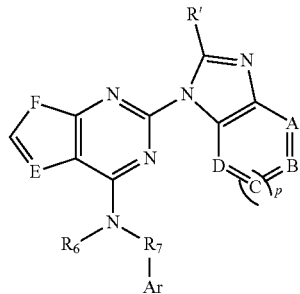

33
E = CR, N;
F = NR, O, S
A, B, C, D = CX, CR, N, O, S
R = H, C1-C6 alkyl or
   substituted C1-C6 alkyl
X = halogen, alkoxy, or nitrile
p = 0, 1

Target compounds of the general structure 34 can be prepared by reacting boronic esters of the general structure 15 with fused chloropyrimidines of the general structure 28 in the presence of a of an organometallic catalyst such as Pd(dba)$_2$ and a phosphine ligand like x-phos.

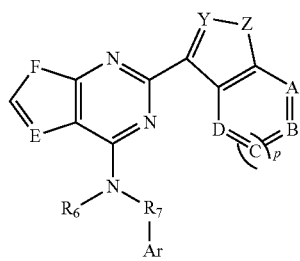

34
E = CR, N;
F = NR, O, S
Y = CR, N;
Z = NR, O, S
A, B, C, D = CX, CR, N, O, S
R = H, C1-C6 alkyl or
   substituted C1-C6 alkyl
X = halogen, alkoxy, or nitrile
p = 0, 1

Compounds of the general structure 35 could be prepared from intermediates and methodology analogous to those used in the preparation of 27 and as outlined in Baraldi P G et al. Biog. Med. Chem. Lett. 2012, 20, 1046-1059. Compounds of the general structure 35 could be used to prepare compounds of the general structures 36-40 using the general methodology previously described.

35

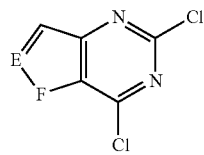

E = CR, N; F = NR, O, S
A, B, C, D =
CH, CR, N, O, S
R = H, C1-C6 alkyl or
C1-C6 substituted alkyl
p = 0, 1

36

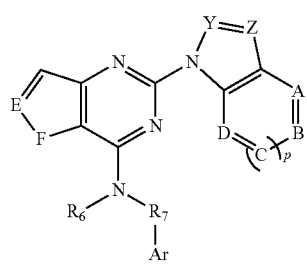

E = CR, N; F = NR, O, S
A, B, C, D =
CR, CX, N, O, S
Y, Z = CR', N
R = H, C1-C6 alkyl
or C1-C6 substituted alkyl
R' = H, alkoxy, C1-C6 alkyl
or C1-C6 substituted alkyl
X = halogen, alkoxy, or nitrile
p = 0,1

37

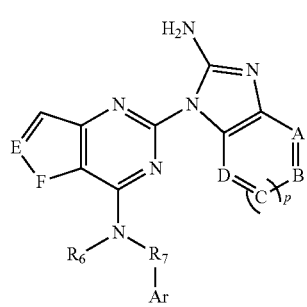

E = CR, N; F = NR, O, S
A, B, C, D =
CX, CR, N, O, S
R = H, C1-C6 alkyl or
substituted C1-C6 alkyl
X = halogen, alkoxy, or nitrile
p = 0, 1

38

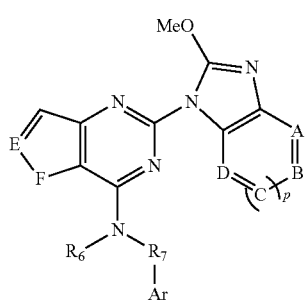

E = CR, N; F = NR, O, S
A, B, C, D =
CX, CR, N, O, S
R = H, C1-C6 alkyl or
substituted C1-C6 alkyl
X = halogen, alkoxy, or nitrile
p = 0, 1

39

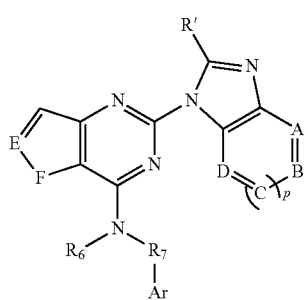

E = CR, N; F = NR, O, S
A, B, C, D =
CX, CR, N, O, S
R = H, C1-C6 alkyl or
substituted C1-C6 alkyl
X = halogen, alkoxy, or nitrile
p = 0, 1

40

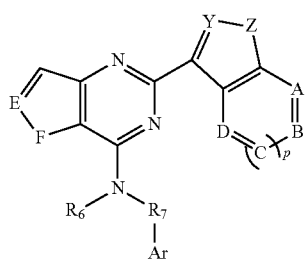

E = CR, N; F = NR, O, S
Y = CR, N;, Z = NR, O, S
A, B, C, D =
CX, CR, N, O, S
R = H, C1-C6 alkyl or
substituted C1-C6 alkyl
X = halogen, alkoxy, or nitrile
p = 0, 1

Compounds of the general structure 41 could be prepared from intermediates and methodology analogous to those used in the preparation of 27 and as outlined in Ali, Amjad et al. J. Med. Chem. 2003 46 1824-1830. Compounds of the general structure 41 could be used to prepare compounds of the general structures 42-46 using the general methodology previously described.

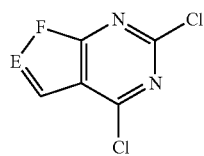

E = CH, N;
F = NR, O, S
R = H, C1-C6 alkyl or
    C1-C6 substituted alkyl

41

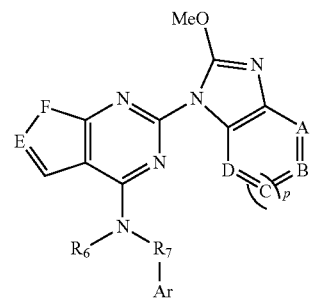

E = CR, N;
F = NR, O, S
A, B, C, D = CR, CX, N, O, S
Y, Z = CR, N
R = H, C1-C6 alkyl or
    C1-C6 substituted alkyl
X = halogen, alkoxy, or nitrile
p = 0, 1

44

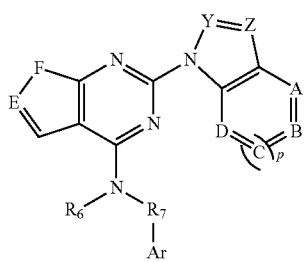

E = CR, N;
F = NR, O, S
A, B, C, D = CR, CX, N, O, S
Y, Z = CR', N
R = H, C1-C6 alkyl or
    C1-C6 substituted alkyl
R' = H, alkoxy, C1-C6 alkyl or
    C1-C6 substituted alkyl
X = halogen, alkoxy, or nitrile
p = 0, 1

42

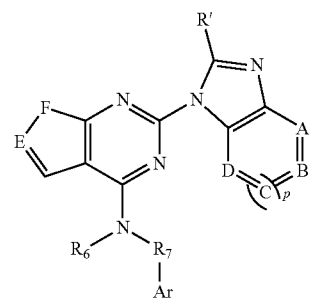

E = CR, N;
F = NR, O, S
A, B, C, D = CR, CX, N, O, S
Y, Z = CR, N
R = H, C1-C6 alkyl or
    C1-C6 substituted alkyl
X = halogen, alkoxy, or nitrile
p = 0, 1

45

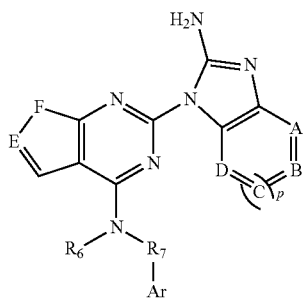

E = CR, N;
F = NR, O, S
A, B, C, D = CR, CX, N, O, S
Y, Z = CR, N
R = H, C1-C6 alkyl or
    C1-C6 substituted alkyl
X = halogen, alkoxy, or nitrile
p = 0, 1

43

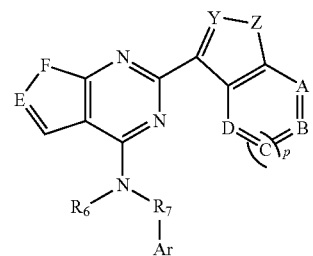

E = CR, N;
F = NR, O, S
A, B, C, D = CR, CX, N, O, S
Y = CR, N;
Z = NR, O, S
R = H, C1-C6 alkyl or
    C1-C6 substituted alkyl
X = halogen, alkoxy, or nitrile
p = 0, 1

46

Compounds of the general structure 47 can be prepared as outlined in Bergeron P et al. PCT Int. Appl., 2010151601 and Asano, S. PCT Int. Appl., 2011152485. Compounds of the general structure 46 can be used to prepare the target compounds 47-51 utilizing the methodology disclosed above.

53

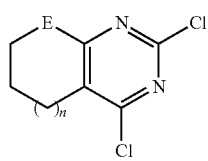

E = NR, O
R = H, C1-C6 alkyl or
C1-C6 substituted alkyl
n = 0-3

54

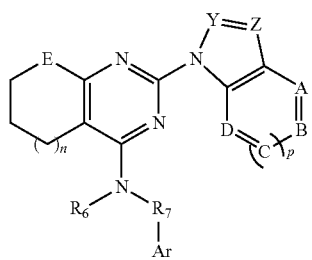

E = NR, O;
A, B, C, D =
CR, CX, N, O, S
Y, Z = CR', N
R = H, C1-C6 alkyl
or C1-C6 substituted alkyl
R' = H, alkoxy, C1-C6 alkyl
or C1-C6 substituted alkyl
X = halogen, alkoxy, or nitrile
n = 0-3
p = 0, 1

49

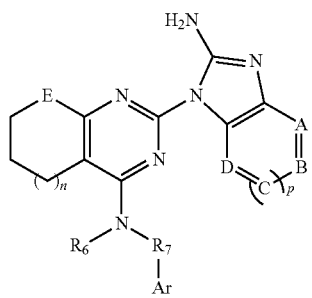

E = NR, O
A, B, C, D =
CR, CX, N, O, S
Y, Z = CR, N
R = H, C1-C6 alkyl
or C1-C6 substituted alkyl
X = halogen, alkoxy, or nitrile
n = 0-3
p = 0, 1

50

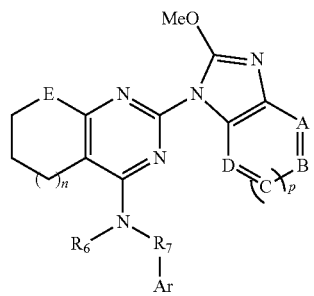

E = NR, O
A, B, C, D =
CR, CX, N, O, S
Y, Z = CR, N
R = H, C1-C6 alkyl
or C1-C6 substituted alkyl
X = halogen, alkoxy, or nitrile
n = 0-3
p = 0, 1

51

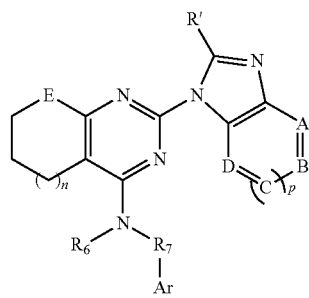

E = NR, O
A, B, C, D =
CR, CX, N, O, S
Y, Z = CR, N
R = H, C1-C6 alkyl
or C1-C6 substituted alkyl
X = halogen, alkoxy, or nitrile
n = 0-3
p = 0, 1

52

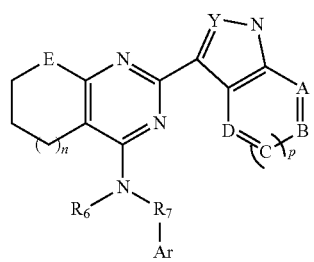

E = NR, O
A, B, C, D =
CR, CX, N, O, S
Y = CR, N; Z = NR, O, S
R = H, C1-C6 alkyl
or C1-C6 substituted alkyl
X = halogen, alkoxy, or nitrile
p = 0, 1

Compounds of the general structure 53 can be prepared using methodology in Srinivasan, A. et. al. J. of Org. Chem. 1982, 47, 4391-6. Compounds of the general structure 53 can be used to prepare the target compounds 54-58 utilizing the methodology disclosed above.

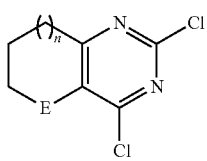

53

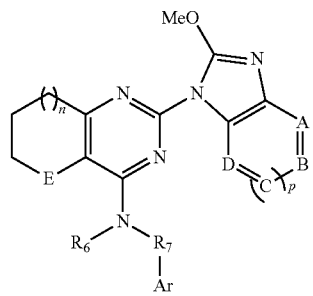

E = NR, O
R = H, C1-C6 alkyl or
C1-C6 substituted alkyl
n = 0-3

-continued

56

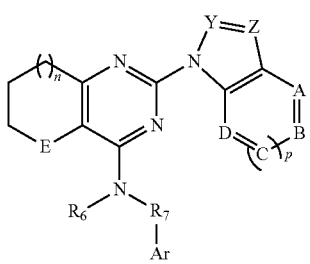

E = NR, O;
A, B, C, D =
CR, CX, N, O, S
Y, Z = CR', N
R = H, C1-C6 alkyl
or C1-C6 substituted alkyl
R' = H, alkoxy, C1-C6 alkyl
or C1-C6 substituted alkyl
X = halogen, alkoxy, or nitrile
n = 0-3
p = 0, 1

54

E = NR, O
A, B, C, D =
CR, CX, N, O, S
Y, Z = CR, N
R = H, C1-C6 alkyl
or C1-C6 substituted alkyl
X = halogen, alkoxy, or nitrile
n = 0-3
p = 0, 1

57

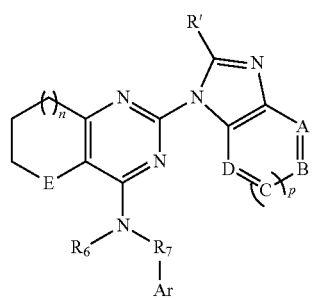

E = NR, O
A, B, C, D =
CR, CX, N, O, S
Y, Z = CR, N
R = H, C1-C6 alkyl
or C1-C6 substituted alkyl
X = halogen, alkoxy, or nitrile
n = 0-3
p = 0, 1

58

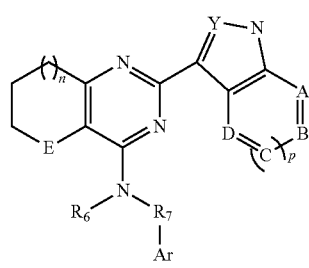

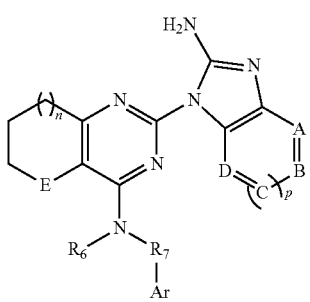

E = NR, O
A, B, C, D =
CR, CX, N, O, S
Y, Z = CR, N
R = H, C1-C6 alkyl
or C1-C6 substituted alkyl
X = halogen, alkoxy, or nitrile
n = 0-3
p = 0, 1

55

E = NR, O;
A, B, C, D =
CR, CX, N, O, S
Y = CR, N; Z = NR, O, S
R = H, C1-C6 alkyl
or C1-C6 substituted alkyl
X = halogen, alkoxy, or nitrile
n = 0-3
p = 0, 1

Compounds of the general structure 59 can be prepared by the methodology outlined for preparing compounds of the general structure 5 and can be converted to compounds of the general structure 60 using an oxidizing agent such as sodium periodate in the presence of a catalytic amount of ruthenium tetroxide. Compounds of the general structure 60 can be converted to compounds of the general structure 61 using methodology outlined in the conversion of compounds 7 to compounds 9. The protecting group can be removed at the appropriate time during the synthetic sequence using HCl in dioxane when the protecting group is Boc, $H_2$ and palladium on carbon if the protecting group is CBZ and ceric ammonium nitrate if the protecting group is 4-methoxy-CBZ.

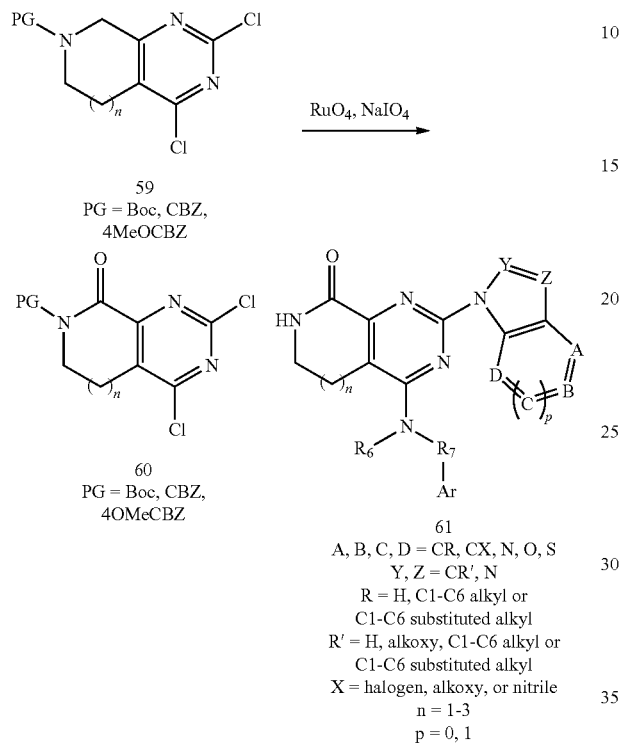

59
PG = Boc, CBZ, 4MeOCBZ

60
PG = Boc, CBZ, 4OMeCBZ

61
A, B, C, D = CR, CX, N, O, S
Y, Z = CR', N
R = H, C1-C6 alkyl or
C1-C6 substituted alkyl
R' = H, alkoxy, C1-C6 alkyl or
C1-C6 substituted alkyl
X = halogen, alkoxy, or nitrile
n = 1-3
p = 0, 1

Compounds of the general structure 60 can be converted to compounds of the general structure 61 using methodology outlined in the conversion of compounds 7 to compounds 11-13. The protecting group can be removed at the appropriate time during the synthetic sequence using HCl in dioxane when the protecting group is Boc, $H_2$ and palladium on carbon if the protecting group is CBZ and ceric ammonium nitrate if the protecting group is 4-methoxy-CBZ.

62

A, B, C, D = CR, CX, N, O, S
Y, Z = CR, N
R = H, C1-C6 alkyl or
C1-C6 substituted alkyl
X = halogen, alkoxy, or nitrile
n = 1-3
p = 0, 1

63

A, B, C, D = CR, CX, N, O, S
Y, Z = CR, N
R = H, C1-C6 alkyl or
C1-C6 substituted alkyl
X = halogen, alkoxy, or nitrile
n = 1-3
p = 0, 1

64

A, B, C, D = CR, CX, N, O, S
Y, Z = CR, N
R = H, C1-C6 alkyl or
C1-C6 substituted alkyl
X = halogen, alkoxy, or nitrile
n = 1-3
p = 0, 1

Compounds of the general structure 60 can be converted to compounds of the general structure 65 using methodology outlined in the conversion of compounds 7 to compounds 16. The protecting group can be removed at the appropriate time during the synthetic sequence using HCl in dioxane when the protecting group is Boc, $H_2$ and palladium on carbon if the protecting group is CBZ and ceric ammonium nitrate if the protecting group is 4-methoxy-CBZ.

65

A, B, C, D = CR, CX, N, O, S
Y = CR, N;
Z = NR, O, S
R = H, C1-C6 alkyl or
C1-C6 substituted alkyl
X = halogen, alkoxy, or nitrile
n = 1-3
p = 0, 1

BIOLOGICAL ASSAYS

The biological activities of the fused pyrimidine compounds of the invention can be determined by their examination in in vitro and cellular assays using protocols well established to identify and select compounds that will exhibit anti-cancer activity. The present invention focuses upon the ability of the fused pyrimidine compounds to intersect with the p97 proteosome complex. As described in the Background, the function of the p97 complex is essential for continued cellular viability. Inhibition of the activity of the complex will cause protein build-up in the cell and consequent apoptosis. The biological assays allow an assessment of the biological activities of the fused pyrimidine compounds of the invention.

The primary biological analyses are in vitro assays and cellular based assays for determining the inhibitory capability of the fused pyrimidine compounds of the invention of the invention against Valosin-containing protein, i.e., p97. The assays also provide a primary indication of bioavailability of the fused pyrimidine compounds of the invention.

The ability to inhibit the p97 complex is studied through use of a p97 in vitro assay using a tagged p97 substrate pursuant to the method of Christianson in Nat Cell Biol. (2011) 14:93 for a p97 cell-based assay. A cell based assay is used to test the anti-tumor effects of inhibitors on cultured cancer cells. This anti-tumor assay is based upon cultured cancer cells using the commercially available cell titer glo assay provided by Promega. Additional assays enable assessment of bioavailability through art recognized model studies designed to demonstrate the ability of the compounds of the invention to reach target cells in vivo. While all compounds tested displayed a degree of anti-tumor activity, the assays also allowed identification of fused pyrimidine compounds as candidates that may be selected for further examined by in vivo anti-tumor testing in mouse, guinea pig and dog models. The selected candidates were shown to have highly desirable pharmacokinetic properties in these in vitro assays.

P97 ATPase Biochemical Assay

The ATPase assay is performed according the following protocol: Purified enzyme (20 nM p97), substrate (20 µM ATP) and a dose titration of compounds are mixed in buffer (50 mM TRIS pH 7.5, 20 mM $MgCl_2$, 0.02% TX-100, 1 mM DTT, 0.2% (v/v) glycerol) and incubated at 37° C. for 15 minutes. The reaction is terminated and the level of product generated is measured using the ADP Glo Assay Kit (Promega, Madison Wis.). Plotting product generated versus compound concentration and using a four-parameter fit model generates an IC50 value for each compounds.

P97 Cell-Based Assay

On target cell-based effects of compounds of the invention are monitored using the reporter cell line HEK-293 TCRα-GFP as described in Christianson et al. Nat. Cell Biol. (2011) 14:93 Inhibition of turnover of the TCRα-GFP reporter is a hallmark of p97 inhibition. The protocol for TCRα-GFP monitoring reporter turnover is as follows: Reporter cells are seeded and incubated with proteasome inhibitor MG132 to accumulate TCRα-GFP. Subsequently, MG132-containing media is removed and a dose titration of compound plus cycloheximide is incubated with the cells. At the end of the incubation, compound and media are removed, cells are fixed and GFP fluorescence is measured by standard epifluorescent microscopy techniques. Plotting fluorescence versus compound concentration and using a four-parameter fit model generates an IC50 value for each compound.

Image-analysis is used to generate quantitative data from these assays that can be fit to a four-parameter sigmoid curve to derive IC50 values. Substrates of the ubiquitin-proteasome system, such as p53, are monitored after tumor cell lines are incubated with compounds for several hours. Accumulation of these proteins indicates an inhibition of proteasome-mediated degradation. Accumulation of lysine-48 chain linkage of poly-ubiquitin is also monitored by immunofluorescence as an indicator of ubiquitin-proteasome system inhibition. Both LC3 and SQSTM1 are mediators of autophagy. The localization and amounts of these proteins are monitored by immunofluorescence and report on the activity and inhibition of autophagy in response to p97 inhibition.

Cultured Cancer Cell Assay

Anti-tumor effects are monitored in cultured cancer cells after several days of compound treatment. The cell titer glo assay (Promega) measures the amount of ATP present as a proxy for cellular viability. Cellular counting is done using high-content microscopy followed by image analysis. A hanging drop 3D-culture system (3D Biomatrix) is used followed by cell titer glo to measure growth in a tumor-like environment.

Absorption Assay

The ability of compounds to be absorbed from the lumen of the gastrointestinal tract after oral administration was assessed by measuring their permeability through Caco-2 cell monolayers. SunD, et al., Curr. Opin. Drug Discov. Develop [(2004) 75. The in vitro permeability of compound (2 µM in Kreb's buffer or HBSS buffer with n=2) was determined using 21-day old Caco-2 cell monolayers. The permeation coefficient was determined for both Apical to Basolateral (A to B) and Basolateral to Apical (B to A) after 120 min at 37° C. The efflux ratio was calculated based on the ratio of permeation coefficient of B to A vs. A to B to determine the potential of compound as substrate for efflux pump (e.g. Pgp). The protocol for this Caco-2 assay and the corresponding detailed description are provided in the following experimental section.

Metabolic Stability Assay

Metabolic stability of compounds can be assessed by measuring their half lives in liver microsomal preparations. Roserts, Sa, et al., Xenobiotica (2001) 37:557. Compounds are applied to a preparation of mouse liver microsomes in the presence of NADPH and their half lives are determined by measuring the rate of disappearance of the compounds from the preparation by determining the concentration at 0, 15, 30 and 60 minutes using LCMS/MS. The protocol for determining metabolic stability in a mouse liver assay and the corresponding detailed description are provided in the following experimental section.

Nonspecific Binding Assay

Many compounds are known to bind nonspecifically to proteins found in high abundance in the plasma. The fraction of unbound drug (free fraction) is available for interaction with targets found in tissues. Banker, M. J. et al., Curr. Drug Metab. (2008) 9:854. The ability of compounds to escape a chamber containing blood plasma to a chamber containing only buffer can be assessed by measuring the concentration that appears in the buffer chamber and the concentration that remains in the plasma chamber. These measurements can be used to determine the fraction of compound bound to plasma proteins and its free fraction (100-percent bound to plasma proteins). The protocol for determining non-specific protein binding in a plasma protein binding assay and the corresponding detailed description are provided in the following experimental section.

The results of the primary assay conducted with selected fused pyrimidine compounds and substituted quinazoline compounds of the invention show that the fused pyrimidine compounds of the invention display significant inhibitory activity ($IC_{50}$) against the enzymatic action of p97 toward its natural substrate. Some of these compounds also have greater potency in cell based assays and have in vitro pharmacokinetic properties consistent with good oral bioavailability.

Table III presents the results of several of these assays conducted upon the fused pyrimidine compounds of the invention. While Table III does not present the data from all assays, all compounds of the invention listed in the compound tables display appropriately affirmative results in these assays. Table III presents a cross-section of such results.

TABLE III

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 1 | | 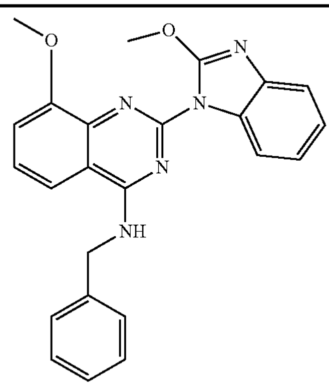 | N-benzyl-8-methoxy-2-(2-methoxy-1H-1,3-benzodiazol-1-yl)quinazolin-4-amine | *** | ND | ND |
| 2 | | 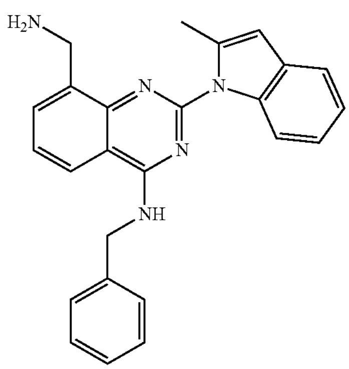 [SMILES: Cc1cc2ccccc2n1-c1nc(NCc2ccccc2)c2cccc(CN)c2n1] | 8-(aminomethyl)-N-benzyl-2-(2-methyl-1H-indol-1-yl)quinazolin-4-amine | * | ND | ND |
| 3 | 21 | 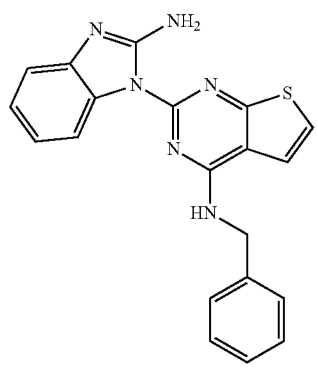 [SMILES: Nc1nc2ccccc2n1-c1nc(NCc2ccccc2)c2ccsc2n1] | 1-[4-(benzylamino)thieno[2,3-d]pyrimidin-2-yl]-1H-1,3-benzodiazol-2-amine | | ND | ND |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 4 | 1 | 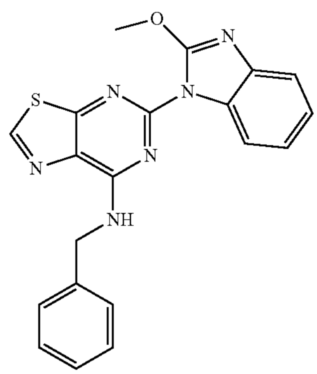 [SMILES: COc1nc2ccccc2n1-c1nc(NCc2ccccc2)c2ncsc2n1] | N-benzyl-5-(2-methoxy-1H-1,3-benzodiazol-1-yl)-[1,3]thiazolo[5,4-d]pyrimidin-7-amine | *** | ND | ND |
| 5 | 22 | 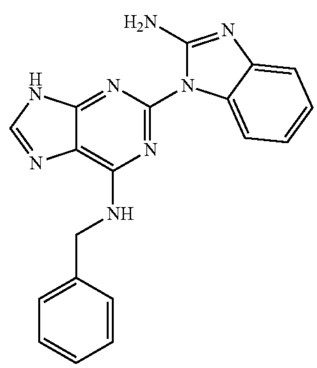 [SMILES: Nc1nc2ccccc2n1-c1nc(NCc2ccccc2)c2nc[nH]c2n1] | 2-(2-amino-1H-1,3-benzodiazol-1-yl)-N-benzyl-9H-purin-6-amine | | ND | ND |
| 6 | 2 | 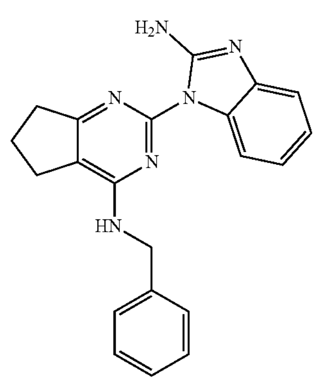 [SMILES: Nc1nc2ccccc2n1-c1nc2c(c(NCc3ccccc3)n1)CCC2] | 1-[4-(benzylamino)-5H,6H,7H-cyclopenta[d]pyrimidin-2-yl]-1H-1,3-benzodiazol-2-amine | | ND | ND |
| 7 | | 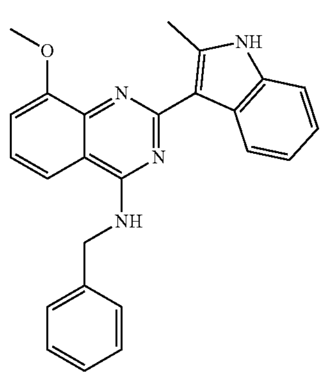 [SMILES: COc1cccc2c(NCc3ccccc3)nc(-c3c(C)[nH]c4ccccc34)nc12] | N-benzyl-8-methoxy-2-(2-methyl-1H-indol-3-yl)quinazolin-4-amine | *** | ND | ND |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 8 | | 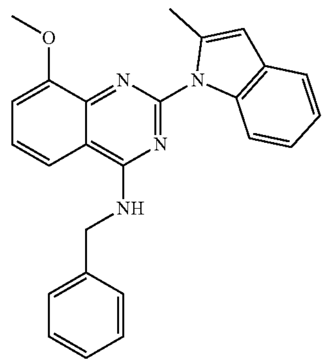 [SMILES: COc1cccc2c(NCc3ccccc3)nc(-n3c(C)cc4ccccc43)nc12] | N-benzyl-8-methoxy-2-(2-methyl-1H-indol-1-yl)quinazolin-4-amine | *** | ND | ND |
| 9 | | 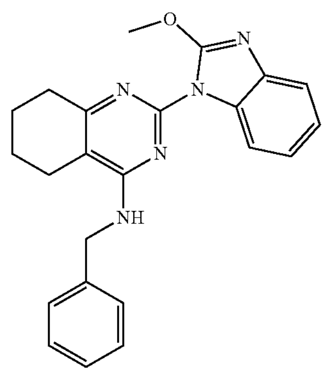 [SMILES: COc1nc2ccccc2n1-c1nc2c(c(NCc3ccccc3)n1)CCCC2] | N-benzyl-2-(2-methoxy-1H-1,3-benzodiazol-1-yl)-5,6,7,8-tetrahydroquinazolin-4-amine | *** | * | |
| 10 | 3 | 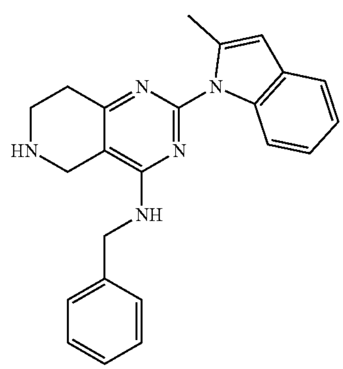 [SMILES: Cc1cc2ccccc2n1-c1nc2c(c(NCc3ccccc3)n1)CNCC2] | N-benzyl-2-(2-methyl-1H-indol-1-yl)-5H,6H,7H,8H-pyrido[4,3-d]pyrimidin-4-amine | ** | * | |
| 11 | 4 | 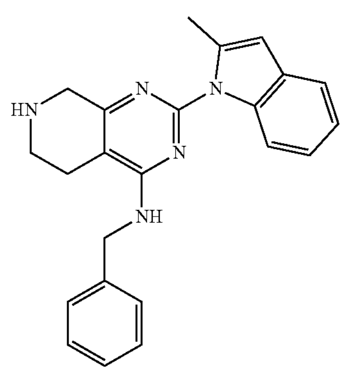 [SMILES: Cc1cc2ccccc2n1-c1nc2c(c(NCc3ccccc3)n1)CCNC2] | N-benzyl-2-(2-methyl-1H-indol-1-yl)-5H,6H,7H,8H-pyrido[3,4-d]pyrimidin-4-amine | ** | ND | ND |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 12 | 5 | 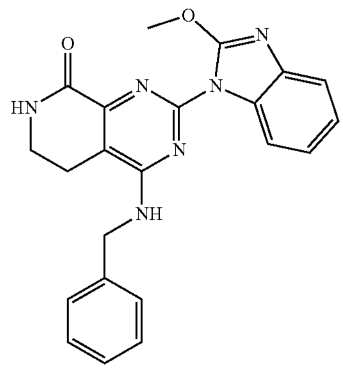 [SMILES: COc1nc2ccccc2n1-c1nc(NCc2ccccc2)c2c(n1)C(=O)NCC2] | 4-(benzylamino)-2-(2-methoxy-1H-1,3-benzodiazol-1-yl)-5H,6H,7H,8H-pyrido[3,4-d]pyrimidin-8-one | | ND | ND |
| 13 | 6 | 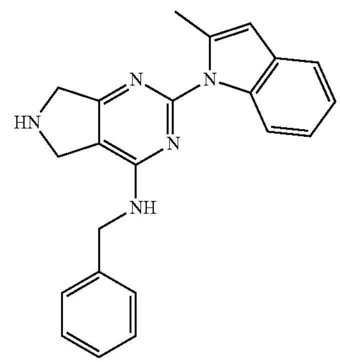 [SMILES: Cc1cc2ccccc2n1-c1nc2c(c(NCc3ccccc3)n1)CNC2] | N-benzyl-2-(2-methyl-1H-indol-1-yl)-5H,6H,7H-pyrrolo[3,4-d]pyrimidin-4-amine | | ND | ND |
| 14 | | 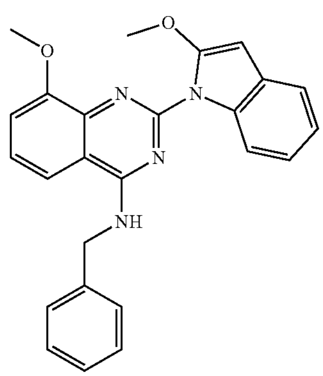 [SMILES: COc1cccc2c(NCc3ccccc3)nc(-n3c(OC)cc4ccccc43)nc12] | N-benzyl-8-methoxy-2-(2-methoxy-1H-indol-1-yl)quinazolin-4-amine | *** | * | |
| 15 | | 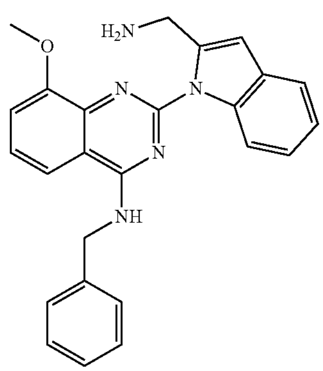 [SMILES: COc1cccc2c(NCc3ccccc3)nc(-n3c(CN)cc4ccccc43)nc12] | 2-[2-(aminomethyl)-1H-indol-1-yl]-N-benzyl-8-methoxyquinazolin-4-amine | *** | | |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 16 | 25 | 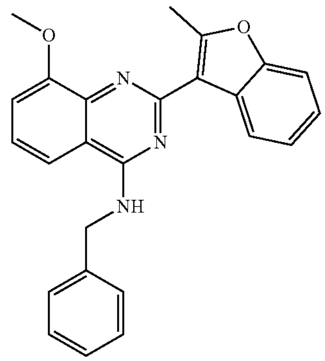 [SMILES: COc1cccc2c(NCc3ccccc3)nc(-c3c(C)oc4ccccc34)nc12] | N-benzyl-8-methoxy-2-(2-methyl-1-benzofuran-3-yl)quinazolin-4-amine | * | ND | ND |
| 17 | | 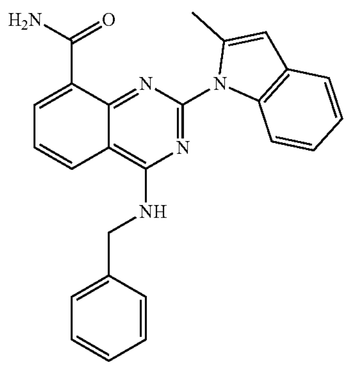 [SMILES: Cc1cc2ccccc2n1-c1nc(NCc2ccccc2)c2cccc(C(N)=O)c2n1] | 4-(benzylamino)-2-(2-methyl-1H-indol-1-yl)quinazoline-8-carboxamide | ** | | |
| 18 | 8 | 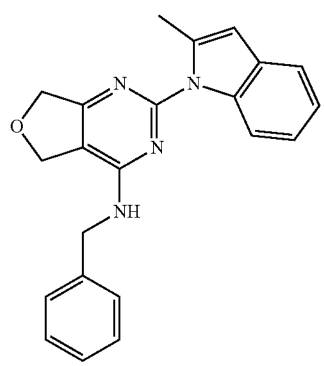 [SMILES: Cc1cc2ccccc2n1-c1nc2c(c(NCc3ccccc3)n1)COC2] | N-benzyl-2-(2-methyl-1H-indol-1-yl)-5H,7H-furo[3,4-d]pyrimidin-4-amine | ** | | |
| 19 | | 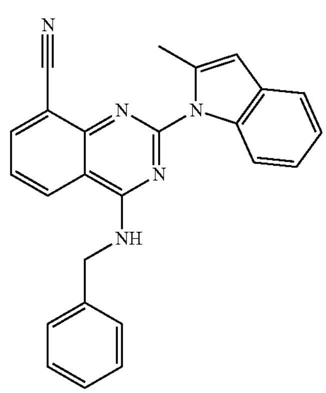 [SMILES: Cc1cc2ccccc2n1-c1nc(NCc2ccccc2)c2cccc(C#N)c2n1] | 4-(benzylamino)-2-(2-methyl-1H-indol-1-yl)quinazoline-8-carbonitrile | * | | |

TABLE III-continued

| Biological Example Number | Synthetic Example Number | Structure | IUPAC | p97 IC50 **** < 30 nM *** < 100 nM ** < 300 nM * < IC50 * < 1000 nM | A549 K48 Cell Intensity | A549 LC3 Increase * > 50% relative to standard |
|---|---|---|---|---|---|---|
| 20 | 7 | 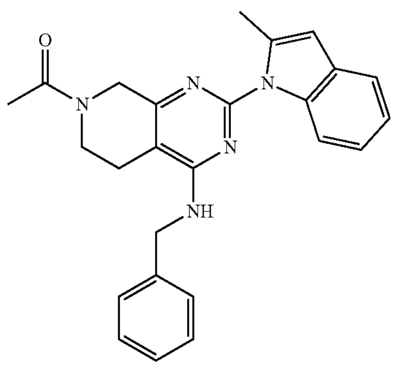 [SMILES: CC(=O)N1CCc2c(nc(-n3c(C)cc4ccccc43)nc2NCc2ccccc2)C1] | 1-[4-(benzylamino)-2-(2-methyl-1H-indol-1-yl)-5H,6H,7H,8H-pyrido[3,4-d]pyrimidin-7-yl]ethan-1-one | *** | | * |
| 21 | | 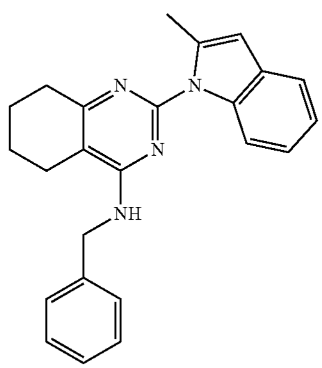 [SMILES: Cc1cc2ccccc2n1-c1nc2c(c(NCc3ccccc3)n1)CCCC2] | N-benzyl-2-(2-methyl-1H-indol-1-yl)-5,6,7,8-tetrahydroquinazolin-4-amine | ** | | * |
| 22 | 24 | 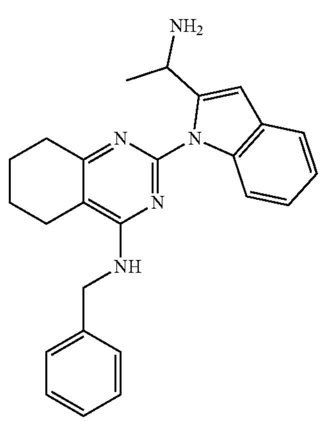 [SMILES: CC(N)c1cc2ccccc2n1-c1nc2c(c(NCc3ccccc3)n1)CCCC2] | 2-[2-(1-aminoethyl)-1H-indol-1-yl]-N-benzyl-5,6,7,8-tetrahydroquinazolin-4-amine | * | | |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 23 | | 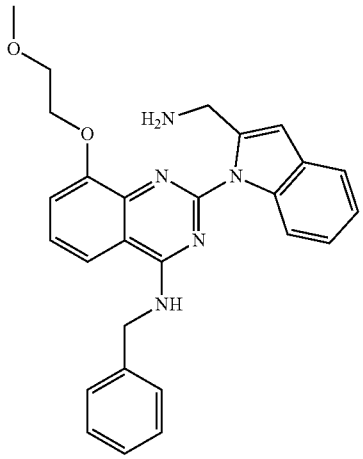 [SMILES: COCCOc1cccc2c(NCc3ccccc3)nc(-n3c(CN)cc4ccccc43)nc12] | 2-[2-(aminomethyl)-1H-indol-1-yl]-N-benzyl-8-(2-methoxyethoxy)quinoazolin-4-amine | ** | | |
| 24 | | 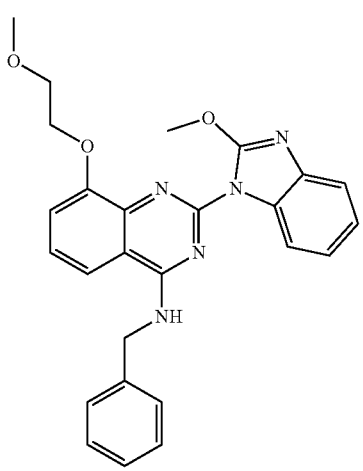 [SMILES: COCCOc1cccc2c(NCc3ccccc3)nc(-n3c(OC)nc4ccccc43)nc12] | N-benzyl-2-(2-methoxy-1H-1,3-benzodiazol-1-yl)-8-(2-methoxyethoxy)quinazolin-4-amine | ** | * | |
| 25 | | 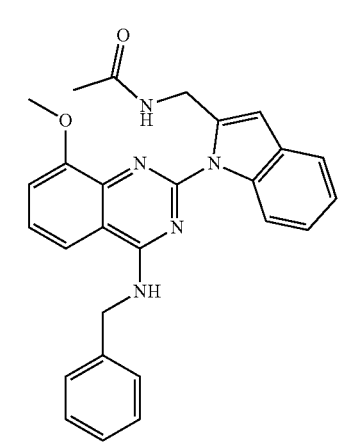 [SMILES: COc1cccc2c(NCc3ccccc3)nc(-n3c(CNC(C)=O)cc4ccccc43)nc12] | N-({1-[4-(benzylamino)-8-methoxyquinazolin-2-yl]-1H-indol-2-yl}methyl)acetamide | ** | | |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 26 | | 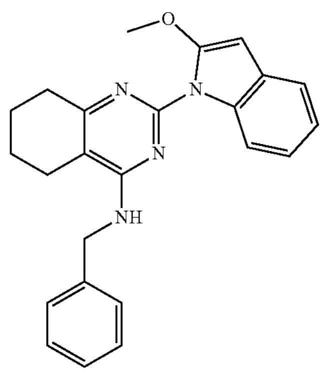 [SMILES: COc1cc2ccccc2n1-c1nc2c(c(NCc3ccccc3)n1)CCCC2] | N-benzyl-2-(2-methoxy-1H-indol-1-yl)-5,6,7,8-tetrahydroquinazolin-4-amine | **** | * | * |
| 27 | | 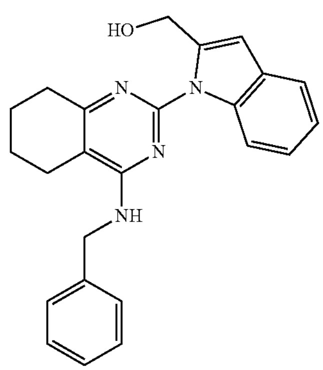 [SMILES: OCc1cc2ccccc2n1-c1nc2c(c(NCc3ccccc3)n1)CCCC2] | {1-[4-(benzylamino)-5,6,7,8-tetrahydroquinazolin-2-yl]-1H-indol-2-yl}methanol | *** | * | * |
| 28 | | 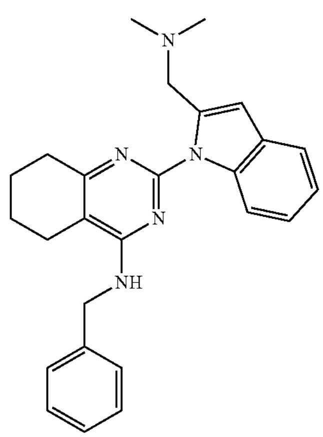 [SMILES: CN(C)Cc1cc2ccccc2n1-c1nc2c(c(NCc3ccccc3)n1)CCCC2] | N-benzyl-2-{2-[(dimethylamino)methyl]-1H-indol-1-yl}-5,6,7,8-tetrahydroquinazolin-4-amine | ** | * | * |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 29 | | 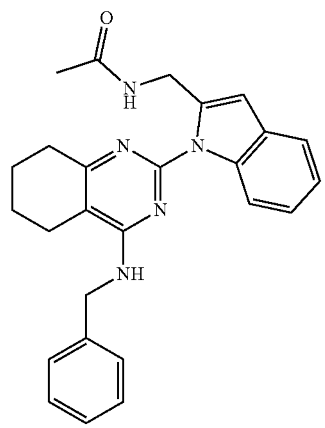 [SMILES: CC(=O)NCc1cc2ccccc2n1-c1nc2c(c(NCc3ccccc3)n1)CCCC2] | N-({1-[4-(benzylamino)-5,6,7,8-tetrahydroquinazolin-2-yl]-1H-indol-2-yl}methyl)acetamide | *** | * | * |
| 30 | | 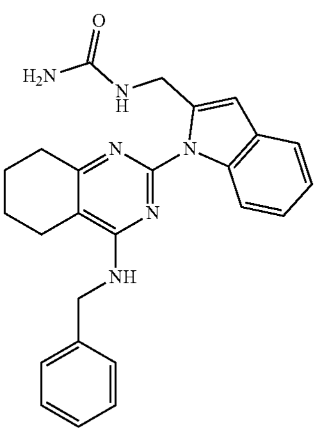 [SMILES: NC(=O)NCc1cc2ccccc2n1-c1nc2c(c(NCc3ccccc3)n1)CCCC2] | ({1-[4-(benzylamino)-5,6,7,8-tetrahydroquinazolin-2-yl]-1H-indol-2-yl}methyl)urea | *** | * | * |
| 31 | | 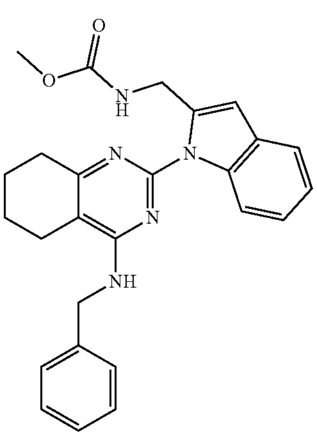 [SMILES: COC(=O)NCc1cc2ccccc2n1-c1nc2c(c(NCc3ccccc3)n1)CCCC2] | methyl N-({1-[4-(benzylamino)-5,6,7,8-tetrahydroquinazolin-2-yl]-1H-indol-2-yl}methyl)carbamate | ** | * | |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 32 | | 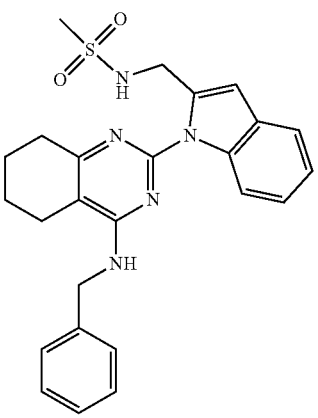 [SMILES: CS(=O)(=O)NCc1cc2ccccc2n1-c1nc2c(c(NCc3ccccc3)n1)CCCC2] | N-({1-[4-(benzylamino)-5,6,7,8-tetrahydroquinazolin-2-yl]-1H-indol-2-yl}methyl)methanesulfonamide | ** | * | |
| 33 | | 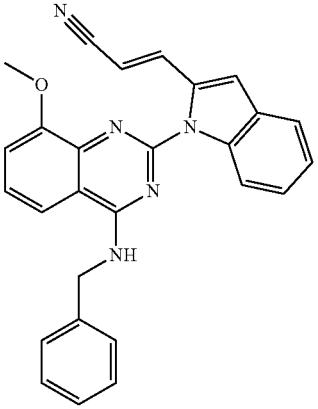 [SMILES: COc1cccc2c(NCc3ccccc3)nc(-n3c(/C=C/C#N)cc4ccccc43)nc12] | (2E)-3-{1-[4-(benzylamino)-8-methoxyquinazolin-2-yl]-1H-indol-2-yl}prop-2-enenitrile | ** | | |
| 34 | | 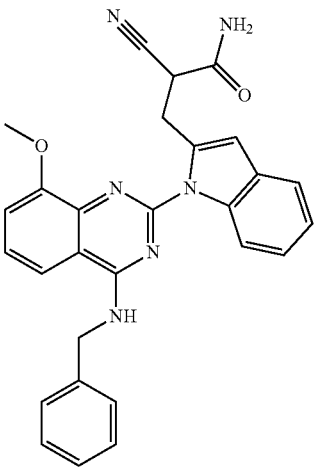 [SMILES: COc1cccc2c(NCc3ccccc3)nc(-n3c(CC(C#N)C(N)=O)cc4ccccc43)nc12] | (2Z)-3-{1-[4-(benzylamino)-8-methoxyquinazolin-2-yl]-1H-indol-2-yl}-2-cyanoprop-2-eneamide | *** | | |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 35 | | 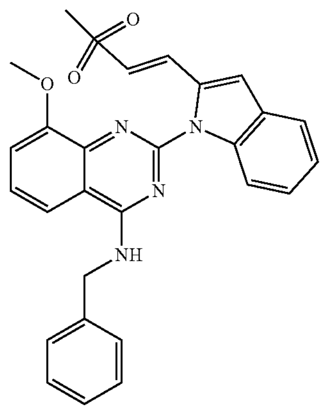 | N-benzyl-2-{2-[(E)-2-methanesulfonylethenyl]-1H-indol-1-yl}-8-methoxyquinazolin-4-amine | ** | * | |
| 36 | 23 | 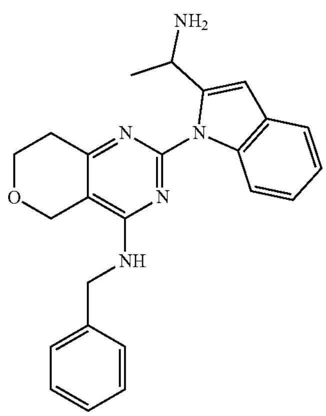 [SMILES: CC(N)c1cc2ccccc2n1-c1nc2c(c(NCc3ccccc3)n1)COCC2] | 2-[2-(1-aminoethyl)-1H-indol-1-yl]-N-benzyl-5H,7H,8H-pyrano[4,3-d]pyrimidin-4-amine | | ND | ND |
| 37 | | 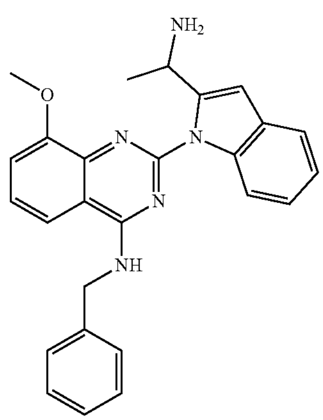 [SMILES: COc1cccc2c(NCc3ccccc3)nc(-n3c(C(C)N)cc4ccccc43)nc12] | 2-[2-(1-aminoethyl)-1H-indol-1-yl]-N-benzyl-8-methoxyquinazolin-4-amine | ** | * | |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 38 | | 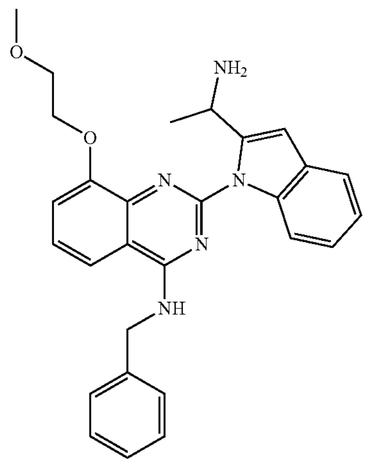 | 2-[2-(1-aminoethyl)-1H-indol-1-yl]-N-benzyl-8-(2-methoxyethoxy)quinazolin-4-amine | ** | | |
| 39 | | 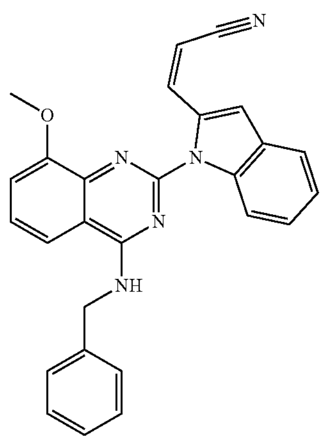 [SMILES: COc1cccc2c(NCc3ccccc3)nc(-n3c(/C=C\C#N)cc4ccccc43)nc12] | (2Z)-3-{1-[4-(benzylamino)-8-methoxyquinazolin-2-yl]-1H-indol-2-yl}prop-2-enenitrile | ** | | |
| 40 | | 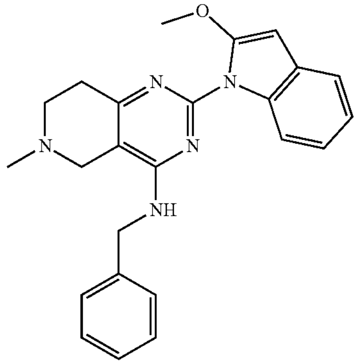 [SMILES: COc1cc2ccccc2n1-c1nc2c(c(NCc3ccccc3)n1)CN(C)CC2] | N-benzyl-2-(2-methoxy-1H-indol-1-yl)-6-methyl-5H,6H,7H,8H-pyrido[4,3-d]pyrimidin-4-amine | * | | |

TABLE III-continued

| Biological Example Number | Synthetic Example Number | Structure | IUPAC | p97 IC50 **** < 30 nM *** < 100 nM ** < 300 nM * < IC50 * < 1000 nM | A549 K48 Cell Intensity * < 10 uM | A549 LC3 Increase * > 50% relative to standard |
|---|---|---|---|---|---|---|
| 41 | | 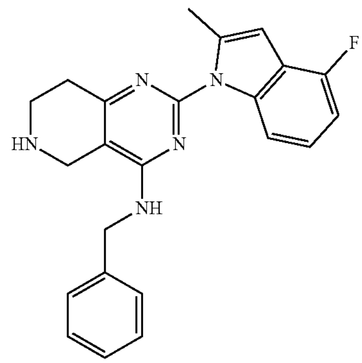 [SMILES: Cc1cc2c(F)cccc2n1-c1nc2c(c(NCc3ccccc3)n1)CNCC2] | N-benzyl-2-(4-fluoro-2-methyl-1H-indol-1-yl)-5H,6H,7H,8H-pyrido[4,3-d]pyrimidin-4-amine | ** | | * |
| 42 | | 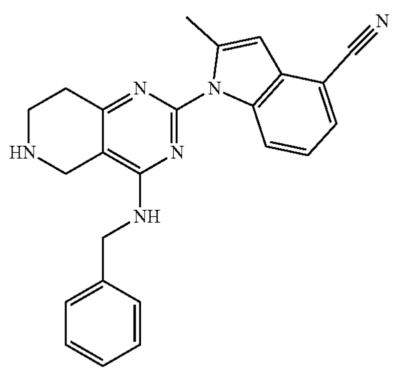 [SMILES: Cc1cc2c(C#N)cccc2n1-c1nc2c(c(NCc3ccccc3)n1)CNCC2] | 1-[4-(benzylamino)-5H,6H,7H,8H-pyrido[4,3-d]pyrimidin-2-yl]-2-methyl-1H-indole-4-carbonitrile | *** | * | |
| 43 | | 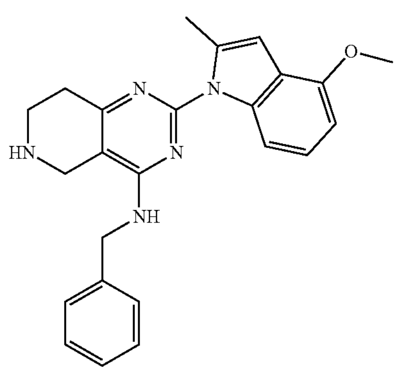 [SMILES: COc1cccc2c1cc(C)n2-c1nc2c(c(NCc3ccccc3)n1)CNCC2] | N-benzyl-2-(4-methoxy-2-methyl-1H-indol-1-yl)-5H,6H,7H,8H-pyrido[4,3-d]pyimidin-4-amine | * | | * |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 44 | | 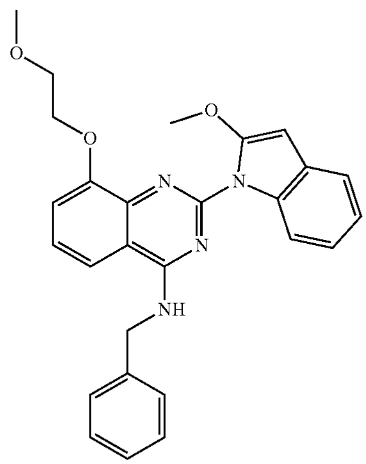 [SMILES: COCCOc1cccc2c(NCc3ccccc3)nc(-n3c(OC)cc4ccccc43)nc12] | N-benzyl-2-(2-methoxy-1H-indol-1-yl)-8-(2-methoxyethoxy)quinazolin-4-amine | *** | | |
| 45 | | 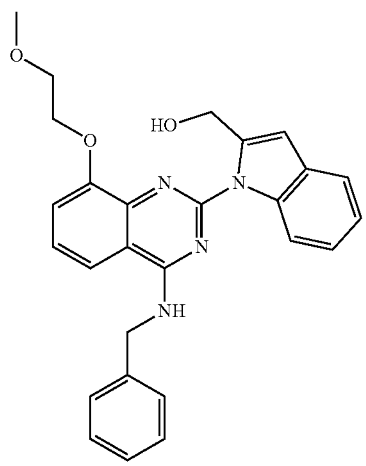 [SMILES: COCCOc1cccc2c(NCc3ccccc3)nc(-n3c(CO)cc4ccccc43)nc12] | {1-[4-(benzylamino)-8-(2-methoxyethoxy)quinazolin-2-yl]-1H-indol-2-yl}methanol | *** | * | |
| 46 | | 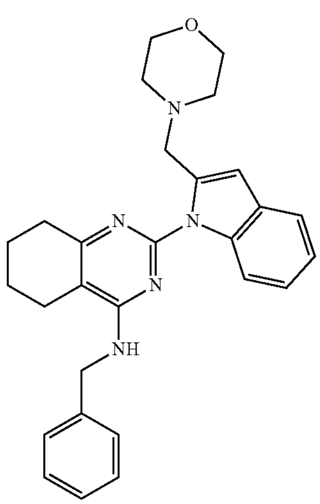 [SMILES: c1ccc(CNc2nc(-n3c(CN4CCOCC4)cc4ccccc43)nc3c2CCCC3)cc1] | N-benzyl-2-[2-(morpholin-4-ylmethyl)-1H-indol-1-yl]-5,6,7,8-tetrahydroquinazolin-4-amine | ** | | |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 47 | | 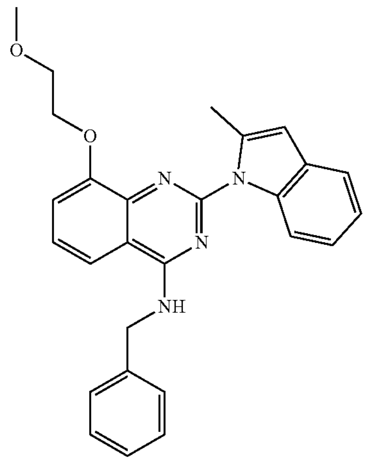 [SMILES: COCCOc1cccc2c(NCc3ccccc3)nc(-n3c(C)cc4ccccc43)nc12] | N-benzyl-8-(2-methoxyethoxy)-2-(2-methyl-1H-indol-1-yl)quinazolin-4-amine | *** | * | |
| 48 | | 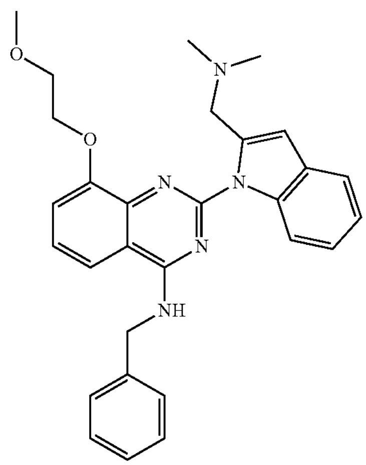 [SMILES: COCCOc1cccc2c(NCc3ccccc3)nc(-n3c(CN(C)C)cc4ccccc43)nc12] | N-benzyl-2-{2-[(dimethylamino)methyl]-1H-indol-1-yl}-8-(2-methoxyethoxy)quinazolin-4-amine | *** | | |
| 49 | | 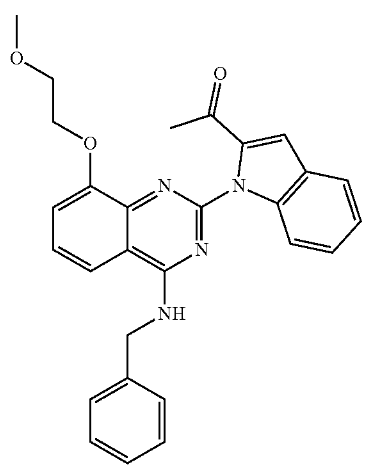 [SMILES: COCCOc1cccc2c(NCc3ccccc3)nc(-n3c(C(C)=O)cc4ccccc43)nc12] | N-({1-[4-(benzylamino)-8-(2-methoxyethoxy)quinazolin-2-yl]-1H-indol-2-yl}methyl)acetamide | ** | | |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity * < IC50 * < 10 uM | A549 LC3 Increase * > 50% relative to standard |
|---|---|---|---|---|---|---|
| 50 | | 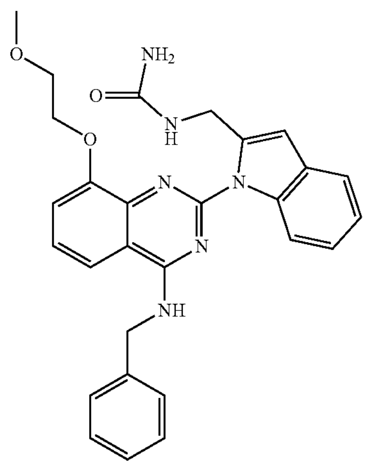 [SMILES: COCCOc1cccc2c(NCc3ccccc3)nc(-n3c(CNC(N)=O)cc4ccccc43)nc12] | ({1-[4-(benzylamino)-8-(2-methoxyethoxy)quinazolin-2-yl]-1H-indol-2-yl}methyl)urea | *** | | |
| 51 | | 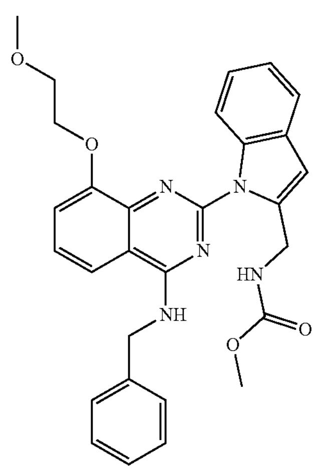 [SMILES: COCCOc1cccc2c(NCc3ccccc3)nc(-n3c(CNC(=O)OC)cc4ccccc43)nc12] | methyl N-({1-[4-(benzylamino)-8-(2-methoxyethoxy)quinazolin-2-yl]-1H-indol-2-yl}methyl)carbamate | ** | | |
| 52 | | 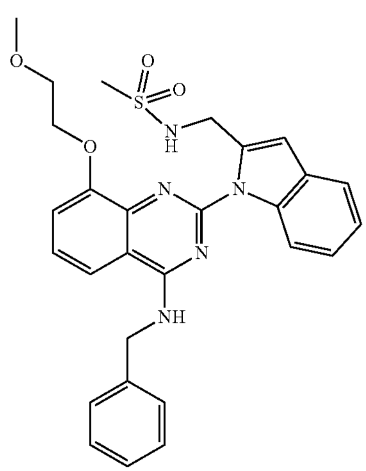 [SMILES: COCCOc1cccc2c(NCc3ccccc3)nc(-n3c(CNS(C)(=O)=O)cc4ccccc43)nc12] | N-({1-[4-(benzylamino)-8-(2-methoxyethoxy)quinazolin-2-yl]-1H-indol-2-yl}methyl)methanesulfonamide | *** | | |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 53 | | 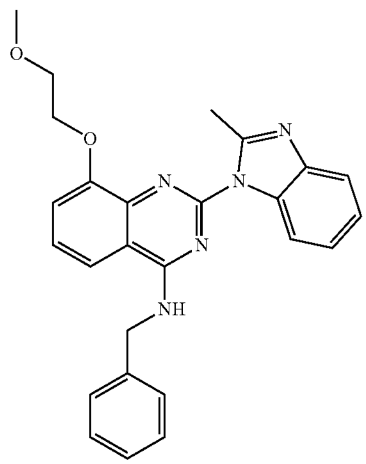 | N-benzyl-8-(2-methoxyethoxy)-2-(2-methyl-1H-1,3-benzodiazol-1-yl)quinazolin-4-amine | ** | | |
| 54 | | 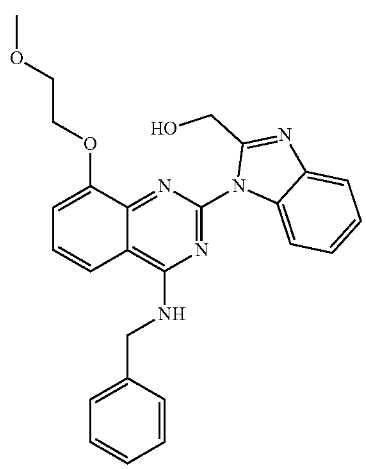 [SMILES: COCCOc1cccc2c(NCc3ccccc3)nc(-n3c(CO)nc4ccccc43)nc12] | {1-[4-(benzylamino)-8-(2-methoxyethoxy)quinazolin-2-yl]-1H-1,3-benzodiazol-2-yl}methanol | ** | | |
| 55 | | 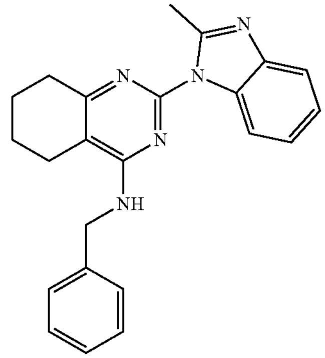 [SMILES: Cc1nc2ccccc2n1-c1nc2c(c(NCc3ccccc3)n1)CCCC2] | N-benzyl-2-(2-methyl-1H-1,3-benzodiazol-1-yl)-5,6,7,8-tetrahydroquinazolin-4-amine | ** | | |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 56 | | 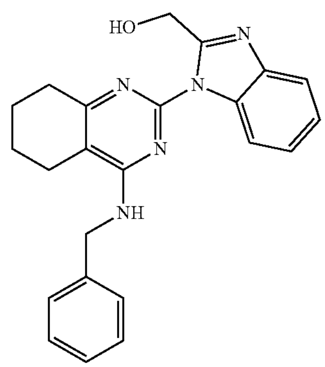 [SMILES: OCc1nc2ccccc2n1-c1nc2c(c(NCc3ccccc3)n1)CCCC2] | {1-[4-(benzylamino)-5,6,7,8-tetrahydroquinazolin-2-yl]-1H-1,3-benzodiazol-2-yl}methanol | * | | |
| 57 | | 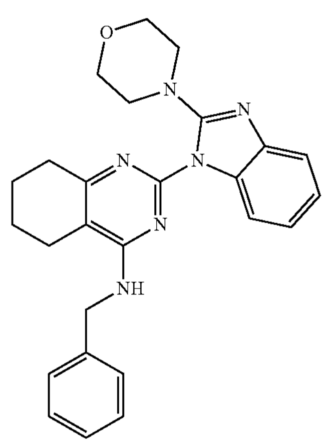 [SMILES: c1ccc(CNc2nc(-n3c(N4CCOCC4)nc4ccccc43)nc3c2CCCC3)cc1] | N-benzyl-2-[2-(morpholin-4-yl)-1H-1,3-benzodiazol-1-yl]-5,6,7,8-tetrahydroquinazolin-4-amine | ** | | |
| 58 | | 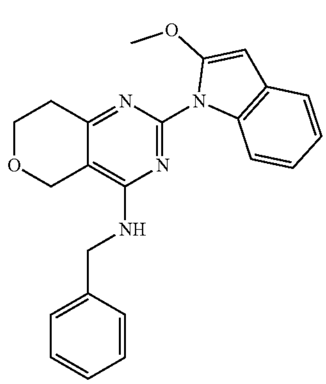 [SMILES: COc1cc2ccccc2n1-c1nc2c(c(NCc3ccccc3)n1)COCC2] | N-benzyl-2-(2-methoxy-1H-indol-1-yl)-5H,7H,8H-pyrano[4,3-d]pyrimidin-4-amine | ** | * | |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 59 | | 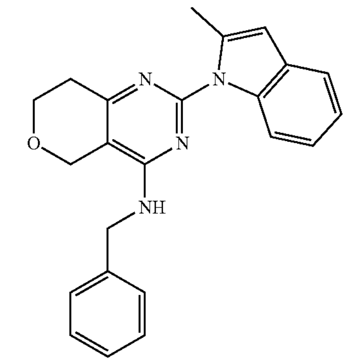 [SMILES: Cc1cc2ccccc2n1-c1nc2c(c(NCc3ccccc3)n1)COCC2] | N-benzyl-2-(2-methyl-1H-indol-1-yl)-5H,7H,8H-pyrano[4,3-d]pyrimidin-4-amine | ** | | |
| 60 | | 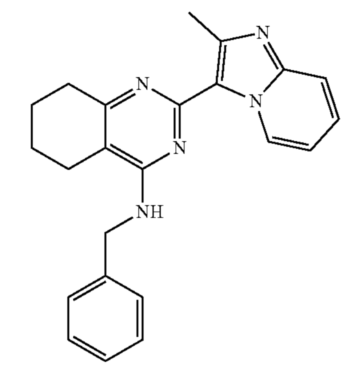 [SMILES: Cc1nc2ccccn2c1-c1nc2c(c(NCc3ccccc3)n1)CCCC2] | N-benzyl-2-{2-methylimidazo[1,2-a]pyridin-3-yl}-5,6,7,8-tetrahydroquinazolin-4-amine | ** | | |
| 61 | | 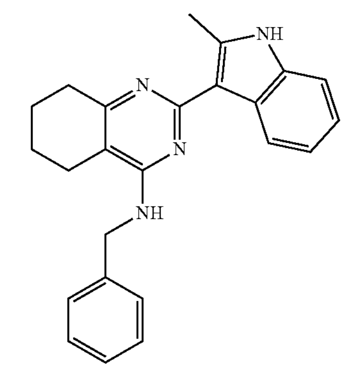 [SMILES: Cc1[nH]c2ccccc2c1-c1nc2c(c(NCc3ccccc3)n1)CCCC2] | N-benzyl-2-(2-methyl-1H-indol-3-yl)-5,6,7,8-tetrahydroquinazolin-4-amine | ** | | * |
| 62 | | 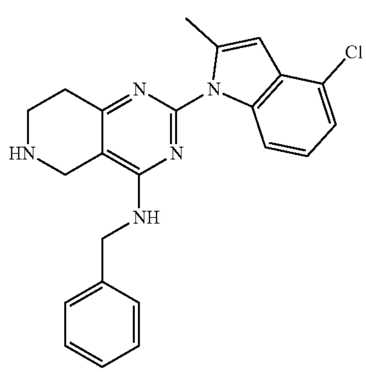 [SMILES: Cc1cc2c(Cl)cccc2n1-c1nc2c(c(NCc3ccccc3)n1)CNCC2] | N-benzyl-2-(4-chloro-2-methyl-1H-indol-1-yl)-5H,6H,7H,8H-pyrido[4,3-d]pyrimidin-4-amine | ** | | * |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 63 | | 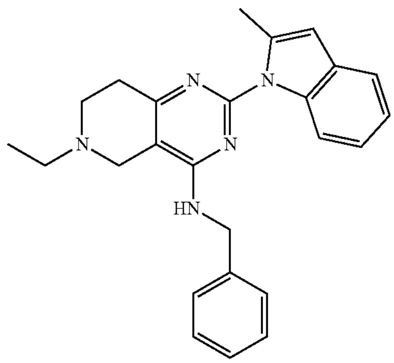 [SMILES: CCN1CCc2nc(-n3c(C)cc4ccccc43)nc(NCc3ccccc3)c2C1] | N-benzyl-6-ethyl-2-(2-methyl-1H-indol-1-yl)-5H,6H,7H,8H-pyrido[4,3-d]pyrimidin-4-amine | * | | * |
| 64 | | 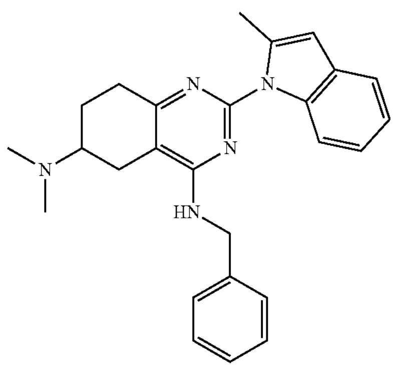 [SMILES: Cc1cc2ccccc2n1-c1nc2c(c(NCc3ccccc3)n1)CC(N(C)C)CC2] | N-benzyl-2-(2-methyl-1H-indol-1-yl)-6-(propan-2-yl)-5H,6H,7H,8H-pyrido[4,3-d]pyrimidin-4-amine | ** | | * |
| 65 | | 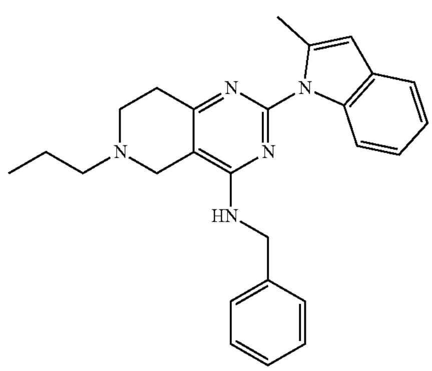 [SMILES: CCCN1CCc2nc(-n3c(C)cc4ccccc43)nc(NCc3ccccc3)c2C1] | N-benzyl-2-(2-methyl-1H-indol-1-yl)-6-propyl-5H,6H,7H,8H-pyrido[4,3-d]pyrimidin-4-amine | * | | |
| 66 | 20 | 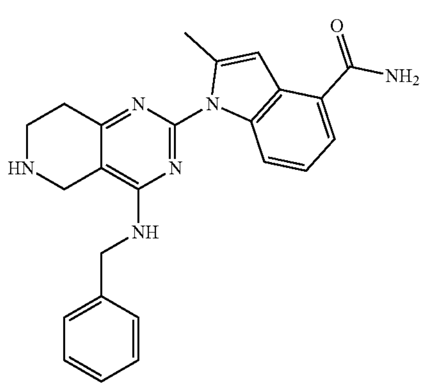 [SMILES: Cc1cc2c(C(N)=O)cccc2n1-c1nc2c(c(NCc3ccccc3)n1)CNCC2] | 1-[4-(benzylamino)-5H,6H,7H,8H-pyrido[4,3-d]pyrimidin-2-yl]-2-methyl-1H-indole-4-carboxamide | *** | * | * |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 67 | | 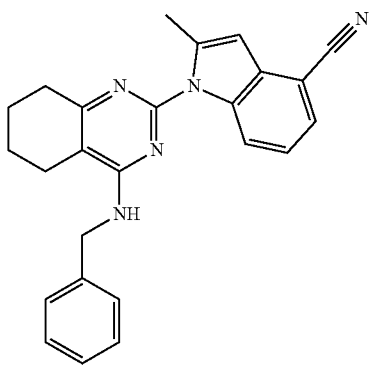 [SMILES: Cc1cc2c(C#N)cccc2n1-c1nc2c(c(NCc3ccccc3)n1)CCCC2] | 1-[4-(benzylamino)-5,6,7,8-tetrahydroquinazolin-2-yl]-2-methyl-1H-indole-4-carbonitrile | *** | | |
| 68 | | 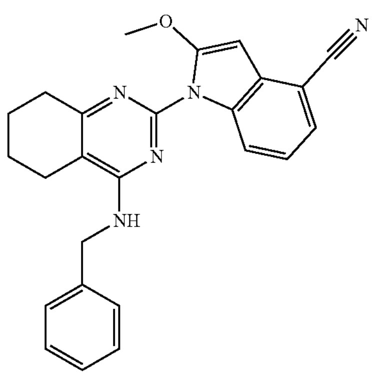 [SMILES: COc1cc2c(C#N)cccc2n1-c1nc2c(c(NCc3ccccc3)n1)CCCC2] | 1-[4-(benzylamino)-5,6,7,8-tetrahydroquinazolin-2-yl]-2-methoxy-1H-indole-4-carbonitrile | *** | * | * |
| 69 | | 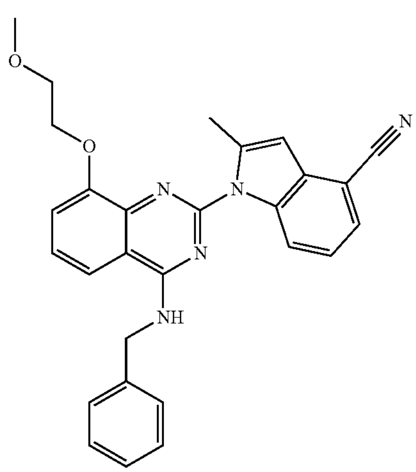 [SMILES: COCCOc1cccc2c(NCc3ccccc3)nc(-n3c(C)cc4c(C#N)cccc43)nc12] | 1-[4-(benzylamino)-8-(2-methoxyethoxy)quinazolin-2-yl]-2-methyl-1H-indole-4-carbonitrile | **** | | |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 70 | | 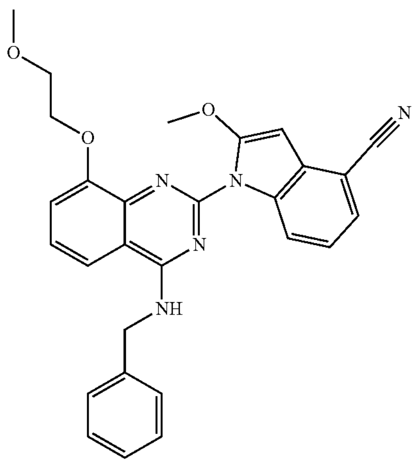 [SMILES: COCCOc1cccc2c(NCc3ccccc3)nc(-n3c(OC)cc4c(C#N)cccc43)nc12] | 1-[4-(benzylamino)-8-(2-methoxyethoxy)quinazolin-2-yl]-2-methoxy-1H-indole-4-carbonitrile | *** | | |
| 71 | | 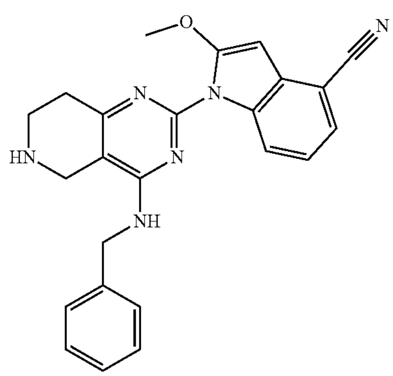 [SMILES: COc1cc2c(C#N)cccc2n1-c1nc2c(c(NCc3ccccc3)n1)CNCC2] | 1-[4-(benzylamino)-5H,6H,7H,8H-pyrido[4,3-d]pyrimidin-2-yl]-2-methoxy-1H-indole-4-carbonitrile | ** | | |
| 72 | | 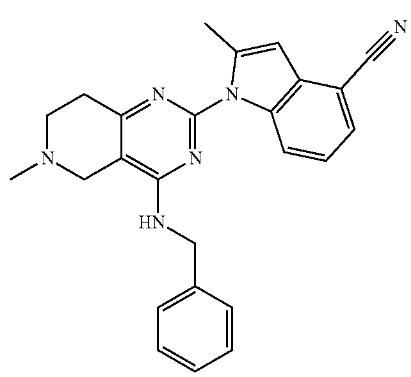 [SMILES: Cc1cc2c(C#N)cccc2n1-c1nc2c(c(NCc3ccccc3)n1)CN(C)CC2] | 1-[4-(benzylamino)-6-methyl-5H,6H,7H,8H-pyrido[4,3-d]pyrimidin-2-yl]-2-methyl-1H-indole-4-carbonitrile | *** | * | * |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 73 | | 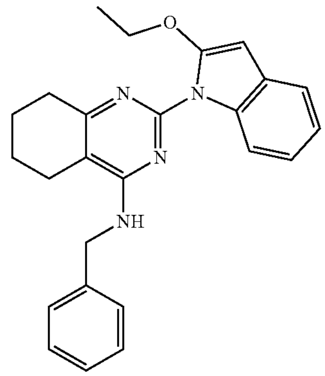 [SMILES: CCOc1cc2ccccc2n1-c1nc2c(c(NCc3ccccc3)n1)CCCC2] | N-benzyl-2-(2-ethoxy-1H-indol-1-yl)-5,6,7,8-tetrahydroquinazolin-4-amine | *** | * | |
| 74 | | 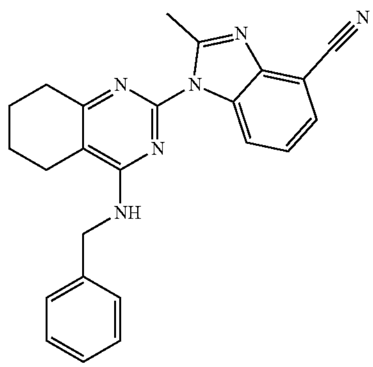 [SMILES: Cc1nc2c(C#N)cccc2n1-c1nc2c(c(NCc3ccccc3)n1)CCCC2] | 1-[4-(benzylamino)-5,6,7,8-tetrahydroquinazolin-2-yl]-2-methyl-1H-1,3-benzodiazole-4-carbonitrile | *** | * | |
| 75 | | 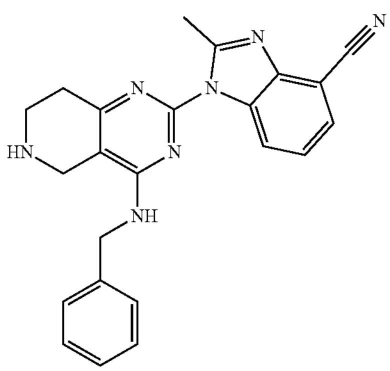 [SMILES: Cc1nc2c(C#N)cccc2n1-c1nc2c(c(NCc3ccccc3)n1)CNCC2] | 1-[4-(benzylamino)-5H,6H,7H,8H-pyrido[4,3-d]pyrimidin-2-yl]-2-methyl-1H-1,3-benzodiazole-4-carbonitrile | *** | * | |
| 76 | | 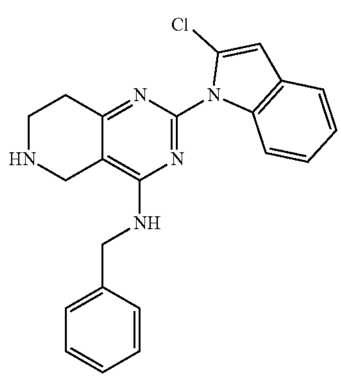 [SMILES: Clc1cc2ccccc2n1-c1nc2c(c(NCc3ccccc3)n1)CNCC2] | N-benzyl-2-(2-chloro-1H-indol-1-yl)-5H,6H,7H,8H-pyrido[4,3-d]pyrimidin-4-amine | ** | * | |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 77 | | 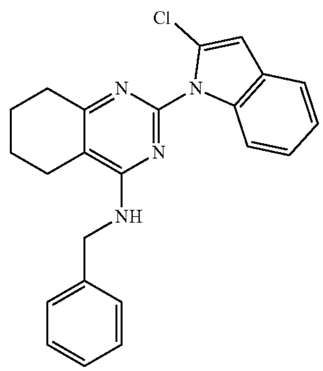 [SMILES: Clc1cc2ccccc2n1-c1nc2c(c(NCc3ccccc3)n1)CCCC2] | N-benzyl-2-(2-chloro-1H-indol-1-yl)-5,6,7,8-tetrahydroquinazolin-4-amine | *** | * | |
| 78 | | 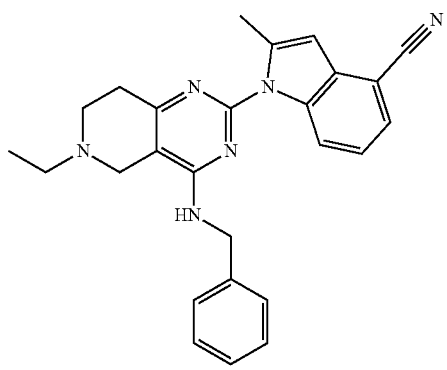 [SMILES: CCN1CCc2nc(-n3c(C)cc4c(C#N)cccc43)nc(NCc3ccccc3)c2C1] | 1-[4-(benzylamino)-6-ethyl-5H,6H,7H,8H-pyrido[4,3-d]pyrimidin-2-yl]-2-methyl-1H-indole-4-carbonitrile | *** | | |
| 79 | | 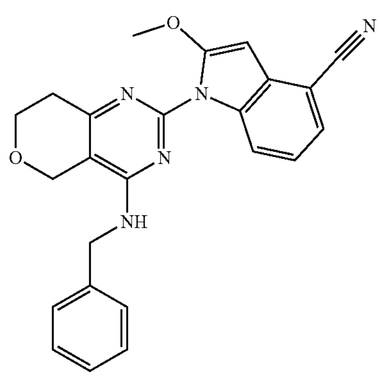 [SMILES: COc1cc2c(C#N)cccc2n1-c1nc2c(c(NCc3ccccc3)n1)COCC2] | 1-[4-(benzylamino)-5H,7H,8H-pyrano[4,3-d]pyrimidin-2-yl]-2-methoxy-1H-indole-4-carbonitrile | *** | * | |
| 80 | | 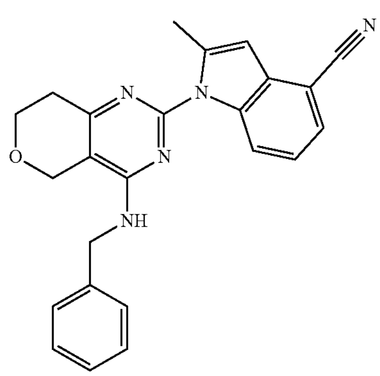 [SMILES: Cc1cc2c(C#N)cccc2n1-c1nc2c(c(NCc3ccccc3)n1)COCC2] | 1-[4-(benzylamino)-5H,7H,8H-pyrano[4,3-d]pyrimidin-2-yl]-2-methyl-1H-indole-4-carbonitrile | *** | | |

| Biological Example Number | Synthetic Example Number | Structure | IUPAC | p97 IC50 ** < 30 nM * < 100 nM ** < 300 nM * < 1000 nM | A549 K48 Cell Intensity IC50 * < 10 uM | A549 LC3 Increase * > 50% relative to standard |
|---|---|---|---|---|---|---|
| 81 | | 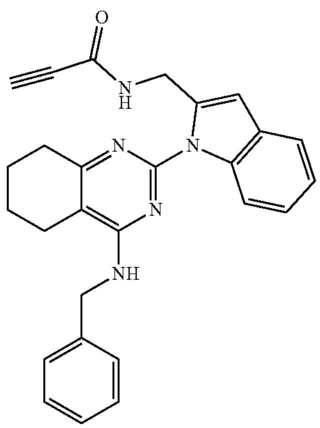 [SMILES: C#CC(=O)NCc1cc2ccccc2n1-c1nc2c(c(NCc3ccccc3)n1)CCCC2] | N-({1-[4-(benzylamino)-5,6,7,8-tetrahydroquinazolin-2-yl]-1H-indol-2-yl}methyl)prop-2-ynamide | | *** | * |
| 82 | | 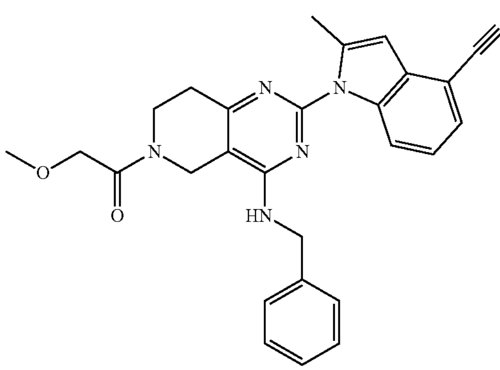 | N-[4-(benzylamino)-6-(2-methoxyacetyl)-5H,6H,7H,8H-pyrido[4,3-d]pyrimidin-2-yl]-2-methyl-1H-indole-4-carbonitrile | **** | | |
| 83 | | 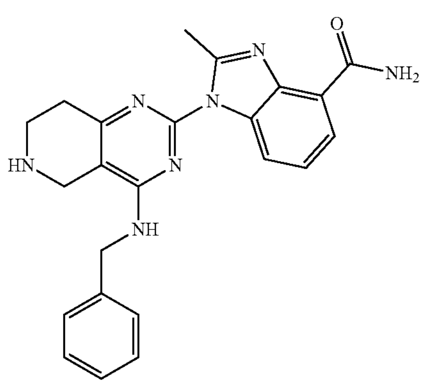 [SMILES: Cc1nc2c(C(N)=O)cccc2n1-c1nc2c(c(NCc3ccccc3)n1)CNCC2] | 1-[4-(benzylamino)-5H,6H,7H,8H-pyrido[4,3-d]pyrimidin-2-yl]-2-methyl-1H-1,3-benzodiazole-4-carboxamide | | * | |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 84 | | 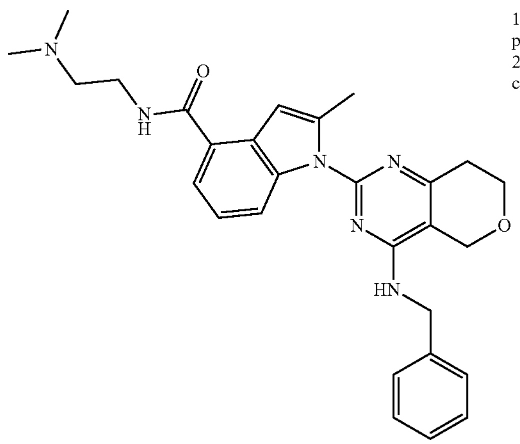 | 1-[4-(benzylamino)-5H,7H,8H-pyrano[4,3-d]pyrimidin-2-yl]-2-methoxy-1H-indole-4-carboxamide | **** | * | |
| 85 | 9 | 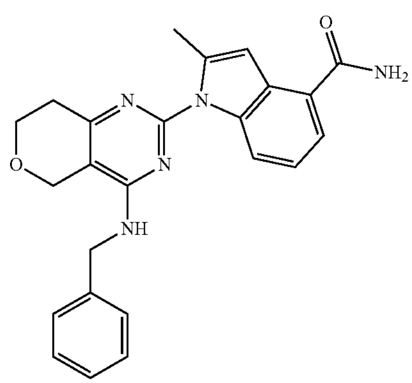 [SMILES: Cc1cc2c(C(N)=O)cccc2n1-c1nc2c(c(NCc3ccccc3)n1)COCC2] | 1-[4-(benzylamino)-5H,7H,8H-pyrano[4,3-d]pyrimidin-2-yl]-2-methyl-1H-indole-4-carboxamide | **** | * | |
| 86 | | 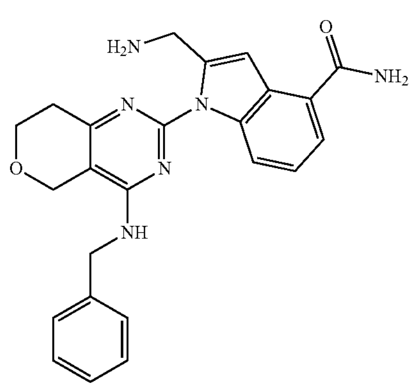 [SMILES: NCc1cc2c(C(N)=O)cccc2n1-c1nc2c(c(NCc3ccccc3)n1)COCC2] | 2-(aminomethyl)-1-[4-(benzylamino)-5H,7H,8H-pyrano[4,3-d]pyrimidin-2-yl]-1H-indole-4-carboxamide | *** | | |

TABLE III-continued

| Biological Example Number | Synthetic Example Number | Structure | IUPAC | p97 IC50 **** < 30 nM *** < 100 nM ** < 300 nM * < IC50 < 1000 nM | A549 K48 Cell Intensity | A549 LC3 Increase * > 50% relative to standard |
|---|---|---|---|---|---|---|
| 87 | | 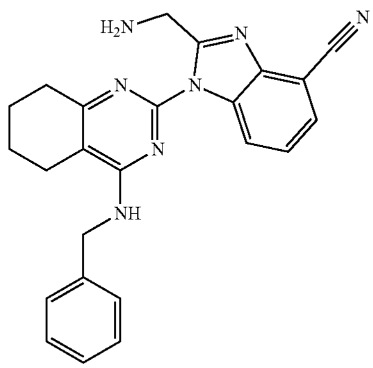 [SMILES: N#Cc1cccc2c1nc(CN)n2-c1nc2c(c(NCc3ccccc3)n1)CCCC2] | 2-(aminomethyl)-1-[4-(benzylamino)-5,6,7,8-tetrahydroquinazolin-2-yl]-1H-1,3-benzodiazole-4-carbonitrile | * | | |
| 88 | | 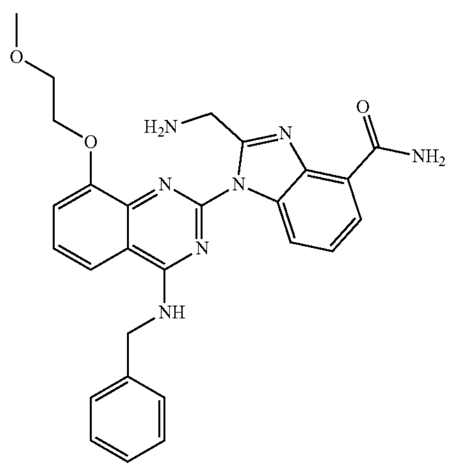 [SMILES: COCCOc1cccc2c(NCc3ccccc3)nc(-n3c(CN)nc4c(C(N)=O)cccc43)nc12] | 2-(aminomethyl)-1-[4-(benzylamino)-8-(2-methoxyethoxy)quinazolin-2-yl]-1H-1,3-benzodiazole-4-carboxamide | * | | |
| 89 | | 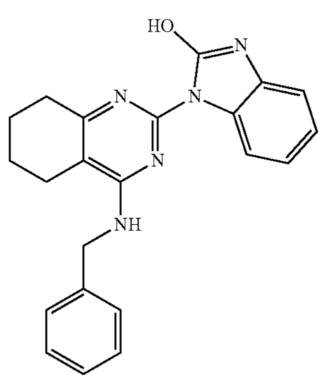 [SMILES: Oc1nc2ccccc2n1-c1nc2c(c(NCc3ccccc3)n1)CCCC2] | 1-[4-(benzylamino)-5,6,7,8-tetrahydroquinazolin-2-yl]-1H-1,3-benzodiazol-2-ol | * | | |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 90 | | 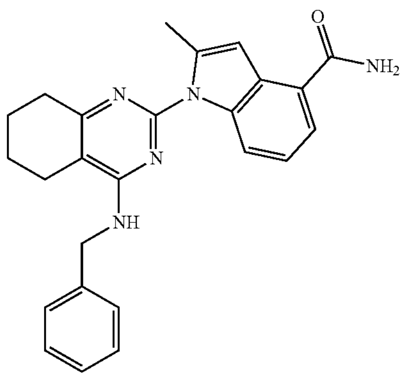 [SMILES: Cc1cc2c(C(N)=O)cccc2n1-c1nc2c(c(NCc3ccccc3)n1)CCCC2] | 1-[4-(benzylamino)-5,6,7,8-tetrahydroquinazolin-2-yl]-2-methyl-1H-indole-4-carboxamide | **** | * | * |
| 91 | | 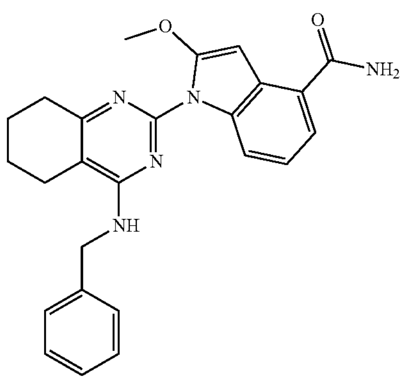 [SMILES: COc1cc2c(C(N)=O)cccc2n1-c1nc2c(c(NCc3ccccc3)n1)CCCC2] | 1-[4-(benzylamino)-5,6,7,8-tetrahydroquinazolin-2-yl]-2-methoxy-1H-indole-4-carboxamide | **** | * | * |
| 92 | | 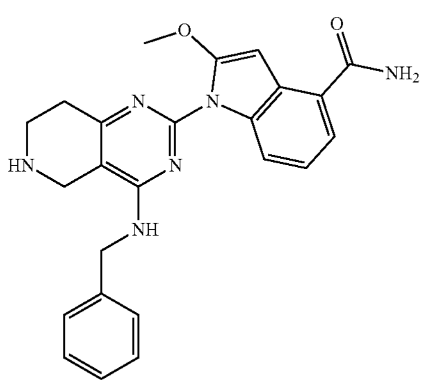 [SMILES: COc1cc2c(C(N)=O)cccc2n1-c1nc2c(c(NCc3ccccc3)n1)CNCC2] | 1-[4-(benzylamino)-5H,6H,7H,8H-pyrido[4,3-d]pyrimidin-2-yl]-2-methoxy-1H-indole-4-carboxamide | * | * | |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 93 | | 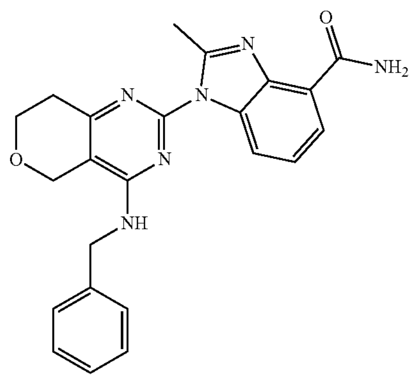 [SMILES: Cc1nc2c(C(N)=O)cccc2n1-c1nc2c(c(NCc3ccccc3)n1)COCC2] | 1-[4-(benzylamino)-5H,7H,8H-pyrano[4,3-d]pyrimidin-2-yl]-2-methyl-1H-1,3-benzodiazole-4-carboxamide | *** | * | * |
| 94 | | 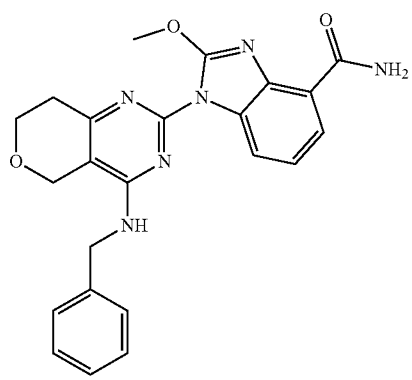 [SMILES: COc1nc2c(C(N)=O)cccc2n1-c1nc2c(c(NCc3ccccc3)n1)COCC2] | 1-[4-(benzylamino)-5H,7H,8H-pyrano[4,3-d]pyrimidin-2-yl]-2-methoxy-1H-1,3-benzodiazole-4-carboxamide | **** | * | |
| 95 | | 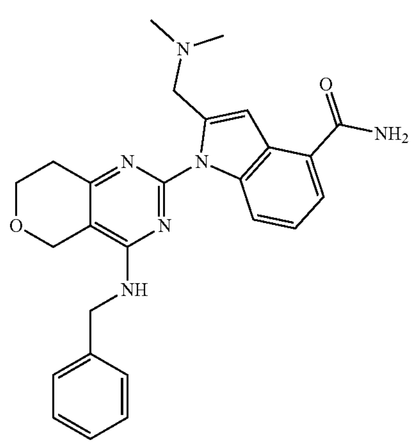 [SMILES: CN(C)Cc1cc2c(C(N)=O)cccc2n1-c1nc2c(c(NCc3ccccc3)n1)COCC2] | 1-[4-(benzylamino)-5H,7H,8H-pyrano[4,3-d]pyrimidin-2-yl]-2-[(dimethylamino)methyl]-1H-indole-4-carboxamide | * | | |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 96 | | 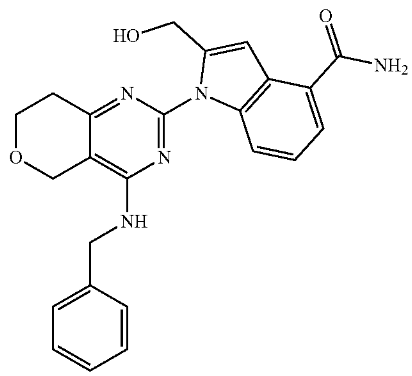 [SMILES: NC(=O)c1cccc2c1cc(CO)n2-c1nc2c(c(NCc3ccccc3)n1)COCC2] | 1-[4-(benzylamino)-5H,7H,8H-pyrano[4,3-d]pyrimidin-2-yl]-2-(hydroxymethyl)-1H-indole-4-carboxamide | *** | * | |
| 97 | | 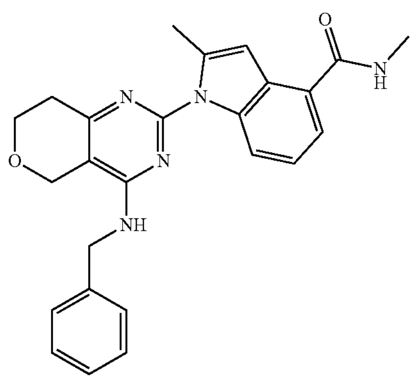 [SMILES: CNC(=O)c1cccc2c1cc(C)n2-c1nc2c(c(NCc3ccccc3)n1)COCC2] | 1-[4-(benzylamino)-5H,7H,8H-pyrano[4,3-d]pyrimidin-2-yl]-N,2-dimethyl-1H-indole-4-carboxamide | *** | * | * |
| 98 | | 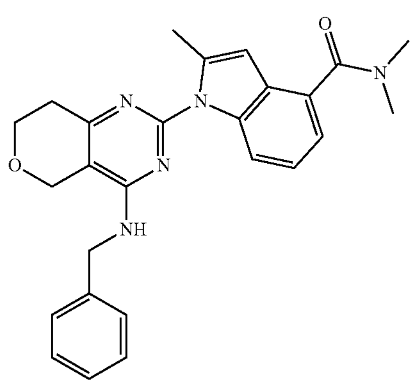 [SMILES: Cc1cc2c(C(=O)N(C)C)cccc2n1-c1nc2c(c(NCc3ccccc3)n1)COCC2] | 1-[4-(benzylamino)-5H,7H,8H-pyrano[4,3-d]pyrimidin-2-yl]-N,N,2-trimethyl-1H-indole-4-carboxamide | | | |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 99 | | 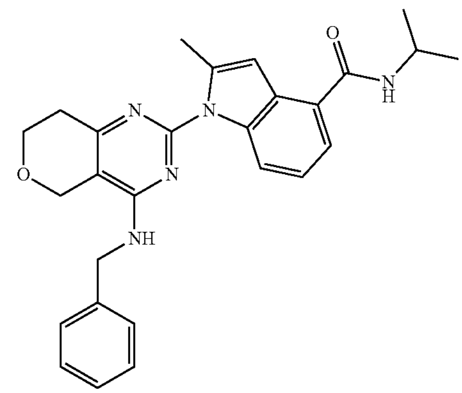 [SMILES: Cc1cc2c(C(=O)NC(C)C)cccc2n1-c1nc2c(c(NCc3ccccc3)n1)COCC2] | 1-[4-(benzylamino)-5H,7H,8H-pyrano[4,3-d]pyrimidin-2-yl]-2-methyl-N-(propan-2-yl)-1H-indole-4-carboxamide | | * | |
| 100 | | 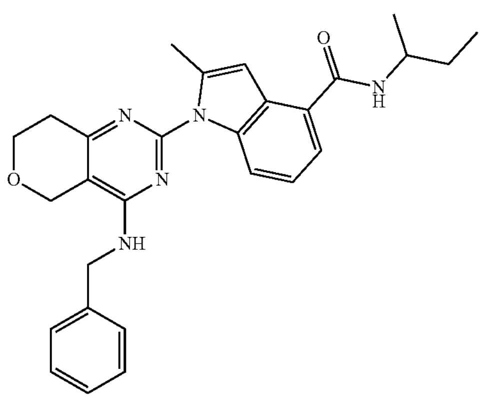 [SMILES: CCC(C)NC(=O)c1cccc2c1cc(C)n2-c1nc2c(c(NCc3ccccc3)n1)COCC2] | 1-[4-(benzylamino)-5H,7H,8H-pyrano[4,3-d]pyrimidin-2-yl]-N-(butan-2-yl)-2-methyl-1H-indole-4-carboxamide | | | |
| 101 | | 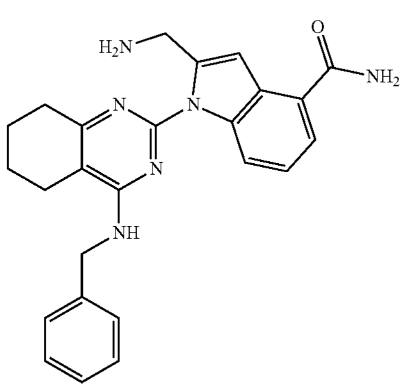 [SMILES: NCc1cc2c(C(N)=O)cccc2n1-c1nc2c(c(NCc3ccccc3)n1)CCCC2] | 2-(aminomethyl)-1-[4-(benzylamino)-5,6,7,8-tetrahydroquinazolin-2-yl]-1H-indole-4-carboxamide | **** | * | * |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 102 | | 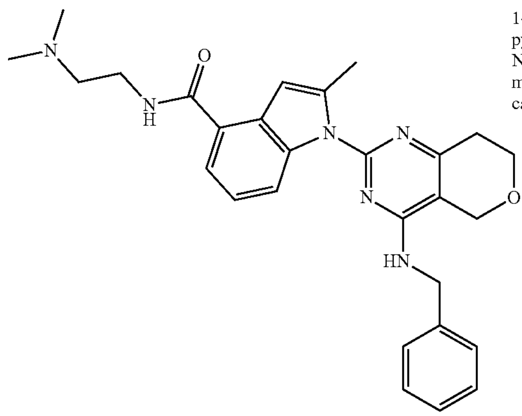 [SMILES: Cc1cc2c(C(=O)NCCN(C)C)cccc2n1-c1nc2c(c(NCc3ccccc3)n1)COCC2] | 1-[4-(benzylamino)-5H,7H,8H-pyrano[4,3-d]pyrimidin-2-yl]-N-[2-(dimethylamino)ethyl]-2-methyl-1H-indole-4-carboxamide | * | * | * |
| 103 | | 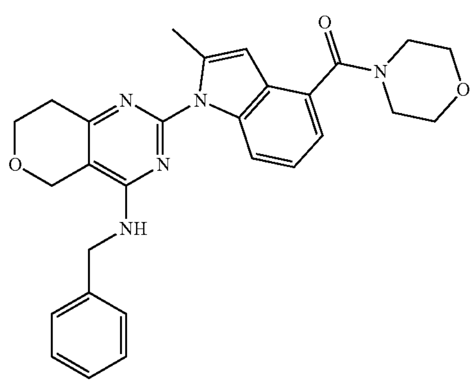 [SMILES: Cc1cc2c(C(=O)N3CCOCC3)cccc2n1-c1nc2c(c(NCc3ccccc3)n1)COCC2] | N-benzyl-2-{2-methyl-4-[(morpholin-4-yl)carbonyl]-1H-indol-1-yl}-5H,7H,8H-pyrano[4,3-d]pyrimidin-4-amine | | | |
| 104 | | 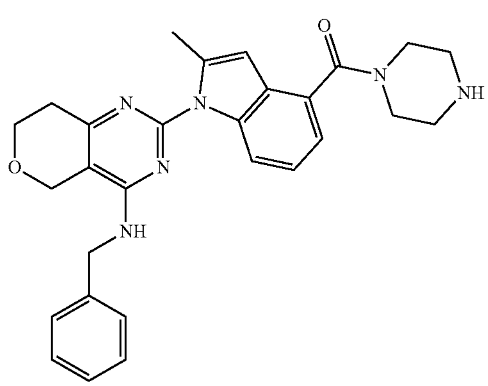 [SMILES: Cc1cc2c(C(=O)N3CCNCC3)cccc2n1-c1nc2c(c(NCc3ccccc3)n1)COCC2] | N-benzyl-2-{2-methyl-4-[(piperazin-1-yl)carbonyl]-1H-indol-1-yl}-5H,7H,8H-pyrano[4,3-d]pyrimidin-4-amine | | | |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 105 | | 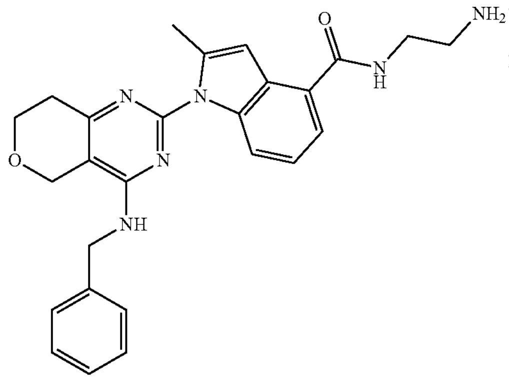 [SMILES: Cc1cc2c(C(=O)NCCN)cccc2n1-c1nc2c(c(NCc3ccccc3)n1)COCC2] | N-(2-aminoethyl)-1-[4-(benzylamino)-5H,7H,8H-pyrano[4,3-d]pyrimidin-2-yl]-2-methyl-1H-indole-4-carboxamide | * | * | * |
| 106 | | 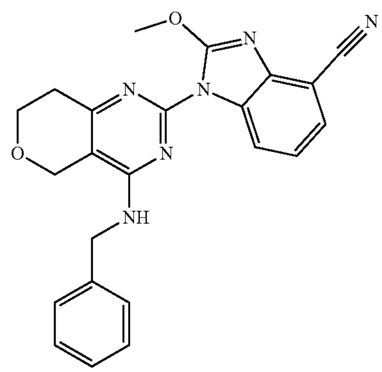 [SMILES: COc1nc2c(C#N)cccc2n1-c1nc2c(c(NCc3ccccc3)n1)COCC2] | 1-[4-(benzylamino)-5H,7H,8H-pyrano[4,3-d]pyrimidin-2-yl]-2-methoxy-1H-1,3-benzodiazole-4-carbonitrile | ** | * | |
| 107 | | 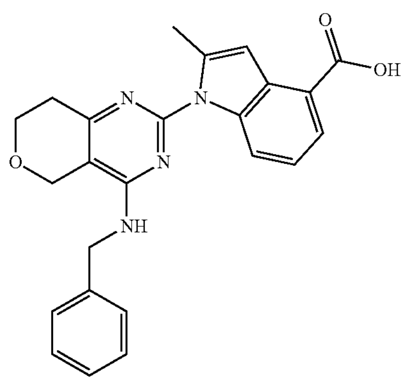 [SMILES: Cc1cc2c(C(=O)O)cccc2n1-c1nc2c(c(NCc3ccccc3)n1)COCC2] | 1-[4-(benzylamino)-5H,7H,8H-pyrano[4,3-d]pyrimidin-2-yl]-2-methyl-1H-indole-4-carboxylic acid | **** | * | |
| 108 | 12 | 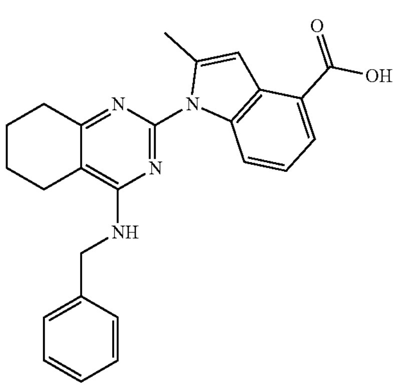 [SMILES: Cc1cc2c(C(=O)O)cccc2n1-c1nc2c(c(NCc3ccccc3)n1)CCCC2] | 1-[4-(benzylamino)-5,6,7,8-tetrahydroquinazolin-2-yl]-2-methyl-1H-indole-4-carboxylic acid | **** | * | |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 109 | 13 | 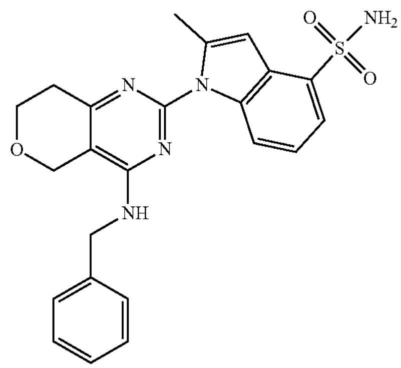 [SMILES: Cc1cc2c(S(N)(=O)=O)cccc2n1-c1nc2c(c(NCc3ccccc3)n1)COCC2] | 1-[4-(benzylamino)-5H,7H,8H-pyrano[4,3-d]pyrimidin-2-yl]-2-methyl-1H-indole-4-sulfonamide | | | |
| 110 | 14 | 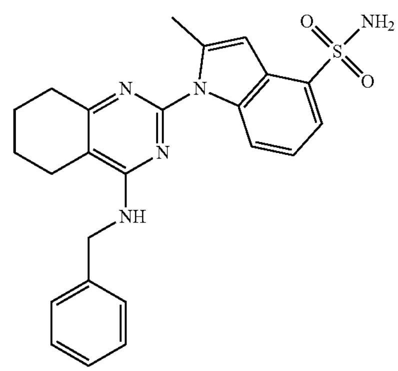 [SMILES: Cc1cc2c(S(N)(=O)=O)cccc2n1-c1nc2c(c(NCc3ccccc3)n1)CCCC2] | 1-[4-(benzylamino)-5,6,7,8-tetrahydroquinazolin-2-yl]-2-methyl-1H-indole-4-sulfonamide | *** | * | |
| 111 | 15 | 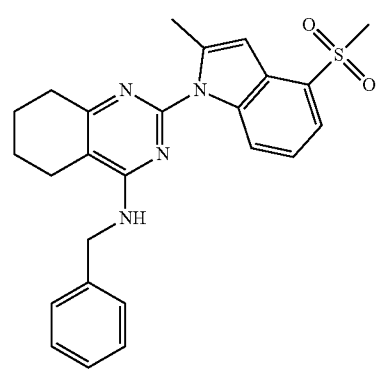 [SMILES: Cc1cc2c(S(C)(=O)=O)cccc2n1-c1nc2c(c(NCc3ccccc3)n1)CCCC2] | N-benzyl-2-(4-methanesulfonyl-2-methyl-1H-indol-1-yl)-5,6,7,8-tetrahydroquinazolin-4-amine | *** | * | * |
| 112 | | 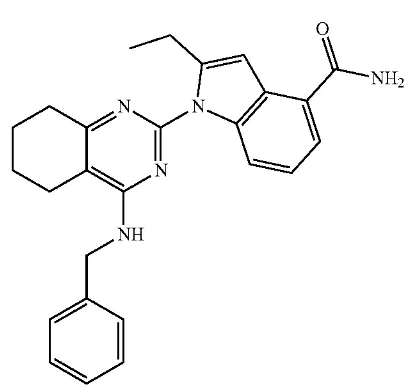 [SMILES: CCc1cc2c(C(N)=O)cccc2n1-c1nc2c(c(NCc3ccccc3)n1)CCCC2] | 1-[4-(benzylamino)-5,6,7,8-tetrahydroquinazolin-2-yl]-2-ethyl-1H-indole-4-carboxamide | *** | * | |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 113 | | 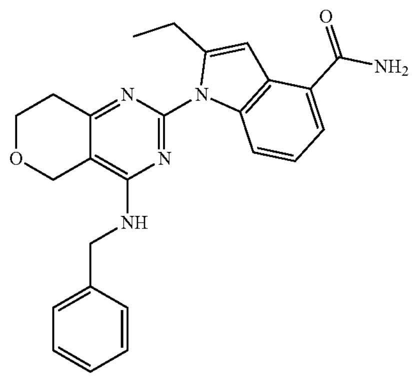 [SMILES: CCc1cc2c(C(N)=O)cccc2n1-c1nc2c(c(NCc3ccccc3)n1)COCC2] | 1-[4-(benzylamino)-5H,7H,8H-pyrano[4,3-d]pyrimidin-2-yl]-2-ethyl-1H-indole-4-carboxamide | ** | * | |
| 114 | 10 | 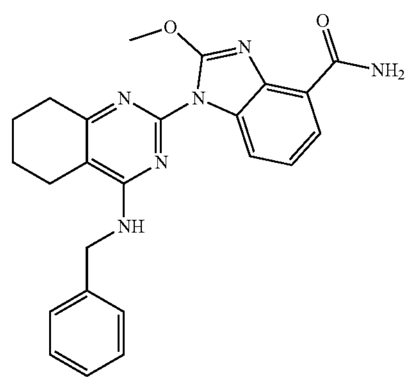 [SMILES: COc1nc2c(C(N)=O)cccc2n1-c1nc2c(c(NCc3ccccc3)n1)CCCC2] | 1-[4-(benzylamino)-5,6,7,8-tetrahydroquinazolin-2-yl]-2-methoxy-1H-1,3-benzodiazole-4-carboxamide | **** | * | * |
| 115 | | 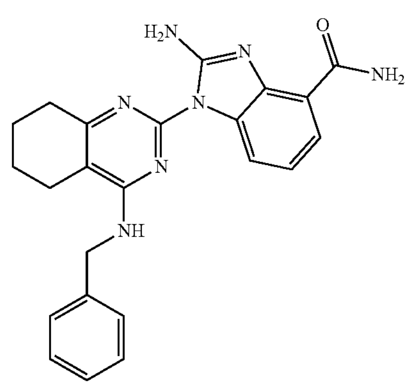 [SMILES: NC(=O)c1cccc2c1nc(N)n2-c1nc2c(c(NCc3ccccc3)n1)CCCC2] | 2-amino-1-[4-(benzylamino)-5,6,7,8-tetrahydroquinazolin-2-yl]-1H-1,3-benzodiazole-4-carboxamide | ** | | |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 116 | | 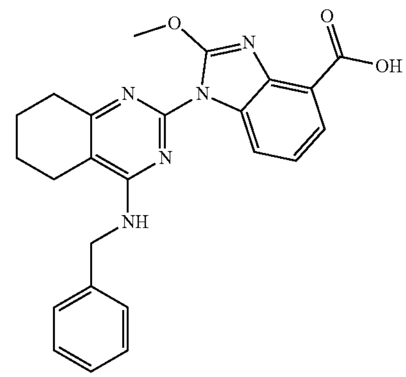 [SMILES: COc1nc2c(C(=O)O)cccc2n1-c1nc2c(c(NCc3ccccc3)n1)CCCC2] | 1-[4-(benzylamino)-5,6,7,8-tetrahydroquinazolin-2-yl]-2-methoxy-1H-1,3-benzodiazole-4-carboxylic acid | **** | | |
| 117 | | 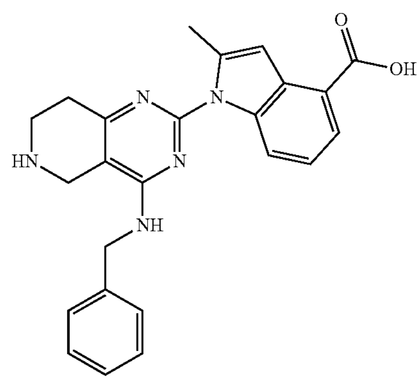 [SMILES: Cc1cc2c(C(=O)O)cccc2n1-c1nc2c(c(NCc3ccccc3)n1)CNCC2] | 1-[4-(benzylamino)-5H,6H,7H,8H-pyrido[4,3-d]pyrimidin-2-yl]-2-methyl-1H-indole-4-carboxylic acid | *** | | |
| 118 | | 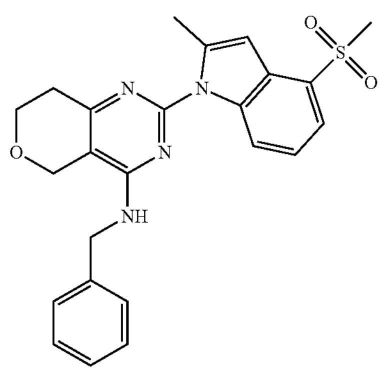 [SMILES: Cc1cc2c(S(C)(=O)=O)cccc2n1-c1nc2c(c(NCc3ccccc3)n1)COCC2] | N-benzyl-2-(4-methanesulfonyl-2-methyl-1H-indol-1-yl)-5H,7H,8H-pyrano[4,3-d]pyrimidin-4-amine | ** | * | |
| 119 | | 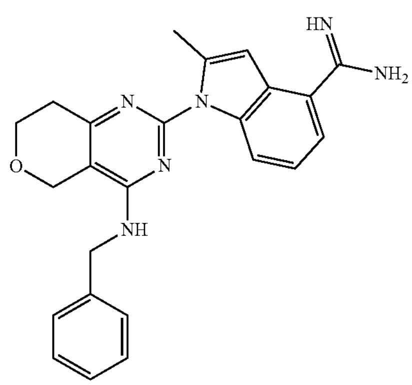 [SMILES: Cc1cc2c(C(=N)N)cccc2n1-c1nc2c(c(NCc3ccccc3)n1)COCC2] | 1-[4-(benzylamnino)-5H,7H,8H-pyrano[4,3-d]pyrimidin-2-yl]-2-methyl-1H-indole-4-carboximidamide | * | | |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 120 | 16 | 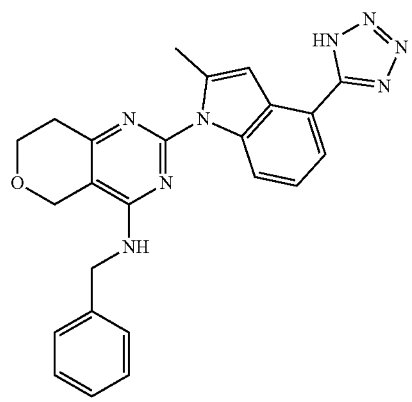 [SMILES: Cc1cc2c(-c3nnn[nH]3)cccc2n1-c1nc2c(c(NCc3ccccc3)n1)COCC2] | N-benzyl-2-[2-methyl-4-(1H-1,2,3,4-tetrazol-5-yl)-1H-indol-1-yl]-5H,7H,8H-pyrano[4,3-d]pyrimidin-4-amine | **** | | ND |
| 121 | | 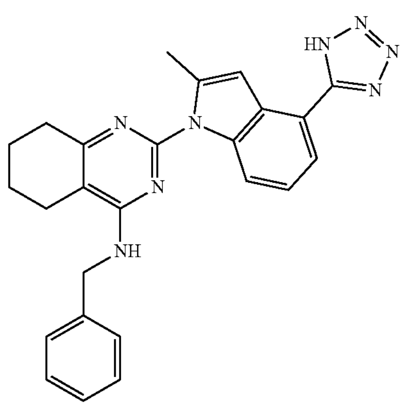 [SMILES: Cc1cc2c(-c3nnn[nH]3)cccc2n1-c1nc2c(c(NCc3ccccc3)n1)CCCC2] | N-benzyl-2-[2-methyl-4-(1H-1,2,3,4-tetrazol-5-yl)-1H-indol-1-yl]-5,6,7,8-tetrahydroquinazolin-4-amine | **** | | |
| 122 | | 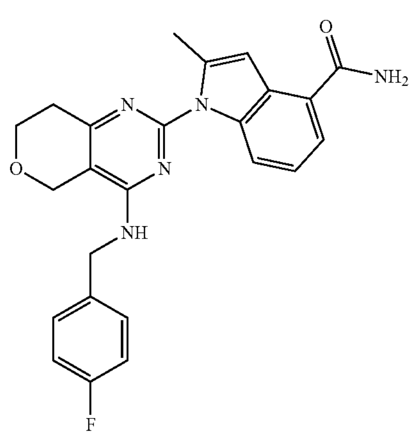 [SMILES: Cc1cc2c(C(N)=O)cccc2n1-c1nc2c(c(NCc3ccc(F)cc3)n1)COCC2] | 1-(4-{[(4-fluorophenyl)methyl]amino}-5H,7H,8H-pyrano[4,3-d]pyrimidin-2-yl)-2-methyl-1H-indole-4-carboxamide | *** | * | |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 123 | | 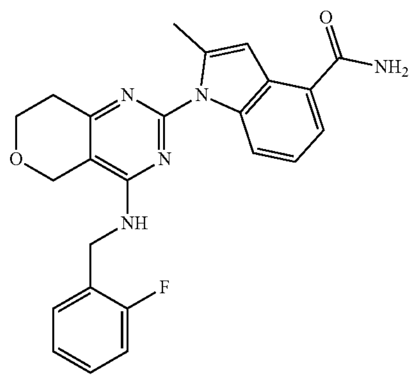 [SMILES: Cc1cc2c(C(N)=O)cccc2n1-c1nc2c(c(NCc3ccccc3F)n1)COCC2] | 1-(4-{[(2-fluorophenyl)methyl]amino}-5H,7H,8H-pyrano[4,3-d]pyrimidin-2-yl)-2-methyl-1H-indole-4-carboxamide | *** | * | |
| 124 | 17 | 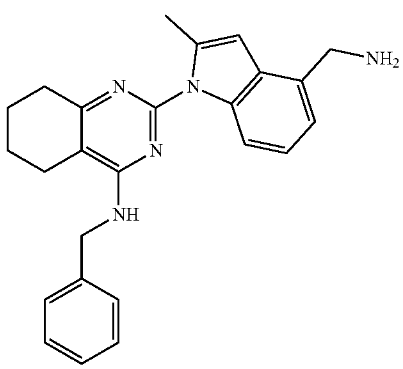 [SMILES: Cc1cc2c(CN)cccc2n1-c1nc2c(c(NCc3ccccc3)n1)CCCC2] | 2-[4-(aminomethyl)-2-methyl-1H-indol-1-yl]-N-benzyl-5,6,7,8-tetrahydroquinazolin-4-amine | *** | * | |
| 125 | | 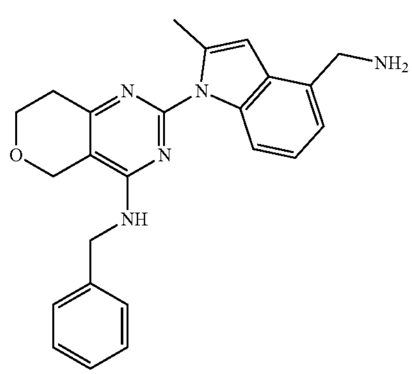 [SMILES: Cc1cc2c(CN)cccc2n1-c1nc2c(c(NCc3ccccc3)n1)COCC2] | 2-[4-(aminomethyl)-2-methyl-1H-indol-1-yl]-N-benzyl-5H,7H,8H-pyrano[4,3-d]pyrimidin-4-amine | ND | * | |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 126 | | 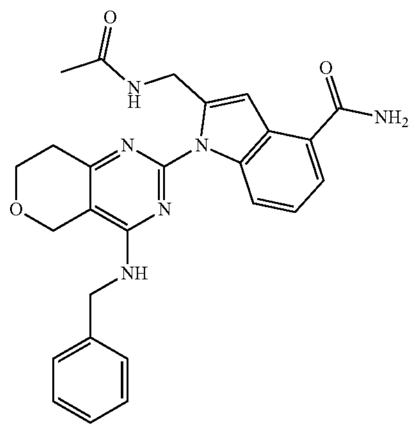 [SMILES: CC(=O)NCc1cc2c(C(N)=O)cccc2n1-c1nc2c(c(NCc3ccccc3)n1)COCC2] | 1-[4-(benzylamino)-5H,7H,8H-pyrano[4,3-d]pyrimidin-2-yl]-2-[(carbamoylamino)methyl]-1H-indole-4-carboxamide | ** | | |
| 127 | | 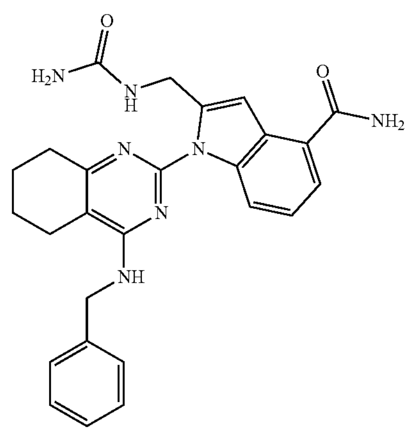 [SMILES: NC(=O)NCc1cc2c(C(N)=O)cccc2n1-c1nc2c(c(NCc3ccccc3)n1)CCCC2] | 1-[4-(benzylamino)-5,6,7,8-tetrahydroquinazolin-2-yl]-2-[(carbamoylamino)methyl]-1H-indole-4-carboxamide | *** | | |
| 128 | | 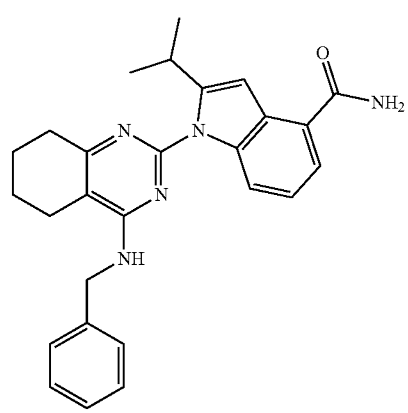 [SMILES: CC(C)c1cc2c(C(N)=O)cccc2n1-c1nc2c(c(NCc3ccccc3)n1)CCCC2] | 1-[4-(benzylamino)-5,6,7,8-tetrahydroquinazolin-2-yl]-2-(propan-2-yl)-1H-indole-4-carboxamide | *** | * | |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 129 | | 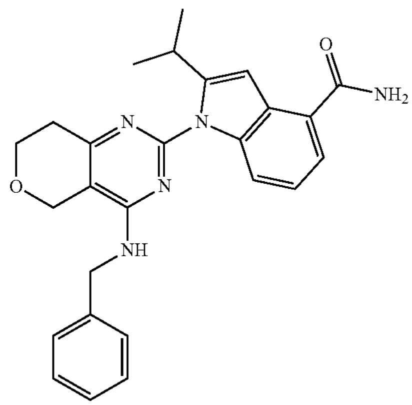 [SMILES: CC(C)c1cc2c(C(N)=O)cccc2n1-c1nc2c(c(NCc3ccccc3)n1)COCC2] | 1-[4-(benzylamino)-5H,7H,8H-pyrano[4,3-d]pyrimidin-2-yl]-2-(propan-2-yl)-1H-indole-4-carboxamide | * | ND | ND |
| 130 | 19 | 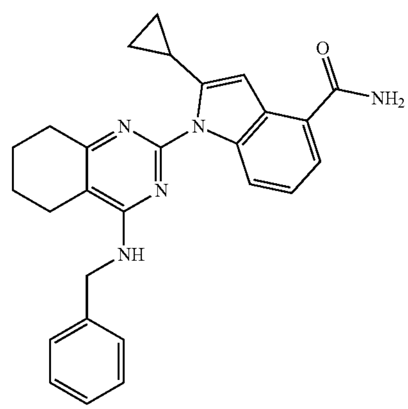 [SMILES: NC(=O)c1cccc2c1cc(C1CC1)n2-c1nc2c(c(NCc3ccccc3)n1)CCCC2] | 1-[4-(benzylamino)-5,6,7,8-tetrahydroquinazolin-2-yl]-2-cyclopropyl-1H-indole-4-carboxamide | **** | * | ND |
| 131 | 18 | 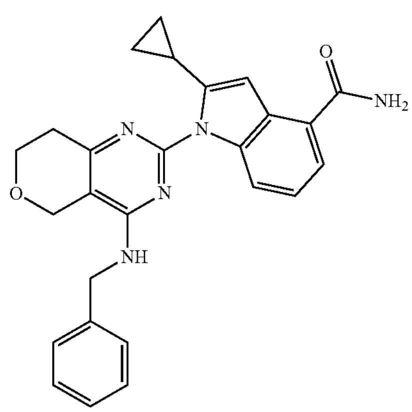 [SMILES: NC(=O)c1cccc2c1cc(C1CC1)n2-c1nc2c(c(NCc3ccccc3)n1)COCC2] | 1-[4-(benzylamino)-5H,7H,8H-pyrano[4,3-d]pyrimidin-2-yl]-2-cyclopropyl-1H-indole-4-carboxamide | **** | | ND |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 132 | 11 | 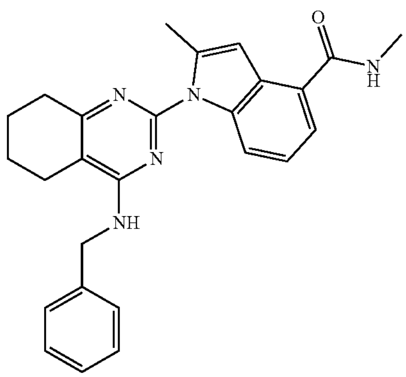 [SMILES: CNC(=O)c1cccc2c1cc(C)n2-c1nc2c(c(NCc3ccccc3)n1)CCCC2] | 1-[4-(benzylamino)-5,6,7,8-tetrahydroquinazolin-2-yl]-N-methyl-2-methyl-1H-indole-4-carboxamide | **** | * | |
| 133 | | 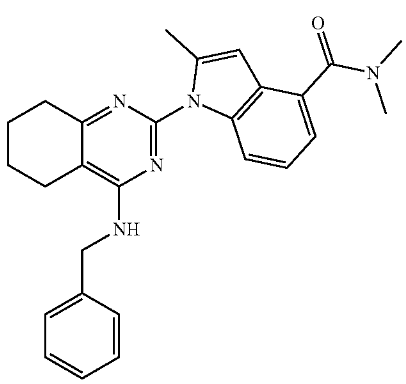 [SMILES: Cc1cc2c(C(=O)N(C)C)cccc2n1-c1nc2c(c(NCc3ccccc3)n1)CCCC2] | 1-(4-(benzylamino)-5,6,7,8-tetrahydroquinazolin-2-yl)-N,N,2-trimethyl-1H-indole-4-carboxamide | | * | |
| 134 | | 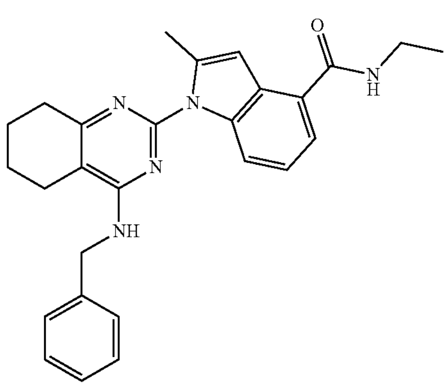 [SMILES: CCNC(=O)c1cccc2c1cc(C)n2-c1nc2c(c(NCc3ccccc3)n1)CCCC2] | 1-[4-(benzylamino)-5,6,7,8-tetrahydroquinazolin-2-yl]-N-ethyl-2-methyl-1H-indole-4-carboxamide | **** | * | |

TABLE III-continued

| Biological Example Number | Synthetic Example Number | Structure | IUPAC | p97 IC50 **** < 30 nM *** < 100 nM ** < 300 nM * < 1000 nM | A549 K48 Cell Intensity IC50 * < 10 uM | A549 LC3 Increase * > 50% relative to standard |
|---|---|---|---|---|---|---|
| 135 | | 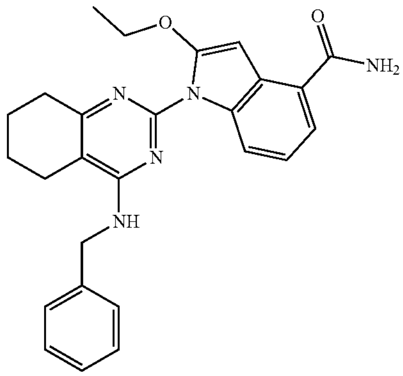 [SMILES: CCOc1cc2c(C(N)=O)cccc2n1-c1nc2c(c(NCc3ccccc3)n1)CCCC2] | 1-[4-(benzylamino)-5,6,7,8-tetrahydroquinazolin-2-yl]-2-ethoxy-1H-indole-4-carboxamide | **** | | |
| 136 | | 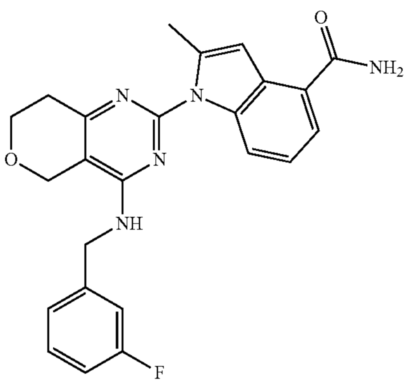 [SMILES: Cc1cc2c(C(N)=O)cccc2n1-c1nc2c(c(NCc3cccc(F)c3)n1)COCC2] | 1-(4-{[(3-fluorophenyl)methyl]amino}-5H,7H,8H-pyrano[4,3-d]pyrimidin-2-yl)-2-methyl-1H-indole-4-carboxamide | **** | | * |
| 137 | | 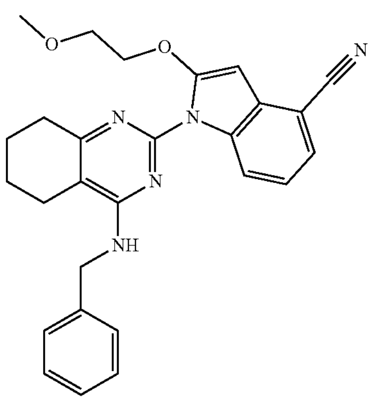 [SMILES: COCCOc1cc2c(C#N)cccc2n1-c1nc2c(c(NCc3ccccc3)n1)CCCC2] | 1-[4-(benzylamino)-5,6,7,8-tetrahydroquinazolin-2-yl]-2-(2-methoxyethoxy)-1H-indole-4-carbonitrile | **** | | * |

Therapeutic and Physiological Treatment

In certain embodiments, the invention is directed to methods of inhibiting p97. Preferred fused pyrimidine compounds and substituted quinazoline compounds for use in the methods disclosed herein bind to the active site of p97, e.g., noncovalently or covalently. In certain such embodiments, the covalent binding may be reversible or irreversible.

The compounds of the invention and their pharmaceutical compositions are capable of acting as "inhibitors" of p97 which means that they are capable of blocking or reducing the activity of an enzyme, for example, inhibition of various activities of p97. An inhibitor can act with competitive, uncompetitive, or noncompetitive inhibition. An inhibitor can bind reversibly or irreversibly, and therefore the term includes compounds that are suicide the enzyme, or it can cause a conformational change elsewhere on the enzyme.

The compounds of the invention and their pharmaceutical compositions function as therapeutic agents in that they are capable of preventing, ameliorating, modifying and/or affecting a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The ability to prevent, ameliorate, modify and/or affect in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The compounds of the invention and their pharmaceutical compositions are capable of functioning prophylacticly and/or therapeutically and include administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The compounds of the invention and their pharmaceutical compositions are capable of prophylactic and/or therapeutic treatments. If a compound or pharmaceutical composition is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof). As used herein, the term "treating" or "treatment" includes reversing, reducing, or arresting the symptoms, clinical signs, and underlying pathology of a condition in manner to improve or stabilize a subject's condition.

The compounds of the invention and their pharmaceutical compositions can be administered in "therapeutically effective amounts" with respect to the subject method of treatment. The therapeutically effective amount is an amount of the compound(s) in a pharmaceutical composition which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

Administration

Compounds prepared as described herein can be administered in various forms, depending on the disorder to be treated and the age, condition, and body weight of the patient, as is well known in the art. For example, where the compounds are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means, and if desired, the active ingredient may be mixed with any conventional additive or excipient, such as a binder, a disintegrating agent, a lubricant, a corrigent, a solubilizing agent, a suspension aid, an emulsifying agent, a coating agent, a cyclodextrin, and/or a buffer. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses. The amount of active ingredient which can be combined with a carrier material to produce a single dosage form will generally be that amount of the compound which produces a therapeutic effect.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A "pharmaceutically acceptable carrier" is a pharmaceutically acceptable material, composition, or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted (3-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions. Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert matrix, such as gelatin and glycerin, or sucrose and acacia) and/or as mouthwashes, and the like, each containing a predetermined amount of a compound of the invention as an active ingredient. A composition may also be administered as a bolus, electuary, or paste.

In solid dosage form for oral administration (capsules, tablets, pills, dragees, powders, granules, and the like), a compound of the invention is mixed with one or more pharmaceutically acceptable carriers, such as sodium citrate or dicalcium phosphate, and/or any of the following:

(1) fillers or extenders, such as starches, cyclodextrins, lactose, sucrose, glucose, mannitol, and/or silicic acid;
(2) binders, such as, for example, carboxymethylcellulose, alginates, gelatin, polyvinyl pyrrolidone, sucrose, and/or acacia;
(3) humectants, such as glycerol;
(4) disintegrating agents, such as agar-agar, calcium carbonate, potato or tapioca starch, alginic acid, certain silicates, and sodium carbonate;
(5) solution retarding agents, such as paraffin;
(6) absorption accelerators, such as quaternary ammonium compounds;
(7) wetting agents, such as, for example, acetyl alcohol and glycerol monostearate; (8) absorbents, such as kaolin and bentonite clay;
(9) lubricants, such a talc, calcium stearate, magnesium stearate, solid polyethylene glycols, sodium lauryl sulfate, and mixtures thereof; and
(10) coloring agents. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered inhibitor(s) moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner.

Examples of embedding compositions which can be used include polymeric substances and waxes. A compound of the invention can also be in micro-encapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more inhibitor(s) with one or more suitable nonirritating excipients or carriers comprising, for example, cocoa butter, polyethylene glycol, a suppository wax or a salicylate, which is solid at room temperature, but liquid at body temperature and, therefore, will melt in the rectum or vaginal cavity and release the active agent.

Formulations which are suitable for vaginal administration also include pessaries, tampons, creams, gels, pastes, foams, or spray formulations containing such carriers as are known in the art to be appropriate.

Dosage forms for the topical or transdermal administration of an inhibitor(s) include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required.

The ointments, pastes, creams, and gels may contain, in addition to a compound of the invention, excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to a compound of the invention, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

A compound of the invention can be alternatively administered by aerosol. This is accomplished by preparing an aqueous aerosol, liposomal preparation, or solid particles containing the composition. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of a compound of the invention together with conventional pharmaceutically acceptable carriers and stabilizers. The carriers and stabilizers vary with the requirements of the particular composition, but typically include nonionic surfactants (Tweens, Pluronics, sorbitan esters, lecithin, Cremophors), pharmaceutically acceptable co-solvents such as polyethylene glycol, innocuous proteins like serum albumin, oleic acid, amino acids such as glycine, buffers, salts, sugars, or sugar alcohols. Aerosols generally are prepared from isotonic solutions.

Transdermal patches have the added advantage of providing controlled delivery of a compound of the invention to the body. Such dosage forms can be made by dissolving or dispersing the agent in the proper medium. Absorption enhancers can also be used to increase the flux of the inhibitor(s) across the skin. The rate of such flux can be controlled by either providing a rate controlling membrane or dispersing the inhibitor(s) in a polymer matrix or gel.

Pharmaceutical compositions of this invention suitable for parenteral administration comprise one or more compounds of the invention in combination with one or more pharmaceutically acceptable sterile aqueous or nonaqueous solutions, dispersions, suspensions or emulsions, or sterile powders which may be reconstituted into sterile injectable solutions or dispersions just prior to isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a compound of the invention, it is desirable to slow the absorption of the compound from subcutaneous or intramuscular injection. For example, delayed absorption of a parenterally administered drug form is accomplished by dissolving or suspending the drug in an oil vehicle.

Injectable depot forms are made by forming microencapsule matrices of inhibitor(s) in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

The pharmaceutical compositions may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion.

The pharmaceutical compositions of the invention may be "systemically administered" "administered systemically," "peripherally administered" and "administered peripherally" meaning the administration of a ligand, drug, or other material other than directly into the central nervous system, such that it enters the patient's system and thus, is subject to metabolism and other like processes, for example, subcutaneous administration.

The compound(s) of the invention may be administered to humans and other animals for therapy by any suitable route of administration, including orally, nasally, as by, for example, a spray, rectally, intravaginally, parenterally, intracisternally, and topically, as by powders, ointments or drops, including buccally and sublingually.

Regardless of the route of administration selected, the compound(s) of the invention, which may be used in a suitable hydrated form, and/or the pharmaceutical compositions of the present invention, are formulated into pharmaceutically acceptable dosage forms by conventional methods known to those of skill in the art.

Actual dosage levels of the compound(s) of the invention in the pharmaceutical compositions of this invention may be varied so as to obtain an amount of the active ingredient which is effective to achieve the desired therapeutic response for a particular patient, composition, and mode of administration, without being toxic to the patient.

The concentration of a compound of the invention in a pharmaceutically acceptable mixture will vary depending on several factors, including the dosage of the compound to be administered, the pharmacokinetic characteristics of the compound(s) employed, and the route of administration.

In general, the compositions of this invention may be provided in an aqueous solution containing about 0.1-10% w/v of a compound disclosed herein, among other substances, for parenteral administration. Typical dose ranges are from about 0.01 to about 50 mg/kg of body weight per day, given in 1-4 divided doses. Each divided dose may contain the same or different compounds of the invention. The dosage will be an effective amount depending on several factors including the overall health of a patient, and the formulation and route of administration of the selected compound(s).

Another aspect of the invention provides a conjoint therapy wherein one or more other therapeutic agents are administered with the compounds and compositions of the invention. Such conjoint treatment will achieve the same or similar treatment accounting for the additive effects of the conjoined therapeutic agents other than the compounds of the invention.

In certain embodiments, a compound of the invention is conjointly administered with one or more proteasome inhibitor(s). In certain embodiments, a compound of the invention is conjointly administered with a chemotherapeutic. Suitable chemotherapeutics may include, natural products such as vinca alkaloids (i.e., vinblastine, vincristine, and vinorelbine), paclitaxel, epidipodophyllotoxins (i.e., etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates (busulfan), nitrosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine); aromatase inhibitors carboplatin), procarbazine, hydroxyurea, mitotane, aminoglutethimide; hormones (i.e. estrogen) and hormone agonists such as leutinizing hormone releasing hormone (LHRH) agonists (goserelin, leuprolide and triptorelin). Other chemotherapeutic agents may include mechlorethamine, camptothecin, ifosfamide, tamoxifen, raloxifene, gemcitabine, navelbine, or any analog or derivative variant of the foregoing.

In certain embodiments, a compound of the invention is conjointly administered with a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, parametasone, prednicarbate, prednisolone, prednisolone 25-diethylaminoacetate, prednisolone, sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof.

In certain embodiments, a compound of the invention is conjointly administered with an immunotherapeutic agent. Suitable immunotherapeutic agents may include, but are not limited to, cyclosporine, thalidomide, and monoclonal antibodies. The monoclonal antibodies can be either naked or conjugated such as rituximab, tositumomab, alemtuzumab, epratuzumab, ibritumomab tiuxetan, gemtuzumab ozogamicin, bevacizumab, cetuximab, erlotinib and trastuzumab.

TREATMENT OF CANCER

Exemplary forms of cancer which may be treated by the methods of the invention include, but are not limited to, prostate cancer, bladder cancer, lung cancer (including either small cell or non-small cell cancer), colon cancer, kidney cancer, liver cancer, breast cancer, cervical cancer, endometrial or other uterine cancer, ovarian cancer, testicular cancer, cancer of the penis, cancer of the vagina, cancer of the urethra, gall bladder cancer, esophageal cancer, or pancreatic cancer.

Additional exemplary forms of cancer which may be treated by the methods of the invention include, but are not limited to, cancer of skeletal or smooth muscle, stomach cancer, cancer of the small intestine, cancer of the salivary gland, anal cancer, rectal cancer, tyroid cancer, parathyroid cancer, pituitary cancer, and nasopharyngeal cancer.

The compounds of the present invention and their salts and solvates, thereof, may be employed alone or in combination with other therapeutic agents for the treatment of the diseases or conditions associated with inappropriate P97 activity.

Additional diseases that can be treated according to the methods of the invention include in addition to cancer, auto-immune disorders, metabolic diseases ( ), infection diseases, neurological diseases, graft versus host disease and other hereditary diseases outlined here: abeta-lipoproteinema, acerulopasminemia, alpha-1-antichymotrypsin (ACT) deficiency, aspartylglucosaminuria, autosomal dominant retinitis pigmentosa, brugada syndrome, Charcot-Marie-Tooth syndrome, congenital adrenal hyperplasia, congenital chloride diarrhea, congenital hypothyroidism, congenital long QT syndrome, congenital nephritic syndrome, congenital sucrase-isomaltase deficiency, Crigler-Najjar type II, cystic fibrosis, diabetes mellitus, diastrophic displasia, Dubin-Johnson syndrome, Fabri disease, familial chylomicronemia, familial glucocorticoid deficiency, familial hypercholesterolemia, Gaucher disease, heavy chain disease, hereditary emphysema, hereditary emphysema with liver injury, hereditary hemochromatosis, hereditary hypofibrinogenemia, hereditary myeloperoxidase, hereditary spherocytosis, hirschprung disease, hypogonadotropic hypogonadism, infantile systemic hyalinosis, infentile neuronal ceroid lipofuscinosis, laron syndrome, liver failure, marfan syndrome, medullary cystic kidney disease, familial juvenile hyperuricemic nephropathy, Menkes disease, nephrogenic diabetes, neurohypophyseal diabetes insipidus, oculocutaneous albinism, osteogenesis imperfect, Pelizaeus-Merzbacher disease, Pendred syndrome, persistent hyperinsulinemic hypoglycemia of infancy, primary hypothyroidism, Protein C deficiency, pseudoachondropla with multiple epiphyseal dysplasia, severe congenital neutropenia, Stargardt-like macular dystrophy, steroid-resistant nephrotic syndrome, Tay-Sachs, Type I hereditary angioedema, tyroxine binding globulin deficiency, von Willebrand disease type IIA, X-linked Charot-Marie-Tooth disease, X-linked hypophosphatemia, Alzheimer disease autosomal recessive juvenile parkinsonism, combined factors V and VIII deficiency, cranio-lenticulo-sutural dysplasia, hypotonia and dysmorphism, inclusion body myopathy Paget's disease of the bone and fronto-temporal dementia (IBMPFD), lipid absorption disorders, Marinesco-Sjoegren syndrome, Parkinson, polycystic liver disease, spondyloepiphyseal dysplasia tarda, Walcott-Rallison syndrome and Lou Gehrig's disease (ALS).

In various embodiments, compounds of the invention may be used to treat neoplastic growth, angiogenesis, infection, inflammation, immune-related diseases, ischemia and reperfusion injury, multiple sclerosis, rheumatoid arthritis, neurodegenerative conditions, or psoriasis.

Neoplastic growth may include cancer. Suitably, the present invention relates to a method for treating or lessening the severity of a cancer selected from: brain (gliomas), glioblastomas, breast, Wilm's tumor, Ewing's sarcoma, rhabdomyosarcoma, ependymoma, medulloblastoma, colon, head and neck, kidney, lung, liver, melanoma, ovarian, pancreatic, prostate, sarcoma, osteosarcoma, giant cell tumor of bone, thyroid, lymphoblastic T cell leukemia, chronic myelogenous leukemia, chronic lymphocytic leukemia, Hairy-cell leukemia, acute lymphoblastic leukemia, acute myelogenous leukemia, chronic neutrophilic leukemia, acute lymphoblastic T cell leukemia, plasmacytoma, immunoblastic large cell leukemia, mantle cell leukemia, multiple myeloma megakaryoblastic leukemia, multiple myeloma, acute megakaryocytic leukemia, promyelocytic leukemia, erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, lung cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

In various embodiments, the cancer is selected from brain cancer (gliomas), glioblastomas, breast cancer, colon cancer, head and neck cancer, kidney cancer, lung cancer, liver cancer, melanoma, ovarian cancer, pancreatic cancer, prostate cancer, sarcoma and thyroid cancer.

In various embodiments, the cancer to be treated is associated with the proteasome. See Voorhees et al., The Proteasome as a Target for Cancer Therapy, Clinical Cancer Research, vol. 9, 6316-6325, December 2003, incorporated by reference in its entirety. In various embodiments, the cancer is associated with a particular target, such as NFkB, p44/42 MAPK, P-gp, TopI, TopIIalpha.

In various embodiments, the cancer is a solid tumor. In various embodiments, the cancer is selected from multiple myeloma, metastatic breast cancer, non-small cell lung cancer, prostate cancer, advanced colorectal cancer, ovarian or primary peritoneal carcinoma, hormone refractory prostate cancer, squamous cell carcinoma of the head and neck, metastatic pancreatic adenocarcinoma, gastroesophageal junction or stomach, or non-Hodgkin's lymphoma.

A method of using the compounds described herein for treating a disorder characterized by an inappropriate level of proteasome activity, or in which a reduction of the normal level of proteasome activity yields a clinical benefit. This disorder can include cancer or immune disorders characterized by excessive cell proliferation or cellular signaling. Among cancers, this includes human cancers that overexpress c-Myc or express an oncogenic form of the K-Ras protein.

Neurodegenerative diseases and conditions may include without limitation stroke, ischemic damage to the nervous system, neural trauma (e.g., percussive brain damage, spinal cord injury, and traumatic damage to the nervous system), multiple sclerosis and other immune-mediated neuropathies (e.g., Guillain-Barre syndrome and its variants, acute motor axonal neuropathy, acute inflammatory demyelinating polyneuropathy, and Fisher Syndrome), HIV/AIDS dementia complex, axonomy, diabetic neuropathy, Parkinson's disease, Huntington's disease, ALS, multiple sclerosis, bacterial, parasitic, fungal, and viral meningitis, encephalitis, vascular dementia, multi-infarct dementia, Lewy body dementia, frontal lobe dementia such as Pick's disease, subcortical dementias (such as Huntington or progressive supranuclear palsy), focal cortical atrophy syndromes (such as primary aphasia), metabolic-toxic dementias (such as chronic hypothyroidism or B12 deficiency), and dementias caused by infections (such as syphilis or chronic meningitis). Compounds of the invention may be used to treat Alzheimer's disease, including administering to a subject an effective amount of an agent or composition (e.g., pharmaceutical composition) disclosed herein.

Compounds of the invention may be used to treat cachexia and muscle-wasting diseases. Compounds of the invention may be used to treat such conditions wherein the condition is related to cancer, chronic infectious diseases, fever, muscle disuse (atrophy) and denervation, nerve injury, fasting, renal failure associated with acidosis, diabetes, and hepatic failure.

Compounds of the invention can be used to treat hyperproliferative conditions such as diabetic retinopathy, macular degeneration, diabetic nephropathy, glomerulosclerosis, IgA nephropathy, cirrhosis, biliary atresia, congestive heart failure, scleroderma, radiation-induced fibrosis, and lung fibrosis (idiopathic pulmonary fibrosis, collagen vascular disease, sarcoidosis, interstitial lung diseases and extrinsic lung disorders). The treatment of burn victims is often hampered by fibrosis, thus, an additional embodiment of the application is the topical or systemic administration of the inhibitors to treat burns. Wound closure following surgery is often associated with disfiguring scars, which may be prevented by inhibition of fibrosis. Thus, in certain embodiments, the application relates to a method for the prevention or reduction of scarring.

Compounds of the invention can be used to treat ischemic conditions or reperfusion injury for example acute coronary syndrome (vulnerable plaques), arterial occlusive disease (cardiac, cerebral, peripheral arterial and vascular occlusions), atherosclerosis (coronary sclerosis, coronary artery disease), infarctions, heart failure, pancreatitis, myocardial hypertrophy, stenosis, and restenosis.

Compounds of the invention can be used for the inhibition of TNFalpha to prevent and/or treat septic shock.

Compounds of the invention can be used for inhibiting antigen presentation in a cell, including exposing the cell to an agent described herein. A compound of the invention may be used to treat immune-related conditions such as allergy, asthma, organ/tissue rejection (graft-versus-host disease), and auto-immune diseases, including, but not limited to, lupus, rheumatoid arthritis, psoriasis, multiple sclerosis, and inflammatory bowel diseases (such as ulcerative colitis and Crohn's disease). Thus, a further embodiment is a method for modulating the immune system of a subject (e.g., inhibiting transplant rejection, allergies, auto-immune diseases, and asthma), including administering to the subject an effective amount of a compound of the invention.

Compounds of the invention can be used in methods for altering the repertoire of antigenic peptides produced by the proteasome or other protein assembly with multicatalytic activity.

Compounds of the invention can be used in methods for inhibiting IKB-alpha degradation, including contacting the cell with an agent identified herein. A further embodiment is a method for reducing the cellular content of NF-KB in a cell, muscle, organ, or subject, including contacting the cell, muscle, organ, or subject with a compound of the invention.

Compounds of the invention can be used in methods for affecting cyclin-dependent eukaryotic cell cycles. Compounds of the invention can be used in methods for treating a proliferative disease in a subject (e.g., cancer, psoriasis, or restenosis). Compounds of the invention can be used for treating cyclin-related inflammation in a subject.

One embodiment is a method for treating p53-related apoptosis, including administering to a subject an effective amount of a compound of the invention.

In another embodiment, the agents of the present application are useful for the treatment of a parasitic infection, such as infections caused by protozoan parasites. In certain such embodiments, the agents are useful for the treatment of parasitic infections in humans caused by a protozoan parasite selected from *Plasmodium* sps., *Trypanosoma* sps., *Leishmania* sps., *Pneumocystis carinii, Toxoplasma gondii, Entamoeba histolytica, Entamoeba invadens*, and *Giardia lamblia*. In certain embodiments, the agents are useful for the treatment of parasitic infections in animals and livestock caused by a protozoan parasite selected from *Plasmodium hermani, Cryptosporidium* sps., *Echinococcus granulosus, Eimeria tenella, Sarcocystis neurona*, and *Neurospora crassa*. Other compounds useful as proteasome inhibitors in the treatment of parasitic diseases are described in WO 98/10779, which is incorporated herein in its entirety.

In particular, the methods of treatment include inhibiting, arresting, ameliorating, minimizing and/or eliminating malconditions associated with the inability of cells to metabolize, degrade or otherwise remove ubiquitin tagged proteins and peptides because the tag has been cleaved, degraded, removed or otherwise rendered disfunctional as a result of P97 metalloprotease domain activity. Included are methods in which a human disorder characterized by abnormal regulatory peptide degradation resulting in excessive cell proliferation or cell signaling. The methods are directed to administration of an effective amount of a compound or pharmaceutical formulation disclosed above so that the abnormal regulatory peptide degradation is ameliorated, reduced or inhibited. In particular, the human disorders include a cancer or immune disorder, a cancer resulting from overexpression of c-Myc or expression of an oncogenic form of the K-Ras protein. The methods also include inhibition or amelioration of P97 metalloprotease domain activity in a human patient suffering from abnormal P97 metalloprotease domain activity on ubiquitin modified proteins. As described above, these methods involve administering to the patient an effective amount of a compound or pharmaceutical formulation disclosed above so that the abnormal P97 metalloprotease domain activity is ameliorated, reduced or inhibited.

DIAGNOSTICS

Various cellular proteins are subject to proteolytic processing during maturation or activation. The compositions identified herein can also be useful as diagnostic agents (e.g., in diagnostic kits or for use in clinical laboratories) for screening for proteins (e.g., enzymes, transcription factors) processed by hydrolases, including the proteasome. The agents are also useful as research reagents for specifically binding the X/MB 1 subunit or alpha-chain and inhibiting the proteolytic activities associated with it. For example, the activity of (and specific inhibitors of) other subunits of the proteasome can be determined.

Compounds of the invention identified herein can be used to determine whether a cellular, developmental, or physiological process or output is regulated by proteolytic activity. One such method includes obtaining an organism, an intact cell preparation, or a cell extract; exposing the organism, cell preparation, or cell extract to an agent identified herein; exposing the agent-exposed organism, cell preparation, or cell extract to a signal, and monitoring the process or output. See, for example, U.S. Pat. No. 7,741,432.

The compounds of this invention may used as a part of a diagnostic assay. For instance cells from a patient may be obtained and an assay may be performed to determine whether the compounds of the invention are likely to be effective therapeutic compounds for that patient. The cells obtained from the patient can be for instance cancerous cells from a tumor. The cells can be cultured and compounds of the invention can be applied to determine how the cancerous cells respond.

The Diagnostics aspect of the invention also includes an assay for the determination of inhibition of P97 activity. The assay involves combining a P97 enzymatic material with a protein substrate and determining whether a potential inhibitory candidate will function in this assay to lessen the enzymatic activity. The P97 enzymatic material is either a standard or taken from a patient's cells. The protein substrate similarly is either standard or taken from a patient's cells. In particular, the protein substrate is selected from the group consisting of a protein modified by a ubiquitin, a protein modified by a ubiquitin-like modifier and a protein modified by a ubiquitin chain that can be isolated from a patient's cells. The combination of the P97 enzymatic material and the protein substrate produces an enzymatic medium. For this medium, the protein substrate is modified with a tag that is detectable by measurement of molecular weight, spectroscopic interaction or chromatographic $R_f$ determination, Following the isolation and tagging, the enzymatic medium is manipulated to conduct a first measurement of the enzymatic medium relative to the protein substrate alone wherein the first measurement is made by a detection of the tag.

Following the first measurement procedure, a potential inhibitory candidate is combined with the tagged protein substrate and the P97 enzymatic material is added to produce a candidate medium.

The candidate medium is manipulated to conduct a second measurement of the candidate medium relative to the protein substrate alone wherein the second measurement is made by detection of the tag.

Finally, the ability of the inhibitory candidate to be effective treatment for the patient in need is assessed by comparing the first and second measurements to identify a candidate that demonstrates at least about a 50% inhibition at a concentration of no more than 500 micromolar in the candidate medium, the difference between the first and second measurements being at least about 50% with the second measurement being greater than the first measurement.

ADDITIONAL EMBODIMENTS OF THE COMPOUNDS OF THE INVENTION

Additional embodiments of the compounds of the invention include the following variations of the core scaffold, the Het moiety and the substituents R³ to R⁶, AH, QH, R¹⁰ and R¹¹. Each of these variations can be combined with any other variation as is appropriate for the final structure of the fused pyrimidine or quinazoline desired to form a full fused pyrimidine compound or quinazoline compound of the invention.

Core scaffold embodiments include those depicted in the following table. In addition, core scaffold embodiments relative to the generic formula X given above include:

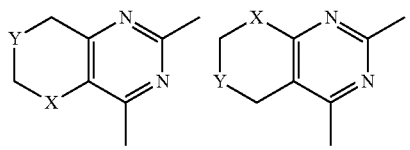

wherein X and Y are independently selected from C, N, O or S. Further embodiments include the following 6:6 bicyclic rings in which X may be S as well as C, N or O. The C, N and O substitutions of X for the 6:6 bicyclic rings without Y are preferred and the C and N substitutions for X without Y in such 6:6 bicyclic rings are especially preferred.

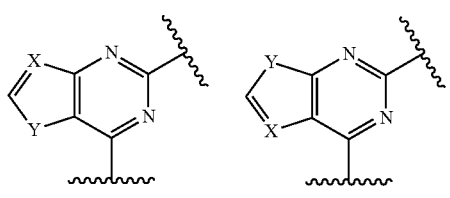

X = C, N; Y = N, O, S     X = C, N; Y = N, O, S

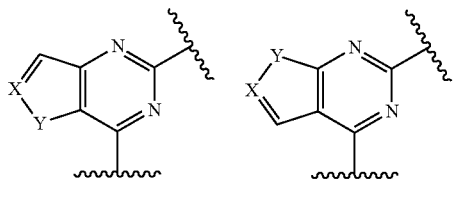

X = C, N; Y = N, O, S     X = C, N; Y = N, O, S

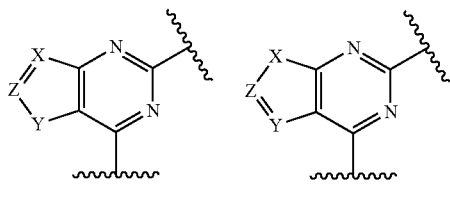

X, Z = C, N; Y = N, O, S     X, Z = C, N; Y = N, O, S

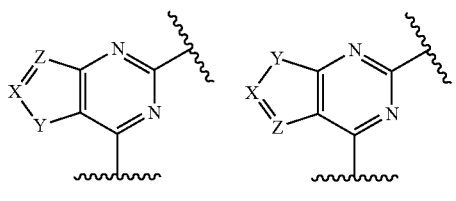

X, Z = C, N; Y = N, O, S     X, Z = C, N; Y = N, O, S

-continued

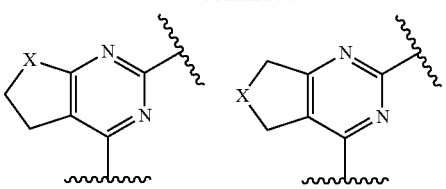

X = C, N, O, S     X = C, N, O, S

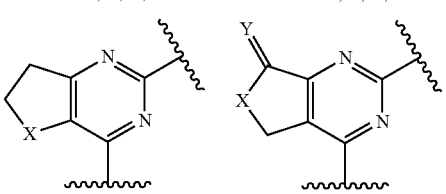

X = C, N, O, S     X = O, N, Y = O, S

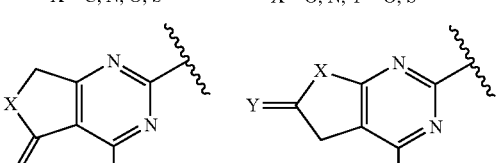

X = O, N, Y = O, S     X = O, N, Y = O, S

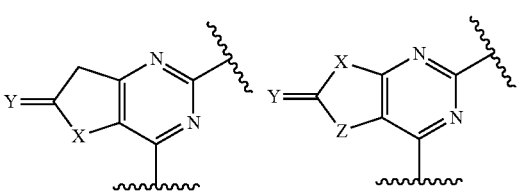

X = O, N, Y = O, S     X, Z = O, N, Y = O, S

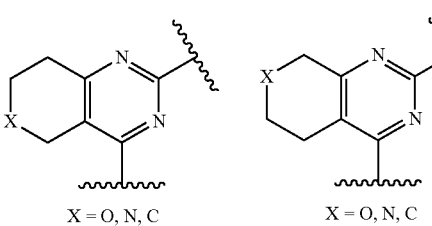

X = O, N, C     X = O, N, C

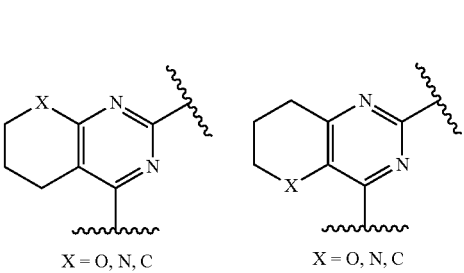

X = O, N, C     X = O, N, C

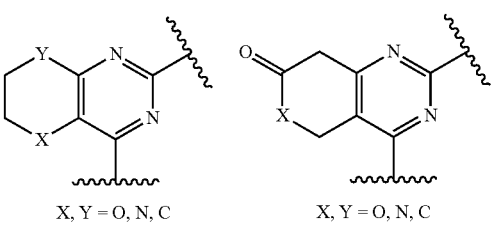

X, Y = O, N, C     X, Y = O, N, C

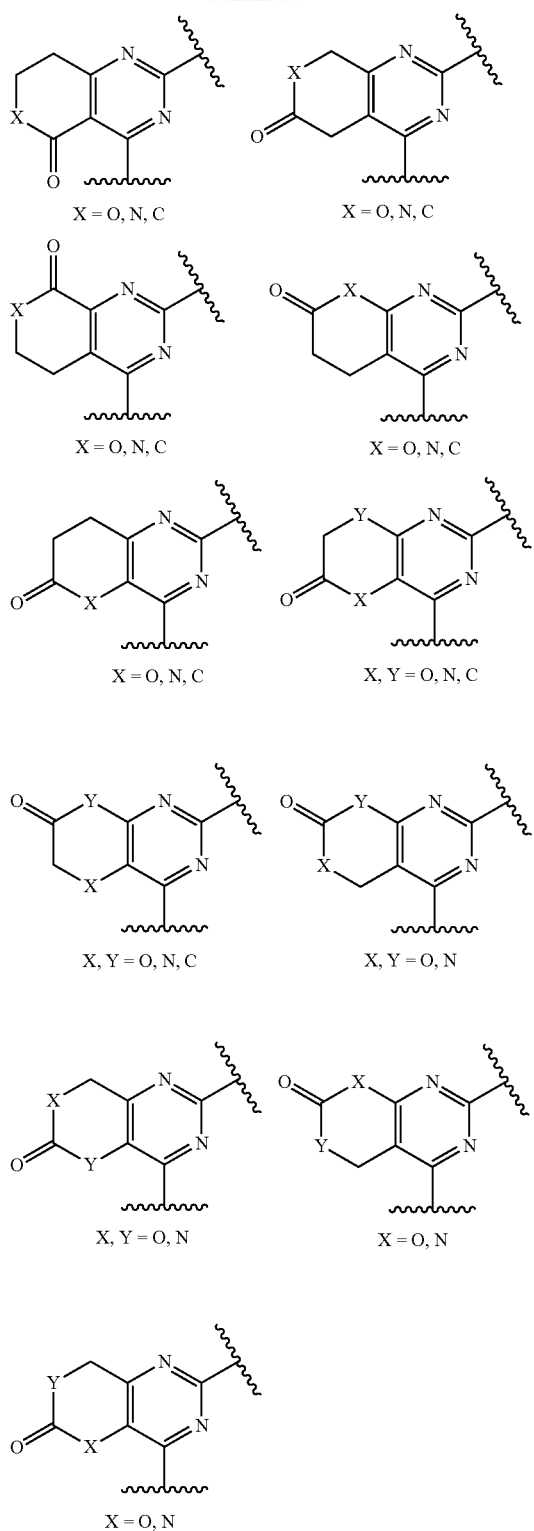

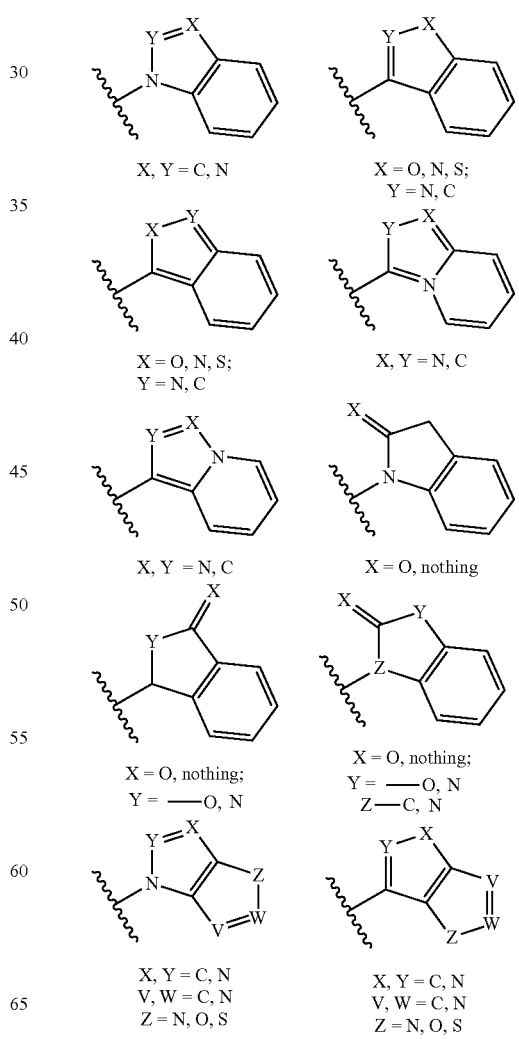

Quinazoline Scaffolds

The first quinazoline scaffold is from the fused pyrimidine formula X. The second structure is from the substituted quinazoline formula XX. Of these fused pyrimidine scaffolds, the more preferred structures are the 6:6 fused pyrimidines depicted above wherein the A ring is saturated or partially saturated and the X designation is C, N or O. The most preferred structures are the 6:6 fused pyrimidines depicted above wherein the A ring is saturated and the X designation is C, N or O.

Each of these core scaffolds can be combined at the 2 position with each of the following Het moieties to form the Het substituted scaffold with G as a bond or to form the QH group of Formula XX.

In addition to the foregoing fused pyrimidine scaffolds in which the A ring is saturated or partially saturated, the quinazoline embodiment of the fused pyrimidine scaffold is also preferred. These quinazoline scaffolds include the following structures

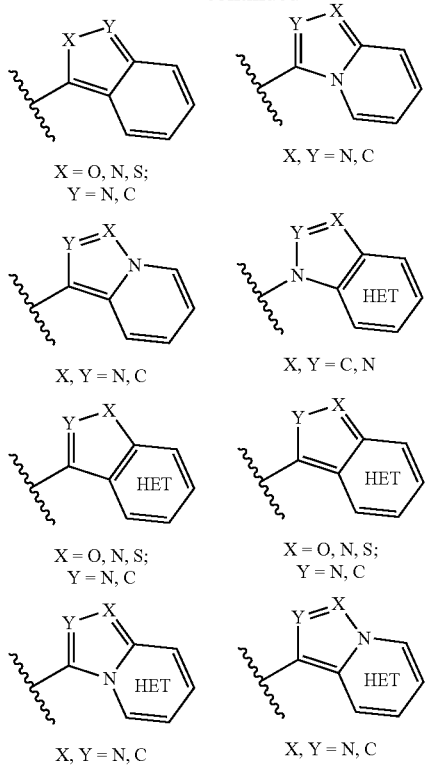

Preferred Het groups include the indole and benzimidazole moieties. For example, the penultimate core scaffold can be combined with the first Het moiety to form a Het substituted scaffold of the following structure wherein X and Y can be N, C or O, preferably X is C or N and Y is C; and X' and Y' can be C or N; preferably Y' is C and X' is C or N.

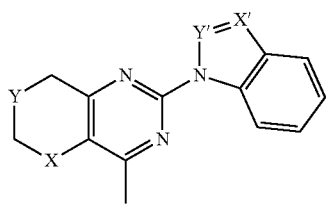

It is understood that in all of these scaffold embodiments, the designation of X or Y as N also signifies that the third substituent on nitrogen is either hydrogen or an alkyl group of 1 to 4 carbons.

To complete these fused pyrimidine compound scaffolds, the substituent at position 4 of the pyrimidine ring can be added. Embodiments of this substituent (—CR³—R⁶—Ar or —AH) include benzyl amine, benzyl, methyl amine, phenethyl amine, phenethyl, methyl amine, phenpropyl amine, phenpropyl methyl amine, aminomethylthiophene, aminoethylthiophene, aminopropylthiophene, aminomethylpyridine, aminoethylpyridine, aminopropylpyridine, aminomethylpyrrole, aminoethylpyrrole, aminopropylpyrrole, the N-methyl derivatives of the thiophene, pyridine and pyrrole compounds, and the substituted versions thereof wherein the substituent is at any position on the phenyl, thiophene, pyridine or pyrrole moiety and is an alkyl of 1 to 4 carbons, halogen, nitrile, hydroxyl, alkoxy of 1 to 4 carbons, carboxyl, carboxamide, amine, alkylamine of 1 to 4 carbons, dialkylamine of 1 to 4 carbons in each alkyl group, methoxyalkylamine of 1 to 4 carbons in the alkyl group, perfluoroalkyl of 1 to 4 carbons, N-alkylcarbamoyl, O-alkylcarbamoyl, ureayl, N-alkylureayl and carboxyl ester of 1 to 4 carbons in the ester group.

The chemical substituents $R^3$ through $R^6$, $R^{10}$ and $R^{11}$ appended to any of these core scaffolds or to the Het moiety or QH specifically delineated above may be positioned at any of the above designated locations of the core scaffold or Het or QH as indicated by the foregoing position numbers. Preferably, one to four chemical substituents are appended, preferably, one or two, more preferably one. The chemical substituents used with any of the foregoing scaffolds and/or Het moieties include any of the following substituents as well as any combination thereof. The number designations for the carbons include all integers between the lowest and highest number. Individual numbers of carbon atoms separate and distinct from other numbers of the same group are also included. For example for an alkyl of 1 to 6 carbons, an alkyl group of 1, 2, 3, 4, 5 or 6 carbons is included as well as each individual number designation separate and distinct from other number designations so that an alkyl of 1 to 6 carbons includes separately, methyl, ethyl, propyl, butyl, pentyl and hexyl.

1) Alkyl and branched alkyl of 1 to 6 carbons,
2) Alkoxy and branched alkoxy of 1 to 6 carbons,
3) Amine and aminoalkyl (e.g., —NHR and —NR₂)
4) Carboxylic acid,
5) Carboxylic ester wherein the alkoxy group of the ester is from 1 to 6 branched or straight carbons or the alcohol esterifying group is phenoxy,
6) Branched or straight alkylenyl carboxylic acid or ester of 2 to 7 carbons in the alkylenyl group and 1 to 6 branched or straight carbons in the ester group,
7) Branched or straight alkylenyl amine of 1 to 6 carbons (eg, —R—NH₂),
8) Branched or straight perfluoroalkyl of 1 to 6 carbons,
9) Branched or straight trifluoroalkyl of 1 to 6 carbons wherein the trifluoro group is on the terminating or end carbon,
10) Hydroxyl,
11) Branched or straight alkylenyl hydroxyl of 1 to 6 carbons,
12) Carboxamide eg., —CONH₂
13) Aminocarbonylalkyl, eg., —NHCOR, wherein R is alkyl of 1 to 6 carbons,
14) Branched or straight alkylenylcarboxyamide of 1 to 6 carbons, e.g., —RCONH₂,
15) Alkyleneaminocarbonylalkyl, eg., —RNHCOR, wherein the alkylenyl is branched or straight and is 1 to 6 carbons and the alkyl is branched or straight and is 1 to 6 carbons,
16) N-substituted carboxamide, wherein the N substituent is an aryl group, heteroaryl group or heterocycle group as defined in the DEFINITIONS section, e.g., —CONHAr or —CONHHet,
17) N-substituted carboxamide wherein the N substituent is an alkaryl group, a alkheteroaryl group or a alkheterocycle group as defined in the DEFINITIONS section, and wherein the "alk" group is an alkylenyl or branched alkylenyl group of 1 to 6 carbons, eg., —CONH—R—Ar or —CONH—R-Het,
18) N-substituted carboxamide wherein the N substituent is a branched or straight alkyl group of 1 to 10 carbons, the polyfluorinated version thereof, or a substituted version thereof, eg., —CONH—R, wherein the substituent of the alkyl group is halogen, cyano, carboxyl, ester of 1 to 6 branched or straight chain carbons in the alkoxy or phenoxy portion, carboxamide, sulfoxamide, alkoxy of 1 to 6 carbons, urea, carbamate of 1 to 10 carbons, amine, mono or dialkyl amine having from 1 to 6 carbons in the alkyl group with the alkyl group being straight or branched, hydroxyalkyl of 1 to 10 branched or straight chain carbons or a cycloalkyl group as defined in the DEFINITIONS section, 19) Preferred aryl, heteroaryl and heterocycle groups for 16 and 17 include phenyl, halogen substituted phenyl, aminophenyl, benzoic acid, tolyl, xylyl, anisolyl, trifluoromethylphenyl, benzyl, tetrahydrofuran, pyrrolidinyl, tetrahydronaphthalene, cyclohexyl or alkyl substituted cyclohexyl with the alkyl group having 1 to 6 carbons, cyclohexyl or alkyl substituted cyclohexyl with the alkyl group having 1 to 6 carbons, cyclopentyl or alkyl substituted cyclopentyl with the alkyl group having 1 to 6 carbons, pyrazolyl, imidazolyl, piperidinyl, piperazinyl, pyrimidinyl, morpholinyl, pyrrolyl, thiophenyl, substituted versions of any of the foregoing aryl, heteroaryl or heterocycle groups wherein the chemical substituent is halogen, cyano, carboxyl, ester of 1 to 10 branched or straight chain carbons in the alkoxy or phenoxy portion, amine, carboxamide, sulfoxamide, urea, carbamate of 1 to 10 carbons, hydroxyl, thiol, alkoxy, anisolyl, phenyl, benzyl or a cycloalkyl group as defined in the DEFINITIONS section, 20) Derivatives of 16, 17 and 18 wherein the N of the carboxamide has a second substituent and the second substituent is a branched or straight chain alkyl of 1 to 6 carbons, 21) N-substituted carboxyamide wherein the N substituent is a mono, di, tri or tetra amino acid and the amino acid moieties include glycinyl, alaninyl, leucinyl, valinyl, phenylalaninyl, lysinyl, argininyl, histidinyl, serinyl, aspariginyl, glutaminyl, aspartic, glutamic such that the amino acid moieties may be combined in any combination of two, three or four moieties including but not limited to a tetramer of four different moieties, a tetramer of two and two different moieties, a tetramer of three of one moiety and one of a different moiety, a trimer of two of one moiety and one of another moiety or a trimer of three different moieties, a dimer of two different moieties of of the same moiety, and a monomer of any of the designated moieties. The nitrogen of an amino acid moiety may serve as the nitrogen of the carboxyamide group. The C-terminus of the amino acid monomer, dimer or trimer may be a carboxylic acid or a carboxamide. The order of amino acid moieties in the tetramer, trimer or dimer may be any order.

22) Any of the substituents designated by items 1, 2, 3, 5, 6, 7, 11, 13, 16, 17 or 18 which additionally includes any functional group selected from F, Cl, Br, I, OR', OC(O)N(R')$_2$, CN, NO, NO$_2$, ONO$_2$, azido, CF$_3$, OCF$_3$, R', O (oxo), S (thiono), methylenedioxy, ethylenedioxy, N(R')$_2$, SR', SOR', SO$_2$R', SO$_2$N(R)$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R)$_2$, (CH$_2$)$_{0-2}$N(R)C(O)R', (CH$_2$)$_{0-2}$N(R)N(R)$_2$, N(R')N(R')C(O)R', N(R)N(R)C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted; for example, wherein R' can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl.

23) In addition to the groups of substituents set forth in 1 through 22 above, each individual substituent and individual combination is included separately and individually as if it were individually recited.

24) Additional embodiments of the compounds of the invention further include each individual compound listed on the compound Tables above.

EXAMPLES

The following describes the preparation of representative compounds of the invention in greater detail. The following examples are offered for illustrative purposes, and are not intended to limit the invention in any manner. Those of skill in the art will readily recognize a variety of noncritical parameters which can be changed or modified to yield essentially the same results.

Those skilled in the art will recognize, or be able to ascertain using no more than routine experimentation, numerous equivalents to the syntheses of the compounds and methods of use thereof described herein. Although certain exemplary embodiments are depicted and described herein, it will be appreciated that compound of the invention can be prepared according to the methods generally available to one of ordinary skill in the art. All of the above-cited references and publications are hereby incorporated by reference.

Unless otherwise noted, all solvents, chemicals, and reagents were obtained commercially and used without purification. The $^1$H NMR spectra were obtained in CDCl$_3$, d$_6$-DMSO, CD$_3$OD, or d$_6$-acetone at 25° C. at 300 MHz on an OXFORD (Varian) spectrometer with chemical shift (δ, ppm) reported relative to TMS as an internal standard. HPLC-MS chromatograms and mass spectra were obtained with Shimadzu LC-MS-2020 system. The prep-HPLC instruments used to purify some compounds were either a Gilson GX-281 (Gilson) or a P230 Preparative Gradient System (Elite). Preparative chira HPLC seperations were performed using an Elite P230 Preparative Gradient System, a Thar Prep-80 or Thar SFC X-5. Reactions using microwave irriadation were performed on a CEM Discover SP instrument.

Example 1

Synthesis of N-benzyl-5-(2-methoxy-1H-benzo[d]imidazol-1-yl)thiazolo[5,4-d]pyrimidin-7-amine (AA)

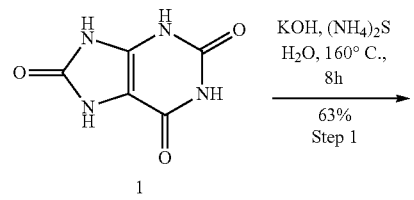

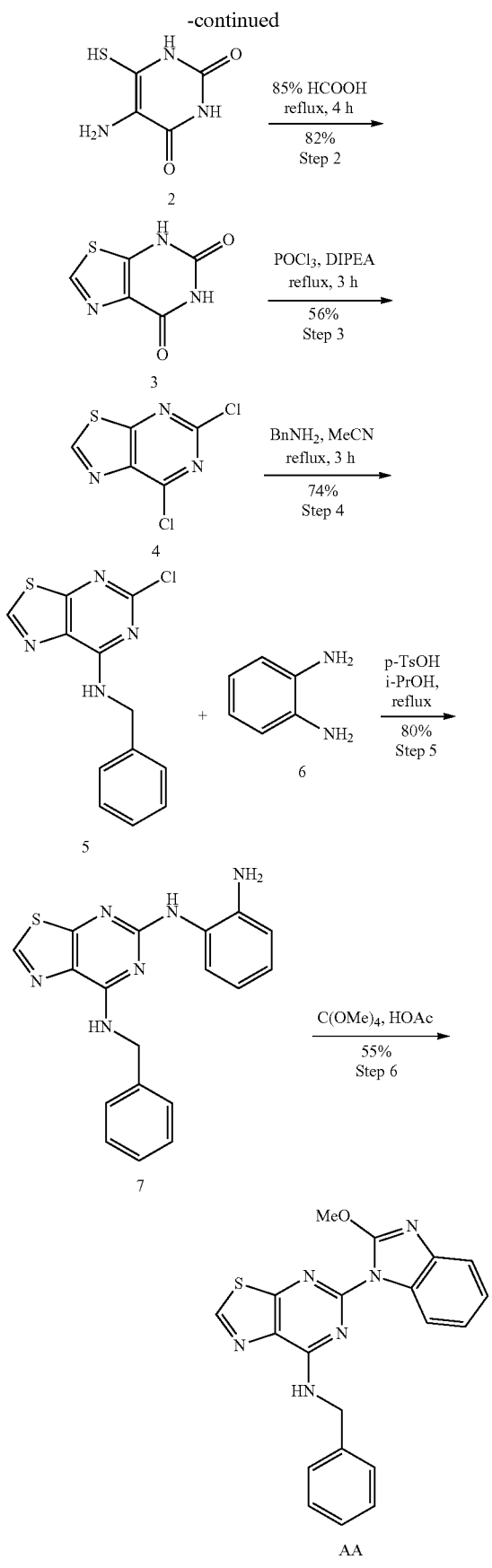

To a 0° C. solution of 1H-purine-2,6,8(3H,7H,9H)-trione 1 (3.0 g, 17.8 mmol) in cold water (30 mL) were added potassium hydroxide (1.0 g, 17.8 mmol) and a solution of aqueous ammonium sulfide (17%, 100 mL). The mixture was stirred and then heated in a cap-sealed reaction vessel for 8 h at 180° C. The reaction mixture was allowed to cool and the golden-yellow crystals of the ammonium salt of 6-thiouramil 2 were collected by filtration and washed with water (50 mL) (2.0 g, 63%). LRMS (M+H$^+$) m/z: calcd 160.01. found 160.11. $^1$H NMR (300 MHz, d$^6$-DMSO): δ 14.09 (br, 1H), 11.79 (s, 1H), 11.61 (s, 3H).

A suspension of 6-thiouramil 2 (1.6 g, 10.1 mmol) in formic acid (40 mL) was refluxed for 4 hours, the resulting mixture was cooled down and filtered to afford intermediate 3 (1.4 g, 82%) as yellow powder. LRMS (M+H$^+$) m/z: calcd 168.99. found 169.0. $^1$H NMR (300 MHz, d$^6$-DMSO): δ 10.43 (s, 1H), 8.68 (s, 2H).

To a 0° C. solution of the aforementioned intermediate 3 (1.4 g, 8.3 mmol) in ethyldiisopropylamine (2.1 g, 16.6 mmol) was added phosphorus oxychloride (30 mL), and the resulting mixture was heated at 110° C. for 3 hours. It was then cooled to the room temperature, the solvents were removed under vacuum, and the residue was diluted with saturated aqueous sodium bicarbonate (50 mL) and ethyl acetate (50 mL). The layers were separated and the aqueous phase was extracted with ethyl acetate (2×50 mL), the combined organic layers were dried over sodium sulfate and then concentrated to give the intermediate 4 (955 mg, 56%) as brown solid. $^1$H NMR (300 MHz, CDCl$_3$): δ 9.17 (s, 1H).

To a 0° C. solution of 5,7-dichlorothiazolo[5,4-d]pyrimidine 4 (950 mg, 4.6 mmol) in acetonitrile (20 mL) was added benzylamine (593 mg, 5.5 mmol). The reaction mixture was stirred at the room temperature for 16 hours and then refluxed for 2 hours. The resulting mixture was cooled down and concentrated under reduced pressure, the residue was purified by column chromatography (silica gel, petroleum ether/ethyl acetate=3:1) to give the compound 5 (950 mg, 74%) as brown oil. $^1$H NMR (300 MHz, CDCl$_3$): δ 8.66 (s, 1H), 7.52-7.27 (m, 5H), 6.63 (br, 1H), 4.80 (s, 2H).

To a 0° C. solution of the intermediate 5 (100 mg, 0.36 mmol) and benzene-1,2-diamine (47 mg, 0.43 mmol) in iso-propanol (10 mL) was added p-toluenesulfonic acid (6.2 mg, 0.036 mmol). Then the mixture was stirred at 80° C. for 3 hours. The reaction mixture was cooled down to the room temperature and quenched with saturated aqueous sodium bicarbonate (20 mL) followed by extraction with ethyl acetate (3×50 mL), the combined organic layers were dried over sodium sulfate and concentrated under reduced pressure, the residue was purified by column chromatography (silica gel, dichloromethane/methanol=20:1) to provide the desired compound 7 (100 mg, 80%) as solid. LRMS (M+H$^+$) m/z: calcd 349.42. found 349.40.

To a 0° C. solution of the aforementioned intermediate 7 (50 mg, 0.14 mmol) in acetic acid (3 mL) was added tetramethoxy methane (40 mg, 0.28 mmol). The reaction mixture was stirred at the room temperature for 12 hours and then quenched with water (3 mL), extracted by ethyl acetate (2×50 mL). The combined organic layers were washed with brine, dried over sodium sulfate. The Na$_2$SO$_4$ was removed by filtration, and the volatiles were removed under reduced pressure. The resulting residue was purified by flash chromatography using a mixture of hexane and ethyl acetate to provide the desired final product AA (30 mg, 55%) as solid. LRMS (M+H$^+$) m/z: calcd 389.11. found 389.45. HPLC purity (214 nm): 95%. $^1$HNMR (300 MHz, CD$_3$OD): δ 8.92 (s, 1H), 7.51 (d, J=8.1 Hz, 1H), 7.41-7.22 (m, 6H), 7.15-7.10 (m, 1H), 6.97-6.94 (m, 1H), 4.92 (s, 2H), 4.12 (s, 3H).

Example 2

Synthesis of 1-(4-(benzylamino)-6,7-dihydro-5H-cyclopenta[d]pyrimidin-2-yl)-1H-benzo[d]imidazol-2-amine (BB)

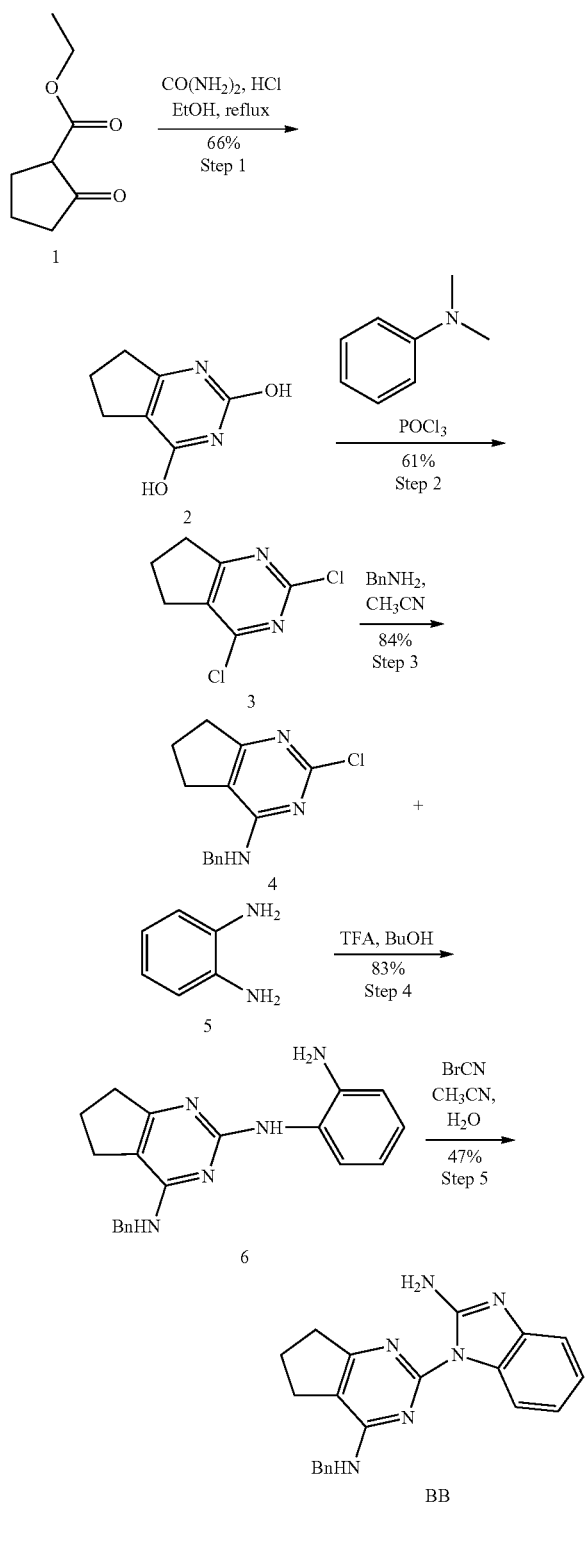

A solution of ethyl 2-oxocyclopentanecarboxylate 1 (10 mL, 67 mmol), urea (6.07 g, 101 mmol) and hydrochloric acid (1 mL) in ethanol (20 mL) was refluxed for 2 hours. The resulting mixture was then cooled down to the room temperature and concentrated in vacuo, the residue was diluted with aqueous sodium hydroxide solution (5%, 25 mL) and the resulting mixture was refluxed for 30 minutes. It was cooled down to the room temperature and the precipitate was collected and dried to give the diol 2 (6.77 g, 66%), which was used in the next step without further purification. LRMS (M+H$^+$) m/z: calcd 153.15. found 153.09.

A solution of the aforementioned diol 2 (4 g, 26 mmol), N,N-dimethylbenzenamine (6.6 mL, 52 mmol) in phosphorus oxychloride (80 mL) was refluxed for 2 hours. The reaction mixture was cooled down to the room temperature and concentrated under reduced pressure. The residue was quenched with ice-water (20 mL), the precipitated solid was collected, washed with hexane (3×50 mL) and dried to yield compound 3 (3 g, 61%), which was used in the next step without further purification. LRMS (M+H$^+$) m/z: calcd 190.04. found 190.10.

To a 0° C. solution of the aforementioned intermediate 3 (2 g, 10.6 mmol) in acetonitrile (25 mL) was added phenylmethanamine (2.9 g, 26.5 mmol). Then the reaction solution was stirred at room temperature for 12 hours. The resulting mixture was concentrated under reduced pressure. The resulting residue was purified by flash chromatography using a mixture of hexane and ethyl acetate to provide the desired 4, (2.3 g, 84%). LRMS (M+H$^+$) m/z: calcd 260.73. found 260.64.

To a 0° C. solution of the immediate 4 (300 mg, 1.16 mmol) and benzene-1,2-diamine (138 mg, 1.38 mmol) in n-butanol (5 mL) was added trifluoroacetic acid (0.05 mL). Then the resulting solution was stirred at 90° C. for 2 hours. It was then cooled to the room temperature, the precipitated solid was collected, washed with hexane and dried to provide the desired product 6 (320 mg, 83%) as solid, which was used in the next step without further purification. LRMS (M+H$^+$) m/z: calcd 332.41. found 332.56.

To a 0° C. solution of the aforementioned intermediate 6 (100 mg, 0.3 mmol) in acetonitrile (1 mL) and water (8 mL) was added cyanic bromide (64 mg, 0.6 mmol). Then the resulting solution was refluxed for 4 hours. The reaction mixture was cooled down to the room temperature and quenched with saturated aqueous ammonium hydroxide (10 mL), followed by extraction with ethyl acetate (3×50 mL). The combined organic layers were dried over sodium sulfate and concentrated, the residue was purified by column chromatography (silica gel, dichloromethane/methanol=10:1) to provide the desired compound BB (50 mg, 47%). LRMS (M+H$^+$) m/z: calcd 357.42. found 357.40. $^1$HNMR (300 MHz, d$^6$-DMSO): δ 8.05 (t, J=6 Hz, 1H), 7.98-7.96 (m, 1H), 7.66 (s, 2H), 7.39-7.31 (m, 4H), 7.26-7.22 (m, 1H), 7.13-7.10 (m, 1H), 7.02-6.97 (m, 1H), 6.80-6.75 (m, 1H), 4.68 (d, J=6 Hz, 2H), 2.90-2.85 (m, 2H), 2.81-2.76 (m, 2H), 2.12-2.05 (m, 2H).

Example 3

Synthesis of N-benzyl-2-(2-methyl-1H-indol-1-yl)-5,6,7,8-tetrahydropyrido[4,3-d]-pyrimidin-4-amine (CC)

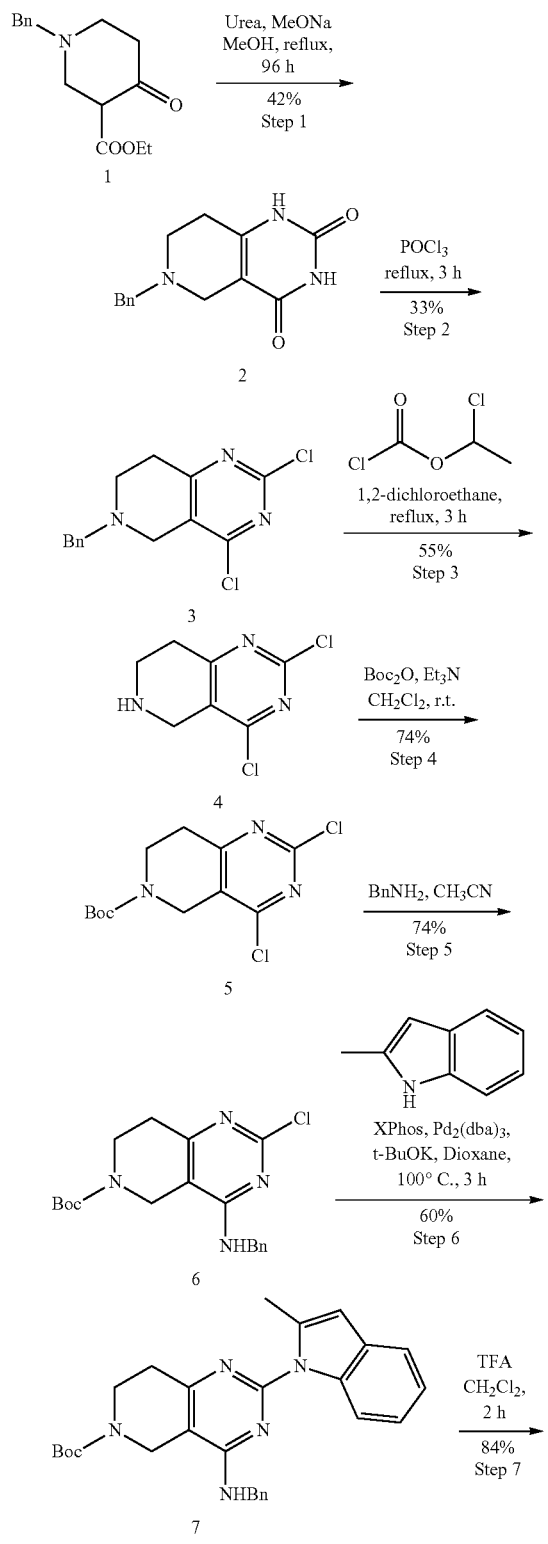

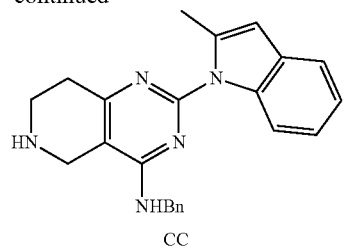

CC

To a 0° C. solution of ethyl 1-benzyl-4-oxopiperidine-3-carboxylate hydrochloride 1 (6.0 g, 20.2 mmol), urea (2.54 g, 42.42 mmol) in MeOH (100 ml) was added NaOMe (6.14 g, 113.7 mmol) under nitrogen atmosphere. The resulting mixture was stirred at 60° C. for 20 hours. The reaction mixture was cooled down to the room temperature and concentrated under reduced pressure, the residue was purified by column chromatography (silica gel, dichloromethane/methanol=10:1) to provide the desired compound 2 (2.2 g, 42%). LRMS (M+H$^+$) m/z: calcd 258.29. found 258.30.

A solution of the intermediate 2 (2.2 g, 8.56 mmol) in POCl$_3$ (25 ml) was stirred at 100° C. for 2 hours. The reaction mixture was cooled down to the room temperature and poured slowly into ice-water (50 mL), followed by extraction with DCM (3×50 mL). The combined organic layers were dried over sodium sulfate and concentrated under reduced pressure, the residue was purified by column chromatography (silica gel, dichloromethane/methanol=10:1) to provide the desired compound 3 (830 mg, 33%). LRMS (M+H$^+$) m/z: calcd 295.18. found 295.20.

To a 0° C. solution of the intermediate 3 (700 mg, 2.39 mmol) in 1,2-dichloroethane (15 mL) was added 1-chloroethyl carbonochloridate (1.02 g, 7.71 mmol), the resulting solution was stirred at 100° C. for 6 hours. The reaction mixture was cooled down to the room temperature and concentrated in vacuo, the residue was dissolved with MeOH (10 mL) and the resulting mixture was stirred at 70° C. for 1 hour. It was then cooled down to the room temperature and concentrated under reduced pressure. The resulting residue was purified by flash chromatography using a mixture of hexane and ethyl acetate to provide the desired product 4 (270 mg, 55%) as solid. LRMS (M+H$^+$) m/z: calcd 205.06. found 205.14.

To a 0° C. solution of the intermediate 4 (270 mg, 1.33 mmol) in DCM (30 mL) were added (Boc)$_2$O (348 mg, 1.6 mmol) and TEA (200 mg, 2.0 mmol). The resulting solution was stirred at the room temperature for 16 hours. It was then diluted with water (30 mL) and DCM (30 mL), the layers were separated and the aqueous phase was extracted with DCM (30 mL×2). The combined organic layers were washed with brine and dried over sodium sulfate. The Na$_2$SO$_4$ was removed by filtration, and the volatiles were removed under reduced pressure. The resulting residue was purified by flash chromatography using a mixture of hexane and ethyl acetate to provide the product 5 (300 mg, 74%). LRMS (M+H$^+$) m/z: calcd 305.17. found 305.24.

To a 0° C. solution of the aforementioned intermediate 5 (300 mg, 1.0 mmol) in acetonitrile (25 mL) was added phenylmethanamine (1.07 g, 10.0 mmol). Then the reaction solution was stirred at room temperature for 12 hours. The resulting mixture was concentrated under reduced pressure. The resulting residue was purified by flash chromatography using a mixture of hexane and ethyl acetate to provide the desired 6 (280 mg, 74%). LRMS (M+H$^+$) m/z: calcd 375.15. found 375.04.

To a 0° C. solution of the intermediate 6 (100 mg, 0.267 mmol), 2-methyl-1H-indole (35 mg, 0.267 mmol) in 1,4-dioxane (15 mL) were added t-BuOK (60 mg, 0.534 mmol), Pd$_2$(dba)$_3$ (24 mg, 0.026 mmol) and x-Phos (13 mg, 0.026 mmol) under nitrogen atmosphere. The resulting mixture was stirred at 80° C. for 3 hours. It was then cooled down to the room temperature and diluted with water (30 mL) and ethyl acetate (30 mL), the layers were separated and the aqueous phase was extracted with ethyl acetate (30 mL×2). The combined organic layers were washed with brine, dried over sodium sulfate. The Na2SO4 was removed by filtration, and the volatiles were removed under reduced pressure. The resulting residue was purified by flash chromatography using a mixture of hexane and ethyl acetate to provide the product 7 (75 mg, 60%). LRMS (M+H$^+$) m/z: calcd 470.58. found 470.63.

The aforementioned intermediate 7 (75 mg, 0.16 mmol) was treated with a solution of HCl in ethyl acetate (2 M, 10 mL) at the room temperature for 1 hour. It was then diluted with saturated aqueous sodium carbonate solution (10 mL) and ethyl acetate (30 mL), the layers were separated and the aqueous phase was extracted with ethyl acetate (30 mL×2). The combined organic layers were washed with brine, dried over sodium sulfate. The Na$_2$SO$_4$ was removed by filtration, and the volatiles were removed under reduced pressure. The resulting residue was purified by preparative-HPLC (water/MeCN) to provide the final product CC (50 mg, 84%). LRMS (M+H$^+$) m/z: calcd 370.46. found 370.43. $^1$H NMR (300 MHz, DMSO) δ 8.27 (s, 1H), 7.63-7.73 (m, 2H), 7.22-7.39 (m, 6H), 6.86-7.01 (m, 2H), 6.30 (s, 1H), 4.65 (d, J=6.0 Hz, 2H), 3.75 (s, 2H), 3.09 (d, J=6.0 Hz, 2H), 2.68 (d, J=6.0 Hz, 2H), 2.37 (s, 3H).

Example 4

Synthesis of N-benzyl-2-(2-methyl-1H-indol-1-yl)-5,6,7,8-tetrahydropyrido-[3,4-d]pyrimidin-4-amine (DD)

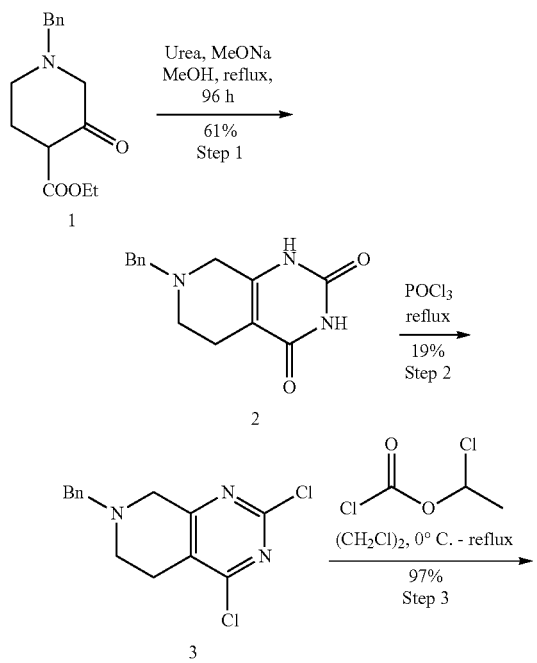

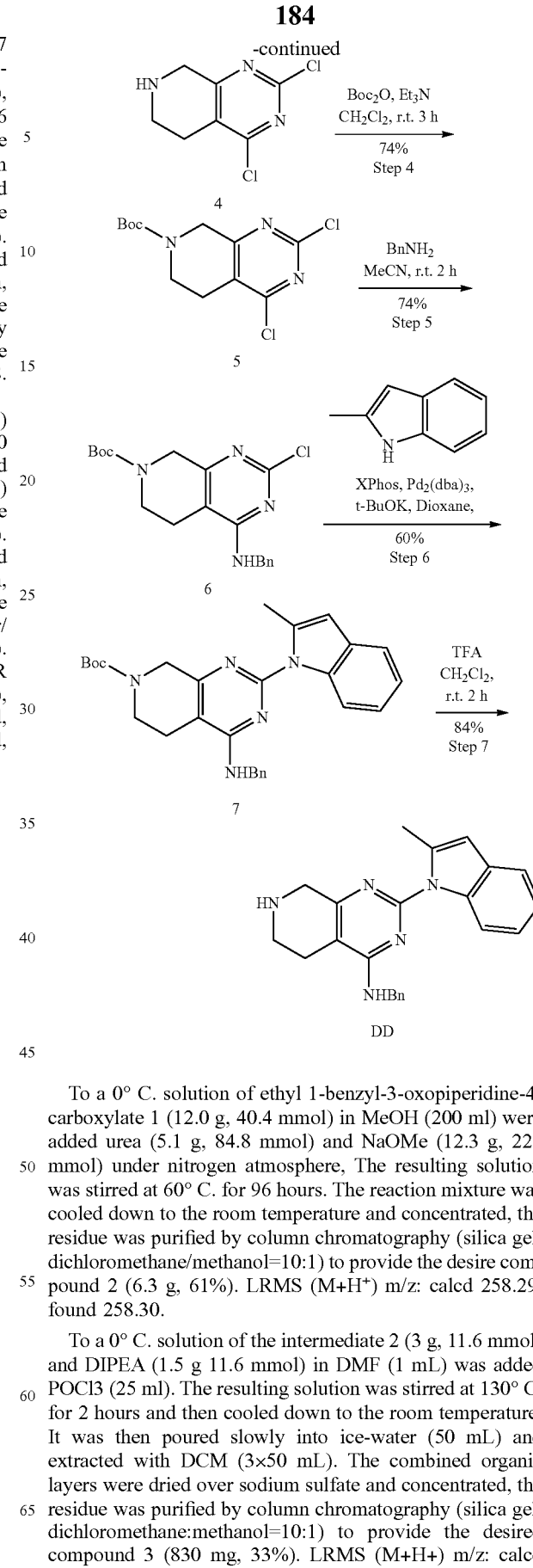

To a 0° C. solution of ethyl 1-benzyl-3-oxopiperidine-4-carboxylate 1 (12.0 g, 40.4 mmol) in MeOH (200 ml) were added urea (5.1 g, 84.8 mmol) and NaOMe (12.3 g, 228 mmol) under nitrogen atmosphere, The resulting solution was stirred at 60° C. for 96 hours. The reaction mixture was cooled down to the room temperature and concentrated, the residue was purified by column chromatography (silica gel, dichloromethane/methanol=10:1) to provide the desire compound 2 (6.3 g, 61%). LRMS (M+H$^+$) m/z: calcd 258.29. found 258.30.

To a 0° C. solution of the intermediate 2 (3 g, 11.6 mmol) and DIPEA (1.5 g 11.6 mmol) in DMF (1 mL) was added POCl3 (25 ml). The resulting solution was stirred at 130° C. for 2 hours and then cooled down to the room temperature. It was then poured slowly into ice-water (50 mL) and extracted with DCM (3×50 mL). The combined organic layers were dried over sodium sulfate and concentrated, the residue was purified by column chromatography (silica gel, dichloromethane:methanol=10:1) to provide the desired compound 3 (830 mg, 33%). LRMS (M+H+) m/z: calcd 295.18. found 295.20. ¹HNMR (300 MHz, DMSO): δ 7.316 (m, 5H), 3.536 (s, 2H), 2.945 (s, 3H), 2.27 (m, 2H), 2.207 (m, 2H).

To a 0° C. solution of the intermediate 3 (1.2 g 4.08 mmol) in 1,2-dichloroethane (15 mL) was added 1-chloroethyl carbonochloridate (700 mg), the resulting solution was stirred at 0° C. for 15 min. The reaction mixture was kept at the room temperature for 16 hours and then concentrated in vacuo, the residue was dissolved with MeOH (10 mL) and the resulting mixture was stirred at 70° C. for 1 hour. It was then cooled to room temperature and concentrated in vacuo. The resulting residue was purified by flash chromatography using a mixture of hexane and ethyl acetate to provide the desired product 4 (810 mg, 97%) as solid. LRMS (M+H+) m/z: calcd. 205.06. found 205.14.

To a 0° C. solution of the intermediate 4 (270 mg, 1.33 mmol) in DCM (30 mL) were added (Boc)₂O (348 mg, 1.6 mmol) and TEA (200 mg, 2.0 mmol). The resulting solution was stirred at the room temperature for 16 hours. It was then diluted with treated water (30 mL) and DCM (30 mL), the layers were separated and the aqueous phase was extracted with DCM (30 mL×2). The combined organic layers were washed with brine, dried over sodium sulfate. The Na₂SO₄ was removed by filtration, and the volatiles were removed under reduced pressure. The resulting residue was purified by flash chromatography using a mixture of hexane and ethyl acetate to provide the product 5 (300 mg, 74%). LRMS (M+H⁺) m/z: calcd 305.17. found 305.24. ¹H-NMR (300 MHz, CDCl₃) δ 4.624 (s, 2H), 3.739-3.700 (t, J=5.9 Hz, 2H), 2.848-2.811 (t, J=5.6 Hz, 2H), 1.472 (s, 9H).

To a 0° C. solution of the aforementioned intermediate 5 (300 mg, 1.0 mmol) in acetonitrile (25 mL) was added phenylmethanamine (1.07 g, 10.0 mmol). Then the reaction solution was stirred at room temperature for 12 hours. The resulting mixture was concentrated under reduces pressure. The resulting residue was purified by flash chromatography using a mixture of hexane and ethyl acetate to provide the desired 6 (280 mg, 74%). LRMS (M+H⁺) m/z: calcd 375.15. found 375.04.

To a 0° C. solution of the intermediate 6 (100 mg, 0.267 mmol), 2-methyl-1H-indole (35 mg, 0.267 mmol) in 1,4-dioxane (15 mL) were added t-BuOK (60 mg, 0.534 mmol), Pd₂(dba)₃ (24 mg, 0.026 mmol) and x-Phos (13 mg, 0.026 mmol) under nitrogen atmosphere. The resulting mixture was stirred at 80° C. for 3 hours. It was then cooled down to the room temperature and diluted with water (30 mL) and ethyl acetate (30 mL), the layers were separated and the aqueous phase was extracted with ethyl acetate (30 mL×2). The combined organic layers were washed with brine, dried over sodium sulfate. The Na2SO4 was removed by filtration, and the volatiles were removed under reduced pressure. The resulting residue was purified by flash chromatography using a mixture of hexane and ethyl acetate to provide the product 7 (79 mg, 62%). LRMS (M+H⁺) m/z: calcd 470.58. found 470.63.

The aforementioned intermediate 7 (75 mg, 0.16 mmol) was treated with a solution of HCl in ethyl acetate (2 M, 10 mL) at the room temperature for 1 hour. It was then diluted with saturated aqueous sodium carbonate solution (10 mL) and ethyl acetate (30 mL), the layers were separated and the aqueous phase was extracted with ethyl acetate (30 mL×2). The combined organic layers were washed with brine, dried over sodium sulfate. The Na₂SO₄ was removed by filtration, and the volatiles were removed under reduced pressure. The resulting residue was purified by preparative-HPLC to provide the final product DD (50 mg, 84%). LRMS (M+H⁺) m/z: calcd 370.46. found 370.43. ¹H-NMR (300 MHz, DMSO) δ 7.686-7.660 (m, 1H), 7.451-7.426 (m, 1H), 7.357-7.268 (m, 5H), 7.130-7.036 (m, 2H), 4.849 (s, 2H), 4.384 (s, 2H), 3.75 (s, 2H), 3.703-3.664 (t, J=6.0 Hz, 2H), 3.955-3.918 (t, J=6.0 Hz, 2H), 2.47 (s, 3H).

Example 5

Synthesis of 4-(benzylamino)-2-(2-methoxy-1H-benzo[d]imidazol-1-yl)-6,7-dihydropyrido[3,4-d]-pyrimidin-8(5H)-one (EE)

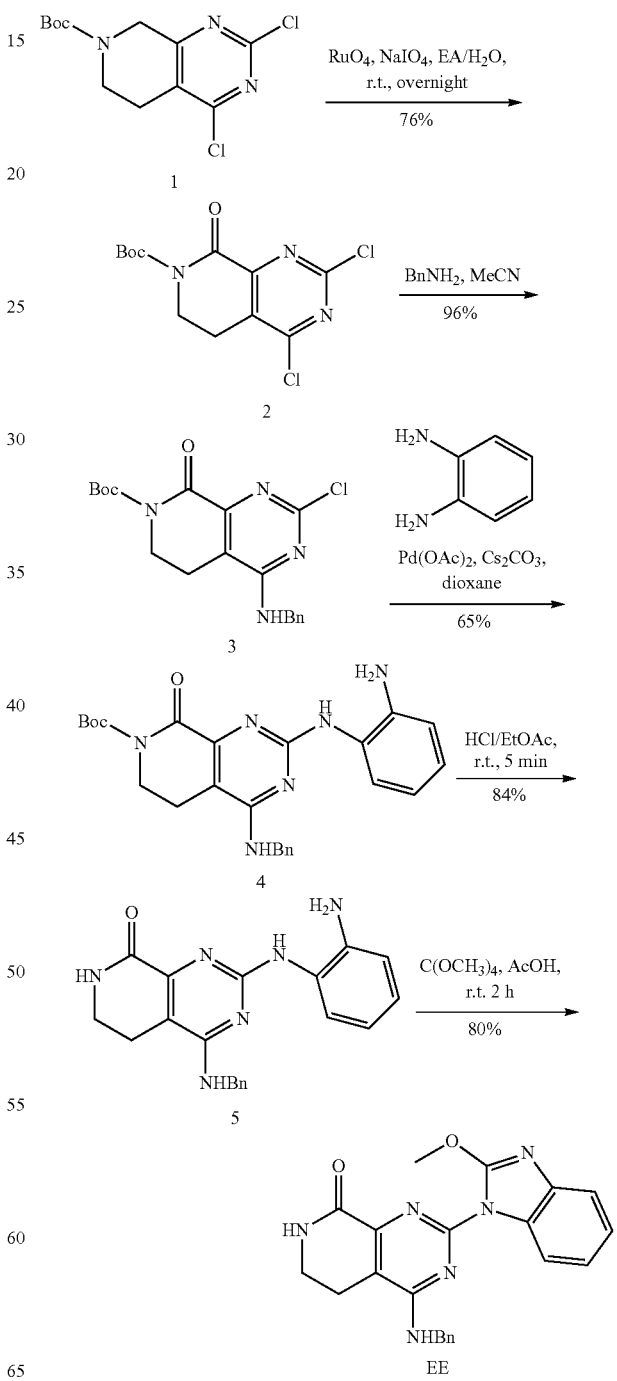

To a 0° C. solution of the intermediate 1 (300 mg, 1.01 mmol) in ethyl acetate (1 Ml) were added ruthenium tetroxide (149 mg, 5%, 0.045 mmol) and an aqueous solution of sodium periodate (0.47M, 2.1 Ml). The resulting mixture was stirred at the room temperature for 16 hours and then diluted with water (10 Ml) and ethyl acetate (10 Ml), the layers were separated and the aqueous phase was extracted with ethyl acetate (10 Ml×2). The combined organic layers were washed with brine, dried over sodium sulfate. The Na$_2$SO$_4$ was removed by filtration, and the volatiles were removed under reduced pressure. The resulting residue was purified by flash chromatography using a mixture of hexane and ethyl acetate to provide the product 2 (238 mg, 76%). LRMS (M+H$^+$) m/z: calcd 319.16. found 319.21. $^1$H NMR (300 MHz, CDCl$_3$) δ 4.093-4.053 (t, J=6.0 Hz, 2H), 3.128-3.089 (t, J=6.0 Hz, 2H), 1.569 (s, 9H).

To a 0° C. solution of the aforementioned intermediate 2 (238 mg, 0.74 mmol) in acetonitrile (20 Ml) was added phenylmethanamine (1.07 g, 10.0 mmol). Then the reaction solution was stirred at room temperature for 2 hours. The resulting mixture was concentrated under reduces pressure. The resulting residue was purified by flash chromatography using a mixture of hexane and ethyl acetate to provide the desired 3 (280 mg, 96%). LRMS (M+H$^+$) m/z: calcd 389.85. found 389.92. $^1$H-NMR (400 MHz, CD$_3$OD) δ 7.353-7.335 (d, J=7.2 Hz, 2H), 7.300-7.263 (t, J=7.4 Hz, 2H), 7.233-7.197 (m, 1H), 4.627 (s, 2H), 4.007-3.976 (t, J=6.2 Hz, 2H), 2.775-2.743 (t, J=6.4 Hz, 2H), 1.537 (s, 9H).

To a 0° C. solution of the immediate 3 (170 mg, 0.43 mmol) and benzene-1,2-diamine (75 mg, 0.7 mmol) in 1,4-dioxane (30 Ml) were added Pd(Oac)$_2$ (12 mg, 0.05 mmol) and Cs$_2$CO$_3$ (400 mg, 1.2 mmol). Then the resulting mixture was stirred at 110° C. for 12 hours. It was then cooled down to the room temperature and the solvents were removed under reduced pressure. The resulting residue was purified by flash chromatography using a mixture of hexane and ethyl acetate to provide the desired 4 (160 mg, 65% yield). LRMS (M+H$^+$) m/z: calcd 461.53. found 461.61.

A solution of the immediate 4 (75 mg, 0.16 mmol) was treated with a solution of HCl in ethyl acetate (2 M, 10 Ml) at the room temperature for one hour. The reaction was then quenched with saturated aqueous sodium carbonate solution (20 Ml) and extracted with ethyl acetate (20 Ml×2). The combined organic layers were dried with sodium sulfate. The Na2SO4 was removed by filtration, and the volatiles were removed under reduced pressure. The resulting residue was purified by pre-HPLC to provide the final product 5 (50 mg, 84%). LRMS (M+H$^+$) m/z: calcd 361.41. found 361.45.

To a 0° C. solution of the aforementioned intermediate 5 (50 mg, 0.14 mmol) in acetic acid (3 Ml) was added tetramethoxymethane (54 mg, 0.4 mmol). Then the resulting solution was stirred at the room temperature for 16 hours. The solvent was then removed under reduced pressure and the residue was purified by preparative-HPLC (MeCN/water with 0.1% TFA) to provide the desired compound EE (44 mg, 80%). LRMS (M+H$^+$) m/z: calcd 401.43. found 401.50. $^1$H-NMR (300 MHz, DMSO) δ7.449-7.310 (m, 7H), 7.156 (m, 1H), 7.021-6.985 (m, 1H), 4.753 (s, 2H), 4.123 (s, 3H), 3.626-3.581 (t, J=6.7 Hz, 2H), 2.881-2.836 (t, J=6.7 Hz, 2H), 2.37 (s, 3H).

Example 6

Synthesis of N-benzyl-2-(2-methyl-1H-indol-1-yl)-6,7-dihydro-5H-pyrrolo[3,4-d]-pyrimidin-4-amine (FF)

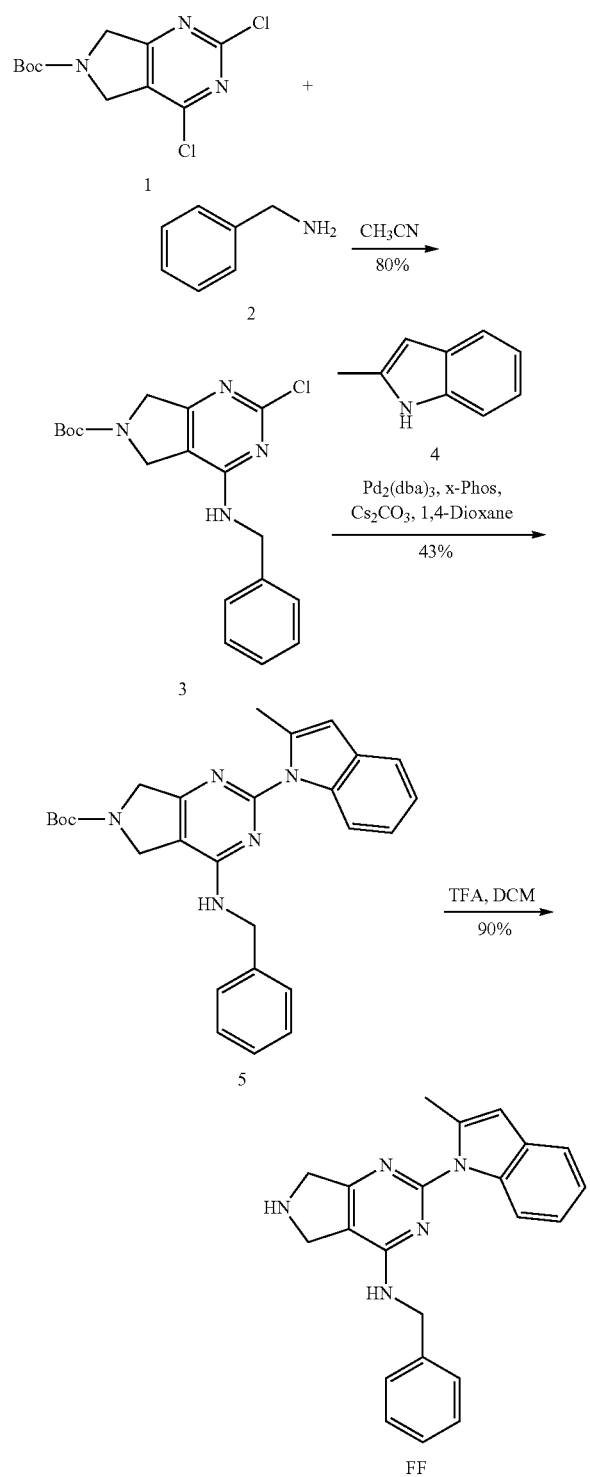

To a 0° C. solution of the aforementioned intermediate 1 (290 mg, 1.0 mmol) in acetonitrile (10 mL) was added phenylmethanamine (150 mg, 1.5 mmol). Then the reaction solution was stirred at room temperature for 12 hours. The resulting mixture was concentrated under reduces pressure. The resulting residue was purified by flash chromatography using a mixture of hexane and ethyl acetate to provide the desired 3 (288 mg, 80%). LRMS (M+H$^+$) m/z: calcd 361.84. found 361.70.

To a 0° C. solution of the intermediate 3 (180 mg, 0.5 mmol) and 2-methyl-1H-indole (100 mg, 0.5 mmol) in 1,4-dioxane (20 mL) were added Cs$_2$CO$_3$ (326 mg, 1.0 mmol), Pd$_2$(dba)$_3$ (105 mg, 0.1 mmol) and x-Phos (50 mg, 0.1 mmol) under nitrogen atmosphere. The resulting mixture was stirred at 100° C. for 3 hours. It was then cooled down to the room temperature and diluted with water (30 mL) and ethyl acetate (30 mL), the layers were separated and the aqueous phase was extracted with Ethyl acetate (30 mL×2). The combined organic layers were washed with brine, dried over sodium sulfate. The Na2SO4 was removed by filtration, and the volatiles were removed under reduced pressure. The resulting residue was purified by flash chromatography using a mixture of hexane and ethyl acetate to provide the product 5 (97 mg, 43%) as a light yellow solid. LRMS (M+H$^+$) m/z: calcd 456.55. found 456.40.

To a 0° C. solution of compound 5 (97 mg, 0.21 mmol) in DCM (3 mL) was added TFA (1 mL), and the resulting solution was stirred at the room temperature for 2 hours. The solvents were removed under reduced pressure, the residue was then dissolved with saturated aqueous sodium carbonate solution (10 mL) and DCM (30 mL), the layers were separated and the aqueous phase was extracted with DCM (30 mL×2). The combined organic layers were washed with brine, dried over sodium sulfate. The Na$_2$SO$_4$ was removed by filtration, and the volatiles were removed under reduced pressure. The resulting residue was purified by preparative-HPLC (solvents?) to provide the final product FF (67 mg, 90%). LRMS (M+H$^+$) m/z: calcd 356.44. found 356.32. $^1$H-NMR (300 MHz, DMSO): δ 7.75 (d, J=8.1 Hz, 1H), 7.43-7.17 (m, 5H), 7.03-6.91 (m, 2H), 6.28 (s, 1H), 4.72 (s, 2H), 4.25 (d, J=19.8 Hz, 4H), 2.45 (s, 3H).

Example 7

Synthesis of 1-(4-(benzylamino)-2-(2-methyl-1H-indol-1-yl)-5,6-dihydropyrido[3,4-d]pyrimidin-7(8H)-yl)ethanone (GG)

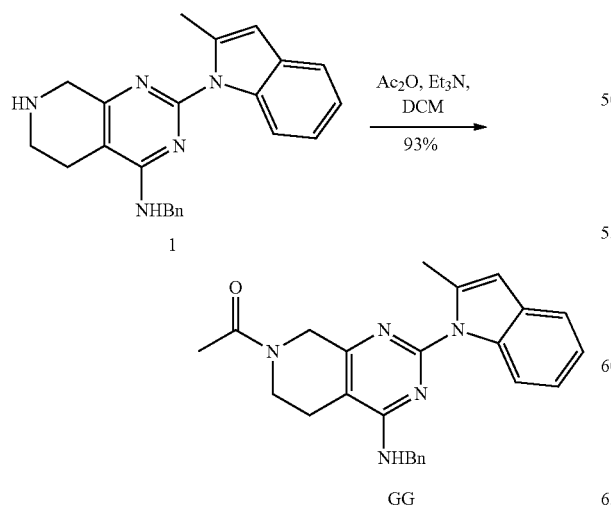

To a 0° C. solution of compound 1 (15 mg, 0.04 mmol) in DCM (3 mL) were added acetic anhydride (102 mg, 1.00 mmol) and Et$_3$N (101 mg, 1.00 mmol). The resulting solution was stirred at the same temperature for 1 hour and at the room temperature for 2 hours. The solvents were removed under reduced pressure. The resulting residue was purified by flash chromatography using a mixture of hexane and ethyl acetate to provide the product GG (15 mg, 93% yield). LRMS (M+H$^+$) m/z: calcd 412.50. found 412.53. $^1$H-NMR (300 MHz, CD$_3$OD) δ 7.75 (d, J=8.1 Hz, 1H), 7.43-7.17 (m, 5H), 7.03-6.91 (m, 2H), 6.28 (s, 1H), 4.72 (s, 2H), 4.25 (d, J=19.8 Hz, 4H), 2.45 (s, 3H), 2.02 (s, 3H).

Example 8

Synthesis of N-benzyl-2-(2-methyl-2H-indol-1(7aH)-yl)-5,7-dihydrofuro[3,4-d]pyrimidin-4-amine (HH)

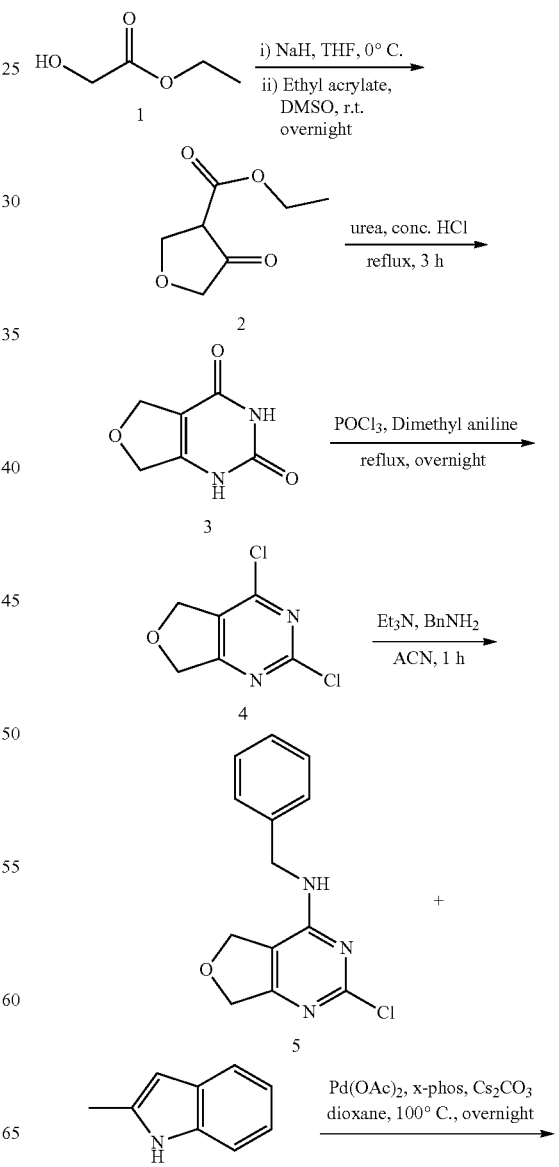

-continued

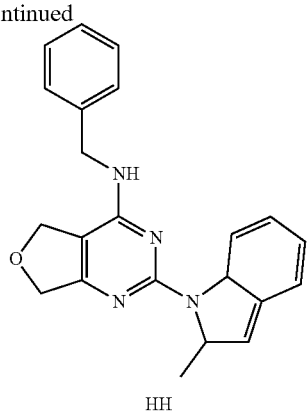

HH

To a 0° °C. solution of ethyl 2-hydroxyacetate 1 (5 mL, 50 mmol) in THF (100 mL) was added NaH (60%, 2.3 g, 58 mmol) under a nitrogen atmosphere. The resulting solution was stirred at the room temperature for 45 minutes. The solvents were removed under reduced pressure. The resulting residue was suspended in dimethyl sulfoxide (65 mL) and cooled to 0° C. Ethyl acrylate (6.8 mL, 63 mmol) was then added dropwisely. The resulting solution was stirred at the room temperature for 12 hours. Then the resulting solution was slowly poured into aqueous hydrochloric acid (10%, 250 mL). It was extracted with diethyl ether (150 mL×3). The combined organic layers were washed with brine, dried over sodium sulfate, filtered and concentrated to give intermediate 2 (3 g, 38%). which was used in the next step without further purification. LRMS (M+H$^+$) m/z: calcd 159.15. found 159.21.

To a 0° C. solution of the aforementioned 2 (3 g, 18 mmol) in methanol (15 mL) were added urea (1.65 g, 27.6 mmol) and concentrated aqueous hydrochloric acid solution (0.75 mL). The resulting solution was refluxed for 2 hours. Then it was cooled down to 0° C. and stirred at this temperature for 15 minutes. The white precipitates were collected and then suspended in aqueous sodium hydroxide solution (15 mL, 2 M), the resulting mixture was refluxed for 1 hour. Then the resulting solution was cooled down to the room temperature and acidified with aqueous hydrochloric acid (10%) slowly. The precipitates were collected, washed with brine and dried to give intermediate 3 (1.5 g, 54%), which was used in the next step without further purification. LRMS (M+H$^+$) m/z: calcd 155.12. found 155.23.

To a 0° C. solution of the aforementioned 3 (500 mg, 3.25 mmol) in phosphorus oxychloride (30 mL) was added dimethyl aniline (500 mg, 4.13 mmol). The resulting solution was refluxed for 12 hours. The solvents were removed under reduced pressure. The resulting residue was poured into ice (100 g) and extracted with dichloromethane (50 mL×3). The combined organic layers were washed with brine, dried over sodium sulfate. The Na2SO4 was removed by filtration, and the volatiles were removed under reduced pressure. The resulting residue was purified by flash chromatography using a mixture of hexane and ethyl acetate to to provide the final product 4 (300 mg, 49%). LRMS (M+H$^+$) m/z: calcd 192.01. found 192.10.

To a 0° C. solution of the aforementioned intermediate 4 (300 mg, 1.58 mmol) in DCM (50 mL) were added phenylmethanamine (300 mg, 3 mmol) and TEA (500 mg, 3.88 mmol). Then the reaction solution was stirred at room temperature for 12 hours. The resulting mixture was concentrated under reduces pressure. The resulting residue was purified by flash chromatography using a mixture of hexane and ethyl acetate to provide the desired 5 (300 mg, 73%). LRMS (M+H$^+$) m/z: calcd 262.71. found 262.85.

To a 0° C. solution of the intermediate 5 (261 mg, 1.0 mmol) and 2-methyl-1H-indole (130 mg, 1.0 mmol) in 1,4-dioxane (30 mL) were added Cs$_2$CO$_3$ (650 mg, 2.0 mmol), Pd$_2$(dba)$_3$ (212 mg, 0.2 mmol) and X-Phos (100 mg, 0.2 mmol) under nitrogen atmosphere. The resulting mixture was treated in microwave at 200° C. for 2 hours. It was then cooled down to the room temperature and diluted with water (30 mL) and ethyl acetate (30 mL), the layers were separated and the aqueous phase was extracted with ethyl acetate (30 mL×2). The combined organic layers were washed with brine, dried over sodium sulfate. The Na2SO4 was removed by filtration, and the volatiles were removed under reduced pressure. The resulting residue was purified by flash chromatography using a mixture of hexane and ethyl acetate to provide the product HH (150 mg, 42%). LRMS (M+H$^+$) m/z: calcd 359.44. found 359.65. $^1$HNMR (300 MHz, CDCl$_3$): δ 8.14-8.11 (m, 1H), 7.39-7.37 (m, 1H), 7.28-7.27 (m, 5H), 7.15-7.14 (m, 2H), 6.40 (s, 1H), 5.09-5.06 (m, 4H), 4.81 (s, 2H), 2.67 (s, 3H), 2.03 (s, 1H).

Example 9

Synthesis of 1-[4-(benzylamino)-5H,7H,8H-pyrano[4,3-d]pyrimidin-2-yl]-2-methyl-1H-indole-4-carboxamide (II)

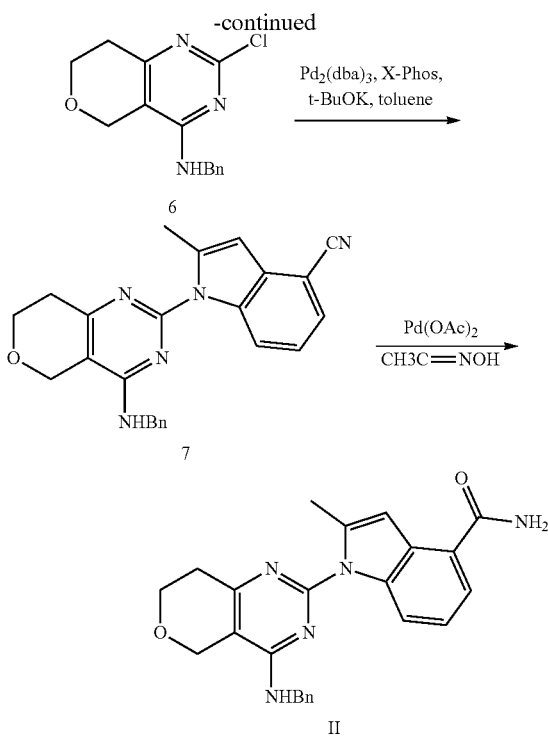

To a room temperature mixture of NaH (60% in hexane, 10.0 g, 250 mmol) in THF (300 mL) were added tetrahydropyran-4-one 1 (10.0 g, 100 mmol) and dimethylcarbonate (21 mL, 250 mmol). Then the mixture was heated to 45° C. overnight. The final mixture was poured into 0.01N HCl and Et$_2$O, filtered over celite, the separated organic layer was dried over anhydrous sodium sulfate and the residue was purified over silica gel (petroleum ether/ethyl acetate=50:1) to give the desired product 2 (7.8 g, 49% yield). $^1$H-NMR (300 MHz, CDCl$_3$) δ: 4.23 (m, 1H), 3.84 (t, 2H), 3.77 (m, 2H), 3.75 (s, 3H), 2.39 (m, 2H).

A mixture of 2 (1.58 g, 10 mmol) and ammonium acetate (2.3 g, 30 mmol) in of MeOH (20 mL) was stirred overnight at room temperature. The mixture was concentrated under vacuum, dichloromethane (100 mL) and water (20 mL) were added, and the separated organic layer was dried over sodium sulfate and concentrated in vacuo. The crude product 3 was dissolved in 20 mL of CH3CN and treated with 2,2,2-trichloro-acetyl isocyanate (3.76 g, 20 mmol) and the mixture was stirred for 30 minutes. The resulting solid was collected by filtration and dissolved in NH$_3$ in MeOH (8 mL, 7 N), the mixture was heated at 70° C. After cooling to room temperature, a solid formed and was collected by filtration to give compound 4 (1.2 g, 71%). 1H NMR (300 MHz, DMSO-d6): δ 10.98 (br, 2H), 4.19 (s, 2H), 3.76 (t, J=5.4 Hz, 2H), 2.38 (t, J=5.4 Hz, 2H).

A solution of compound 4 (1.68 g, 10 mmol) in POCl$_3$ (10 mL) was heated to reflux and stirred for 2 h. After cooled to room temperature, the mixture was concentrated under vacuum. DCM (100 mL) and water (10 mL) were added, the separated organic layer was dried over anhydrous sodium sulfate and concentrated under vacuum to give the desired product 5 (0.7 g, 34%).

A solution of compound 5 (1.03 g, 5 mmol) in 50 mL of CH3CN was treated with benzyl amine (2.68 g, 25 mmol). The mixture was stirred overnight at room temperature, concentrated in vacuo and the residue was purified by flash chromatography (PE/EA=1:1) to give the product 6 (1.0 g, 72%). 1H-NMR (300 MHz, CDCl3): δ 7.34 (m, 5H), 4.70 (d, J=5.1 Hz, 2H), 4.61 (br, 1H), 4.42 (s, 2H), 3.96 (t, J=5.4 Hz, 2H), 2.79 (t, J=5.4 Hz, 2H).

To a solution of 2-methyl-1H-indole-4-carbonitrile (85 mg, 0.54 mmol) compound 6 (150 mg, 0.54 mmol) in dioxane (10 mL) was added Pd$_2$(dba)$_3$ (100 mg, 0.11 mmol), X-Phos (52 mg, 0.11 mmol) and CsCO$_3$ (358 mg 1 mmol). The mixture was degassed 3 times, then stirred at 100° C. for 2 hours. The resulting mixture was concentrated in vacuo and the residue was purified by flash chromatography (silica gel, petroleum ether/ethyl acetate=5:1) to give the desired product 7 (150 mg, 70% yield). 1H-NMR (400 MHz, CD3OD): δ 7.81 (d, J=8.4 Hz, 1H), 7.40 (d, J=7.2 Hz, 1H), 7.34-7.30 (m, 4H), 7.28-7.24 (m, 1H), 7.02-6.98 (m, 1H), 6.48 (s, 1H), 4.72 (s, 2H), 4.66 (s, 2H), 4.07 (t, J=5.6 Hz, 2H), 2.83 (t, J=5.6 Hz, 2H), 2.50 (s, 3H).

To a solution of compound 7 (180 mg, 0.46 mmol) in ethanol (8 mL) and water (1 mL) was added Pd(OAc)$_2$ (11 mg, 0.046 mmol), PPh$_3$ (14 mg, 0.053 mmol) and acetaldehyde oxime (53 mg, 0.92 mmol). Then the reaction mixture was heated to reflux for 2 hours. The resulting mixture was concentrated and the residue was purified by flash chromatography (silica gel, dichloromethane/methanol=20:1) to give the desired product II (110 mg, 58% yield). LRMS (M+H$^+$) m/z: calcd 414.19. found 414.20; $^1$H-NMR (300 MHz, D$_3$COD) δ 7.72 (d, 1H), 7.44 (d, 1H), 7.41 (m, 1H), 7.31 (m, 3H), 7.25 (m, 1H), 6.96 (t, 1H), 6.77 (s, 1H), 4.71 (d, 2H), 4.63 (s, 1H), 4.05 (t, 2H), 2.11, (t, 2H), 2.45 (s, 3H).

Example 10

Synthesis of 1-(4-(benzylamino)-7,8-dihydro-5H-pyrano[4,3-d]pyrimidin-2-yl)-2-methoxy-1H-benzo[d]imidazole-4-carbonitrile (JJ)

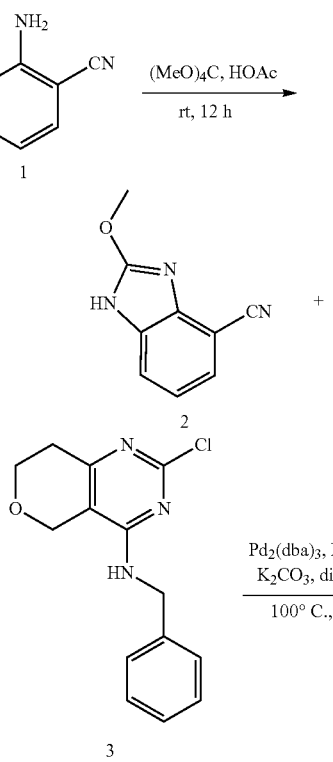

5.40-5.25 (m, 2H), 4.77 (d, J=5.4 Hz, 2H), 4.60 (s, 2H), 4.27 (s, 3H), 4.06 (t, J=5.4 Hz, 2H), 3.02 (t, J=5.4 Hz, 2H).

Example 11

Synthesis of 1-(4-(benzylamino)-7,8-dihydro-5H-pyrano[4,3-d]pyrimidin-2-yl)-N,2-dimethyl-1H-indole-4-carboxamide (KK)

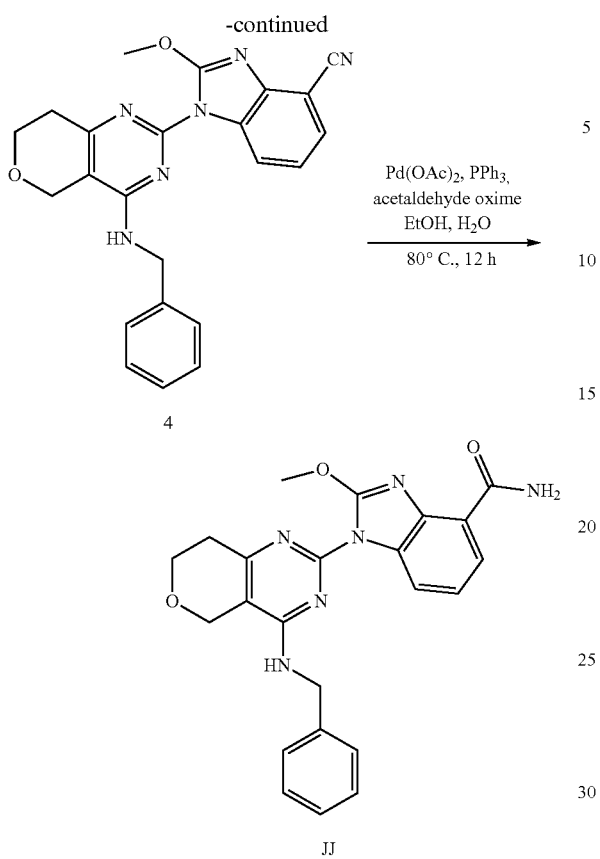

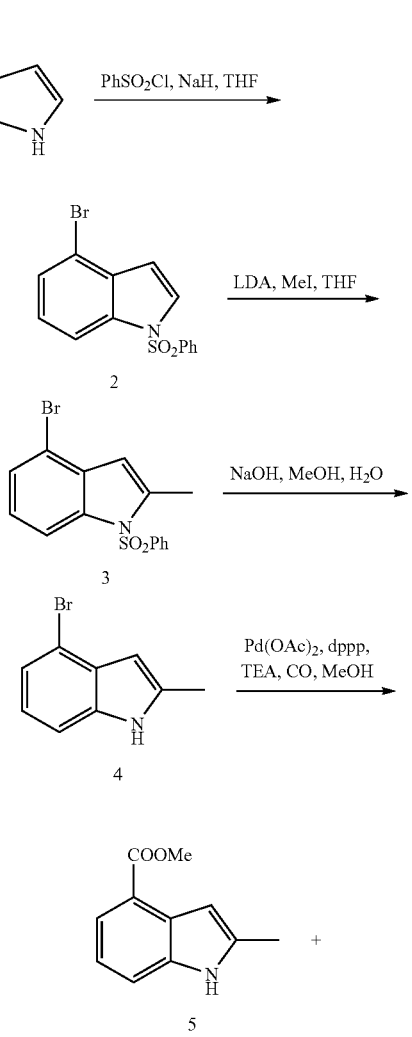

To a 0° C. solution of 2,3-diaminobenzonitrile 1 (0.532 g, 4.0 mmol) in acetic acid (10 mL) was added tetramethylorthocarbonate (0.544 g, 4.0 mmol). The mixture was stirred at the room temperature for 12 hours and then concentrated under reduced pressure. The residue was purified by flash chromatography (silica gel, petroleum ether/ethyl acetate=10:1) to give 2-methoxy-1H-benzo[d]imidazole-4-carbonitrile 2 (0.61 g, 88%). LRMS (M+H+) m/z: calcd 174.06. found 174.17.

A mixture of 2-methoxy-1H-benzo[d]imidazole-4-carbonitrile 2 (63 mg, 0.36 mmol) and N-benzyl-2-chloro-7,8-dihydro-5H-pyrano[4,3-d]pyrimidin-4-amine 3 (100 mg, 0.36 mmol), tris(dibenzylideneacetone) dipalladium(0) (33 mg, 0.036 mmol), X-phos (34 mg, 0.072 mg) and $K_2CO_3$ (100 mg, 0.72 mmol) in dioxane (4 mL) was heated at 100° C. for 12 hours under nitrogen atmosphere. The reaction mixture was cooled down to the room temperature and concentrated, and the resulting residue was then purified by flash chromatography (silica gel, petroleum ether/ethyl acetate=4:1) to give intermediate 4 (100 mg, 67%). LRMS (M+H+) m/z: calcd 413.16. found 413.20.

To a solution of intermediate 4 (50 mg, 0.12 mmol) in ethanol (4 mL) and water (0.4 mL) were added Pd(OAc)$_2$ (2.7 mg, 0.012 mmol), PPh$_3$ (6.3 mg, 0.024 mmol) and acetaldehyde oxime (14 mg, 0.24 mmol). Then the reaction mixture was stirred at 80° C. for 12 hours. The resulting mixture was cooled down and concentrated, the resulting residue was purified by flash chromatography (silica gel, dichloromethane/methanol=20:1) to give the desired compound JJ (32 mg, 62%) as solid. LRMS (M+H+) m/z: calcd 431.46. found 431.51. $^1$H-NMR (300 MHz, CDCl$_3$): δ 9.30-9.29 (m, 1H), 8.03 (d, J=7.8 Hz, 1H), 7.68 (d, J=8.1 Hz, 1H), 7.37-7.35 (m, 4H), 7.13 (t, J=8.1 Hz, 1H), 5.97 (s, 1H),

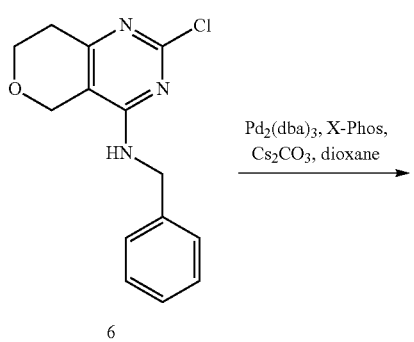

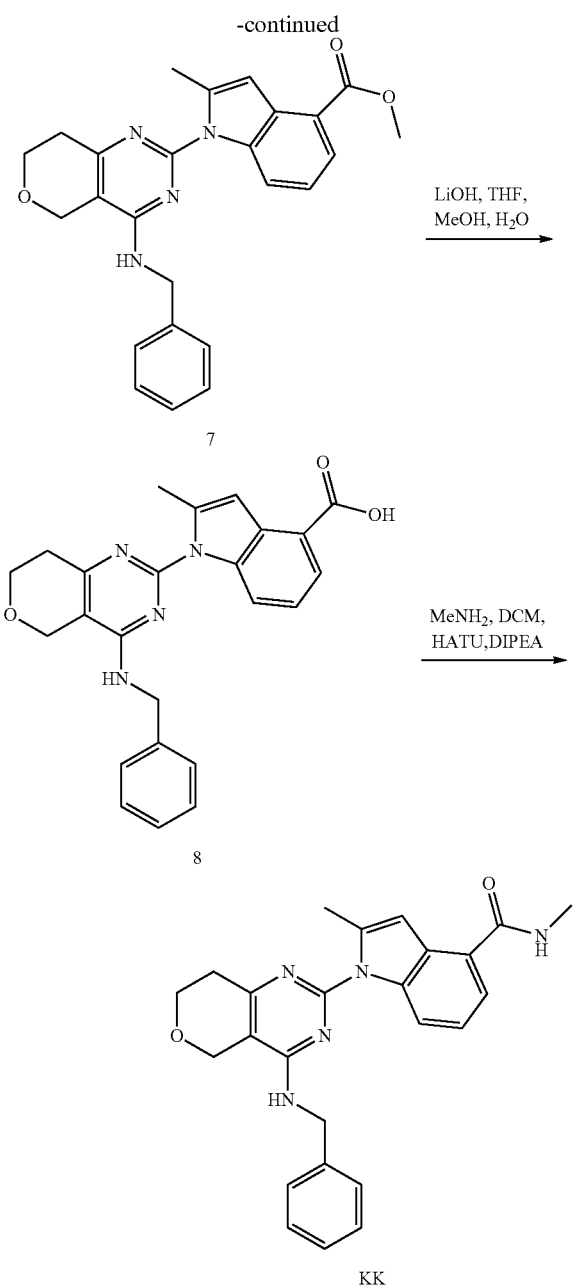

To a 0° C. solution of 4-bromo-1H-indole (10 g, 50 mol) in THF (100 mL) was added NaH (96%, 1.4 g, 56 mol). The mixture was stirred at the room temperature for 30 min, and PhSO$_2$Cl (8.8 g, 0.05 mol) was then added slowly. The resulting mixture was stirred at the same temperature for 6 hours. It was then quenched with water (20 mL) and extracted with ethyl acetate (3×100 mL). The combined organic layers were washed with brine, dried over sodium sulfate. The Na2SO4 was removed by filtration, and the volatiles were removed under reduced pressure. The resulting residue was purified by flash chromatography (silica gel, petroleum ether/ethyl acetate=5:1) to give 4-bromo-1-(phenylsulfonyl)-1H-indole 2 (10 g, 60%). LRMS (M+H$^+$) m/z: calcd 335.96. found 336.10.

To a −45° C. solution of the aforementioned intermediate 2 (8 g, 23.9 mmol) in THF (100 mL) was added LDA (1.6 M, 18 mL, 28.9 mmol). The mixture was stirred at the same temperature for 1 hour, then MeI (4.04 g, 28.7 mmol) was added. The resulting mixture was warmed up to the room temperature and stirred for one more hour. It was then quenched with NH$_4$Cl saturated solution (30 mL) and extracted with ethyl acetate (3×50 mL). The combined organic layers were washed with water and brine, dried over anhydrous MgSO$_4$ and concentrated under reduced pressure. The residue was purified by flash chromatography (silica gel, petroleum ether/ethyl acetate=5:1) to give the intermediate 3 (7.0 g, 84%). LRMS (M+H$^+$) m/z: calcd 348.98. found 349.10.

To a solution of the aforementioned intermediate 3 (7.0 g, 20.1 mmol) in MeOH (80 mL) and water (40 mL) was added NaOH (4.01 g, 0.1 mol). The resulting solution was stirred at 50° C. for 6 h. it was then cooled down and concentrated under vacuum; the residue was extracted with DCM (3×50 mL). The combined organic layers were washed with water and brine, dried over anhydrous MgSO$_4$ and concentrated under vacuum. The residue was purified by flash chromatography (silica gel, petroleum ether/ethyl acetate=5:1) to give 4-bromo-2-methyl-1H-indole 4 (3.0 g, 71%). LRMS (M+H$^+$) m/z: calcd 209.98. found 210.12.

A mixture of the aforementioned intermediate 4 (1.2 g, 5.74 mmol), Pd(OAc)$_2$ (122 mg, 0.58 mmol), dppp (238 mg, 0.58 mmol), TEA (1.6 mL, 11.48 mmol) in MeOH (40 mL) was sealed under CO atmosphere and heated at 90° C. overnight. The resulting mixture was cooled down and concentrated, the residue was then purified by flash chromatography (silica gel, petroleum ether/ethyl acetate=5:1) to give methyl 2-methyl-1H-indole-4-carboxylate 5 (0.9 g, 83%). LRMS (M+H$^+$) m/z: calcd 190.08. found 190.12.

A mixture of the aforementioned intermediate 5 (1.02 g, 3.70 mmol), methyl 2-methyl-1H-indole-4-carboxylate 6 (700 mg, 3.70 mmol), tris(dibenzylidene-acetone) dipalladium(0) (677 mg, 0.74 mmol), X-Phos (352 mg, 0.74 mmol) and Cs$_2$CO$_3$ (2.4 g, 7.4 mmol) in dioxane (35 mL) was heated at 100° C. for 12 hours under nitrogen atmosphere. The resulting reaction mixture was cooled to the room temperature and concentrated under vacuum, the residue was purified by flash chromatography (silica gel, petroleum ether/ethyl acetate=2:1) to give methyl 1-(4-(benzylamino)-7,8-dihydro-5H-pyrano[4,3-d]pyrimidin-2-yl)-2-methyl-1H-indole-4-carboxylate 7 (1.2 g, 76%). LRMS (M+H$^+$) m/z: calcd 429.48. found 429.59.

To a solution of the aforementioned intermediate 7 (600 mg, 1.4 mmol) in THF (15 mL), methanol (5 mL) and water (5 mL) was added LiOH (177 mg, 4.2 mmol). Then the reaction mixture was refluxed for 3 hours. It was then cooled down and the solvents were removed under vacuum, and the residue was acidified with HCl (2 M) to pH=2-3 and extracted with DCM (3×50 mL). The combined organic layers were dried over anhydrous MgSO$_4$, filtered and concentrated to give the intermediate 8 which was used for next step without further purification. LRMS (M+H$^+$) m/z: calcd 415.17. found 415.25.

To a 0° C. solution of the aforementioned crude intermediate 8 (70 mg, 0.17 mmol) in DCM (10 mL) were added methylamine in THF (2 M, 0.17 mL), HATU (78 mg, 0.20 mmol) and DIPEA (44 mg, 0.34 mmol). The reaction solution was stirred at the room temperature for 2 hours and then quench with water (30 mL) and DCM (100 mL), the organic layer was separated, dried over sodium sulfate and concentrated in vacuo and the residue was purified by flash chromatography (silica gel, dichloromethane/methanol=20: 1) to give 1-(4-(benzylamino)-7,8-dihydro-5H-pyrano[4,3-d]pyrimidin-2-yl)-N,2-dimethyl-1H-indole-4-carboxamide KK (35 mg, 48%). LRMS (M+H$^+$) m/z: calcd 428.20. found 428.25. ¹HNMR (300 MHz, CD₃OD): δ 7.73 (d, J=8.1 Hz, 1H), 7.37-7.24 (m, 6H), 6.96 (t, J=7.5 Hz, 1H), 6.71 (s, 1H), 4.71 (s, 2H), 4.64 (s, 2H), 4.05 (t, J=5.7 Hz, 2H), 2.95 (s, 3H), 2.82 (t, J=5.7 Hz, 2H), 2.45 (s, 3H).

Example 12

Synthesis of 1-(4-(benzylamino)-5,6,7,8-tetrahydro-quinazolin-2-yl)-2-methyl-1H-indole-4-carboxylic acid (LL)

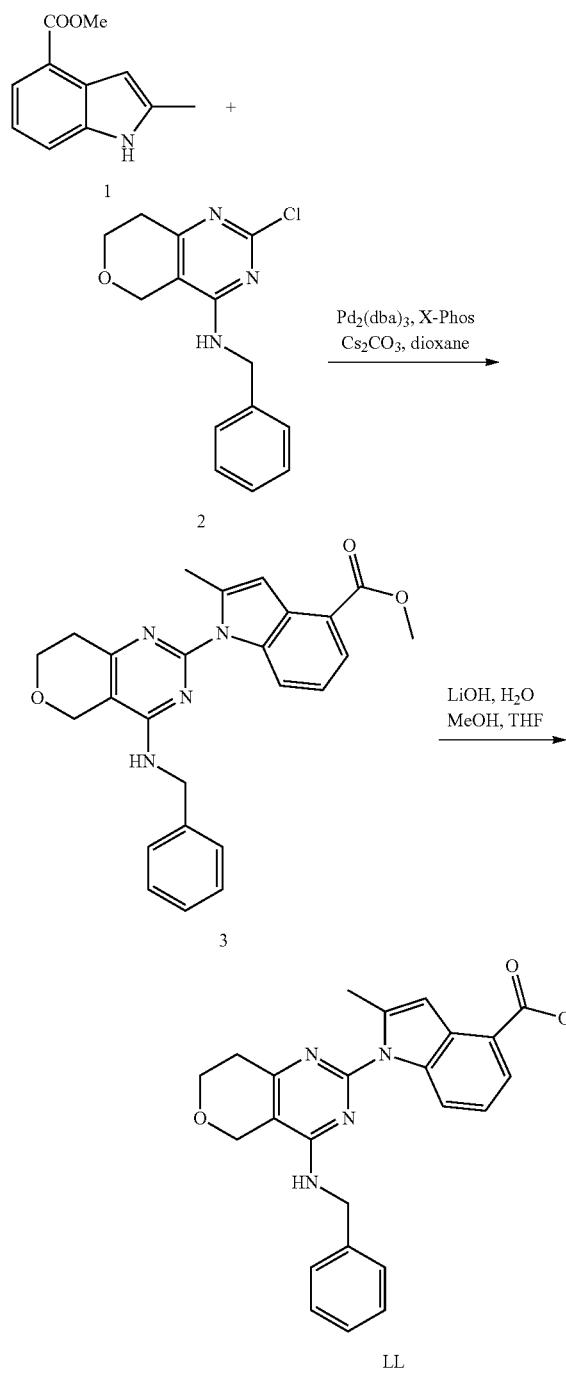

A mixture of methyl 2-methyl-1H-indole-4-carboxylate 1 (60 mg, 0.32 mmol), N-benzyl-2-chloro-5,6,7,8-tetrahydro-quinazolin-4-amine 2 (87 mg, 0.32 mmol), tris(dibenzylideneacetone) dipalladium(0) (59 mg, 0.064 mmol), X-Phos (30 mg, 0.064 mmol) and Cs₂CO₃ (208 mg, 0.64 mmol) in dioxane (5 mL) was heated at 100° C. for 12 hours under nitrogen atmosphere. It was then cooled down to the room temperature and concentrated in vacuo, the residue was purified by flash chromatography (silica gel, petroleum ether/ethyl acetate=2:1) to give the intermediate 3 (100 mg, 73.5%). LRMS (M+H⁺) m/z: calcd 427.21. found 427.26.

To a solution of the aforementioned crude intermediate 3 (100 mg, 0.23 mmol) in a THF (12 mL), methanol (4 mL) and water (4 mL) was added LiOH (30 mg, 0.7 mmol). Then the mixture was refluxed for 3 hours. Then the reaction mixture was refluxed for 3 hours. It was then cooled down and the solvents were removed under vacuum, and the residue was acidified with HCl (2 M) to pH=2-3 and extracted with DCM (3×50 mL). The combined organic layers were dried over anhydrous MgSO₄, filtered and concentrated in vacuo, the residue was purified by flash chromatography (silica gel, dichloromethane/methanol=20:1) to give 1-(4-(benzylamino)-5,6,7,8-tetrahydroquinazolin-2-yl)-2-methyl-1H-indole-4-carboxylic acid LL (60 mg, 63%) as light yellow solid. LRMS (M+H⁺) m/z: calcd 413.19. found 413.25. ¹HNMR (400 MHz, CD₃OD): δ 7.76 (dd, J=7.5 Hz, J=0.9 Hz, 1H), 7.65 (d, J=8.4 Hz, 1H), 7.32-7.24 (m, 5H), 6.98-6.93 (m, 2H), 4.72 (s, 2H), 2.75-2.72 (m, 2H), 2.55-2.51 (m, 2H), 2.42 (s, 3H), 1.94-1.92 (m, 4H).

Example 13

Synthesis of 1-(4-(benzylamino)-5,6,7,8-tetrahydro-quinazolin-2-yl)-2-methyl-1H-indole-4-sulfonamide (MM)

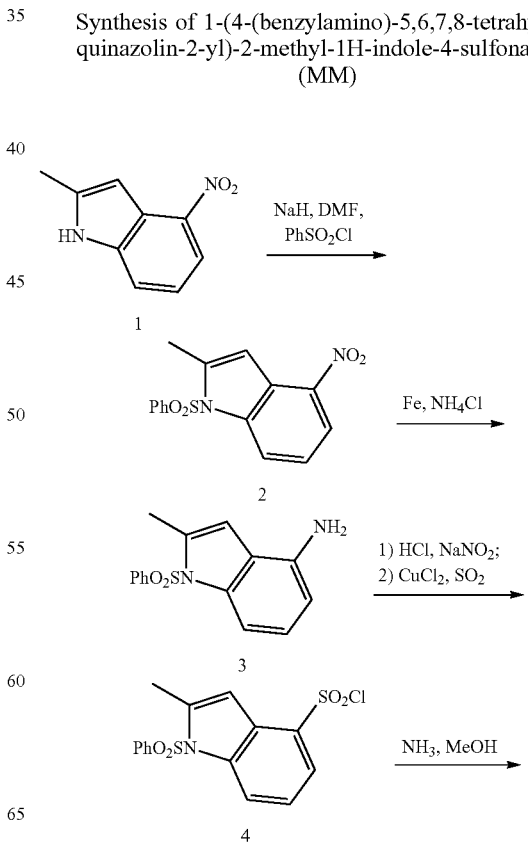

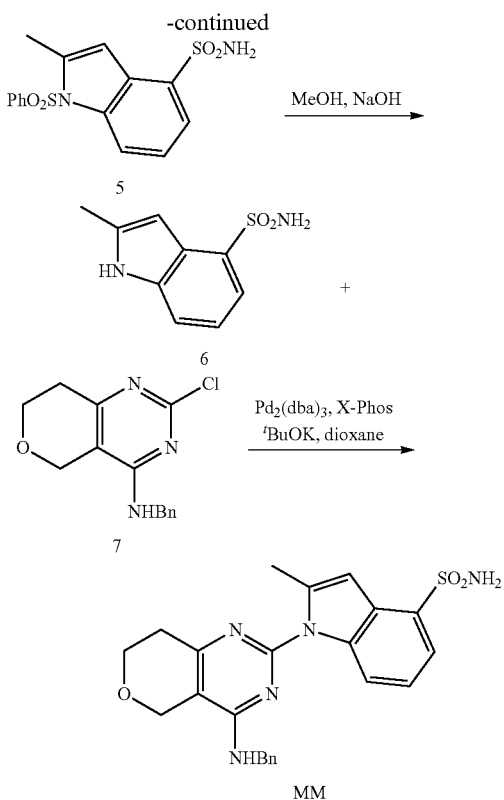

To a 0° C. solution of 2-methyl-4-nitro-1H-indole (6.34 g, 36 mmol) in DMF (40 mL) was added NaH (1.29 g, 54 mmol). The reaction mixture was stirred at the same temperature for 15 minutes, and then benzenesulfonyl chloride (9.54 g, 54 mmol) was added. The mixture was stirred for 2 h at the room temperature. And then quenched with NH$_4$Cl (aq.) (10 mL) and H$_2$O (50 mL), the solid was collected by filtration to give 2-methyl-4-nitro-1-(phenylsulfonyl)-1H-indole as a yellow solid 2 (10 g, 88%) which was used in the next step without further purification.

To a solution of the aforementioned intermediate 2 (10 g, 31 mmol) in ethanol (300 mL) were added saturated NH$_4$Cl (aq) (60 mL) and Fe (8.7 g, 155 mmol). The reaction mixture was stirred at 60° C. for 2 h. It was then cooled down and the solid was filtered off and the filtrate was concentrated under vacuum. The residue was purified by flash chromatography (silica gel, petroleum ether/ethyl acetate=1:2) to give 2-methyl-1-(phenylsulfonyl)-1H-indol-4-amine 3 (8.8 g, 97%). LRMS (M+H$^+$) m/z: calcd 287.08. found 287.19. $^1$H NMR (300 MHz, DMSO): δ 7.81-7.78 (m, 2H), 7.67-7.64 (m, 1H), 7.59-7.54 (m, 2H), 7.18 (d, J=8.1 Hz, 1H), 6.92 (t, J=8.0 Hz, 1H), 6.64 (s, 1H), 6.34 (d, J=7.8 Hz, 1H), 5.40 (s, 2H), 2.49 (s, 3H).

To a 0° C. suspension of the aforementioned intermediate 3 (2.86 g, 0.01 mol) in concentrated aq. HCl (20 mL, 36%) was added a solution of NaNO$_2$ (1.6 g) in water (6 mL) dropwisely over 30 minutes and the mixture is then stirred for another 60 minutes. A solution of CuCl$_2$ (0.27 g) in water (0.5 mL) was added to a solution of glacial acetic acid (50 mL) saturated with SO$_2$. Then the resulting diazoniumchloride suspension was pumped into this aforementioned reaction mixture at the room temperature., the reaction mixture was poured onto ice/water (55 mL) when the nitrogen gas evolution ceased (about 60 minutes) and the precipitated solid 4 (3.5 g crude product) was collected by filtration which was used in the next step without further purification.

To a 0° C. solution of the aforementioned intermediate 4 (3.5 g) in MeOH (50 mL) was added NH$_3$ in MeOH (20 mL, 7 N). The resulting mixture was stirred at the room temperature overnight. The reaction mixture was concentrated in vacuo, and the residue was purified by flash chromatography (silica gel, petroleum ether/ethyl acetate=5:3) to give 2-methyl-1-(phenylsulfonyl)-1H-indole-4-sulfonamide 5 (500 mg, 15%). LRMS (M+H$^+$) m/z: calcd 351.04. found 351.16. $^1$H NMR (400 MHz, CDCl$_3$): δ 8.44 (d, J=11.2 Hz, 1H), 7.84-7.78 (m, 7H), 4.76 (s, 2H), 2.74 (t, J=5.6 Hz, 2H), 2.67 (s, 3H).

To a 0° C. solution of the aforementioned intermediate 5 (500 mg, 1.4 mmol)) in MeOH (20 mL) were added NaOH (168 mg, 4.2 mmol) and water (2 mL). The resulting solution was then heated to reflux overnight. It was cooled down to the room temperature and concentrated in vacuo. The residue was purified by flash chromatography (silica gel, petroleum ether/ethyl acetate=5:3) to give desired product 6 as a yellow solid (245 mg, 82%). LRMS (M+H+) m/z: calcd 211.05. found 211.08. $^1$H NMR (400 MHz, CD$_3$OD): δ 7.56 (d, J=10 Hz, 1H), 7.49 (d, J=10 Hz, 1H), 7.10 (t, J=10 Hz, 1H), 6.61 (s, 1H), 2.48 (s, 3H).

To a 0° C. solution of the aforementioned 6 (50 mg, 0.18 mmol) in dioxane (10 mL) were added N-benzyl-2-chloro-7,8-dihydro-5H-pyrano[4,3-d]pyrimidin-4-amine (50 mg, 0.18 mmol), tris(dibenzylidene-acetone) dipalladium(0) (30 mg, 0.03 mmol), X-Phos (30 mg, 0.06 mmol) and KO$^t$-Bu (40 mg, 0.36 mmol), and the reaction mixture was then heated at 100° C. for 2 hours under nitrogen atmosphere. It was cooled down to the room temperature and concentrated in vacuo, and the residue was purified by flash chromatography (silica gel, DCM/MeOH=30:1) to give the desired product MM (10 mg, 12%). LRMS (M+H$^+$) m/z: calcd 450.15. found 450. $^1$HNMR (400 MHz, CD$_3$OD): δ 7.56 (d, J=8.8 Hz, 1H), 7.54 (d, J=8.8 Hz, 1H), 7.27-7.20 (m, 3H), 7.04-7.02 (m, 2H), 6.84 (t, J=8.0 Hz, 1H), 6.60 (s, 1H), 4.23-4.21 (m, 4H), 3.84 (t, J=5.6 Hz, 2H), 2.57 (t, J=5.6 Hz, 2H), 2.37 (s, 3H).

Example 14

Synthesis of 1-(4-(benzylamino)-5,6,7,8-tetrahydroquinazolin-2-yl)-2-methyl-1H-indole-4-sulfonamide (NN)

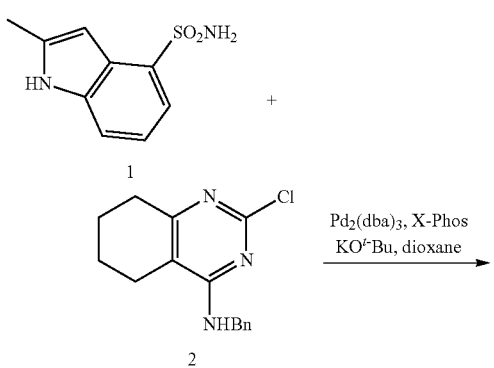

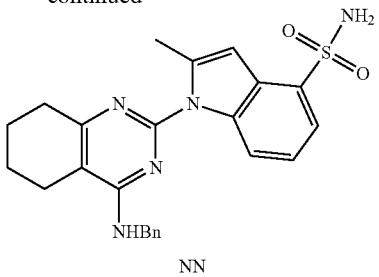

Following the procedures of Example 13 and using the reagents and reactions depicted, Example 14 is prepared.

Example 15

Synthesis of N-benzyl-2-(2-methyl-4-(methylsulfonyl)-1H-indol-1-yl)-5,6,7,8-tetrahydroquinazolin-4-amine (OO)

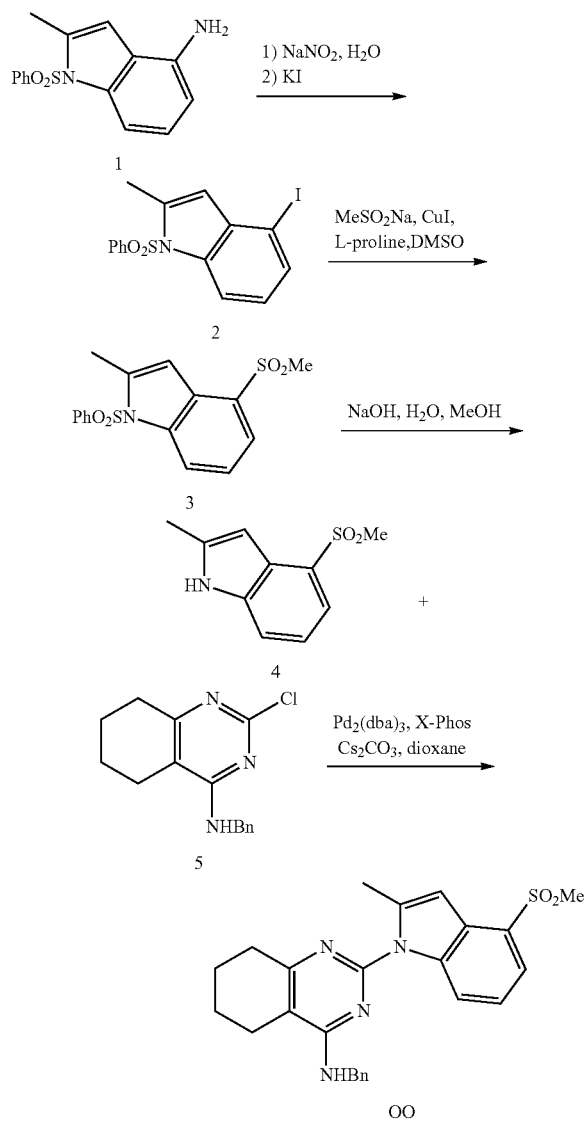

To a 0° C. suspension of 2-methyl-1-(phenylsulfonyl)-1H-indol-4-amine (572 mg, 2 mmol) in $H_2O$ (10 mL) were added a solution of $NaNO_2$ (305 mg, 4.4 mmol) in $H_2O$ (10 mL) and aq. HCl (10 mL, 10%). 30 min later, the resulting reaction mixture was added to a 0° C. solution of KI (8.53 g, 51.4 mmol) in $H_2O$ (20 mL). then it was kept at the same temperature for another 1.5 h and heated at 85° C. for 10 min. The solution was cooled down and extracted with ethyl acetate (2×100 mL), the combined organic layers were dried over $Na_2SO_4$ and filtered. The filtrate was concentrated in vacuo. The residue was purified by flash chromatography (petroleum ether/ethyl acetate=3/1) to give 4-iodo-2-methyl-1-(phenylsulfonyl)-1H-indole 2 as a white solid (600 mg, 76% yield). $^1$H NMR (300 MHz, DMSO): δ 8.05 (d, J=8.4 Hz, 1H), 7.90-7.87 (m, 2H), 7.72-7.69 (m, 1H), 7.65-7.57 (m, 3H), 7.07 (t, J=8.1 Hz, 1H), 6.46 (s, 1H), 2.63 (s, 3H).

To a solution of the aforementioned intermediate 2 (0.6 g, 1.51 mmol) in DMSO (10 mL) were added sodium methanesulfinate, CuI (58 mg, 0.3 mmol) and L-proline (70 mg, 0.6 mmol) under $N_2$ atmosphere. The mixture was stirred at 80° C. for 2 days. It was cooled down and quenched with saturated aqueous $NH_4Cl$ (10 mL), diluted with water (20 mL), extracted with ethyl acetate (30 mL×2), dried over $Na_2SO_4$ and filtered. The filtrate was concentrated in vacuo. The residue was purified by flash chromatography (petroleum ether/ethyl acetate=2/1) to give 2-methyl-4-(methylsulfonyl)-1-(phenylsulfonyl)-1H-indole 3 as a yellow solid (320 mg, 60% yield). $^1$H NMR (400 MHz, DMSO): δ 8.40 (d, J=8.4 Hz, 1H), 7.98-7.96 (m, 2H), 7.77-7.72 (m, 2H), 7.62 (t, J=8.0 Hz, 2H), 7.52 (t, J=8.0 Hz, 1H), 6.99 (s, 1H), 3.20 (s, 3H), 2.69 (s, 3H).

To a solution of the aforementioned intermediate 3 (320 mg, 0.92 mmol) in MeOH (20 mL) were water (2 mL) and NaOH (110 mg, 2.75 mmol). The mixture was heated at 60° C. for 0.5 h. it was cooled down and the solvent was removed in vacuo and the residue was purified by flash chromatography (petroleum ether/ethyl acetate=1/1) to give 2-methyl-4-(methylsulfonyl)-1H-indole 4 as a white solid (170 mg, 88% yield). LRMS (M+H$^+$) m/z: calcd 209.05. found 209.

To a 0° C. solution of the aforementioned 4 (77 mg, 0.365 mmol) in dioxane (20 mL) were added N-benzyl-2-chloro-5,6,7,8-tetrahydroquinazolin-4-amine (100 mg, 0.365 mmol), $Pd_2(dba)_3$ (67 mg, 0.073 mmol), X-Phos (35 mg, 0.073 mmol) and $Cs_2CO_3$ (357 mg, 1.095 mmol), and the reaction mixture was then heated at 100° C. for 2 hours under nitrogen atmosphere. The reaction was cooled down and quenched by adding water (20 mL) and extracted with ethyl acetate (30 mL×2), the combined organic layers were dried over $Na_2SO_4$ and filtered. The filtrate was concentrated in vacuo. The residue was purified by flash chromatography (silica gel, MeOH/DCM=1/15) to give N-benzyl-2-(2-methyl-4-(methylsulfonyl)-1H-indol-1-yl)-5,6,7,8-tetrahydroquinazolin-4-amine (00) as a white solid (90 mg, 55% yield). LRMS (M+H$^+$) m/z: calcd 447.18. found 446.30. $^1$H NMR (400 MHz, CDCl$_3$): δ 8.17 (d, J=8.0 Hz, 1H), 7.71 (d, J=7.6 Hz, 1H), 7.37-7.32 (m, 5H), 7.15 (t, J=8.0 Hz, 1H), 6.82 (s, 1H), 5.09 (s, 1H), 4.75 (d, J=5.6 Hz, 2H), 3.08 (s, 3H), 2.82 (t, J=5.0 Hz, 2H), 2.64 (s, 3H), 2.42 (t, J=5.4 Hz, 2H), 1.93-1.91 (m, 4H).

Example 16

Synthesis of N-benzyl-2-(2-methyl-4-(1H-tetrazol-5-yl)-1H-indol-1-yl)-7,8-dihydro-5H-pyrano[4,3-d]pyrimidin-4-amine (PP)

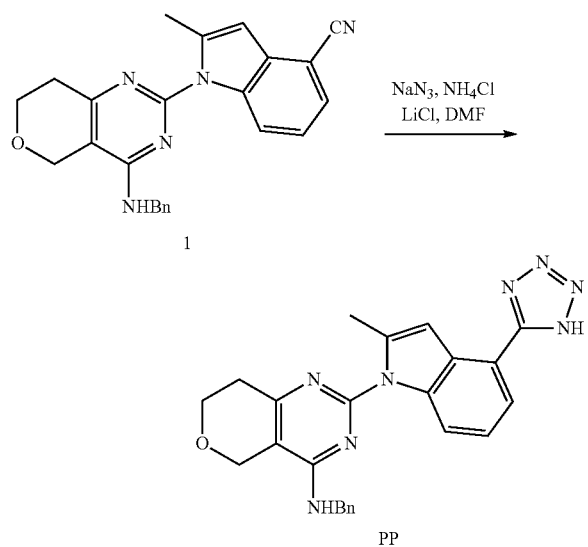

A mixture of 1-(4-(benzylamino)-7,8-dihydro-5H-pyrano[4,3-d]pyrimidin-2-yl)-2-methyl-1H-indole-4-carbonitrile 1 (340 mg, 0.86 mmol), NaN$_3$ (560 mg, 8.6 mmol), NH$_4$Cl (465 mg, 8.6 mmol), LiCl (110 mg, 2.58 mmol) and DMF (20 mL) was stirred at 120° C. for 14 hours under N$_2$ atmosphere. The mixture was cooled down and diluted with water (30 mL) and extracted with ethyl acetate (50 mL×3), the combined organic layers were dried over Na$_2$SO$_4$ and filtered. The filtrate was concentrated in vacuo. The residue was purified by flash chromatography (silica gel, MeOH/DCM=1:8) to give N-benzyl-2-(2-methyl-4-(1H-tetrazol-5-yl)-1H-indol-1-yl)-7,8-dihydro-5H-pyrano[4,3-d]pyrimidin-4-amine PP as yellow solid (40 mg, 11% yield). LRMS (M+H$^+$) m/z: calcd 439.19. found 439.20. $^1$H-NMR (400 MHz, CD$_3$OD): δ 7.77 (d, J=8.0 Hz, 1H), 7.60 (d, J=7.6 Hz, 1H), 7.34-7.26 (m, 5H), 7.09 (t, J=8.0 Hz, 1H), 6.98 (s, 1H), 4.73 (s, 2H), 4.66 (s, 2H), 4.07 (t, J=5.6 Hz, 2H), 2.84 (t, J=5.6 Hz, 2H), 2.5 (s, 3H).

Example 17

Synthesis of 2-(4-(aminomethyl)-2-methyl-1H-indol-1-yl)-N-benzyl-5,6,7,8-tetrahydro-quinazolin-4-amine (QQ)

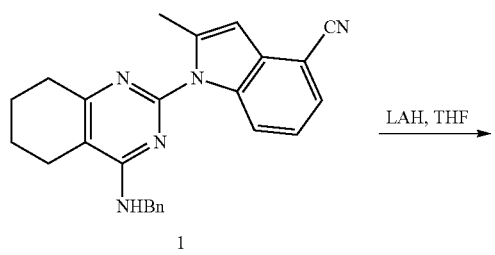

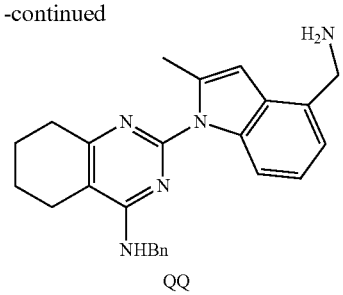

To a 0° C. solution of 1-(4-(benzylamino)-7,8-dihydro-5H-pyrano[4,3-d]pyrimidin-2-yl)-2-methyl-1H-indole-4-carbonitrile 1 (50 mg, 0.13 mmol) in THF (5 mL) was added lithium aluminum hydride (10 mg, 0.26 mmol). The resulting mixture was stirred at the room temperature for 12 hours. The reaction mixture was quenched by Na$_2$SO$_4$.10H$_2$O, and filtered. The filtrate was concentrated under vacuum, and the residue was purified by column chromatography (silica gel, DCM/MeOH=20:1) to afford 2-(4-(aminomethyl)-2-methyl-1H-indol-1-yl)-N-benzyl-5,6,7,8-tetrahydroquinazolin-4-amine QQ (30 mg, 59%) as a white solid. LRMS (M+H$^+$) m/z: calcd 398.23. found 398.23. $^1$HNMR (400 MHz, CD$_3$OD): δ 7.44 (d, J=8.0 Hz, 1H), 7.31-7.23 (m, 5H), 7.02 (d, J=8.0 Hz, 1H), 6.94 (t, J=8.0 Hz, 1H), 6.41 (s, 1H), 4.72 (s, 2H), 4.05 (s, 2H), 2.74 (t, J=5.6 Hz, 2H), 2.50 (t, J=5.6 Hz, 2H), 2.40 (s, 3H), 1.95-1.89 (m, 4H).

Example 18

Synthesis of 1-(4-(benzylamino)-7,8-dihydro-5H-pyrano[4,3-d]pyrimidin-2-yl)-2-cyclopropyl-1H-indole-4-carboxamide (SS)

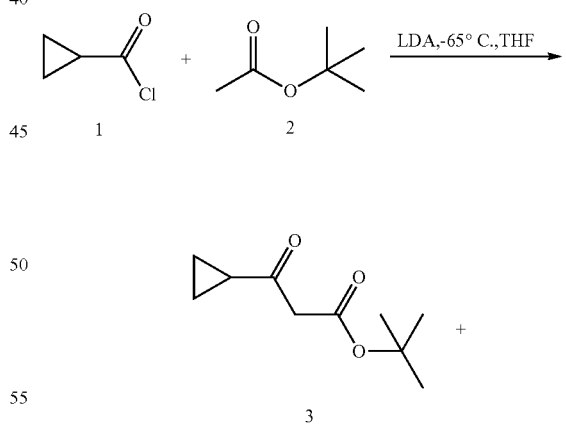

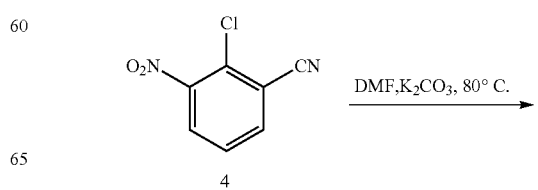

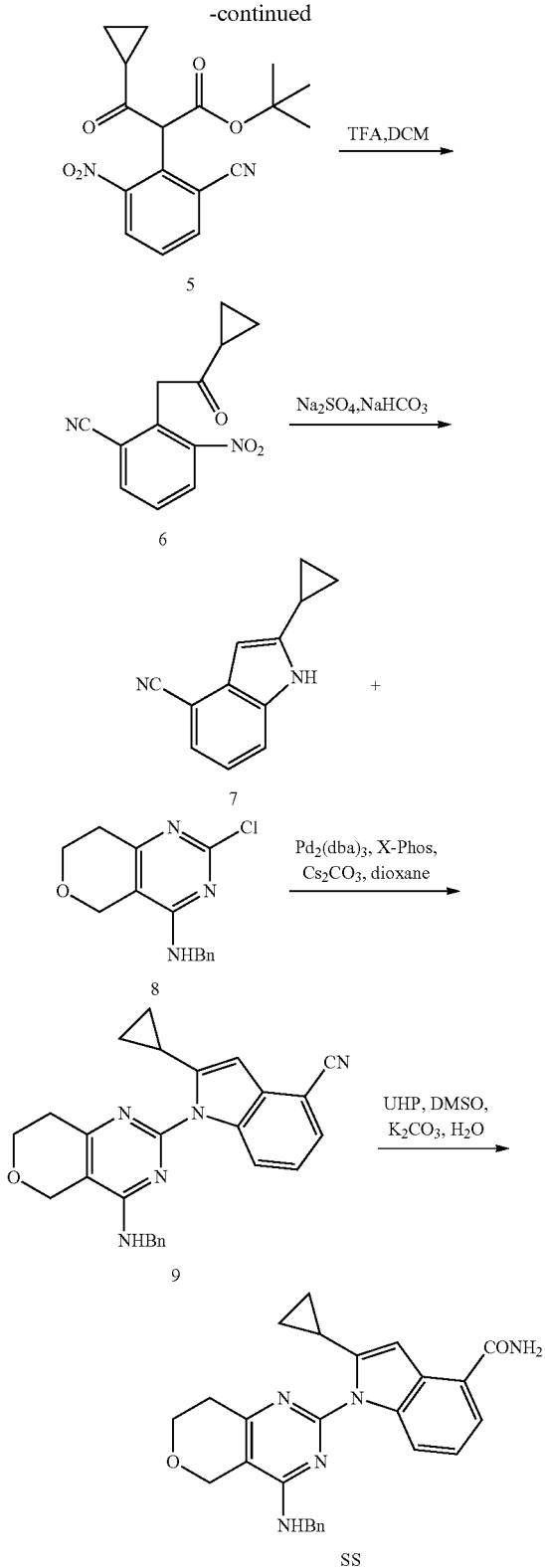

kept at the same temperature for 2 hours and then allowed to warm slowly to 0° C. It's then quenched with saturated ammonium chloride (100 mL) and extracted with ethyl acetate (200 mL×2). The combined organic layers were washed with aq. hydrochloric acid (200 mL, 1N) and brine (200 mL), dried with anhydrous sodium sulfate and concentrated. The residue was purified by flash chromatography (petroleum ether/ethyl acetate=4:1) to give tert-butyl 3-cyclopropyl-3-oxopropanoate 3 (2.1 g, 60%) as a yellow liquid. $^1$H-NMR (300 MHz, CDCl$_3$): δ 3.42 (s, 1H), 2.03-1.97 (m, 1H), 1.43 (s, 9H), 1.06-1.03 (m, 2H), 0.93-0.88 (m, 2H).

A solution of the aforementioned intermediate 3 (1 g, 5.4 mmol), 2-chloro-3-nitrobenzonitrile 4 (1.6 g, 8.8 mmol) and potassium carbonate (2.2 g, 15.9 mmol) in N,N-dimethylacetamide (30 mL) was heated at 80° C. for 4 hours under nitrogen atmosphere. the reaction solution was cooled down and concentrated in vacuo, and the residue was purified by flash chromatography (petroleum ether/ethyl acetate=4:1) to give tert-butyl 2-(2-cyano-6-nitrophenyl)-3-cyclopropyl-3-oxopropanoate 5 (1.2 g, 67%) as a brown solid. $^1$H-NMR (300 MHz, CDCl$_3$): δ 13.53 (s, 1H), 8.10 (dd, J=1.2 Hz, J=8.4 Hz, 1H), 7.91 (dd, J=1.2 Hz, J=8.4 Hz, 1H), 7.57 (3.42 J=7.8 Hz, 1H),1.48 (m, 1H), 1.34 (s, 9H), 1.30 (d, J=7.2 Hz, 4H).

To a 0° C. solution of the aforementioned intermediate 5 (400 mg, 0.233 mol) in dichloromethane (20 mL) was added trifluoroacetic acid (5 mL). the reaction was kept at room temperature for 2 hour and then concentrated to give 2-(2-cyclopropyl-2-oxoethyl)-3-nitrobenzonitrile 6 (270 mg, 91%), which was used for next step without further purification. $^1$H-NMR (300 MHz, CDCl$_3$): δ 12.84 (s, 1H), 8.20 (dd, J=1.2 Hz, J=8.1 Hz, 1H), 7.97 (dd, J=1.2 Hz, J=8.1 Hz, 1H), 7.66 (t, J=8.1 Hz, 1H), 1.50 (m, 1H), 1.38-1.24 (m, 4H).

To a 0° C. solution of the aforementioned intermediate 6 (270 mg, 1.17 mmol) in dioxane (8 mL) were added sodium dithionite (880 mg, 5.06 mmol) in water (6 mL) and saturated aq. sodium bicarbonate (2 mL). The mixture was kept at room temperature for overnight. The reaction was diluted with water (20 mL) and extracted with ethyl acetate (40 mL×2). The combined organic layers were concentrated and the residue was purified by prep-TLC (petroleum ether/ethyl acetate=4:1) to give 2-cyclopropyl-1H-indole-4-carbonitrile 7 and 3-amino-2-(2-cyclopropyl-2-oxoethyl)benzonitrile (approximately 1:1 ratio by $^1$H-NMR), which was used for next step without further purification. $^1$H-NMR (300 MHz, CDCl$_3$): δ 8.43 (s, 1H), 7.46 (d, J=8.4 Hz, 1H), 7.31 (d, J=8.1 Hz, 1H), 7.07 (t, 1H), 6.20 (s, 1H), 2.00-1.96 (m, 1H), 0.90-0.79 (m, 1H).

To a 0° C. solution of the aforementioned 7 (70 mg, 0.38 mmol containing with 3-amino-2-(2-cyclopropyl-2-oxoethyl)benzonitrile in approximately 1:1 ratio) in dioxane (20 mL) were added N-benzyl-2-chloro-7,8-dihydro-5H-pyrano[4,3-d]pyrimidin-4-amine 8 (110 mg, 0.38 mmol), tris(dibenzylideneacetone) dipalladium(0) (40 mg, 0.04 mmol), X-Phos (40 mg, 0.08 mmol) and Cs$_2$CO$_3$ (250 mg, 0.76 mmol), and the reaction mixture was then heated at 100° C. for 2 hours under nitrogen atmosphere. The reaction was cooled down and quenched by adding water (20 mL) and extracted with ethyl acetate (30 mL×2), the combined organic layers were dried over Na$_2$SO$_4$ and filtered. The filtrate was concentrated in vacuo. The residue was purified by flash chromatography (silica gel, petroleum ether/ethyl acetate=2:1) to give 1-(4-(benzylamino)-7,8-dihydro-5H-pyrano[4,3-d]pyrimidin-2-yl)-2-cyclopropyl-1H-indole-4-carbonitrile 9 (110 mg, 69%). $^1$H-NMR (300 MHz, CDCl$_3$): δ 8.03-8.00 (m, 1H), 7.43-7.29 (m, 6H), 7.34-7.30 (m, 4H), 7.08 (d, J=8.4 Hz, 1H), 6.43 (s, 1H), 4.76 (d, J=4.5 Hz, 2H), 4.62 (s, 2H), 4.09 (t, J=6.0 Hz, 2H), 2.97 (m, 2H), 2.53 (m, 1H), 1.26 (m, 2H), 0.97 (m, 2H).

To a solution of 1-(4-(benzylamino)-7,8-dihydro-5H-pyrano[4,3-d]pyrimidin-2-yl)-2-cyclopropyl-1H-indole-4-carbonitrile (100 mg, 0.3 mmol) in DMSO (2 mL) was added UHP (226 mg, 2.4 mmol) and $K_2CO_3$ (20 mg, 0.15 mmol). Then water (0.17 mL) was added to the mixture and stirred at room temperature for overnight. Water (50 mL) was added to the mixture. The mixture was filtrated to give crude product (30 mg) which was purified by prep-TLC (dichloromethane/methanol=20:1) to give 1-(4-(benzylamino)-7,8-dihydro-5H-pyrano[4,3-d]pyrimidin-2-yl)-2-cyclopropyl-1H-indole-4-carboxamide SS (30 mg, 48%) as light yellow solid. LRMS (M+H$^+$) m/z: calcd 440.20. found 440.25. $^1$H-NMR (300 MHz, CD$_3$OD): δ 7.67 (d, J=8.4 Hz, 1H), 7.46 (d, J=7.2 Hz, 1H), 7.28 (m, 5H), 7.01 (t, J=8.4 Hz, 1H), 6.64 (s, 1H), 4.71 (s, 2H), 4.67 (s, 2H), 4.06-4.07 (m, 2H), 2.83 (m, 2H), 2.20 (m, 1H), 0.54-0.57 (m, 4H).

Following the procedures of Examples 1-17 and using the reagents and reactions depicted, Examples 18-29 were prepared.

Example 19

Synthesis of 1-(4-(benzylamino)-5,6,7,8-tetrahydroquinazolin-2-yl)-2-methyl-1H-indole-4-carboxamide (TT)

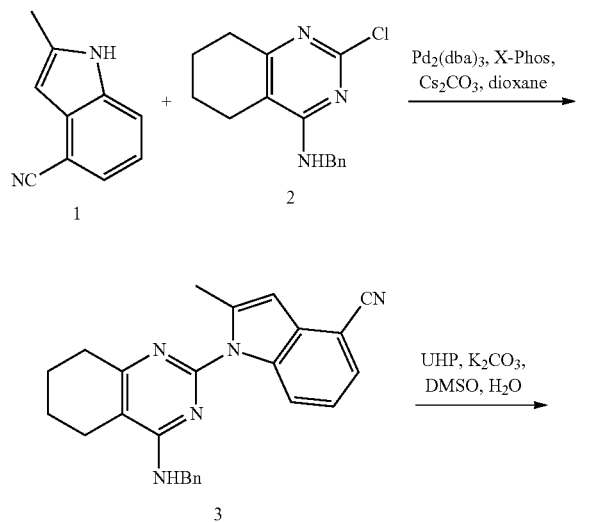

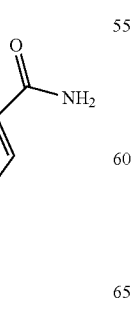

Example 20

Synthesis of 1-(4-(benzylamino)-5,6,7,8-tetrahydropyrido[4,3-d]pyrimidin-2-yl)-2-methyl-1H-indole-4-carboxamide (UU)

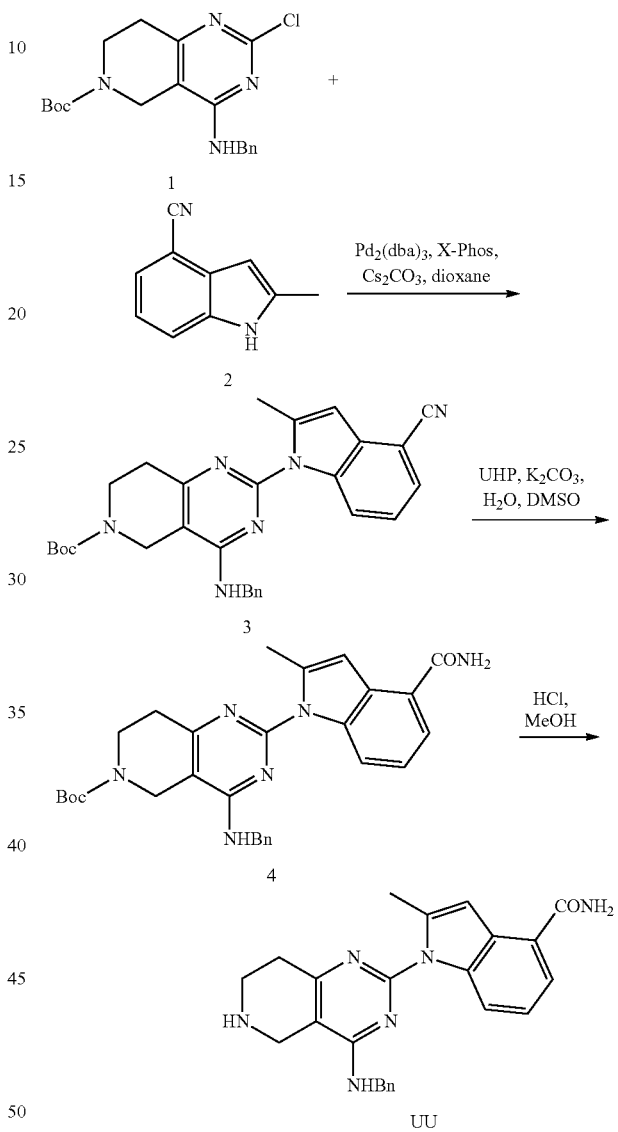

Example 21

Synthesis of 2-(2-amino-1H-benzo[d]imidazol-1-yl)-N-benzylthieno[2,3-d]pyrimidin-4-amine (VV)

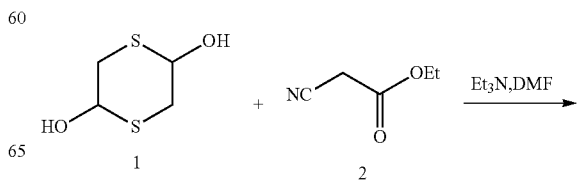

211
-continued
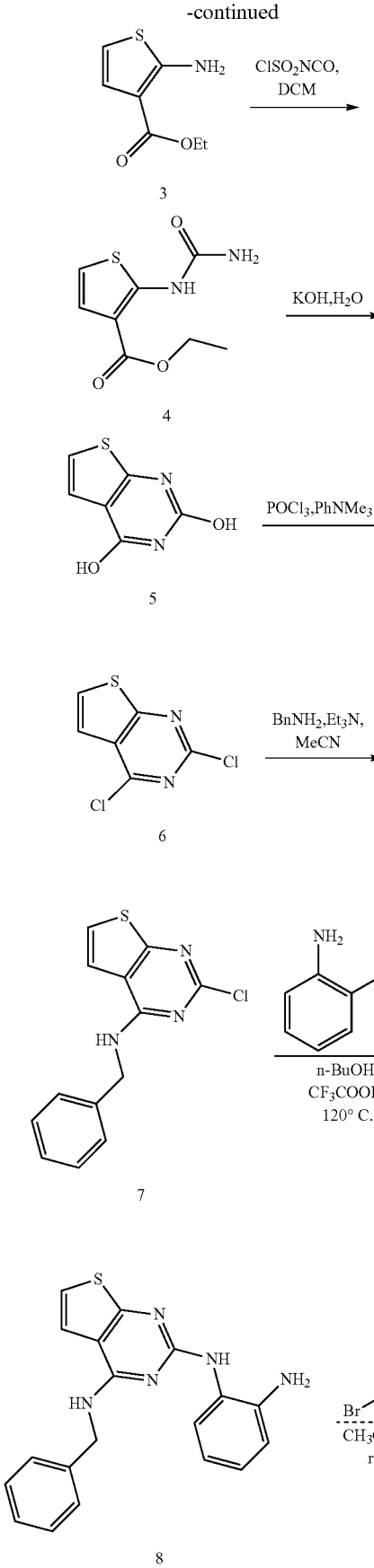
212
-continued
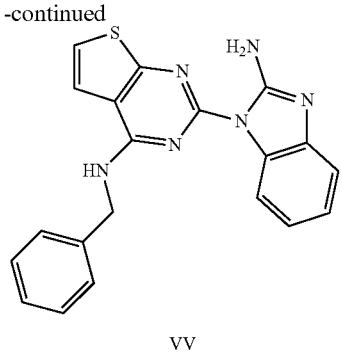
VV
Example 22
Synthesis of 2-(2-amino-1H-benzo[d]imidazol-1-yl)-N-benzyl-9H-purin-6-amine (WW)
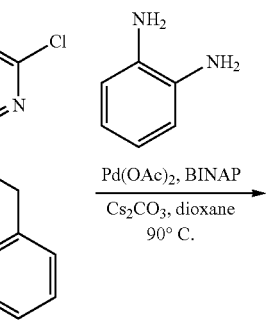

213
-continued
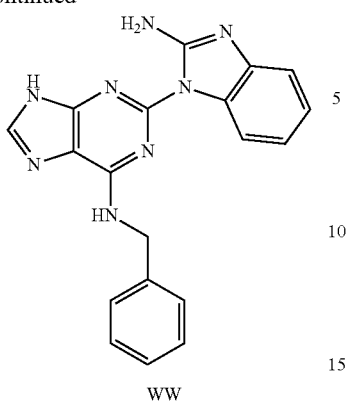
WW
Example 23
Synthesis of 2-(5-(aminomethyl)-4H-thieno[3,2-b]pyrrol-4-yl)-N-benzyl-8-methoxyquinazolin-4-amine (ZZ)
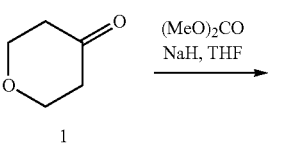
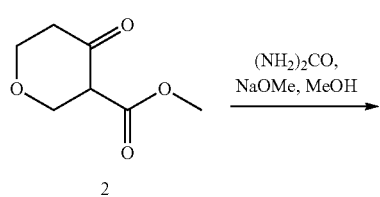
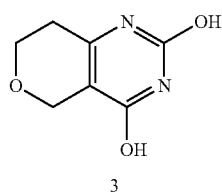
214
-continued
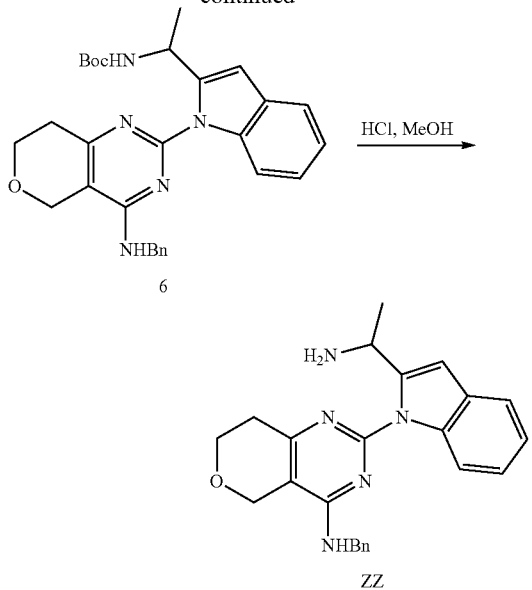
ZZ
Example 24
Synthesis of 2-(2-(1-aminoethyl)-1H-indol-1-yl)-N-benzyl-5,6,7,8-tetrahydroquinazolin-4-amine (AC)

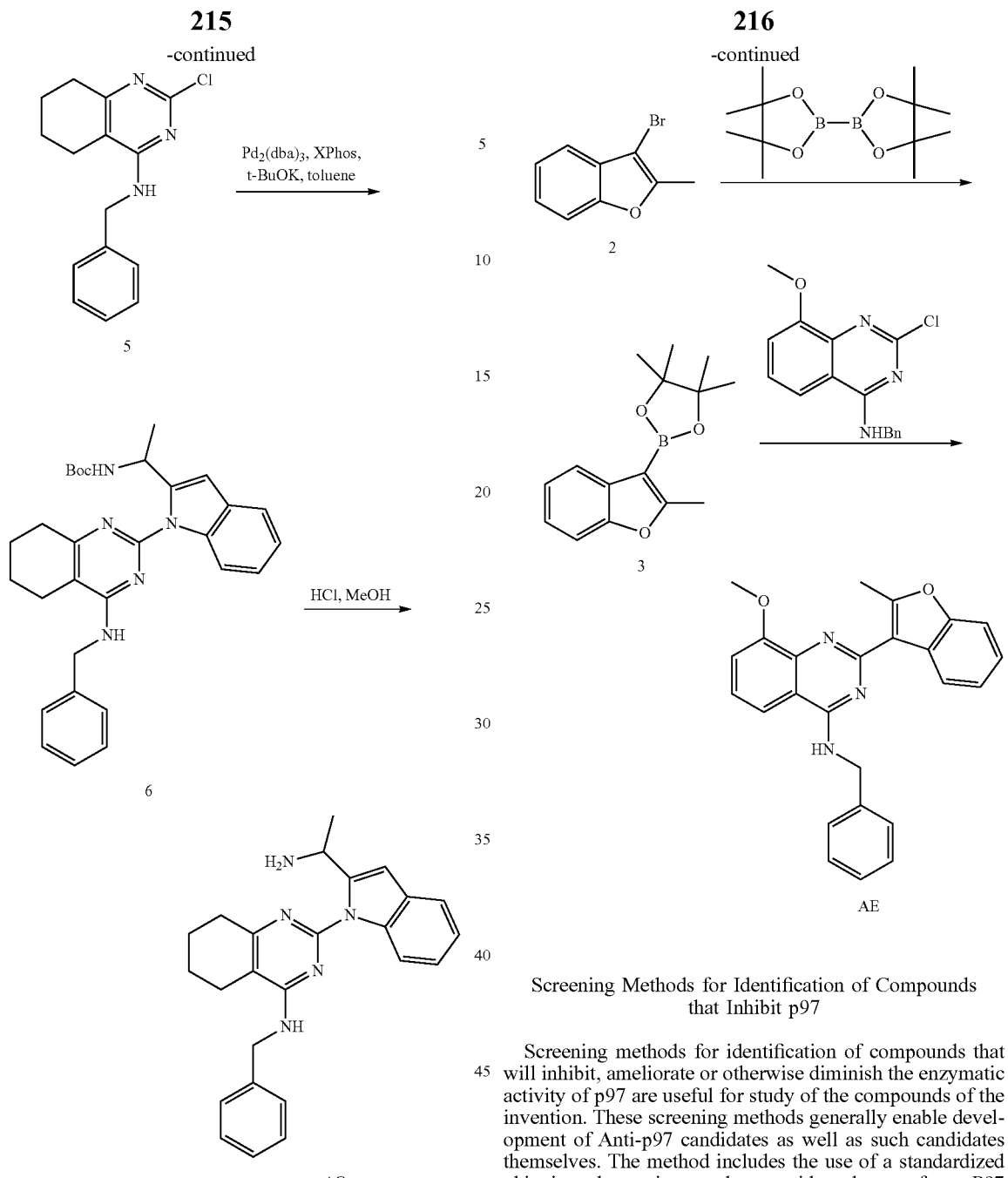

Example 25

Synthesis of N-benzyl-8-methoxy-2-(2-methylbenzofuran-3-yl)quinazolin-4-amine (AE)

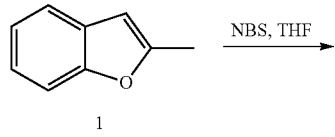

Screening Methods for Identification of Compounds that Inhibit p97

Screening methods for identification of compounds that will inhibit, ameliorate or otherwise diminish the enzymatic activity of p97 are useful for study of the compounds of the invention. These screening methods generally enable development of Anti-p97 candidates as well as such candidates themselves. The method includes the use of a standardized ubiquinated protein or other peptide substrate for a P97 enzyme. The standardized substrate is tagged with a detectable moiety that will enable differentiation between (a) the substrate having, for example, a ubiquitin or ubiquitin chain or other p97 substrate and (b) the cleaved substrate missing all or part of the substrate moiety that is susceptible to p97 cleavage. In particular, the methods for screening for a compound that inhibits the enzymatic activity of P97 enzyme include the assays described above as Biological Assays.

Screening methods are also provided for measuring the activity of any test agent on p97 that involves monitoring the effect of the test agent on the ability of p97 to engage in enzymatic activity.

In one aspect, such a method comprises modifying ubiquitin with a fluorescent molecule and cleaving the fluorescent ubiquitin conjugate. The course of the cleavage reaction is monitored by a decrease in fluorescence polarization of the fluorescent molecule.

In one aspect, such a method involves modification of ubiquitin with fluorescent dyes that undergo fluorescence resonance energy transfer (FRET). Cleavage of the conjugate is monitored by loss of FRET signal (i.e., reduced fluorescence of the acceptor dye or dequenching of the donor dye).

In one aspect, the chosen assay method is used to screen a library of small molecules to identify those that inhibit the enzymatic activity of p97.

In one aspect, cleavage of labeled ubiquitin is monitored by sodium dodecylsulfate-polyacrylamide gel electrophoresis followed by detection of the ubiquitin.

Compounds determined to be inhibitors of the enzymatic activity of '97 include those described above under the COMPOUNDS section.

BIOLOGICAL PROTOCOLS

The in vitro and in vivo biological assays to determine the anti-cancer properties of the fused pyrimidine compounds of the invention are summarized above. The details of these protocols show how the assays are carried out.

P97 Biochemical Assay Protocol

The p97 assay is an initial screening assay used to determine inhibitory activity of the fused pyrimidine compounds of the invention against the p97 complex. As discussed above, inhibition of activity of the p97 proteosome complex can enable apoptosis and cause elimination of neoplastic cells (cancer cells). The method follows that of Christianson in Nat. Cell Biol., (2011) 14:93.

The Reagents Used for the p97 Assay Include:

Assay Buffer is a mixture of 50 mM TRIS pH 7.5, 20 mM $MgCl_2$, 0.02% TX-100, 1 mM DTT and 0.2% (v/v) Glycerol. The well plate is Platetype: Corning 3674, 384w plate. The identification kit is an ADP glo kit (Promega): stop buffer, detection reagent.

The Assay Protocol is Conducted as Follows:

Serial dilute compound in DMSO in a 1:3.33-fold 10 point serial dilution.

in each well of 384w plate add the following reagents:
0.5 µL compound serial diluted in DMSO (Final Conc. 10%)
2 µL ATP (Final Conc.=20 uM, diluted in assay buffer)
2.5 µL p97 (Final Conc.=20 nM, diluted in assay buffer)
Incubate at 37 degC for 15 min.
Add 5 µL of stop buffer, incubate at RT for 40 min.
Add 10 µL of detection reagent, incubate at RT for 30 min.
Read luminescence on Envision plate reader.

Upon obtaining the data from the luminescence reading, the data may be analyzed as follows:

Normalize luminescence data using no enzyme (full inhibition) and no compound (no inhibition) controls. Plot normalized luminescence data against log-transformed concentration values and fit to a sigmoidal curve to determine IC50 values (done in Collaborative Drug Discovery software).

Caco-2 Permeability Assay

This assay is designed as a model to indicate the permeability of a fused pyrimidine compound of this invention through the gut-blood barrier. The result will yield indications of whether or not the fused pyrimidine compound may be efficiently absorbed into the blood stream of a patient. Efficient, effective absorption of an orally administered drug determines in part its bioavailability. For the fused pyrimidine compounds of the invention, this assay is a model to evaluate the bioavailability of the compounds as a result of their ability to pass through biological barriers to entry into the physiological system of the patient.

The experimental goal of the Caco-2 assay is to measure directional Caco-2 permeability of test compounds in cultured Caco-2 monolayer.

The test compounds are the fused pyrimidine compounds of the invention.

Set-Up

Instruments
Tissue culture $CO_2$ incubator with humidity control
Liquid handler
Orbital shaker
EVOM Epithelial Volt-ohmmeter fitted with planar electrodes (World Precision Instruments, Sarasota, Fla.) required for measuring transepithelial electrical resistance (TEER)
Bench top centrifuge with 96-well plate adaptor
Caco-2 cells (Human colorectal adenocarcinoma, ATCC #37-HTB, passage 30-45)
Cells seeded onto PET membranes (1 µm pore size, 0.31 $cm^2$ surface area) inside Falcon HTS multiwell Insert system using 24-well plates (Becton Dickinson plates, Part #351181, Fisher Scientific, Inc.) at a density of 23,000 cells/well. Cells grown 20-23 days with medium changed every 2-3 days

Reagents

Ringers buffer solution (pH 7.4 at 25° C.)
Ringers buffer with 1% Methanol
Blk solution: Ringers buffer: Methanol=2:1 (v/v); 100% Methanol including internal standard (IS); 10 mM stock dosing solution in DMSO; 100 µM dosing solution in buffer.

Protocol Summary

Caco-2 permeability: 20-23 day/Passage 30-45
24-well format transwell: 0.31 cm2 surface area
Donor conc: 100 µM including 1% DMSO
A: 300 µL pH 7.4/B: 1200 µL pH 7.4 Ringers buffer
Directionality: A B and B A (N=4)
Donor side sampling: 20 µL at beginning and end (90 min)
Receiver side sampling: 100 µL at 30, 50, 70, and 90 min
Incubation at 50 oscillations per minute, 37° C., 5% $CO_2$, 95% humidity
Analysis: LC-UV, LC-MS, or LSC
Output: Peff (cm/sec)=(dX/dt)/(A*Co*60), dX/dt: transported amount (nmole) versus time (minute) profile in the receiver chamber; A: surface area ($cm^2$); and Co: initial donor concentration (gM)
Positive control: Atenolol and propranolol
Membrane integrity: TEER >200 $Ocm^2$
Amount required: Approximately 1 mg or 100 µl of 10 mM test compound in DMSO
Instruments: $CO_2$ incubator with humidity control, liquid handler, epithelial volt-ohmmeter for TEER, Caco-2 cells (ATCC #37-HTB), and 24-well insert plates (PET membranes, 1 µm pore size, 0.31 $cm^2$ plates, Part #351181) surface area, Becton Dickinson
Throughput: 6 compounds/2 Caco-2 plates/1 FTE/day Preparation

TABLE 24

Preparation of Ringers with Glucose (Isotonic = 290 mOsm/kg), pH 7.4

| Chemical | Molecular Wt | Concentration | Mass(g) for 1 L | Mass(g) for 2 L | Mass(g) for 4 L |
|---|---|---|---|---|---|
| $CaSO_4 2H_2O$ | 172.2 | 1.25 mM | 0.2152 | 0.4305 | 0.861 |
| $MgSO_4 7H2O$ | 246.5 | 1.1 mM | 0.2712 | 0.5423 | 1.0846 |
| KCl | 74.55 | 5 mM | 0.3728 | 0.7455 | 1.491 |
| $Na_2HPO_4$ | 142.0 | 1.15 mM | 0.1633 | 0.3266 | 0.6532 |
| $NaH_2PO_4 H_2O$ | 138.0 | 0.3 mM | 0.0414 | 0.0828 | 0.1656 |
| $NaHCO_3$ | 84.01 | 25 mM | 2.100 | 4.200 | 8.401 |
| Glucose($C_6H_{12}O_6$) | 180.2 | 25 mM | 4.505 | 9.01 | 18.02 |
| NaCl | 58.44 | 110 mM | 6.428 | 12.86 | 25.71 |

Preparation of 4 L Solution

1. To 3.5 L distilled water, add Calcium Sulfate and Magnesium Sulfate.
   Note: Add Calcium Sulfate and Magnesium Sulfate first due to low solubility and add the remaining ingredients in the order listed in Table 1.
2. Adjust the final volume of the solution to 4 L with distilled water, with continuous stirring.
3. Adjust final solution to a pH of 7.4 using 1N HCl or 1N NaOH.
4. Make the buffer iso-osmotic using NaCl. Measure tonicity of the solution using a tonometer. Given that an isotonic solution is equivalent to 0.9% NaCl (290 mOsm/L),
   Y={(290−x)/290}×9 mg×4000 mL, where y=NaCl required (in mg) to make the solution isotonic and x=observed tonicity of solution (reported as mOsm/L).

Preparation of Dosing Solution in 15 ml PP Tube 1. 100 µM dosing solution in RG: 140 µL 10 mM stock+(14 mL−140 µL) RG Preparation of Calibration in 96 Shallow Well 1. Prepare 10 µM standard: 100 µL of 100 µM dosing solution+0.9 mL Ringers with 1% Methanol.
2. Prepare analytical standard solutions 10, 5, 2, 1, 0.5, 0.2, 0.1, 0.05, 0.02, 0.01, and 0 µM. (See Table 26)

Transport Studies

Dosing and Sampling

1. Equilibrate both sides of the monolayers for 10 minutes with prewarmed (37° C.) drug-free Ringers buffer (300 µL apical side, 1,200 µL basolateral side) supplemented with glucose (25 mM).
2. Measure TEER under 37° C. water bath conditions.
   Note: The TEER value serves as a quality control check for monolayer integrity. At 21 days post-seeding, each Caco-2 cell monolayer should have a TEER value of greater than or equal to 2000×$cm^2$ and those not meeting this criteria are not suitable for permeability evaluations.
3. When studying A to B transport: Fill basolateral side with 1,200 µL of Ringers buffer. Initiate transport experiments by transferring test drug dosing solution (320 µL) to apical side.
4. When studying B to A transport: Fill apical side with 300 µl of Ringers buffer. Initiate transport experiments by transferring test drug dosing solution (1,220 µL) to basolateral side. Transport studies for each direction (A to B, B to A) are performed in quadruplicate for each test drug.
5. Start timer after dosing last donor well.
6. Remove 20 µL aliquots from the donor wells at 0 minutes ($D_O$) and transfer these aliquots to the donor site of the 96-well plate containing 180 µL buffer with 1% Methanol. This step effectively dilutes the $D_0$ ten times.

TABLE 25

Preparation of analytical calibration in 96 shallow well

| | 1 | 2 | 3 | 4 | 5 | 6 | 7 | 8 | 9 | 10 | 11 | 12 |
|---|---|---|---|---|---|---|---|---|---|---|---|---|
| | 0 | 20 µL of 0.1 µM 180 µL | 20 µL of 0.2 µM 180 µL | 20 µL of 0.5 µM 180 µL | 20 µL of 1 µM 180 µL | 20 µL of 2 µM 180 µL | 20 µL of 5 µM 180 µL | 20 µL of 10 µM 180 µL | 40 µL of 10 µM 160 µL | 100 µL of 10 µM 100 µL | 200 µL of 10 µM 0 | Source solution 1% MeOH in buffer |
| Comp 1 | Blk | 0.01 µM | 0.02 µM | 0.05 µM | 0.1 µM | 0.2 µM | 0.5 µM | 1 µM | 2 µM | 5 µM | 10 µM | |
| Comp 2 | | | | | | | | | | | | |
| Comp 3 | | | | | | | | | | | | |

7. Initiate transport studies by placing plate on orbital shaker maintained inside a prewarmed (37° C.) and humidified (5% $CO_2$) incubator. Studies are performed under stirring conditions at 50 oscillations per minute.

8. Remove 100 μL aliquots from the receiver side of the monolayer at 30, 50, 70, and 90 minutes postdosing and transfer these aliquots to the corresponding 96-well sample plate (See Table 26). Replace with an equivalent volume of prewarmed buffer.

9. Remove 20 μL aliquots from the donor side of the monolayer at 90 minutes postdosing ($D_f$) and transfer these aliquots to a donor site of a 96-well plate containing 180 μL Ringers buffer with 1% Methanol. This step effectively dilutes the $D_f$ ten times.

10. Replace both sides of monolayer with fresh, drug-free, prewarmed Ringers buffer (300 μL apical side, 1,200 μL basolateral side) and equilibrate for 10 minutes.

11. Measure TEER under 37° C. water bath conditions.

Sample Handling

The following steps refer to 96-well analytical plate for Caco-2, Table 26.

1. Transfer 20 μL of diluted $D_0$ and $D_f$ to corresponding 96-well sample plate with each well containing 80 μL buffer with 1% Methanol. This step effectively dilutes the samples five times further. Therefore, donor samples are diluted 50 times from their initial concentration.

2. Transfer 100 μL of analytical calibration (from 0 to 10 μM) to the sample plate row 1.

3. Add 50 μL Methanol including IS to all sample wells and mix (standards, samples, and $D_0$ and $D_f$).

4. Transfer 150 μl of Blk solution to the analytical plate row 2.

5. Seal the analytical plate with adhesive sealing film and store samples with label at −80° C. for LC-UV or LC-MS analysis.

6. Analyze 20 μL aliquots of the individual permeability samples and the standards using a suitable analytical instrument.

7. $Peff=(dX/dt)/(A \times C_0 \times 60)$, where $P_{eff}$ is the effective permeability in cm/sec, X=mass transported, A is the surface area $(cm)^2$ available for transport, $C_0$ is the initial donor drug concentration (μM), and dX/dt is the slope of the best fit line through the transported amount (nmole) versus time (min) profile in the receiver chamber.

Positive Control Data

Mean data in Table 27 represent the mean value from 12 separate inter-day experiments.

TABLE 27

| $P_{eff}$ (×E−6 cm/sec) in pH 7.4 Caco-2 | | |
|---|---|---|
| | A B | B A |
| Atenolol | | |
| Mean | 1.08 | 2.29 |
| Range | 0.69-1.80 | 1.69-2.68 |
| Propranolol | | |
| Mean | 28.53 | 20.91 |
| Range | 18.50-36.80 | 16.30-31.40 |

Mouse Liver Microsome Assay

The liver microsome assay is a model for studying the metabolic stability of the fused pyrimidine compounds of the invention. Metabolic stability is another aspect determining bioavailability. The facility of a compound to be bioabsorbed into the blood stream as shown by the Caco-2 model indicates the degree to which an oral dose of the compound will reach the blood stream. The body efficiently metabolizes substances to rid them from the body and/or to utilize them as nutrients. This aspect of bioavailability can be determined by such model studies as liver microsomal metabolism. Whether by oxidation, conjugation or any other biological pathway, metabolism of a drug determines at least in part the lifetime of the drug in the body.

The mouse liver microsome assay is a model designed to establish drug half-life in vivo. The liver enzymes are responsible to conversion of substances to materials that can be readily excreted by the body. Other routes for such metabolism include kidney metabolism, cellular metabolism and the like.

In this protocol, the compound is combined with a liver microsomal preparation (protein) and NADPH. The mixture is incubated and the rate of disappearance of the compound from the test solution is measured. Measurement is made by screening for the compound concentration at specified times using liquid chromatography in combination with mass spectroscopy.

TABLE 26

| Analytical Plate for Caco-2 (96-well plate) | | | | | | | | | | | |
|---|---|---|---|---|---|---|---|---|---|---|---|
| 0 | 0.01 μM | 0.02 μM | 0.05 μM | 0.1 μM | 0.2 μM | 0.5 μM | 1 μM | 2 μM | 5 μM | 10 μM | |
| Blk | Blk | Blk | Blk | A to B | | | B to A | Blk | Blk | Blk | Blk |
| 1-30 | 2-30 | 3-30 | 4-30 | | | | | 5-30 | 6-30 | 7-30 | 8-30 |
| 1-50 | 2-50 | 3-50 | 4-50 | | | | | 5-50 | 6-50 | 7-50 | 8-50 |
| 1-70 | 2-70 | 3-70 | 4-70 | | | | | 5-70 | 6-70 | 7-70 | 8-70 |
| 1-90 | 2-90 | 3-90 | 4-90 | | | | | 5-90 | 6-90 | 7-90 | 8-90 |
| 1-Do | 2-Do | 3-Do | 4-Do | | | | | 5-Do | 6-Do | 7-Do | 8-Do |
| 1-Df | 2-Df | 3-Df | 4-Df | | | | | 5-Df | 6-Df | 7-Df | 8-Df |

Concentrations of Reactants Ready for Formulation as the Test Solution:
 Protein: 1.0 mg/ml
 Compound: 1 um
 Organic solvent: 0.4% DMSO
 Medium: 0.1 M Potassium Phosphate (KB)
 1 mM NADPH (sigma N1630, FW 833.3, make freshly)
 Prepare test article (TA, i.e., a compound of the invention) by dissolving solid TA in DMSO to make a 0.25 mM solution Amounts of Reactant Solutions to be Combined to Form the Test Solution:

| | |
|---|---|
| 423 ul | KB (potassium phosphate) |
| +25 ul | MLM (20 mg/ml) (mouse liver microsomal preparation) |
| 448 ul | |
| +2 ul | Test compound (a fused pyrimidine compound at 0.25 mM DMSO) |
| +50 ul | NADPH stock (10 mM, 10 x) |
| 500 ul | |

Test Protocol for Conducting the Assay
1. Add 423 ul KB to an 8-strip deep well tubes
2. Add 25 ul of MLM for condition 1
3. Place on ice, add 2 ul cmpds (250×stock in DMSO, stock at 0.25 mM)
4. Preincubate the reaction mixture at 37 C for 3 to 5 minutes (shaking at 150 rpm)
5. Initiate reaction by adding 50 ul NADPH for condition 1
6. Add 50 ul KB for condition 2
7. An aliquot of samples of 100 ul were collected at 0, 15, 30, and 60 min time point, and 200 ul of acetonitrile mixture containing IS was added to quench the reaction.
8. Centrifuge for 10 min at 4000 rpm
9. The supernatant were injected for liquid chromatographic tandem mass spectrometry (LC-MS/MS) analysis Procedure of Protein Binding Using 96-Well Equilibrium Dialyzer Non-specific protein binding is another facet affecting bioavailability and effectiveness of a drug. To assay a compound for non-specific binding, the compound is combined with human blood plasma and the solution dialyzed against a membrane constructed to prevent passage of larger molecules such as human plasma proteins but allow passage of small molecules such as the compounds of the invention. Typically, such membranes allow passage of such compounds irrespective of their salt or neutral form. The dialysate (solution passing through the membrane) is examined by liquid chromatography mass spectrometric techniques to determine the identity and concentration of the compound present. The concentration of compound in the dialysate compared with the concentration of compound combined with blood plasma indicates whether or not non-specific protein binding has occurred.

Equipment and Reagent:
96-Well Equilibrium Dialyzer (made by: Harvard Apparatus)
Plate Rotator with DIALYZER plates secured in clamp fixture
Buffer: DPBS (gibco, 1×)
Compound Concentration: 1 µM (~0.5 in µg/mL) in Human Plasma Procedure:
1. Seal the empty Sample Side well on the colored side with cap strips.
2. Invert the plate and carefully pipet a volume of buffer, 200 µL equal to the sample volume into the wells on the Buffer Side (clear frame) without touching the membranes by allowing the liquid to flow along the inner side wall of each well.
3. Gently seal the filled buffer wells with cap strips.
4. Invert the plate and carefully remove the cap strips from the sample side wells. Pipet desired samples, without touching the membranes.
5. Reseal the sample wells with the cap strips.
6. Slide the assembled DIALYZER Plate into a Plate Rotator and hand tighten the snobs. Turn on and allow rotating until equilibrium has been reached (24 hours at 37 C), remove the DIALYZER Plate from the Rotator.
7. After equilibrium has been reached, remove the DIALYZER Plate from the rotator.
8. Carefully remove the cap strips from the Buffer Side of the Plated (clear frame) and slowly pipet out the analysis samples from the wells taking care not to touch or puncture the membranes.

Samples will include control at 4 C and stability at 37 C samples in PBS and plasma.

MS Analysis:
 Prepare standard range 5, 10, 50, 100, 500 and 1000 ng/mL in Plasma
 Pipet 10 µL each of standard and sample into 404 of blank buffer/blank plasma them (ratio: 1 plasma/4 DPBS), mix them.
 Add 200 µL of Is (internal standard) in ACN, mix well.
 Centrifuge the samples and transfer supernatant solution for LC/MS analysis.

The Cell Assay Protocol

The cellular assay provides information about the antineoplastic activity of the compounds of the invention. The compounds are tested against cultured cancer cells to determine whether or not the compounds of the invention are capable of intersecting with cancer cells to minimize or eliminate such cells.

The assay involves establishing colonies of such cells and then treating them with the test compound under specified conditions and analysis regima to determine results.

Day 1, Cell Plating to Establish Colonies of Cancer Cells
Cell Plating:
 Seed cells ~16 hrs prior to compound treatment
 Plate 25 µL of A549 cells in every well of 384-well plate using multidrop.
 Two (2) black plates for IF at 2500 cells/well
 Let plate sit at room temp for 10-15 minutes prior to putting in incubator to allow cells to stick in middle of plate.
 One (1) white plate for viability at 500 cells/well.

Day 2 Treatment of Cultured Cells with Test Compounds
Treat Cells:
 Serial dilute compounds with a 10 point 2-fold serial dilution in DMSO to make 250× stock compound solution
 Dilute compounds 1:125 in cell culture media to make a 2× solution Add 25 µl of dilution compounds to cell plates in well duplicates
 Put cells back in incubator (6 hr incubation for black plates, 72 hr incubation for white plates).

Fix/Stain Black Plates:
Incubate cells in black plates with compound at 37 degC for 6 hrs.
add 15 μL of 16% Paraformaldehyde (PFA) directly into media of each well,
incubate at room temp for 5 min, flick plate and wash in 50 μL of PBS
block in 50 μL of Blocking Buffer for 30 minutes (can go up to several hours)
Blocking buffer: 1×PBS, 1% BSA, 0.3% Triton-X100, Hoechst (1:10,000) incubate in 25 μL of primary antibody in blocking buffer at 4 degC over night
Primary Antibodies:
Plate A K48-Ub 1:20,000 (millipore 05-1307 Lot 2049282) Rabbit
CHOP/Gadd153 1:2,000 (SC-7351) Mouse
Plate B P53 1:2,000 (SC-6243) Rabbit
p62/SQSTM1 1:2,000 (SC-28359) Mouse
overnight at 4 degC
Secondary Antibodies:
AlexaFluor488 Goat anti-Rabbit 1:2,000 (Life Tech A11008)
AlexaFluor555 Goat anti-Mouse 1:2,000 (Life Tech A21422)
Day 3/4
Black Plate Staining (cont):
wash black plates 3× in 50 μL PBS (~5 min each)
incubate in 25 μl of secondary antibody (1:2,000) in blocking buffer for 1-2 hrs at room temp (alexafluor488-anti-Rabbit/alexafluor555-anti-Mouse)
wash 4× in 50 μL PBS (~5 min each)
leave plates in PBS for imaging
clean bottom of plates with 70% EtOH
Imaging:
Image plates in high content microscope with 405 nm, 488 nm and 555 nm filters
Data Analysis:
Nuclear counts and cellular intensities of each markers are measured using Hoechst as a nuclear marker with an automated image analysis protocol using Matlab software (Math Works)
Day 5
Viability assay:
Thaw an aliquot of frozen cell titer glo (Promega G7572) at room temperature.
Add 45 mL of NaCl/PBS solution to 5 ml of cell titer glo (10×).
Remove white plates from incubator, leave at room temp for 30 minutes.
Add 25 μl of diluted cell titer glo to each well.
Shake plate for >1 minute.
Incubate plate for >5 minutes to stabilize luminescence.
Luminescence is stable for up to 3 hours.
Read luminescence on plate reader Summary Statements The inventions, examples, biological assays and results described and claimed herein have may attributes and embodiments include, but hot limited to, those set forth or described or referenced in this application.

All patents, publications, scientific articles, web sites and other documents and material references or mentioned herein are indicative of the levels of skill of those skilled in the art to which the invention pertains, and each such referenced document and material is hereby incorporated by reference to the same extent as if it had been incorporated verbatim and set forth in its entirety herein. The right is reserved to physically incorporate into this specification any and all materials and information from any such paten, publication, scientific article, web site, electronically available information, text book or other referenced material or document.

The written description of this patent application includes all claims. All claims including all original claims are hereby incorporated by reference in their entirety into the written description portion of the specification and the right is reserved to physically incorporated into the written description or any other portion of the application any an all such claims. Thus, for example, under no circumstances may the patent be interpreted as allegedly not providing a written description for a claim on the assertion that the precise wording of the claim is not set forth in haec verba in written description portion of the patent.

All features disclosed in this specification may be combined in any order and in any combination with any of the formulas I, II and/or III.

While the invention has been described in conjunction with the detailed description thereof, the foregoing description is intended to illustrate and not limit the scope of the invention, which is defined by the scope of the appended claims. Thus, from the foregoing, it will be appreciated that, although specific nonlimiting embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred nonlimiting embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in nonlimiting embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various nonlimiting embodiments and/or preferred nonlimiting embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, for example, the term "X and/or Y" means "X" or "Y" or both "X" and "Y", and the letter "s" following a noun designates both the plural and singular forms of that noun. In addition, where features or aspects of the invention are described in terms of Markush groups, it is intended, and those skilled in the art will recognize, that the invention embraces and is also thereby described in terms of any individual member and any subgroup of members of the Markush group, and the right is reserved to revise the application or claims to refer specifically to any individual member or any subgroup of members of the Markush group.

What is claimed is:

1. A fused pyrimidine compound of Formula I

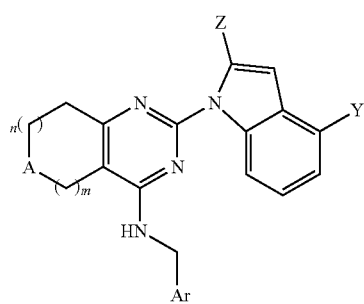

Formula I or a pharmaceutically acceptable salt thereof, wherein:
A is $CH_2$, $NR^1$, O or S;
m is an integer of 1-3;
n is 0 or an integer of 1-2;
the ring containing A is a five or six member ring and the sum of m and n is no greater than 2;
Y is selected from the group consisting of halogen, $OR^c$, CN, $CO_2H$, $CON(R^c)_2$, $C(NR^c)N(R^c)_2$, $CH_2N(R^c)2$, $SO_2N(R^c)_2$, tetrazolyl, $SO_2R^c$ and $SO_3H$ wherein each $R^c$ is independently selected from the group consisting of hydrogen and alkyl of 1 to 4 carbons;
Z is selected from the group consisting of methyl, ethyl, propyl, cyclopropyl, methoxy, ethoxy, propoxy, methoxymethyl, methoxyethyl, methoxymethoxy, methoxyethoxy, morpholinyl, piperidinyl, piperazinyl, pyrrolidonyl, pyrrolidinyl, trifluoromethyl, pentafluoroethyl;
$R^1$ is selected from a group consisting of hydrogen and unsubstituted alkyl of 1 to 6 carbons; and,
Ar is phenyl or fluorophenyl.

2. A fused pyrimidine compound according to claim 1 wherein $R^c$ of Y is hydrogen or methyl.

3. A fused pyrimidine compound according to claim 1 wherein Y is selected from the group consisting of cyano, fluoro, chloro, bromo, carboxyl, sulfo, methylsulfonyl, aminomethyl, carboxamido sulfonamido, carboxamido, N,N-dialkylcarboxamido, N-alkylsulfonamido, N,N-dialkylsulfonamido, wherein the alkyl group is 1 to 4 carbons.

4. The fused pyrimidine compound of claim 1 wherein Ar is an unsubstituted phenyl.

5. A fused pyrimidine compound having any one of the following names or a salt or hydrate thereof:
1-[4-(benzylamino)-5,6,7,8-tetrahydroquinazolin-2-yl]-2-methyl-1H-indole-4-carbonitrile;
1-[4-(benzylamino)-5,6,7,8-tetrahydroquinazolin-2-yl]-2-methoxy-1H-indole-4-carbonitrile;
1-[4-(benzylamino)-5,6,7,8-tetrahydroquinazolin-2-yl]-2-methyl-1H-indole-4-carboxamide;
1-[4-(benzylamino)-5,6,7,8-tetrahydroquinazolin-2-yl]-2-methoxy-1H-indole-4-carboxamide;
1-[4-(benzylamino)-5,6,7,8-tetrahydroquinazolin-2-yl]-2-ethyl-1H-indole-4-carboxylic acid;
1-[4-(benzylamino)-5,6,7,8-tetrahydroquinazolin-2-yl]-2-methyl-1H-indole-4-sulfonamide;
N-benzyl-2-(4-methanesulfonyl-2-methyl-1H-indol-1-yl)-5,6,7,8-tetrahydroquinazolin-4-amine;
1-[4-(benzylamino)-5,6,7,8-tetrahydroquinazolin-2-yl]-2-ethyl-1H-indole-4-carboxamide;
N-benzyl-2-[2-methyl-4-(1H-1,2,3,4-tetrazol-5-yl)-1H-indol-1-yl]-5,6,7,8-tetrahydroquinazolin-4-amine;
1-[4-(benzylamino)-5,6,7,8-tetrahydroquinazolin-2-yl]-2-(2-methoxyethoxy)-1H-indole-4-carboxamide;
1-[4-(benzylamino)-5,6,7,8-tetrahydroquinazolin-2-yl]-2-(propan-2-yl)-1H-indole-4-carboxamide;
1-[4-(benzylamino)-5,6,7,8-tetrahydroquinazolin-2-yl]-2-cyclopropyl-1H-indole-4-carboxamide;
1-[4-(benzylamino)-5,6,7,8-tetrahydroquinazolin-2-yl]-N,2-dimethyl-1H-indole-4-carboxamide;
1-[4-(benzylamino)-5,6,7,8-tetrahydroquinazolin-2-yl]-N,N,2-trimethyl-1H-indole-4-carboxamide;
1-[4-(benzylamino)-5,6,7,8-tetrahydroquinazolin-2-yl]-N-ethyl-2-methyl-1H-indole-4-carboxamide;
1-[4-(benzylamino)-5,6,7,8-tetrahydroquinazolin-2-yl]-N-(2-methoxyethyl)-2-methyl-1H-indole-4-carboxamide;
1-[4-(benzylamino)-5,6,7,8-tetrahydroquinazolin-2-yl]-2-ethoxy-1H-indole-4-carboxamide;
1-[4-(benzylamino)-5,6,7,8-tetrahydroquinazolin-2-yl]-2-(2-methoxyethoxy)-1H-indole-4-carboxamide
1-[4-(benzylamino)-5H,7H,8H-pyrano[4,3-d]pyrimidin-2-yl]-2-methoxy-1H-indole-4-carbonitrile;
1-[4-(benzylamino)-5H,7H,8H-pyrano[4,3-d]pyrimidin-2-yl]-2-methyl-1H-indole-4-carbonitrile;
1-[4-(benzylamino)-5H,7H,8H-pyrano[4,3-d]pyrimidin-2-yl]-2-methoxy-1H-indole-4-carboxamide;
1-[4-(benzylamino)-5H,7H,8H-pyrano[4,3-d]pyrimidin-2-yl]-2-methyl-1H-indole-4-carboxamide;
1-[4-(benzylamino)-5H,7H,8H-pyrano[4,3-d]pyrimidin-2-yl]-N,2-dimethyl-1H-indole-4-carboxamide;
1-[4-(benzylamino)-5H,7H,8H-pyrano[4,3-d]pyrimidin-2-yl]-N,N,2-trimethyl-1H-indole-4-carboxamide;
1-[4-(benzylamino)-5H,7H,8H-pyrano[4,3-d]pyrimidin-2-yl]-2-methyl-N-(propan-2-yl)-1H-indole-4-carboxamide;
1-[4-(benzylamino)-5H,7H,8H-pyrano[4,3-d]pyrimidin-2-yl]-N-(butan-2-yl)-2-methyl-1H-indole-4-carboxamide;
1-[4-(benzylamino)-5H,7H,8H-pyrano[4,3-d]pyrimidin-2-yl]-2-methyl-1H-indole-4-carboxylic acid;
1-[4-(benzylamino)-5H,7H,8H-pyrano[4,3-d]pyrimidin-2-yl]-2-methyl-1H-indole-4-sulfonamide;

1-[4-(benzylamino)-5H,7H,8H-pyrano[4,3-d]pyrimidin-2-yl]-2-ethyl-1H-indole-4-carboxamide;
N-benzyl-2-(4-methanesulfonyl-2-methyl-1H-indol-1-yl)-5H,7H,8H-pyrano[4,3-d]pyrimidin-4-amine;
1-[4-(benzylamino)-5H,7H,8H-pyrano[4,3-d]pyrimidin-2-yl]-2-methyl-1H-indole-4-carboximidamide;
N-benzyl-2-[2-methyl-4-(1H-1,2,3,4-tetrazol-5-yl)-1H-indol-1-yl]-5H,7H,8H-pyrano[4,3-d]pyrimidin-4-amine;
1-(4-{[(4-fluorophenyl)methyl]amino}-5H,7H,8H-pyrano[4,3-d]pyrimidin-2-yl)-2-methyl-1H-indole-4-carboxamide;
1-(4-{[(2-fluorophenyl)methyl]amino}-5H,7H,8H-pyrano[4,3-d]pyrimidin-2-yl)-2-methyl-1H-indole-4-carboxamide;
2-[4-(aminomethyl)-2-methyl-1H-indol-1-yl]-N-benzyl-5H,7H,8H-pyrano[4,3-d]pyrimidin-4-amine;
1-[4-(benzylamino)-5H,7H,8H-pyrano[4,3-d]pyrimidin-2-yl]-2-(propan-2-yl)-1H-indole-4-carboxamide;
1-[4-(benzylamino)-5H,7H,8H-pyrano[4,3-d]pyrimidin-2-yl]-2-cyclopropyl-1H-indole-4-carboxamide;
1-(4-{[(3-fluorophenyl)methyl]amino}-5H,7H,8H-pyrano[4,3-d]pyrimidin-2-yl)-2-methyl-1H-indole-4-carboxamide;
N-benzyl-2-(4-fluoro-2-methyl-1H-indol-1-yl)-5H,6H,7H,8H-pyrido[4,3-d]pyrimidin-4-amine;
1-[4-(benzylamino)-5H,6H,7H,8H-pyrido[4,3-d]pyrimidin-2-yl]-2-methyl-1H-indole-4-carbonitrile;
1-[4-(benzylamino)-5H,6H,7H,8H-pyrido[4,3-d]pyrimidin-2-yl]-2-methyl-1H-indole-6-carbonitrile;
N-benzyl-2-(4-methoxy-2-methyl-1H-indol-1-yl)-5H,6H,7H,8H-pyrido[4,3-d]pyrimidin-4-amine;
1-[4-(benzylamino)-5H,6H,7H,8H-pyrido[4,3-d]pyrimidin-2-yl]-2-methyl-1H-indole-4-carboxamide;
1-[4-(benzylamino)-5H,6H,7H,8H-pyrido[4,3-d]pyrimidin-2-yl]-2-methoxy-1H-indole-4-carbonitrile;
1-[4-(benzylamino)-6-methyl-5H,6H,7H,8H-pyrido[4,3-d]pyrimidin-2-yl]-2-methyl-1H-indole-4-carbonitrile;
1-[4-(benzylamino)-6-ethyl-5H,6H,7H,8H-pyrido[4,3-d]pyrimidin-2-yl]-2-methyl-1H-indole-4-carbonitrile;
N-{1-[4-(benzylamino)-5H,6H,7H,8H-pyrido[4,3-d]pyrimidin-2-yl]-2-methyl-1H-indol-4-yl}acetamide;
1-[4-(benzylamino)-5H,6H,7H,8H-pyrido[4,3-d]pyrimidin-2-yl]-N,2-dimethyl-1H-indole-4-carboxamide;
1-[4-(benzylamino)-5H,6H,7H,8H-pyrido[4,3-d]pyrimidin-2-yl]-N,N,2-trimethyl-1H-indole-4-carboxamide;
1-[4-(benzylamino)-5H,6H,7H,8H-pyrido[4,3-d]pyrimidin-2-yl]-2-methyl-N-(propan-2-yl)-1H-indole-4-carboxamide;
1-[4-(benzylamino)-5H,6H,7H,8H-pyrido[4,3-d]pyrimidin-2-yl]-N-(butan-2-yl)-2-methyl-1H-indole-4-carboxamide;
1-[4-(benzylamino)-5H,6H,7H,8H-pyrido[4,3-d]pyrimidin-2-yl]-1H-indole-4-carboxamide;
1-[4-(benzylamino)-5H,6H,7H,8H-pyrido[4,3-d]pyrimidin-2-yl]-2-methoxy-1H-indole-4-carboxamide;
1-[4-(benzylamino)-5H,6H,7H,8H-pyrido[4,3-d]pyrimidin-2-yl]-2-methyl-1H-indole-4-sulfonamide;
1-[4-(benzylamino)-5H,6H,7H,8H-pyrido[4,3-d]pyrimidin-2-yl]-2-methyl-1H-indole-4-carboxylic acid;
N-benzyl-2-(4-methanesulfonyl-2-methyl-1H-indol-1-yl)-5H,6H,7H,8H-pyrido[4,3-d]pyrimidin-4-amine; or
1-[4-(benzylamino)-5H,6H,7H,8H-pyrido[4,3-d]pyrimidin-2-yl]-2-(2-methoxyethoxy)-1H-indole-4-carboxamide.

6. A fused pyrimidine compound according to claim 1, wherein A is $CH_2$.

7. A fused pyrimidine compound according to claim 1, wherein A is $NR^1$.

8. A fused pyrimidine compound according to claim 1, wherein A is O.

9. A fused pyrimidine compound according to claim 5 having any one of the following names:
a) 1-[4-(benzylamino)-5,6,7,8-tetrahydroquinazolin-2-yl]-2-methyl-1H-indole-4-carbonitrile;
b) 1-[4-(benzylamino)-5,6,7,8-tetrahydroquinazolin-2-yl]-2-methyl-1H-indole-4-carboxamide;
c) 1-[4-(benzylamino)-5,6,7,8-tetrahydroquinazolin-2-yl]-2-methoxy-1H-indole-4-carboxamide;
d) 1-[4-(benzylamino)-5,6,7,8-tetrahydroquinazolin-2-yl]-2-ethoxy-1H-indole-4-carboxamide;
e) 1-[4-(benzylamino)-5,6,7,8-tetrahydroquinazolin-2-yl]-2-(2-methoxyethoxy)-1H-indole-4-carbonitrile;
f) 1-[4-(benzylamino)-5,6,7,8-tetrahydroquinazolin-2-yl]-2-cyclopropyl-1H-indole-4-carboxamide;
h) N-benzyl-2-[2-methyl-4-(1H-1,2,3,4-tetrazol-5-yl)-1H-indol-1-yl]-5,6,7,8-tetrahydroquinazolin-4-amine;
i) 1-[4-(benzylamino)-5H,7H,8H-pyrano[4,3-d]pyrimidin-2-yl]-2-methoxy-1H-indole-4-carboxamide;
j) 1-[4-(benzylamino)-5H,7H,8H-pyrano[4,3-d]pyrimidin-2-yl]-2-methyl-1H-indole-4-carboxamide;
k) 1-(4-{[(3-fluorophenyl)methyl]amino}-5H,7H,8H-pyrano[4,3-d]pyrimidin-2-yl)-2-methyl-1H-indole-4-carboxamide;
l) 1-[4-(benzylamino)-5H,7H,8H-pyrano[4,3-d]pyrimidin-2-yl]-2-methyl-1H-indole-4-carboxylic acid;
n) 1-[4-(benzylamino)-5H,6H,7H,8H-pyrido[4,3-d]pyrimidin-2-yl]-2-methyl-1H-indole-4-carboxylic acid;
o) 1-[4-(benzylamino)-5,6,7,8-tetrahydroquinazolin-2-yl]-2-methyl-1H-indole-4-sulfonamide;
p) N-benzyl-2-(4-methanesulfonyl-2-methyl-1H-indol-1-yl)-5,6,7,8-tetrahydroquinazolin-4-amine;
q) 1-[4-(benzylamino)-5,6,7,8-tetrahydroquinazolin-2-yl]-N-methyl-2-methyl-1H-indole-4-carboxamide; or
r) 1-[4-(benzylamino)-5H,7H,8H-pyrano[4,3-d]pyrimidin-2-yl]-N,2-dimethyl-1H-indole-4-carboxamide.

10. A fused pyrimidine compound according to claim 9 having any one of the following names:
1-[4-(benzylamino)-5,6,7,8-tetrahydroquinazolin-2-yl]-2-methy-1H-indole-4-carboxamide;
1-[4-(benzylamino-5H,7H,8H-pyrano[4,3-d]pyrimidin-2-yl]-2-methyl-1H-indole-4-carboxamide;
1-(4-{[(3-fluorophenyl)methyl]amino}-5H,7H,8H-pyrano[4,3-d]pyrimidin-2-yl)-2-methyl-1H-indole-4-carboxamide;
[4-(benzylamino)-5H,6H,7H,8H-pyridino[4,3-d]pyrimidin-2-yl]-2-methyl-1H-indole-4-carboxamide; or
1-[4-(benzylamino)-5H,7H,8H-pyrano[4,3-]pyrimidin-2-yl]-2-methoxy-1H-indole-4-carboxamide.

11. A fused pyrimidine compound according to claim 2 or 3 wherein A is $CH_2$.

12. A fused pyrimidine compound according to claim 2 or 3 wherein A is $N^1$.

13. A fused pyrimidine compound according to claim 2 or 3 wherein A is O.

14. A fused pyrimidine compound according to claim 10 having the name 1-[4-(benzylamino)-5H,7H,8H-pyrano[4,3-d]pyrimidin-2-yl]-2-methyl-1H-indole-4-carboxamide.

* * * * *